(12) United States Patent
Shah et al.

(10) Patent No.: US 11,857,539 B2
(45) Date of Patent: Jan. 2, 2024

(54) GEL OPHTHALMIC FORMULATIONS OF PILOCARPINE AND BRIMONIDINE COMPOUNDS AND RELATED METHODS

(71) Applicant: Somerset Therapeutics, LLC, Hollywood, FL (US)

(72) Inventors: Mandar V. Shah, Rockaway, NJ (US); Ilango Subramanian, Warren, NJ (US); Veerappan Subramanian, Warren, NJ (US); Aman Trehan, Hillsborough, NJ (US)

(73) Assignee: Somerset Therapeutics, LLC, Hollywood, FL (US)

( * ) Notice: Subject to any disclaimer, the term of this patent is extended or adjusted under 35 U.S.C. 154(b) by 0 days.

(21) Appl. No.: 18/167,059

(22) Filed: Feb. 9, 2023

(65) Prior Publication Data

US 2023/0248701 A1     Aug. 10, 2023

Related U.S. Application Data

(60) Provisional application No. 63/308,382, filed on Feb. 9, 2022, provisional application No. 63/308,394, filed on Feb. 9, 2022, provisional application No. 63/308,418, filed on Feb. 9, 2022, provisional application No. 63/308,402, filed on Feb. 9, 2022, provisional application No. 63/308,417, filed on Feb. 9, 2022, provisional application No. 63/308,390, filed on Feb. 9, 2022.

(51) Int. Cl.
| | |
|---|---|
| A61K 31/4178 | (2006.01) |
| A61K 31/498 | (2006.01) |
| A61K 9/00 | (2006.01) |
| A61K 47/26 | (2006.01) |
| A61K 31/14 | (2006.01) |
| A61K 47/44 | (2017.01) |

(52) U.S. Cl.
CPC ........ *A61K 31/4178* (2013.01); *A61K 9/0048* (2013.01); *A61K 31/14* (2013.01); *A61K 31/498* (2013.01); *A61K 47/26* (2013.01); *A61K 47/44* (2013.01)

(58) Field of Classification Search
CPC .. A61K 31/4178; A61K 31/498; A61K 47/44; A61K 9/0048
See application file for complete search history.

(56) References Cited

U.S. PATENT DOCUMENTS

| | | | |
|---|---|---|---|
| 6,410,544 B1 | 6/2002 | Gwon | |
| 8,299,079 B2 * | 10/2012 | Kaufman | A61K 31/498 514/249 |
| 10,610,518 B2 | 4/2020 | Robinson | |
| 10,639,297 B2 | 5/2020 | Feinbaum | |
| 11,285,134 B2 | 3/2022 | Robinson | |
| 2019/0008832 A1 | 1/2019 | Pinelli | |
| 2020/0246310 A1 | 8/2020 | Pitlick | |

FOREIGN PATENT DOCUMENTS

WO    WO2022/169959    8/2022

OTHER PUBLICATIONS

Isopto® Product Label (Alcon Laboratories, Inc., Revised Jun. 2010, 5 pages) (Year: 2010).*
Vuity® Product Label (Allergan, Revised Oct. 2021, 8 pages) (Year: 2021).*
Alphagan® Product Label (Allergan, Revised Mar. 2016, 8 pages) (Year: 2016).*
Pilocarpine Hs® Product Label (Alcon Laboratories, Inc., Revised Oct. 2007, 7 pages) (Year: 2007).*
Gil-Cazorla et al., 2016, British Journal of Ophthalmology 100(1): 62-70, Apr. 23, 2015, Gil-Cazorla, Raquel.
Charman, 2014, Ophthalmic & Physiological Optics: the Journal of the College of Optometrists 34(4): 397-426, Apr. 10, 2014, Charman, W. Neil.
Charman, 2014, Ophthalmic & Physiological Optics: the Journal of the College of Optometrists 34(1): 8-29, Nov. 10, 2013, Charman, W. Neil.
Katz, et al. "Presbyopia—A Review of Current Treatment Options and Emerging Therapies." Clin Ophthalmol. 2021; 15:2167-2178, May 24, 2021, Katz, James A.
Patel et al., 2007, Community Eye Health/International Centre for Eye Health 20(63): 40-41, Sep. 1, 2007, Patel, Ilesh.
Goertz et al., 2014, Acta Ophthalmologica 92(6): 497-500, Nov. 13, 2013, Goertz, Ariana D.
Frick et al., 2015, Ophthalmology 122(8): 1706-10, Aug. 15, 2015, Frick, Kevin D.
Non-Final Office Action dated Apr. 11, 2023 for U.S. Appl. No. 18/154,470, Apr. 11, 2023, Mitchell, Edwin Coleman.
Non-Final Office Action dated Mar. 23, 2023 for U.S. Appl. No. 18/154,524, Mar. 23, 2023, Truong, Quanglong N.

(Continued)

*Primary Examiner* — James D. Anderson
(74) *Attorney, Agent, or Firm* — Transformative Legal LLC; Len S. Smith; Denise M. Brown

(57) ABSTRACT

The present invention provides, stable, pharmaceutically acceptable and ophthalmologically suitable gel compositions comprising therapeutically effective amounts of both a pilocarpine compound and a brimonidine compound and effective amount(s) of at least one polyethoxylated castor oil, which in aspects is/are present in a defined ratio with one or more active pharmaceutical ingredients. In aspects, such compositions are formulated as gel compositions. In certain embodiments, provided compositions are free of both a borate buffer and a citrate buffer. Compositions provided by the invention demonstrate stability, e.g., pH and active pharmaceutical ingredient stability, when stored under controlled room temperature conditions for an extended period of time. Further, the invention provides methods of manufacturing such compositions and methods of their use in treating ocular conditions, such as presbyopia.

22 Claims, No Drawings

(56) References Cited

OTHER PUBLICATIONS

Non-Final Office Action dated Apr. 11, 2023 for U.S. Appl. No. 18/167,057, Apr. 11, 2023, Anderson, James D.
Non-Final Office Action dated May 10, 2023 for U.S. Appl. No. 18/167,056, May 10, 2023, Alawadi, Sarah.

* cited by examiner

GEL OPHTHALMIC FORMULATIONS OF PILOCARPINE AND BRIMONIDINE COMPOUNDS AND RELATED METHODS

RELATED APPLICATIONS/PRIORITY

This patent application claims priority to U.S. Provisional Patent Application No. 63/308,382, filed Feb. 9, 2022, entitled, "Formulations of Pilocarpine and Brimonidine Compounds and Quaternary Ammonium Salts with Defined Tonicity Characteristics and Methods of Their use in Treating Presbyopia,"; U.S. Provisional Patent Application No. 63/308,390, filed Feb. 9, 2022, entitled, "Tonicity Defined, Saccharide-Free Formulations of Pilocarpine and Brimonidine Compounds and Methods of Their Use in Treating Presbyopia,"; U.S. Provisional Patent Application No. 63/308,394, filed Feb. 9, 2022, entitled, "Saccharide-Free Formulations of Pilocarpine and Brimonidine Compounds, With Quaternary Ammonium Salts and Methods of Their Use in the Treatment of Presbyopia,"; U.S. Provisional Patent Application No. 63/308,417, filed Feb. 9, 2022, entitled, "Low pH Formulations of Pilocarpine and Brimonidine Compounds and Methods of Their Use in the Treatment of Presbyopia,"; U.S. Provisional Patent Application No. 63/308,402, filed Feb. 9, 2022, entitled, "Selective Combination Formulations of Pilocarpine and Brimonidine Compounds and Methods of Their Use in the Treatment of Presbyopia,"; and U.S. Provisional Patent Application No. 63/308,418, filed Feb. 9, 2022, entitled, "Ophthalmic Gel Formulations of Pilocarpine Compounds and Brimonidine Compounds,". This application claims the benefit of priority to, and incorporates by reference the entirety of, these above-referenced priority applications.

FIELD OF THE INVENTION

The invention primarily relates to new and useful ophthalmic composition(s) that are useful for the treatment of ophthalmic conditions or related symptoms, wherein the composition(s) comprise pilocarpine compound(s) and brimonidine compound(s) and have unexpected or otherwise innovative properties. The present invention also relates to process(es) for manufacturing such composition(s) and method(s) of their use in treating ophthalmic condition(s) such as presbyopia.

BACKGROUND OF THE INVENTION

Presbyopia, commonly known as age-related blurry near vision, is a condition associated with and typically caused by age-related eye deterioration. Presbyopia typically develops with age and is associated with a natural progressive loss of visual accommodation. A presbyopic eye loses the ability to focus on objects rapidly and easily at near distances. Presbyopia progresses over the lifetime of an individual, usually becoming noticeable, and often bothersome or even disabling after the age of 45 years.

Presbyopia is the most common physiological change occurring in the adult eye and the condition can significantly affect quality of life and productivity when left uncorrected (See, e.g., Frick et al., 2015, Ophthalmology 122(8): 1706-10; Goertz et al., 2014, Acta Ophthalmologica 92(6): 497-500; and Patel et al., 2007, Community Eye Health/International Centre for Eye Health 20(63): 40-41). The main symptom of this condition is a progressive blurring of vision when performing near tasks (e.g., reading, sewing, viewing a computer screen, etc.). This can occur in the absence of any visual symptoms associated with distance vision. According to Katz, et. al., in "Presbyopia—A Review of Current Treatment Options and Emerging Therapies," Clin Ophthalmol. 2021; 15:2167-2178, and references cited therein, about 85% of people aged 40 years or older develop presbyopia. In 2015, it was estimated that 1.8 billion people globally suffered from presbyopia and its prevalence was predicted to reach approximately 2.1 billion in 2030 (Katz, supra)

For many years, the only means for addressing presbyopia has been corrective lens systems and surgical interventions. The methods available for correcting presbyopia have provided fixed and variable-focus lens systems ("glasses" or "spectacles" or contact lenses with monofocal, bifocal or multifocal design), and surgical procedures which modify the optics of the cornea, replace the crystalline lens with different fixed optics, or attempt to at least partially restore active accommodation (See, e.g., Charman, 2014, Ophthalmic & Physiological Optics: Journal of the College of Optometrists 34(1): 8-29; Charman, 2014, Ophthalmic & Physiological Optics: the Journal of the College of Optometrists 34(4): 397-426; and, e.g., Gil-Cazorla et al., 2016, British Journal of Ophthalmology 100(1): 62-70). However, corrective lens systems can be cumbersome or provide inadequate treatment, while surgical methods can be invasive and bring with them additional risks and potential side effects. For example, a patient may have trouble with night vision after a surgical intervention to treat presbyopia.

Topical pharmaceutical ophthalmic preparations have been marketed for a number of different ophthalmic conditions for many years. These preparations often comprise a parasympathomimetic drug (also referenced as a cholinomimetic drug or, e.g., a cholinergic receptor stimulating agent or cholinergic agonist). Most such agents act either directly by stimulating the nicotinic or muscarinic receptors (mimicking acetylcholine) or by inhibiting cholinesterase. Cholinergic agonists, such as the compound pilocarpine, were known within the field of ophthalmic disease for their ability to lower intraocular pressure (IOP), e.g., useful in the treatment of primary open angle glaucoma were commonly used treatments for lowering intraocular pressure (IOP) until the late 1970s.

In subsequent decades, and with the introduction of topical carbonic anhydrase inhibitors, alpha agonists, and prostaglandin agonists for lowering IOP, e.g., particularly the introduction of timolol in 1978, pilocarpine became less frequently prescribed, since newer drugs had a much lower incidence of side effects such as, e.g., reduced visual acuity and ocular discomfort (Allingham et al., Shields' Textbook of Glaucoma, $5^{th}$ edition, Lippincott Williams & Wilkins (Philadelphia), 2005, pp. 501-503).

There has remained, however, a void in treatment options for ameliorating or reducing presbyopia in patients that do not wish to undergo surgery (intra-ocular lenses, laser ablation, etc.) or use corrective glasses, as no topical solution has been available. This, in part, is due to the broadly accepted challenges facing ophthalmological composition formulators; that is, generating stable, safe, tolerable, and efficacious compositions, as it has been well demonstrated that even slight modifications of compositional elements leads to remarkably different results.

In late 2021, pilocarpine was approved by the United States Food and Drug Administration (NDA Number 214028) for the treatment of presbyopia. Abbvie, Inc. currently markets a product, VUITY® (approved under US FDA NDA Number 214028), which is a 1.25% pilocarpine ophthalmic solution. The product presently marketed as VUITY® is indicated for the treatment of presbyopia in adults with dosage of one drop in each eye once daily and represents the first and currently only FDA approved eye drop to treat this common and progressive eye condition affecting 128 million Americans, at least half of the U.S. adult population.

Each milliliter of VUITY® contains pilocarpine hydrochloride 1.25% (12.5 mg) as the active ingredient, equivalent to 1.06% (10.6 mg) pilocarpine free base. Inactive ingredients present in VUITY® include benzalkonium chloride (0.0075%), boric acid, sodium citrate dihydrate, sodium chloride, purified water, and may also include hydrochloric acid and/or sodium hydroxide for pH adjustment to a pH of between 3.5 and 5.5, if necessary.

U.S. Pat. No. 10,610,518 (Allergan), an Orange Book-listed patent associated with the above-referenced NDA that VUITY® is currently sold under, discloses a method of treating an ocular condition in a patient in need thereof, comprising administering to the patient a pharmaceutically acceptable ophthalmic composition comprising pilocarpine hydrochloride at a concentration of 1.0 to 1.5% w/v, 1.0% w/v boric acid, 0.015% w/v sodium citrate dihydrate, 0.03 to 0.37% w/v sodium chloride, hydrochloric acid and/or sodium hydroxide, and water.

U.S. Pat. No. 6,410,544 (also to Allergan) discloses a method for increasing or decreasing parasympathetic/cholinergic/ciliary tonic contraction by administering a composition to the eye in order to restore the resting portion of the eye and allow normal positive and negative accommodation, which includes administering a composition to a myopic or hyperopic presbyope. The patent discloses pilocarpine as a possible muscarinic agent for use in such compositions in a concentration 0.001-2%. The examples and abbreviated clinical study included in the patent disclose use of pilocarpine at either 0.1% or 0.3%.

U.S. Pat. No. 10,639,297 (Orasis Pharma.) discloses an ophthalmic pharmaceutical composition consisting of pilocarpine or a pharmaceutically acceptable salt thereof at a concentration of about 0.01% to about 0.45%, a lubricant, and one or more pharmaceutically acceptable carriers. The lubricant is selected from the group consisting of hyaluronic acid or pharmaceutically acceptable salt thereof, cellulose, carboxymethyl cellulose sodium, hydroxyethyl cellulose, methylcellulose, dextran, gelatin, a polyol, glycerin, polyethylene glycol 300, polyethylene glycol 400, polysorbate, propylene glycol, polyvinyl alcohol, hydroxypropyl methylcellulose, or povidone, or mixtures thereof.

All the above-referenced patent documents specifically disclose ophthalmic pharmaceutical compositions of pilocarpine. The general field of ophthalmic drug delivery has contemplated combination compositions, e.g., combinations of parasympathomimetic drugs (e.g., pilocarpine) with alpha-2 adrenergic receptor agonists. However, such compositions are not always preferred or easily achievable. In fact, the Orange Book listed VUITY® patent (U.S. Pat. No. 10,610,518) described above specifically recites the following in this regard: "Some teachings have also advocated combining pilocarpine with other active ingredients, such as alpha-2 adrenergic receptor agonists. However, such combinations may implicate additional side effects on top of those related to pilocarpine." The VUITY® label provides a list of possible side effects of the composition as determined by clinical trials, including, e.g., greater than 5% of all users experiencing headache and conjunctival hyperemia; and blurred vision, eye pain, visual impairment, eye irritation, and increased lacrimation experienced by 1.5% of clinical trial patients. The possibility of increasing such side effects reduces the advantageous nature of treating presbyopia using a topical application versus the more known invasive treatments.

Nonetheless, U.S. Pat. No. 8,299,079 (Kaufman; "the '079 patent"), which contains disclosures dating back to 2009 or 2010, proposes the combination of one or more parasympathomimetic drugs and one or more alpha agonists for treating, ameliorating, or reducing presbyopia. The '079 patent discloses ophthalmic compositions comprising a parasympathomimetic drug, such as, e.g., pilocarpine, in a concentration of anywhere from 0.0001% to about 5%, and further comprising one or more alpha agonists, such as, e.g., brimonidine, at a concentration of about 0.2% or less. Specific embodiments described therein provide pilocarpine in a concentration of about 3% or less and brimonidine in an amount of about 0.2% or less; however, the only specifically exemplified preparations of pilocarpine and brimonidine disclose brimonidine in an amount of 0.1, 0.15, 0.2, or 0.25 g/100 mL (0.1, 0.15, 0.2, or 0.35%), pilocarpine in an amount of 3, 2.8, 2.6, 2.5, 2.3, 2.0, 1.8, 1.6, 1.5, 1.2, 1, 0.9, 0.8, 0.7, 0.6, 0.5, 0.4, 0.3, 0.2, or 0.1 g/100 mL, and further comprise 0.4 g/100 mL of sodium chloride and 0.04% of a saccharide (specifically D-Glucose), presumably as a stabilizer. The '079 patent further discloses specific formulation(s) used in a study designed to compare the efficacy of pilocarpine alone to the efficacy of pilocarpine in combination with brimonidine in treating visual acuity (VA). Administration of this study comprised providing a first single composition comprising low amounts of pilocarpine, specifically pilocarpine in concentrations of 0.25%, 0.5%, or 1% pilocarpine, followed by the provision of a second single composition comprising 0.2% brimonidine, the second composition administered as a separate drop from the pilocarpine composition. No composition was utilized in the efficacy study comprising both pilocarpine and brimonidine in a single formulation. A second larger study was similarly conducted, wherein two separate compositions were again provided. In the follow-on study, pilocarpine was provided only in a concentration of 0.5%. Despite such clinical studies and other disclosure in the '079 patent, in more than a decade since the disclosures that led to the '079 patent no product has been approved utilizing the technology of the patent or any similar formulation, suggesting the art did not view the disclosure of the '079 patent as sufficiently promising for further development and, further reflecting, that despite such detailed disclosures of various proposed formulations in the art, developing a product that has sufficient practical utility to be useful as an approved ophthalmological product for the treatment of presbyopia remains significantly challenging.

At least in part, as stated briefly above, this is because formulating ophthalmological compositions that are safe, efficacious, and stable for commercially relevant periods of time is extremely challenging due to the particularly nuanced balance required for treating such delicate tissue as the mammalian eye, with any slight modification to composition(s) often yielding unacceptable results related to one or more of safety, efficacy, and stability. WO 2022/169959 (to Sydnexis, Inc.) is just one example of this. The WO 2022/169959 publication is put forth in response to the fact that ophthalmic formulations continue to suffer from significant stability problems. The application seeks to overcome such known stability challenges primarily via use of deuterated water. WO 2022/169959 discloses ophthalmic compositions comprising one or more ophthalmic agents (e.g., aceclidine, pilocarpine, and tropicamide or combinations thereof), that is, optionally combination-API compositions comprising pilocarpine, for the treatment of presbyopia, wherein compositions utilize deuterated water to provide improved stability and, further, at least in part, address the known challenge of ophthalmic compositions commonly being irritating to recipient eye(s) by reducing the buffer capacity of such proposed compositions. In reducing the buffer capacity via use of deuterated water, compositions allegedly adjust to the pH of the natural eye environment more quickly, hence potentially reducing associated irritation resulting in tearing. While disclosing numerous possible active ingredients, the WO 2022/169959 art specifically discloses pilocarpine compositions, and exemplifies the comparison of pilocarpine compositions comprising deuterated and non-deuterated water. The data demonstrate the benefit of using deuterated water in improving stability of ophthalmic compositions, a challenge which is, again, well recognized in the art and the source of frustration for ophthalmic composition formulators. As stated previously, as is also well recognized in the art, even the slightest of modifications to ophthalmic compositions, e.g., an amount of API, excipient, or both, often yields detrimental effect(s) in terms of stability, safety, efficacy, tolerability, etc. and combinations thereof. In fact, the WO 2022/169959 art exemplifies this fact, as even simply modifying the water of the composition, not even an API or an excipient, yields very different performance results.

Thus, formulating ophthalmologically suitable and commercially viable composition(s), such as composition(s) comprising pilocarpine in addition to one or more additional active pharmaceutical ingredients, efficacious in treating a growing population of people suffering from ophthalmic conditions such as presbyopia, is an ongoing and everpresent problem that will require the application of inventive ingenuity to solve.

Construction, Terms, and Acronyms

This section offers guidelines for reading this disclosure. The intended audience for this disclosure ("readers") are persons having ordinary skill in the practice of technologies discussed or used herein. Readers may also be called "skilled persons," and such technologies called "the art." Terms such as "understood," "known," and "ordinary meaning," refer to the general knowledge of skilled persons.

The term "uncontradicted" means not contradicted by this disclosure, logic, or plausibility based on knowledge of skilled persons.

Disclosed here are several different but related exemplary aspects of the invention (referred also to as, e.g., "cases," "facets," or "embodiments"). The invention encompasses all aspects as described individually and as can be arrived at by any combination of such individual aspects. The breadth and scope of the invention should not be limited by any exemplary embodiment(s). No language in this disclosure should be construed as indicating any element/step is essential to the practice of the invention unless such a requirement is explicitly stated. Uncontradicted, any aspect(s) can be combined with any other aspect(s).

Uncontradicted, all technical/scientific terms used here generally have the same meanings as commonly understood by skilled persons, regardless of any narrower examples or descriptions provided here (including any term introduced initially in quotations). However, aspects characterized by the inclusion of elements, steps, etc., associated with specific descriptions provided here are distinct embodiments of the invention. Uncontradicted, disclosure of any aspect using known terms, which terms are narrowed by example or otherwise in this disclosure, implicitly discloses related aspects in which such terms are alternatively interpreted using the broadest reasonable interpretation of skilled persons.

Uncontradicted, "or" means "and/or" here, regardless of any occasional inclusion of "and/or" (e.g., phrases such as "A, B, or C" and "A, B, and/or C" simultaneously disclose aspects including (1) all of A, B, and C; (2) A and C; (3) A and B; (4) B and C; (5) only A; (6) only B; and (7) only C (and also support sub-groupings, such as "A or B," "A or C," etc.)).

Uncontradicted, "also" means "also or alternatively." Uncontradicted, "here" & "herein" mean "in this disclosure." The term "i.a." means "inter alia" or "among other things." "Also known as" is abbreviated "aka" or "AKA." "Elsewhere" means "elsewhere herein."

For conciseness, symbols are used where appropriate. E.g., "&" is used for "and," & "~" for "about." Symbols such as < and > are given their ordinary meaning (e.g., "≤" means "less than or equal to" & "≥" means "greater than or equal to"). A slash "/" can represent "or" ("A/B" means "A or B") or identify synonyms of an element, as will be clear from context.

The inclusion of "(s)" after an element or a step indicates that ≥1 of such an element is present, step performed, and the like. E.g., "element(s)" means both 1 element or ≥2 elements, with the understanding that each thereof is an independent aspect of the invention.

Use of the abbreviation "etc." (or "et cetera") in association with a list of elements/steps means any or all suitable combinations of the recited elements/steps or any known equivalents of such recited elements/steps for achieving the function(s) of such elements/steps that are known in the art. Terms such as "and combinations," or "or combinations" regarding listed elements/steps means any or all possible/suitable combinations of such elements/steps.

Aspects may be described as suitable for use(s) disclosed herein. Uncontradicted, terms such as "suitability" means acceptable or appropriate for performing a particular function/achieving particular state(s)/outcome(s), and typically means effective, practical, and non-deleterious/harmful in the context the term is used. E.g., uncontradicted, the term "suitable" means appropriate, acceptable, or in contexts sufficient, or providing at least generally or substantially all of an intended function, without causing or imparting significant negative/detrimental impact.

Uncontradicted, heading(s) (e.g., "Construction, Terms . . . ") and subheadings are included for convenience and do not limit the scope of any aspect(s). Uncontradicted, aspect(s), step(s), or element(s) described under one heading can apply to other aspect(s) or step(s)/element(s) here.

Ranges of values are used to represent each value falling within such range that are within an order of magnitude of the smallest endpoint of the range without having to explicitly write each value of the range. E.g., a recited range of 1-2 implicitly discloses each of 1.0, 1.1, 1.2, . . . 1.9, and 2.0 and 10-100 implicitly discloses each of 10, 11, 12, . . . 98, 99, and 100). Uncontradicted, all ranges include the range's endpoints, regardless of how a range is described. E.g., "between 1-5" includes 1 and 5 in addition to 2, 3, and 4 (and all numbers between such numbers within an order of magnitude of such endpoints, e.g., 1.0, 1.1, . . . 4.9, and 5.0). For the avoidance of doubt, any number within a range, regardless of the order of magnitude of the number, is covered by the range (e.g., a range of 2-20 covers 18.593).

Terms of approximation (e.g., "about," "~," or "approximately") are used (1) to refer to a set of related values or (2)

where a precise value is difficult to define (e.g., due to limits of measurement). Uncontradicted, all exact values provided here simultaneously/implicitly disclose corresponding approximate values and vice versa (e.g., disclosure of "about 10" provides explicit support for the use of 10 exactly in such aspect/description). Ranges described with approximate value(s) include all values encompassed by each approximate endpoint, regardless of presentation (e.g., "about 10-20" has the same meaning as "about 10-about 20"). The scope of value(s) encompassed by an approximate term typically depends on the context of the disclosure, criticality or operability, statistical significance, understanding in the art, etc. In the absence of guidance here or in the art for an element, terms such as "about" when used in connection with an element should be interpreted as ±10% of the indicated value(s) and implicitly disclosing ±5%, ±2%, ±1%, and ±0.5%.

Lists of aspects, elements, steps, and features are sometimes employed for conciseness. Unless indicated, each member of each list should be viewed as an independent aspect. Each aspect defined by any individual member of a list can have, and often will have, nonobvious properties vis-a-vis aspects characterized by other members of the list.

Uncontradicted, the terms "a" and "an" and "the" and similar referents encompass both the singular and the plural form of the referenced element, step, or aspect. Uncontradicted, terms in the singular implicitly convey the plural and vice versa herein (in other words, disclosure of an element/step implicitly discloses corresponding use of such/similar elements/steps and vice versa). Hence, e.g., a passage regarding an aspect including X step supports a corresponding aspect including several X steps. Uncontradicted, any mixed use of a referent such as "a" in respect of one element/step or characteristic and "one or more of" with respect to another element/step or characteristic in a paragraph, sentence, aspect, or claim, does not change the meaning of such referents. Thus, for example, if a paragraph describes a composition comprising "an X" and "one or more Ys," the paragraph should be understood as providing disclosure of "one or more Xs" and "one or more Ys."

"Significant" and "significantly" mean results/characteristics that are statistically significant using ≥1 appropriate test(s)/trial(s) in the given context (e.g., p≤0.05/0.01). "Detectable" means measurably present/different using known detection tools/techniques. The acronym "DOS" (or "DoS") means "detectable(ly) or significant(ly)."

Uncontradicted, any value here that is not accompanied by a unit of measurement (e.g., a weight of 50 or a length of 20), any previously provided unit for the same element/step or the same type of element/step will apply, or, in cases where no such disclosure exists, the unit most commonly used in association with such an element/step in the art will apply.

Uncontradicted, the terms "including," "containing," "comprising," and "having" mean "including, but not limited to" or "including, without limitation." Uncontradicted, use of terms such as comprising and including regarding elements/steps means including any detectable number or amount of an element or including any detectable performance of a step/number of steps (with or without other elements/steps).

For conciseness, description of an aspect "comprising" or "including" an element, with respect to a collection/whole (e.g., a system, device, or composition), implicitly provides support for any detectable amount/number or ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the whole/collection being made up of the element, or essentially all of the whole/collection being made up of the element (i.e., that the collection consists essentially of the referenced element). Similarly, a method described as including a step with respect to an effect/outcome implicitly provides support for the referenced step providing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the effect/outcome, representing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the steps/effort performed, or both. Explicit listing of percentages of elements/steps in connection with aspects does not limit or contradict such implicit disclosure.

Uncontradicted, terms such as "comprising" when used in connection with a step of a method provide implicit support for performing the step once, ≥2 times, or until an associated function/effect is achieved.

Uncontradicted, the term "one" means a single type, single iteration/copy/thing, of a recited element or step, or both, which will be clear from context. For example, the referent "one" used with a component of a composition can refer to one type of element (which may be present in numerous copies, as in the case of an ingredient in a composition), one unit of the element, or both. Similarly, "one" component, a "single" component, or the "only component" of a system typically means 1 type of element (which may be present in numerous copies), 1 instance/unit of the element, or both. Further, "one" step of a method typically means performing one type of action (step), one iteration of a step, or both. Uncontradicted, a disclosure of "one" element provides support for both, but uncontradicted, any claim to any "one" element means one type of such an element (e.g., a component of a composition/system).

The term "some" means ≥2 copies/instances or ≥5% of a listed collection/whole is, or is made up of, an element. Regarding method(s), some means ≥5% of an effect, effort, or both, is made up of or is attributable to a step (e.g., as in "some of the method is performed by step Y") or indicates a step is performed ≥2 times (e.g., as in "step X is repeated some number of times"). "Predominately," "most," or "mostly," means detectably >50% (e.g., mostly comprises, predominately includes, etc., mean >50%) (e.g., a system that mostly includes element X is composed of >50% of element X). The term "generally" means ≥75% (e.g., generally consists of, generally associated with, generally comprises, etc., means ≥75%) (e.g., a method that generally consists of step X means that 75% of the effort or effect of the method is attributable to step X). "Substantially" or "nearly" means ≥95% (e.g., nearly all, substantially consists of, etc., mean ≥95%) (e.g., a collection that nearly entirely is made up of element X means that at least 95% of the elements in the collection are element X). Terms such as "generally free" of an element or "generally lacking" an element mean comprising ≤~25% of an element and terms such as "substantially free" of an element mean comprising ≤~5% of an element.

In certain embodiments describing API(s), excipient(s), or both present in amounts of "at least" or "greater than" a given amount or, e.g., present in amounts of "no more than" or "no greater than" or "less than" a given amount, the reader should interpret such disclosure as disclosing, e.g., encompassing and explicitly including, such undefined low or high amount(s) ranging to the opposite amount (high or low) that is maximally/minimally therapeutically effective, typically suitable, or both. For example, use of the phrase "at least" (and similar descriptors) in connection with an amount of a component of a formulation or of an entire formulation/composition can be interpreted as at least the amount described but that is no more than a maximally suitable or therapeutically effective amount (in the individual or in a population, such as determined in a clinical study). Similarly, phrases such as "less than" (and similar descriptors) an indicated amount can be interpreted referring to an amount that is still suitable (including, where appropriate, no amount, e.g., 0 units of the indicated component) or therapeutically effective (e.g., an amount that results in a DOS result in a significant number of individuals in a well-controlled and adequate study), but is less than the indicated amount.

The phrase "substantially identical" may be used in certain contexts to reflect that tests that would be considered substantially identical by those of skill in the art (not differing meaningfully in terms of outcome) or that component(s) or step(s) can achieve the same result in a similar way as a referenced set of component(s)/step(s) so as to not meaningfully differ in intended result and manner of achieving such a result. It will be appreciated that the phrase "substantially identical" in such contexts comprises the use of identical amounts, identical formulations, and identical conditions, or, e.g., in other respects, composition(s) demonstrate an identical performance as a comparator.

Uncontradicted, any aspect described with respect to an optionally present element(s)/step(s) also provides implicit support for corresponding aspect(s) in which one, some, most, generally all, nearly all, essentially all, or all of such element(s) are lacking/step(s) not performed, in respect of the relevant aspect. E.g., disclosure of a system comprising element X implicitly also supports a system lacking element X.

Uncontradicted, changes to tense or presentation of terms (e.g., using "comprises predominately" in place of "predominately comprises") do not change the meaning of the corresponding term/phrase.

Uncontradicted, all methods provided here can be performed in any suitable order regardless of presentation (e.g., a method comprising steps A, B, and C, can be performed in the order C, B, and A; B and A and C simultaneously, etc.). Uncontradicted, elements of a composition can be assembled in any suitable manner by any suitable method. In general, any method(s) and materials similar or equivalent to those described here can be used in the practice of embodiments. Uncontradicted, the use of ordinal numbers such as "first," "second," "third," etc. is to distinguish respective elements rather than to denote a particular order of those elements.

Uncontradicted, any elements, steps, components, or features of aspects and all variations thereof, etc., are within the scope of the invention.

Elements associated with a function can be described as "means for" performing a function in a composition/device/system or a "step for" performing a part of a method, and parts of this disclosure refer to "equivalents," which means equivalents known in the art for achieving a referenced function associated with disclosed mean(s)/step(s). However, no element of this disclosure or claim should be interpreted as limited to a "means-plus-function" construction unless such intent is clearly indicated by the use of the terms "means for" or "step for." Terms such as "configured to" or "adapted to" do not indicate "means-plus-function" interpretation, but, rather, describe element(s)/step(s) configured to, designed to, selected to, or adapted to achieve a certain performance, characteristic, property, etc. using teachings provided here or in the art.

All references (e.g., publications, patent applications, and patents) cited herein are hereby incorporated by reference as if each reference were individually and specifically indicated to be incorporated by reference and set forth in its entirety herein. Uncontradicted, any suitable principles, methods, or elements of such references (collectively "teachings") can be combined with or adapted to aspects. However, citation/incorporation of patent documents is limited to the technical disclosure thereof and does not reflect any view regarding the validity, patentability, etc., thereof. In the event of any conflict between this disclosure and the teachings of such documents, the content of this disclosure controls regarding aspects of the invention. Numerous references are cited here to concisely incorporate known information and aid skilled persons in putting aspects into practice. While efforts have been made to include the most relevant references for such purposes, readers will understand that not every aspect of every cited reference will apply to every aspect of the invention.

All original claims contained in this disclosure when filed are incorporated into this specification as if they were a part of the description.

Additional Terms, Concepts, and Acronyms

The following description of certain terms and acronyms is provided to assist readers in understanding the invention. Additional acronyms may be only provided in other parts of this disclosure and acronyms that are well known in the art may not be provided here.

Uncontradicted, any description of ingredient representation as percentage of a composition is percent weight/volume (% w/v).

Uncontradicted, the term "composition" as used herein, is interchangeable with pharmaceutical formulation, liquid composition, liquid formulation, and formulation, and refers to preparations comprising pilocarpine in a form suitable for ophthalmic administration to a patient or subject. At times herein, the term "formulation" is used to describe a composition wherein exemplary ranges of composition constituents are provided, and "composition" is used where specific composition constituents are provided in specific exemplary amounts. A composition can have any suitable form, such as an ointment or a solution. In aspects, a composition is a solution, a gel, or both. Uncontradicted, disclosure of a composition, formulation, and the like, provides implicit support for any of the various specific types of composition(s) described herein as if separately stated (e.g., disclosure of a composition or formulation should be understood to disclose "a gel, a solution, or other type of composition . . . ").

Except where explicitly indicated or clearly indicated by context, "improved" herein means detectably or significantly "increased." In aspects, "improved" means detectably or significantly "reduced," such as with respect to the toxicity of a composition. Uncontradicted, terms such as "enhanced," "improved," and the like are used synonymously herein.

"Pharmaceutical suitability", "pharmaceutically suitable", "ophthalmologically suitable" or "ophthalmological suitability" are phrases typically used to refer to composition(s) that are safe and effective for pharmaceutical administration and application, and particularly ophthalmological application(s), having sufficient potency, purity, strength, quality, and safety, stability, and tolerability, for pharmaceutical application, in cases specifically to the eye, as may be judged by regulatory authority review, and as established by, e.g., one or more well-controlled and adequate clinical studies performed in compliance with generally prevailing regulatory authority standards. Composition(s) described as "ophthalmologically suitable" should be interpreted to mean suitable for ophthalmic delivery when provided in a potency, purity, strength, or quality making it safe for ophthalmic use. Components described as "ophthalmologically suitable" should be interpreted in a similar manner Uncontradicted, a description of "suitability" implicitly means that the referenced element, step, etc., is ophthalmologically/pharmaceutically suitable or otherwise medically suitable (e.g., safe and effective and otherwise suitable, such as tolerable in most, generally all, nearly all or essentially all recipients in one or more studies, or otherwise suitable for applications to the eye or treatment of eye conditions, as determined by proper nonclinical/clinical testing).

Excipients herein are typically present in "effective amounts," and uncontradicted, any described class/type of excipient (often referred to as a "component" herein—e.g., a "buffer component" may include one or more buffers) or specific excipient is understood to be present in the associated composition/formulation in an effective amount, which generally means, in this context, an amount that is effective for the described function(s) associated with the excipient (it being understood that some excipient compound(s)/ingredient(s) exhibit more than one effect). E.g., a tonicity agent will be understood to be present in a composition/formulation in an amount that is effective to impart an indicated tonicity effect, a tonicity effect that is required for suitability of the composition, or an effect that imparts a detectable or significant tonicity effect on a composition (with respect to a comparator composition lacking the compound(s)/ingredient(s)).

Aspects of the invention are described broadly and generically herein, as well as in narrower species and examples. Each of the narrower species, examples, and subgeneric groupings falling within the generic disclosure also form part of the invention. This includes the generic description of the invention with a proviso or negative limitation removing one or more specific matters from the genus, regardless of whether or not the excised (specifically excluded) material is specifically recited herein.

SUMMARY

The inventions described and claimed herein have many attributes and aspects including, but not limited to, those set forth in, e.g., described or referenced in, this Summary This Summary of the Invention ("Summary") is not intended to be all-inclusive, and the scope of the invention is not limited to or by the aspects, features, elements, or embodiments provided in this Summary, which is included for illustrative purposes only and not restriction. Any of the aspects described under this section can be combined with any other aspect described in this section or with any other aspect of this disclosure.

In aspects, the invention provides new and unexpected/innovative ways of ameliorating or reducing an ophthalmic condition, e.g., presbyopia, such as or including, e.g., one or more symptoms of the ophthalmic condition such as presbyopia, for patients, e.g., for patients who do not wish to undergo surgery (intra-ocular lenses, laser ablation, etc.) or use corrective glasses. The invention described herein provides composition(s) comprising pilocarpine compound(s), e.g., a salt of pilocarpine, e.g., pilocarpine HCl, and brimonidine compound(s), e.g., a salt of brimonidine, e.g., brimonidine tartrate, which provide an alternative to existing compositions.

In aspects, the invention provides composition(s) such as those exemplified in this Summary comprising a buffer component. In aspects, the invention provides composition(s) such as those exemplified in this Summary wherein the composition(s) comprise a buffer component. Alternatively, in aspects, the invention provides composition(s) such as those exemplified in this Summary wherein the composition(s) are characterizable as lacking a buffer component. In aspects, the invention provides composition(s) such as those exemplified in this Summary, wherein the composition(s) further comprise one or more non-buffer, excipients, such as one or more excipients selected from a penetration enhancer component, a solubilization component, a demulcent component, a tonicity component, a thickening component, a chelation component, a pH adjusting component, a preservative component, and a carrier component. In aspects, composition(s) provided by the invention exemplified in this Summary can comprise a tonicity component, such as, e.g., sodium chloride, which, in aspects, is present in a limited concentration, e.g., a concentration that is significantly lower than in formulations in the patent references cited in the background, such as at least about 10%, at least about 20%, or at least about 33% lower than any of the concentrations disclosed in the cited patent art, or as further described elsewhere. In aspects, compositions can comprise a tonicity component which does not comprise more than about 0.001% w/v of any free monosaccharide not characterizable as a sugar alcohol. In aspects, the tonicity component can be, e.g., mannitol. In aspects, composition(s) provided by the invention such as those described in this Summary can comprise a preservation component, such as a preservation component comprising a quaternary ammonium salt, e.g., benzalkonium chloride. Further, in aspects, composition(s) provided by the invention such as those described in this Summary can comprise a penetration enhancer component, wherein the penetration enhancer provides detectable or significant activity as a penetration enhancer, a solubilizer, and a demulcent, such as, for example polysorbate 80.

In aspects, composition(s) provided herein comprises a demulcent (uncontradicted aspects described herein as "comprising" an element of a composition are understood as implicitly disclosing, inter alia, the presence of an effective amount of such an element). In aspects, composition(s) comprise a demulcent that also provides a detectable or significant penetration enhancement effect of one or more active pharmaceutical ingredient(s) of the composition(s), such as, e.g., pilocarpine compound(s), brimonidine compound(s), or both.

In aspects, a penetration enhancer which does not provide a detectable or significant demulcent effect is provided as a constituent of composition(s).

In certain aspects, composition(s) are provided as aqueous solutions. In alternative aspects, composition(s) are provided as a gel. In aspects, providing composition(s) as a gel increases the length of time that an API, e.g., pilocarpine compound, e.g., pilocarpine HCl, or a brimonidine compound, e.g., brimonidine tartrate, is retained in the eye over similar aqueous solution compositions.

In general and uncontradicted, any aspects described herein as composition(s) having "none" of an element/ingredient/constituent or component or "no" element, etc., are to be understood as implicitly simultaneously disclosing aspects wherein the amount of the referenced element in the composition is not an effective amount (as described in connection with the feature of the element/excipient/constituent or component), is not a significant amount, is not a detectable amount (using standard methods), or is otherwise present, at most, in very low amounts (e.g., making up less than about 0.01%, less than about 0.001%, less than about 0.0001%, less than about 0.00001%, less than about 0.000001%, or less than about 0.0000001% of a relevant unit of the composition, such as the w/v % of the composition).

In aspects, composition(s) provided by the invention comprise very specific characteristic(s) providing unique alternatives to previously envisioned compositions. In aspects, such a characteristic or characteristics can include one or more of, e.g., composition(s) comprising a low pH such as a pH below 5.5; composition(s) comprising a pH closer to physiological pH, such as, e.g., a pH at about 7; or composition(s) having a pH that is higher than 7; composition(s) comprising an amount of a tonicity agent(s), e.g., sodium chloride, which, in aspects, represents less than about 0.1% w/v of the composition(s); composition(s) comprising an amount of a quaternary ammonium salt, e.g., benzalkonium chloride; composition(s) comprising a penetration enhancer component, such as, e.g., a penetration enhancer component which also provides a detectable or significant solubilization effect, demulcent effect, or both; and, e.g., composition(s) being characterizable as lacking a particular one or more components, such components described herein.

In certain aspects, the invention provides pharmaceutically acceptable and ophthalmologically suitable composition(s) comprising both pilocarpine compound(s) and brimonidine compound(s) in the form of a gel (such a composition, or other composition that is in the form of a gel or that can conditionally take the form of a gel can be referred to as a "gel composition"). In aspects, the pilocarpine compound(s), brimonidine compound(s), or both pilocarpine and brimonidine compound(s) of gel composition(s) are retained in the eye for a detectably or significantly longer period of time than a comparable composition providing the same amount of pilocarpine compound(s) and brimonidine compound(s) provided in the form of a liquid (e.g., aqueous) solution which does not gel when administered to the eye. In aspects, composition(s) provided in the form of a gel causes detectably or significantly less blurriness (in an individual or in a patient population, e.g., as determined by a clinical study) than a comparable composition providing the same amount of pilocarpine compound (s), brimonidine compound(s), or both pilocarpine and brimonidine compound(s) provided in another form, such as in the form of a liquid (e.g., aqueous) solution (e.g., a solution which does not gel when administered to the eye), even when such an alternative composition form comprises a substantially similar or identical amount of one or both active ingredients.

According to certain specific aspects, the invention herein provides pharmaceutically acceptable and ophthalmologically suitable gel composition(s) for treating an ocular condition via administration to a mammalian eye. In aspects, such composition(s) comprise a pilocarpine compound in an amount greater than about 1% w/v and a brimonidine compound in an amount of about 0.05% w/v-0.2% w/v.

In other aspects, the invention provides pharmaceutically acceptable and ophthalmologically suitable composition(s) for treating an ocular condition, such as, or including, one or more symptoms of an ocular condition, comprising a pilocarpine compound in an amount of about 1% w/v-about 3% w/v; a brimonidine compound in an amount of about 0.05% w/v-about 0.2% w/v; a solubilization component in an amount of between about 0.1% w/v-about 1.3% w/v; a preservation component in an amount of about 0.003% w/v-about 0.02% w/v; a tonicity component in an amount of between about 3% w/v-about 6% w/v; and a viscosity enhancement component (thickening component) in an amount of about 0.05% w/v-about 1% w/v. In aspects, such a composition is provided as or can be in the form of (or conditionally forms) a gel. E.g., in aspects such a composition forms a gel when administered to an eye or when placed under some, most, or all of the conditions associated with the environment of the typical mammalian eye, such as the eye of a typical human, e.g., the eye of a middle-aged or older human or middle-aged or older presbyopia patient.

In further specific aspects, the invention provides a gel composition such as a gel composition described in this Summary section, wherein the pilocarpine compound is a salt of pilocarpine, such as pilocarpine hydrochloride, and is present in an amount of about 1.25% w/v of a composition, and the brimonidine compound is a salt of brimonidine, e.g., brimonidine tartrate, present in an amount of about 0.1% w/v of a composition. In aspects, the invention provides the gel composition described here wherein the composition is effective in treating a significant number of patients having an ocular condition, such as an ocular condition that is selected from the group consisting of presbyopia, hyperopia, mydriasis, anisocoria, accommodative esotropia, myopia, and astigmatism.

In aspects, the pH of gel composition(s) provided by the invention is maintained within a range of between about 3.5-about 5.5, or, alternatively, between about 5.5 and about 8.5. In aspects, the pilocarpine compound of gel composition(s), the brimonidine compound of gel composition(s), or both the pilocarpine compound and the brimonidine compound of gel composition(S) is or are retained in the eye for a detectably or significantly longer period of time than such actives are retained from a comparable composition providing the same amount of pilocarpine compound, the same amount of brimonidine compound, or the same amount of both the pilocarpine compound and brimonidine compound provided in another dosage form, such as the form of a liquid solution (e.g., an aqueous solution), e.g., a solution which does not form a gel when administered to the eye, such as described in the art or elsewhere herein. Further, as previously described, in aspects, the composition provided in the form of a gel causes detectably or significantly less blurriness than a comparable composition providing the same amount of pilocarpine compound provided in the form of a liquid (e.g., aqueous) solution.

In one particular aspect, the invention provides a pharmaceutically acceptable and ophthalmologically suitable gel composition for treating an ocular condition via administration to a mammalian eye, the composition comprising (1) a pilocarpine compound in an amount greater than about 1% w/v and (2) a brimonidine compound in an amount of about 0.05% w/v-0.2% w/v, wherein when the composition maintains a pH of between about 3 and about 8.5.

In aspects, composition(s) provided by the invention exhibit commercially relevant levels of stability, e.g., levels of stability considered suitable and acceptable physical and chemical stability with respect to typical standards applicable to ophthalmological compositions. In aspects, the invention provides composition(s) such as composition(s) exemplified in this Summary section, wherein the composition(s) maintain at least about 98% of the pilocarpine compound(s), at least about 98% of the brimonidine compound(s), or at least about 98% of the pilocarpine compound(s) and brimonidine compound(s) when stored at between about 15° C. and about 27° C. (e.g., between about 15° C. and about 27° C. and about 60% relative humidity); when stored at about 25° C.±2° C., e.g., at about 25° C.±2° C. and about 40%±5% relative humidity (e.g., for long term storage); when stored at about 30° C.±2° C. and about 35%±5% relative humidity (e.g., for long term storage); when stored at about 30° C.±2° C. and about 65%±5% relative humidity; when stored at about 40° C.±2° C. and not more than ("NMT") about 25% relative humidity (e.g., for accelerated storage); or when stored at a combination of any or all such conditions, for at least about three months, such as ≥~6 months, ≥~12 months, ≥~18 months, ≥~24 months, or, e.g., ≥~36 months. In aspects, the invention provides composition(s) such as a composition exemplified in this Summary section, wherein the composition(s) comprise less than about 0.5% total impurities after storage of the composition (e.g., in a suitable closed container) at between about 15° C. and about 27° C. (e.g., between about 15° C. and about 27° C. and about 60% relative humidity); after storage at about 25° C.±2° C., e.g.; after storage at about 25° C.±2° C. and about 40%±5% relative humidity (e.g., for long term storage); after storage at about 30° C.±2° C. and about 35%±5% relative humidity (e.g., for long term storage); after storage at about 30° C.±2° C. and about 65%±5% relative humidity; after storage at about 40° C.±2° C. and not more than ("NMT") about 25% relative humidity (e.g., for accelerated storage); or after storage at a combination of any or all such conditions, for a period of at least about 1 month, such as ≥~3 months, ≥~6 months, ≥~12 months, ≥~18 months, ≥~24 months, or, e.g., ≥~36 months.

In certain aspects, composition(s) provided by the invention, or, e.g., method(s) of their use, provide a detectable or significant increase in the efficacy in treating one or more ophthalmic conditions or related symptoms (such as, e.g., presbyopia) compared to compositions directed to treating the same condition which do not comprise both pilocarpine compound(s) and brimonidine compound(s) or, also or alternatively, do not comprise one or more of the characteristics of compositions described herein. In aspects, the pharmaceutically acceptable and ophthalmologically suitable composition(s) provided by the invention are suitable for treating an ocular condition or one or more symptoms related to such an ocular condition, selected from the group consisting of presbyopia, hyperopia, mydriasis, anisocoria, accommodative esotropia, myopia, and astigmatism.

In another specific aspect, the invention provides method(s) of treating an ophthalmic condition or symptom related thereto in a mammalian eye, the ophthalmic condition selected from the group consisting of presbyopia, hyperopia, mydriasis, anisocoria, accommodative esotropia, myopia, and astigmatism, the method comprising administration of an effective amount of composition(s), an effective amount being about 1-about 2 drops of the composition(s) to the mammalian eye once or twice daily, and optionally repeating for a number of times demonstrated to provide a significant clinical effect in visual improvement in a significant number of patients in a well-controlled and adequate study or that is shown to be bioequivalent to a product that has been demonstrated to achieve effectively the same improvement in vision, wherein the composition comprises (1) a pilocarpine compound in an amount greater than about 1% w/v and (2) a brimonidine compound in an amount of about 0.05% w/v-0.2% w/v. In aspects, composition(s) maintain a pH of between about 3 and about 8.5 at least about 97% of the pilocarpine compound and at least 97% of the brimonidine compound when stored at between about 15° C. and about 27° C. (e.g., between about 15° C. and about 27° C. and about 60% relative humidity); when stored at about 25° C.±2° C., e.g., when stored at about 25° C.±2° C. and about 40%±5% relative humidity (e.g., for long term storage); when stored at about 30° C.±2° C. and about 35%±5% relative humidity (e.g., for long term storage); when stored at about 30° C.±2° C. and about 65%±5% relative humidity; when stored at about 40° C.±2° C. and not more than ("NMT") about 25% relative humidity (e.g., for accelerated storage); or when stored at a combination of any or all such conditions, for at least about one month, e.g., at least about 3 months, at least about 6 months, at least about 12 months, at least about 18 months, at least about 24 months, or, e.g., at least about 36 months.

In certain aspects, composition(s) provided by the invention provide a reduced level of irritation compared to marketed pilocarpine composition(s) for the treatment of presbyopia or as compared to such compositions described in the cited art that differ from the characteristics of compositions of this disclosure in one or more respects, such as, e.g., comprising a plurality of buffers (which is a feature optionally lacking in compositions of aspects of the invention). In certain aspects, compositions provided by the invention provide/are associated with a reduced level (i.e., are associated with a detectably or significantly reduced level) of irritation compared to marketed pilocarpine composition(s) for the treatment of presbyopia or compositions described in the cited art that comprise no effective amount or no amount (i.e., no detectable amount) of any demulcent.

In aspects, the invention provides method(s) of improving vision, method(s) of reducing visual impairment, method(s) of treating an ophthalmic condition, including, e.g., one or more symptoms related to the ophthalmic condition, selected from the group consisting of presbyopia, hyperopia, mydriasis, anisocoria, accommodative esotropia, myopia, and astigmatism, or any combination of such methods, the method(s) comprising administering an effective amount of any one or more of the compositions described in this Summary section, for an effective period of time to treat the target indication, e.g., for an acute or chronic treatment period. In aspects, the invention provides method(s) of improving vision, method(s) of reducing visual impairment, method(s) of treating an ophthalmic condition, including, e.g., one or more symptoms related to the ophthalmic condition, selected from the group consisting of presbyopia, hyperopia, mydriasis, anisocoria, accommodative esotropia, myopia, and astigmatism, or any combination of such methods/indications, wherein the method(s) comprise the administration of an effective amount of any one or more of the compositions described in this Summary section, and the method(s) is/are clinically demonstrated to be as effective or detectably or significantly more effective than treatment with the product approved under US Food and Drug Administration NDA Number 214028 (as of Jan. 1, 2022) (such product being described herein as "VUITY" for sake of convenience) or a product that is substantially similar thereto (e.g., having about the same amount of the same ingredients and producing significantly similar results thereto) or a product that is bioequivalent thereto (according to US FDA standards), for the same or similar indication (e.g., improving vision) and for at least substantially the same administration period. In aspects, the invention provides a method of treating presbyopia, including one or more symptoms related to presbyopia, wherein the method(s) comprise administration of an effective amount of composition(s) described in this section, and wherein the method(s) result in detectably or significantly reduced ocular blurring, ocular discomfort, eye pain, brow ache, blurry vision, light sensitivity, stinging, itching, or any combination of any or all thereof compared to treatment of presbyopia with the product approved under US Food and Drug Administration NDA Number 214028 (VUITY) for at least substantially the same administration period.

Although elements, such as indications are, for convenience, sometimes grouped herein using Markush language (a group consisting of), uncontradicted, readers should understand that each members of any such described group provided in this disclosure, such as the indications so linked as described above, are, actually, nonetheless, unique and distinguishable aspects of the invention, which can exhibit unexpected, innovative, and substantially, markedly, or significantly different properties from each other and, accordingly, should not be substantively viewed as grouped together in terms of assessing the novelty or inventiveness of any one thereof.

In further aspects, the invention provides method(s) of manufacturing both liquid solution and gel compositions, e.g., including composition(s) described in this Summary section, and kits providing composition(s). Readers should note that additional embodiments, aspects, features, results, etc., associated with the various elements of the invention are described in the following Detailed Description and such elements can be combined with the elements of this Summary to arrive at additional aspects of the invention.

EXEMPLARY ASPECTS OF THE INVENTION

The following is a non-limiting list of exemplary aspects of the invention, which illustrates embodiments of the invention in a summary form to aid readers in quickly understanding the overall scope of the invention. Similar to patent claims, listed aspects described in the paragraphs of this section may make reference to (depend on/from) one or more other paragraphs. Readers will understand that such references mean that the features/characteristics or steps of such referenced aspects are incorporated into/combined with the referring aspect. E.g., if an aspect in a paragraph (e.g., a paragraph indicated by text at the end of the paragraph as aspect 2) refers to another aspect by one or more aspect numbers (e.g., aspect 1 or "any one of aspects 1-3"), it will be understood to include the elements, steps, or characteristics of such referenced aspects (e.g., aspect 1) in addition to those of the aspect in which the reference is made (e.g., if aspect 2 refers to aspect 1, it provides a description of a composition, method, system, device, etc., including the features of both aspect 1 and aspect 2).

Lists of aspects describing specific exemplary embodiments of the invention are sometimes employed for aiding the reader in understanding the invention. Such aspects can, within them, reference other exemplary aspects, either individually or as groups of aspects (e.g., via reference to a range within a list of numbered aspects when such aspects are provided as a numbered list). Reference to ranges of aspects should be interpreted as referencing all such aspects individually, each as unique embodiments of the invention, and in combination with one another as unique embodiment(s) of the invention, according to the presentation provided of such aspects unless such an aspect within such a referenced range is either contradictory or non-sensical. If contradicted, reference to the contradictory aspect should be excluded.

In aspects, the invention provides a pharmaceutically acceptable and ophthalmologically suitable gel composition for treating an ocular condition via administration to a mammalian eye, the composition comprising (1) a pilocarpine compound in an amount greater than about 1% w/v and (2) brimonidine compound in an amount of about 0.05% w/v-0.2% w/v, wherein the composition maintains a pH of between about 3 and about 8.5 at least about 97% of the pilocarpine compound and at least 97% of the brimonidine compound when stored at between about 15° C. and about 27° C. (e.g., between about 15° C. and about 27° C. and about 60% relative humidity); when stored at about 25° C.±2° C. (e.g., when stored at about 25° C.±2° C. and about 40%±5% relative humidity), when stored at about 30° C.±2° C. and about 35%±5% relative humidity, when stored at about 30° C.±2° C. and about 65%±5% relative humidity; when stored at about 40° C.±2° C. and not more than ("NMT") about 25% relative humidity; or when stored at a combination of any or all such conditions, for at least about one month (aspect 1).

In aspects, the invention provides the composition of aspect 1, wherein the pilocarpine compound is a salt of pilocarpine (aspect 2).

In aspects, the invention provides the composition of any one or both of aspect 1 or aspect 2, wherein the pilocarpine compound is pilocarpine hydrochloride (aspect 3).

In aspects, the invention provides the composition of any one or more of aspect 1-aspect 3, wherein the composition comprises pilocarpine hydrochloride in an amount greater than about 1.15% w/v but less than about 1.7% w/v (aspect 4).

In aspects, the invention provides the composition of any one or more of aspect 1-aspect 4, wherein the composition comprises pilocarpine hydrochloride in an amount representing about 1.2% w/v to about 1.6% w/v of the composition (aspect 5).

In aspects, the invention provides the composition of any one or more of aspect 1-aspect 5, wherein the composition comprises pilocarpine hydrochloride in an amount representing about 1.5% w/v of the composition (aspect 6).

In aspects, the invention provides the composition of any one or more of aspect 1-aspect 6, wherein the brimonidine compound is a salt of brimonidine (aspect 7).

In aspects, the invention provides the composition of any one or more of aspect 1-aspect 7, wherein the brimonidine compound is brimonidine tartrate (aspect 8).

In aspects, the invention provides the composition of any one or more of aspect 1-aspect 8, wherein the composition comprises brimonidine tartrate in an amount between about 0.05% w/v to about 0.15 wt. % (aspect 9).

In aspects, the invention provides the composition of any one or more of aspect 1-aspect 9, wherein the composition comprises brimonidine tartrate in an amount representing about 0.075% w/v to about 0.125% w/v of the composition (aspect 10).

In aspects, the invention provides the composition of any one or more of aspect 1-aspect 10, wherein the composition comprises brimonidine tartrate in an amount representing about 0.1% w/v of the composition (aspect 11).

In aspects, the invention provides the composition of any one or more of aspect 1-aspect 11, wherein the ocular condition is selected from the group consisting of presbyopia, hyperopia, mydriasis, anisocoria, accommodative esotropia, myopia, and astigmatism (aspect 12).

In aspects, the invention provides the composition of any one or more of aspect 1-aspect 12, wherein the ocular condition is presbyopia (aspect 13).

In aspects, the invention provides the composition of any one or more of aspect 1-aspect 13, wherein the pH of the composition is maintained between about 3.5-about 8.5 (aspect 14).

In aspects, the invention provides the composition of any one or more of aspect 1-aspect 14, wherein the pH of the composition is maintained between about 3.5-about 6.5 (aspect 15).

In aspects, the invention provides the composition of any one or more of aspect 1-aspect 15, wherein the pH of the composition is maintained between about 3.5-about 5.5 (aspect 16).

In aspects, the invention provides the composition of any one or more of aspect 1-aspect 16, wherein the pH of the composition is maintained between about 3.5-about 4.5 (aspect 17).

In aspects, the invention provides the composition of aspect 14, wherein the pH of the composition is maintained between about 5.5-about 8.5 (aspect 18).

In aspects, the invention provides the composition of aspect 18, wherein the pH of the composition is maintained between about 6.5-about 8.5 (aspect 19).

In aspects, the invention provides the composition of any one or both of aspect 18 or aspect 19, wherein the pH of the composition is maintained between about 7.4-about 8.5 (aspect 20).

In aspects, the invention provides the composition of any one or more of aspect 1-aspect 20, wherein the composition comprises a buffer component (aspect 21).

In aspects, the invention provides the composition of aspect 21, wherein the buffer component comprises a single buffer constituent (aspect 22).

In aspects, the invention provides the composition of aspect 22, wherein the single buffer component constituent is boric acid or sodium borate (aspect 23).

In aspects, the invention provides the composition of aspect 23, wherein the boric acid or sodium borate is present in the composition in an amount of about 0.5% w/v-about 1.5% w/v (aspect 24).

In aspects, the invention provides the composition of aspect 24, wherein the boric acid or sodium borate is present in the composition in an amount of about 1% w/v (aspect 25).

In aspects, the invention provides the composition of any one or more of aspect 23-aspect 25, wherein the ratio of the pilocarpine compound to the buffer component is between about 3.4:1-about 1:1.4 (aspect 26).

In aspects, the invention provides the composition of aspect 26, wherein the ratio of the pilocarpine compound to the buffer component is about 1.5:1 (aspect 27).

In aspects, the invention provides the composition of any one or more of aspect 23-aspect 27, wherein the ratio of the brimonidine compound to the buffer component is between about 1:2.5-about 1:30 (aspect 28).

In aspects, the invention provides the composition of aspect 28, wherein the ratio of the brimonidine compound to the buffer component is about 1:10 (aspect 29).

In aspects, the invention provides the composition of any one or more of aspect 23-aspect 29, wherein the ratio of the total amount of API in the composition, consisting of a pilocarpine compound and a brimonidine compound, to the buffer component is between about 3.8:1-1:1.4-about 1:1.5 (aspect 30).

In aspects, the invention provides the composition of aspect 30, wherein the ratio of the total amount of API in the composition, consisting of a pilocarpine compound and a brimonidine compound, to the buffer component is about 1.6:1 (aspect 31).

In aspects, the invention provides the composition of aspect 22, wherein the single buffer component constituent is a citrate buffer (e.g., a sodium citrate compound, e.g., sodium citrate dihydrate) (aspect 32).

In aspects, the invention provides the composition of aspect 32, wherein the citrate buffer is present in the composition in an amount of about 0.005% w/v-about 0.4% w/v (aspect 33).

In aspects, the invention provides the composition of aspect 33, wherein the citrate buffer is present in the composition in an amount of about 0.02% w/v-about 0.25% w/v (aspect 34).

In aspects, the invention provides the composition of any one or more of aspect 32-aspect 34, wherein the citrate buffer is present in the composition in an amount of about 0.2% w/v (aspect 35).

In aspects, the invention provides the composition of any one or more of aspect 32-aspect 35, wherein the ratio of the pilocarpine compound to the buffer component is between about 234:1-about 2.7:1 (aspect 36).

In aspects, the invention provides the composition of aspect 36, wherein the ratio of the pilocarpine compound to the buffer component is between about 10:1-about 2.5:1 (aspect 37).

In aspects, the invention provides the composition of aspect 37, wherein the ratio of the pilocarpine compound to the buffer component is about 7.5:1 (aspect 38).

In aspects, the invention provides the composition of any one or more of aspect 32-aspect 38, wherein the ratio of the brimonidine compound to the buffer component is between about 40:1-about 1:8 (aspect 39).

In aspects, the invention provides the composition of aspect 39, wherein the ratio of the brimonidine compound to the buffer component is between about 10:1-about 1:5 (aspect 40).

In aspects, the invention provides the composition of aspect 40, wherein the ratio of the brimonidine compound to the buffer component is about 1:2 (aspect 41).

In aspects, the invention provides the composition of any one or more of aspect 32-aspect 41, wherein the ratio of the total amount of API in the composition, consisting of a pilocarpine compound and a brimonidine compound, to the buffer component is between about 38:1-about 5.75:1 (aspect 42).

In aspects, the invention provides the composition of aspect 42, wherein the ratio of the total amount of API in the composition, consisting of a pilocarpine compound and a brimonidine compound, to the buffer component is between about 20:1 to about 5.75:1 (aspect 43).

In aspects, the invention provides the composition of aspect 43, wherein the ratio of the total amount of API in the composition, consisting of a pilocarpine compound and a brimonidine compound, to the buffer component is about 8:1 (aspect 44).

In aspects, the invention provides the composition of aspect 21, wherein the buffer component does not comprise boric acid, sodium borate, or sodium citrate (aspect 45).

In aspects, the invention provides the composition of aspect 45, wherein the buffer component comprises a single buffer constituent (aspect 46).

In aspects, the invention provides the composition of aspect 46, wherein the single buffer constituent is sodium acetate or sodium phosphate depending on the target pH range of the composition (aspect 47).

In aspects, the invention provides the composition of aspect 47, wherein the sodium acetate or sodium phosphate is present in the composition in an amount of about 0.2% w/v-about 1.5% w/v (aspect 48).

In aspects, the invention provides the composition of aspect 48, wherein the sodium acetate or sodium phosphate is present in the composition in an amount of about 0.75% w/v (aspect 49).

In aspects, the invention provides the composition of any one or more of aspect 47-aspect 49, wherein the ratio of the pilocarpine compound to the buffer component is between about 8.5:1-about 1:1.4 (aspect 50).

In aspects, the invention provides the composition of aspect 50, wherein the ratio of the pilocarpine compound to the buffer component is about 2:1 (aspect 51).

In aspects, the invention provides the composition of any one or more of aspect 47-aspect 51, wherein the ratio of the brimonidine compound to the buffer component is between about 1:1-about 1:30 (aspect 52).

In aspects, the invention provides the composition of aspect 40, wherein the ratio of the brimonidine compound to the buffer component is about 1:7.5 (aspect 53).

In aspects, the invention provides the composition of any one or more of aspect 47-aspect 53, wherein the ratio of the total amount of API in the composition, consisting of a pilocarpine compound and a brimonidine compound, to the buffer component is between about 9.5:1-about 1:1.4 (aspect 54).

In aspects, the invention provides the composition of aspect 54, wherein the ratio of the total amount of API in the composition, consisting of a pilocarpine compound and a brimonidine compound, to the buffer component is about 2.1:1 (aspect 55).

In aspects, the invention provides the composition of any one or more of aspect 1-aspect 20, wherein the composition does not comprise a buffer component (aspect 56).

In aspects, the invention provides the composition of any one or more of aspect 1-aspect 56, wherein the composition is not provided in the form of a solution, suspension, ointment, cream, or any dosage form other than a gel (aspect 57).

In aspects, the invention provides the composition of aspect 57, wherein the viscosity of the composition detectably or significantly increases (1) upon exposure to the environment of the mammalian eye to which it is administered, (2) upon exposure to temperatures of at least about 32 degrees Celsius (° C.), (3) upon exposure to an environment having an ionic strength detectably or significantly greater than that of one or more gelling agents present in the composition (e.g., gellan gum), (4) exposure to an environment having a pH of greater than about 5, or (5) any combination of (1)-(4), over the viscosity of the composition prior to administration to the eye (e.g., upon completion of manufacturing and while stored prior to administration at a temperature of between about 15° C. to about 25° C.+/−2° C.) (aspect 58).

In aspects, the invention provides the composition of any one or more of aspect 1-aspect 58, wherein the composition further comprises one or more non-buffer excipients (aspect 59).

In aspects, the invention provides the composition of aspect 59, wherein the one or more excipients is/are selected from the group consisting of a penetration enhancer component, a solubilization component, a demulcent component, a tonicity component, a thickening component, a chelation component, a pH adjusting component, a preservative component, and a carrier component (aspect 60).

In aspects, the invention provides the composition of any one or both of aspect 59 or aspect 60, wherein the composition comprises a tonicity component (aspect 61).

In aspects, the invention provides the composition of any one or more of aspect 59-aspect 61, wherein the tonicity component comprises a constituent characterizable as a sugar alcohol (aspect 62).

In aspects, the invention provides the composition of any one or more of aspect 59-aspect 62, wherein the composition comprises mannitol in an amount representing about 3% w/v to about 6% w/v of the composition (aspect 63).

In aspects, the invention provides the composition of any one or more of aspect 59-aspect 63, wherein the composition comprises mannitol in an amount of about 4.5% w/v (aspect 64).

In aspects, the invention provides the composition of any one or more of aspect 1-aspect 64, wherein the osmolality of the composition is about 171 mOsm/Kg-about 1171 mOsm/Kg, such as, e.g., about 200 mOsm/Kg-about 1000 mOsm/Kg, about 250 mOsm/Kg-about 500 mOsm/Kg, or, e.g., about 280 mOsm/Kg-about 370 mOsm/Kg (aspect 65).

In aspects, the invention provides the composition of aspect 65, wherein the osmolality of the composition is about 250 mOsm/Kg-about 350 mOsm/Kg or about 270 mOsm/Kg-about 330 mOsm/Kg (aspect 66).

In aspects, the invention provides the composition of any one or more of aspect 59-aspect 66, wherein the composition comprises a preservation component (aspect 67).

In aspects, the invention provides the composition of any one or more of aspect 59-aspect 67, wherein the preservation component comprises one or more quaternary ammonium salts (aspect 68).

In aspects, the invention provides the composition of any one or more of aspect 59-aspect 68, wherein the one or more quaternary ammonium salts is benzalkonium chloride (aspect 69).

In aspects, the invention provides the composition of any one or more of aspect 59-aspect 69, wherein the composition comprises benzalkonium chloride in an amount of about 0.005% w/v-about 0.01% w/v, such as about 0.0075% w/v (aspect 70).

In aspects, the invention provides the composition of any one or more of aspect 59-aspect 70, wherein the composition comprises a penetration enhancer component (aspect 71).

In aspects, the invention provides the composition of aspect 71, wherein the penetration enhancer component comprises at least one constituent which provides detectable or significant activity as two or more of a penetration enhancer, a solubilizer, a demulcent, a buffer, a tonicity agent, a thickener, a chelator, a pH adjusting agent, a preservative, or a carrier (aspect 72).

In aspects, the invention provides the composition of aspect 72, wherein the penetration enhancer component comprises at least one constituent which provides detectable or significant activity as a penetration enhancer, a solubilizer, a demulcent, or any combination of two or more thereof (aspect 73).

In aspects, the invention provides the composition of aspect 73, wherein the penetration enhancer component comprises at least one constituent which provides detectable or significant activity as a penetration enhancer, a solubilizer, and a demulcent (aspect 74).

In aspects, the invention provides the composition of any one or more of aspect 59-aspect 74, wherein the penetration component comprises one or more of polyoxyethylene sorbitan fatty acid ester(s), tocopheryl polyethylene glycol succinate (TPGS), poly-arginine, polyserine, tromethamine (tris), sesame seed oil, or oils having similar compositions and functional characteristics suitable for ophthalmic use (aspect 75).

In aspects, the invention provides the composition of aspect 75, wherein the polyoxyethylene sorbitan fatty acid ester(s) include polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65), or a polyoxyethylene sorbitan oleate/polyoxyethylene sorbitan mono-oleate ester (e.g., polysorbate 80) (aspect 76).

In aspects, the invention provides the composition of aspect 76, wherein the penetration component is present in an amount of about 0.1% w/v-about 5% w/v (aspect 77).

In aspects, the invention provides the composition of aspect 77, wherein the penetration component is present in an amount of about 0.1% w/v-about 3% w/v (aspect 78).

In aspects, the invention provides the composition of any one or more of aspect 59-aspect 78, wherein the penetration component comprises polysorbate 80 (aspect 79).

In aspects, the invention provides the composition of aspect 79, wherein the polysorbate 80 is present in the composition in an amount of about 0.25% w/v (aspect 80).

In aspects, the invention provides the composition of any one or more of aspect 59-aspect 80, wherein the composition comprises a solubilization component comprising at least one constituent which does not provide detectable or significant penetration enhancement, detectably or significant demulcent effect, or both (aspect 81).

In aspects, the invention provides the composition of aspect 81, wherein the solubilization component comprises at least one constituent characterizable as a polyoxyethylated castor oil (aspect 82).

In aspects, the invention provides the composition of aspect 81, wherein the solubilization component comprises at least one constituent characterizable as an alkalizing organic compound (aspect 83).

In aspects, the invention provides the composition of any one or more of aspect 81-aspect 83, wherein the solubilization component comprises at least one constituent characterizable as a polyoxyethylated castor oil and at least one constituent characterizable as an alkalizing organic compound (aspect 84).

In aspects, the invention provides the composition of any one or all of aspect 81-aspect 84, wherein the composition comprises a cremophor (aspect 85).

In aspects, the invention provides the composition of aspect 85, wherein the composition comprises a cremophor in an amount of about 0.05% w/v-about 0.8% w/v (aspect 85).

In aspects, the invention provides the composition of aspect 85, wherein the composition comprises a cremophor in an amount of about 0.25% w/v (aspect 87).

In aspects, the invention provides the composition of any one or all of aspect 81-aspect 84, wherein the composition comprises tromethamine (aspect 88).

In aspects, the invention provides the composition of aspect 88, wherein the composition comprises tromethamine in an amount of about 0.05% w/v-about 0.5% w/v (aspect 89).

In aspects, the invention provides the composition of aspect 89, wherein the composition comprises tromethamine in an amount of about 0.185% w/v (aspect 90).

In aspects, the invention provides the composition of any one or all of aspect 81-aspect 90, wherein the composition comprises a cremophor and tromethamine (aspect 91).

In aspects, the invention provides the composition of aspect 91, wherein the composition comprises a cremophor in an amount of about 0.05% w/v-about 0.8% w/v and tromethamine in an amount of about 0.05% w/v-about 0.5% w/v (aspect 92).

In aspects, the invention provides the composition of one or more of aspect 59-aspect 92, wherein the penetration component comprises at least one constituent which further provides detectable or significant demulcent effect, and wherein the constituent detectably or significantly reduces the amount of irritation caused by the product over a corresponding product comprising the same amount of pilocarpine compound provided in the same dosage form, for the same indication, and for substantially the same administration period as reported in an appropriately administered clinical trial (aspect 93).

In aspects, the invention provides the composition of aspect 93, wherein the constituent is polysorbate 80 (aspect 94).

In aspects, the invention provides the composition of any one or more of aspect 1-aspect 94, wherein the composition comprises a gel component comprising at least one constituent which detectably or significantly increases the viscosity of the composition when the composition is administered to the mammalian eye compared to the viscosity of the composition prior to administration to the eye (e.g., upon completion of manufacturing and while stored prior to administration at a temperature of between about 15° C. to about 25° C.+/−2° C.) (aspect 95)

In aspects, the invention provides the composition of any one or more of aspect 1-aspect 95, wherein the composition comprises a gel component comprising at least one constituent which detectably or significantly increases the viscosity of the composition when the composition is exposed to a temperature of at least about 28 degrees Celsius (° C.) compared to the viscosity of the composition prior to administration to the eye (e.g., upon completion of manufacturing and while stored prior to administration at a temperature of between about 15° C. to about 25° C.+/−2° C.) (aspect 96).

In aspects, the invention provides the composition of any one or more of aspect 1-aspect 96, wherein the composition comprises a gel component comprising at least one constituent which detectably or significantly increases the viscosity of the composition when the composition is exposed to an environment having an ionic strength detectably or significantly greater than that of one or more gelling agents present in the composition (e.g., gellan gum) compared to the viscosity of the composition prior to administration to the eye (e.g., upon completion of manufacturing and while stored prior to administration at a temperature of between about 15° C. to about 25° C.+/−2° C.) (aspect 97).

In aspects, the invention provides the composition of any one or more of aspect 1-aspect 97, wherein the composition comprises a gel component comprising at least one constituent which detectably or significantly increases the viscosity of the composition when the composition is exposed to an environment having a pH of greater than about 5 compared to the viscosity of the composition prior to administration to the eye (e.g., upon completion of manufacturing and while stored prior to administration at a temperature of between about 15° C. to about 25° C.+/−2° C.) (aspect 98).

In aspects, the invention provides the composition of any one or more of aspect 1-aspect 95, wherein the composition comprises a gel component comprising at least one constituent which detectably or significantly increases the viscosity of the composition when the composition is exposed to any of the environments of aspect 95-aspect 98 compared to the viscosity of the composition prior to administration to the eye (e.g., upon completion of manufacturing and while stored prior to administration at a temperature of between about 15° C. to about 25° C.+/−2° C.) (aspect 99).

In aspects, the invention provides the composition of any one or more of aspect 1-aspect 99, wherein the composition comprises a gel component comprising gellan gum (aspect 100).

In aspects, the invention provides the composition of any one or more of aspect 1-aspect 100, wherein the composition comprises a gel component wherein the gel component comprises one or more constituents capable of detectably or significantly increasing the viscosity of the composition (1) upon exposure of the composition to the environment of the mammalian eye to which it is administered, (2) upon exposure of the composition to temperatures of at least about 32 degrees Celsius (° C.), (3) upon exposure of the composition to an environment having an ionic strength detectably or significantly greater than that of one or more gelling agents present in the composition, (4) exposure of the composition to an environment having a pH of greater than about 5, or (5) any combination of (1)-(4), over the viscosity of the composition prior to administration to the eye (e.g., upon completion of manufacturing and while stored prior to administration at a temperature of between about 15° C. to about 25° C.+/−2° C.), wherein the gel component is present in an amount representing about 0.1% w/v to about 1% w/v of the composition (aspect 101).

In aspects, the invention provides the composition of aspect 101, wherein the composition comprises a gel component wherein the gel component comprises one or more constituents capable of detectably or significantly increasing the viscosity of the composition (1) upon exposure of the composition to the environment of the mammalian eye to which it is administered, (2) upon exposure of the composition to temperatures of at least about 32 degrees Celsius (° C.), (3) upon exposure of the composition to an environment having an ionic strength detectably or significantly greater than that of one or more gelling agents present in the composition, (4) exposure of the composition to an environment having a pH of greater than about 5, or (5) any combination of (1)-(4), over the viscosity of the composition prior to administration to the eye (e.g., upon completion of manufacturing and while stored prior to administration at a temperature of between about 15° C. to about 25° C.+/−2° C.), wherein the gel component is present in an amount representing about 0.3% w/v to about 0.8% w/v of the composition (aspect 102).

In aspects, the invention provides the composition of any one or more of aspect 1-aspect 102, wherein the composition comprises a gel component wherein the gel component comprises one or more constituents capable of detectably or significantly increasing the viscosity of the composition (1) upon exposure of the composition to the environment of the mammalian eye to which it is administered, (2) upon exposure of the composition to temperatures of at least about 32 degrees Celsius (° C.), (3) upon exposure of the composition to an environment having an ionic strength detectably or significantly greater than that of one or more gelling agents present in the composition, (4) exposure of the composition to an environment having a pH of greater than about 5, or (5) any combination of (1)-(4), over the viscosity of the composition prior to administration to the eye (e.g., upon completion of manufacturing and while stored prior to administration at a temperature of between about 15° C. to about 25° C.+/−2° C.), wherein the gel component is present in an amount representing about 0.5% w/v to about 0.7% w/v of the composition (aspect 103).

In aspects, the invention provides the composition of any one or more of aspect 1-aspect 103, wherein the composition comprises a gel component wherein the gel component comprises one or more constituents capable of detectably or significantly increasing the viscosity of the composition (1) upon exposure of the composition to the environment of the mammalian eye to which it is administered, (2) upon exposure of the composition to temperatures of at least about 32 degrees Celsius (° C.), (3) upon exposure of the composition to an environment having an ionic strength detectably or significantly greater than that of one or more gelling agents present in the composition, (4) exposure of the composition to an environment having a pH of greater than about 5, or (5) any combination of (1)-(4), over the viscosity of the composition prior to administration to the eye (e.g., upon completion of manufacturing and while stored prior to administration at a temperature of between about 15° C. to about 25° C.+/−2° C.), wherein the gel component is present in an amount representing about 0.6% w/v of the composition (aspect 104).

In aspects, the invention provides the composition of any one or more of aspect 101-aspect 104, wherein the composition comprises gellan gum in an amount of about 0.6% w/v (aspect 105).

In aspects, the invention provides the composition of any one or more of aspect 1-aspect 105, wherein the gel composition retains the amount of pilocarpine compound in the eye, retains the amount of brimonidine compound in the eye, or retains the amount of both the pilocarpine compound and brimonidine compound in the eye, for a detectably or significantly longer period of time than a comparable composition providing at least generally the same, at least substantially the same, at least essentially the same, essentially the same, or the same amount of pilocarpine compound, brimonidine compound, or both provided in the form of a liquid (e.g., an aqueous) solution (aspect 106).

In aspects, the invention provides the composition of any one or more of aspect 1-aspect 106, wherein the gel composition causes detectably or significantly less visual blurring (detectably or significantly less blurriness) than a composition providing at least generally the same, at least substantially the same, at least essentially the same, essentially the same, or the same amount of pilocarpine compound, brimonidine compound, or both provided in the form of a liquid (e.g., an aqueous) solution (aspect 107).

In aspects, the invention provides the composition of any one or more of aspect 1-aspect 107, wherein the composition comprises no non-ionic saccharide which detectably or significantly promotes microbial growth (aspect 108).

In aspects, the invention provides the composition of aspect 108, wherein the composition comprises no saccharide characterizable as a glucose compound, e.g., glucose or D-glucose (dextrose) (aspect 109).

In aspects, the invention provides the composition of any one or more of aspect 1-aspect 109, wherein the composition comprises no free monosaccharide not characterizable as a sugar alcohol (aspect 110).

In aspects, the invention provides the composition of any one or more of aspect 1-aspect 110, wherein the composition comprises no free monosaccharide not characterizable as a sugar alcohol and further comprises no free disaccharide (aspect 111).

In aspects, the invention provides the composition of any one or more of aspect 1-aspect 111, wherein the composition comprises no free monosaccharide not characterizable as a sugar alcohol, no free disaccharide, and no free oligosaccharide (aspect 112).

In aspects, the invention provides the composition of any one or more of aspect 1-aspect 94, wherein the only free monosaccharide in the composition is mannitol (aspect 113).

In aspects, the invention provides the composition of any one or more of aspect 1-aspect 113, wherein the composition maintains at least about 98% of the pilocarpine compound, the brimonidine compound, or both the pilocarpine and the brimonidine compound when stored at between about 15° C. and about 27° C. (e.g., between about 15° C. and about 27° C. and about 60% relative humidity), when stored at about 25° C.±2° C., e.g., when stored at about 25° C.±2° C. and about 40%±5% relative humidity, when stored at about 30° C.±2° C. and about 35%±5% relative humidity, or when stored under any combination of such conditions, for at least about three months, such as, e.g., about 3 months to about 9 months (aspect 114).

In aspects, the invention provides the composition of any one or more of aspect 1-aspect 114, wherein the composition maintains at least about 98% of the pilocarpine compound, the brimonidine compound, or both the pilocarpine and the brimonidine compound when stored at between about 15° C. and about 27° C. (e.g., between about 15° C. and about 27° C. and about 60% relative humidity), when stored at about 25° C.±2° C., e.g., when stored at about 25° C.±2° C. and about 40%±5% relative humidity, when stored at about 30° C.±2° C. and about 35%±5% relative humidity, or when stored under any combination of such conditions, for at least about six months, such as, e.g., about 6 months to about 12 months (aspect 115).

In aspects, the invention provides the composition of any one or more of aspect 1-aspect 115, wherein the composition maintains at least about 98% of the pilocarpine compound, the brimonidine compound, or both the pilocarpine and the brimonidine compound when stored at between about 15° C. and about 27° C. (e.g., between about 15° C. and about 27° C. and about 60% relative humidity), when stored at about 25° C.±2° C., e.g., when stored at about 25° C.±2° C. and about 40%±5% relative humidity, when stored at about 30° C.±2° C. and about 35%±5% relative humidity, or when stored under any combination of such conditions, for at least about nine months such as, e.g., about 9 months to about 18 months (aspect 116).

In aspects, the invention provides the composition of any one or more of aspect 1-aspect 116, wherein the composition maintains at least about 98% of the pilocarpine compound, the brimonidine compound, or both the pilocarpine and the brimonidine compound when stored at between about 15° C. and about 27° C. (e.g., between about 15° C. and about 27° C. and about 60% relative humidity), when stored at about 25° C.±2° C., e.g., when stored at about 25° C.±2° C. and about 40%±5% relative humidity, when stored at about 30° C.±2° C. and about 35%±5% relative humidity, or when stored under any combination of such conditions, for at least about 12 months, such as, e.g., about 12 months-about 24 months (aspect 117).

In aspects, the invention provides the composition of any one or more of aspect 1-aspect 117, wherein the composition maintains at least about 98% of the pilocarpine compound, the brimonidine compound, or both the pilocarpine and the brimonidine compound when stored at between about 15° C. and about 27° C. (e.g., between about 15° C. and about 27° C. and about 60% relative humidity), when stored at about 25° C.±2° C., e.g., when stored at about 25° C.±2° C. and about 40%±5% relative humidity, when stored at about 30° C.±2° C. and about 35%±5% relative humidity, or when stored under any combination of such conditions, for at least about 18 months, such as, e.g., about 18 months-about 32 months (aspect 118).

In aspects, the invention provides the composition of any one or more of aspect 1-aspect 118, wherein the composition maintains at least about 98% of the pilocarpine compound, the brimonidine compound, or both the pilocarpine and the brimonidine compound when stored at between about 15° C. and about 27° C. (e.g., between about 15° C. and about 27° C. and about 60% relative humidity), when stored at about 25° C.±2° C., e.g., when stored at about 25° C.±2° C. and about 40%±5% relative humidity, when stored at about 30° C.±2° C. and about 35%±5% relative humidity, or when stored under any combination of such conditions, for at least about 24 months, such as, e.g., about 24 months-about 36 months (aspect 119).

In aspects, the invention provides the composition of any one or more of aspect 1-aspect 119, wherein the composition maintains at least about 98% of the pilocarpine compound, the brimonidine compound, or both the pilocarpine and the brimonidine compound when stored at between about 15° C. and about 27° C. (e.g., between about 15° C. and about 27° C. and about 60% relative humidity), when stored at about 25° C.±2° C., e.g., when stored at about 25° C.±2° C. and about 40%±5% relative humidity, when stored at about 30° C.±2° C. and about 35%±5% relative humidity, or when stored under any combination of such conditions, for at least about 36 months (aspect 120).

In aspects, the invention provides the composition of any one or more of aspect 1-aspect 120, wherein the composition maintains at least about 98% of the pilocarpine compound, the brimonidine compound, or both the pilocarpine and the brimonidine compound when stored at about 15° C.-about 27° C. and about 60% relative humidity, when stored at between about 15° C. and about 27° C. (e.g., between about 15° C. and about 27° C. and about 60% relative humidity), when stored at about 25° C.±2° C., e.g., when stored at about 25° C.±2° C. and about 40%±5% relative humidity, when stored at about 30° C.±2° C. and about 35%±5% relative humidity, or when stored under any combination of such conditions (aspect 121).

In aspects, the invention provides the composition of any one or more of aspect 1-aspect 121, wherein the composition comprises less than about 2.5% total impurities after storage at between about 15° C. and about 27° C. (e.g., between about 15° C. and about 27° C. and about 60% relative humidity); after storage at about 25° C.±2° C. (e.g., after storage at about 25° C.±2° C. and about 40%±5% relative humidity), after storage at about 30° C.±2° C. and about 35%±5% relative humidity, after storage at about 30° C.±2° C. and about 65%±5% relative humidity; after storage at about 40° C.±2° C. and not more than ("NMT") about 25% relative humidity; or after storage at a combination of any or all such conditions, for a period of at least about 1 month, such as, e.g., about 1 month to about 3 months (aspect 122).

In aspects, the invention provides the composition of any one or more of aspect 1-aspect 122, wherein the composition comprises less than about 2.5% total impurities after storage at between about 15° C. and about 27° C. (e.g., between about 15° C. and about 27° C. and about 60% relative humidity), after storage at about 25° C.±2° C., e.g., after storage at about 25° C.±2° C. and about 40%±5% relative humidity, after storage at about 30° C.±2° C. and about 35%±5% relative humidity, or after storage under any combination of such conditions, for a period of at least about 3 months, such as, e.g., about 3 months to about 6 months (aspect 123).

In aspects, the invention provides the composition of any one or more of aspect 1-aspect 123, wherein the composition comprises less than about 2.5% total impurities after storage at between about 15° C. and about 27° C. (e.g., between about 15° C. and about 27° C. and about 60% relative humidity), after storage at about 25° C.±2° C., e.g., after storage at about 25° C.±2° C. and about 40%±5% relative humidity, after storage at about 30° C.±2° C. and about 35%±5% relative humidity, or after storage under any combination of such conditions, for a period of at least about 6 months, such as, e.g., about 6 months to about 9 months (aspect 124).

In aspects, the invention provides the composition of any one or more of aspect 1-aspect 124, wherein the composition comprises less than about 2.5% total impurities after storage at between about 15° C. and about 27° C. (e.g., between about 15° C. and about 27° C. and about 60% relative humidity), after storage at about 25° C.±2° C., e.g., after storage at about 25° C.±2° C. and about 40%±5% relative humidity, after storage at about 30° C.±2° C. and about 35%±5% relative humidity, or after storage under any combination of such conditions, for a period of at least about 9 months, such as, e.g., about 9 months to about 12 months (aspect 125).

In aspects, the invention provides the composition of any one or more of aspect 1-aspect 125, wherein the composition comprises less than about 2.5% total impurities after storage at between about 15° C. and about 27° C. (e.g., between about 15° C. and about 27° C. and about 60% relative humidity), after storage at about 25° C.±2° C., e.g., after storage at about 25° C.±2° C. and about 40%±5% relative humidity, after storage at about 30° C.±2° C. and about 35%±5% relative humidity, or after storage under any combination of such conditions, for a period of at least about 12 months, such as, e.g., about 12 months to about 18 months (aspect 126).

In aspects, the invention provides the composition of any one or more of aspect 1-aspect 126, wherein the composition comprises less than about 2.5% total impurities after storage at between about 15° C. and about 27° C. (e.g., between about 15° C. and about 27° C. and about 60% relative humidity), after storage at about 25° C.±2° C., e.g., after storage at about 25° C.±2° C. and about 40%±5% relative humidity, after storage at about 30° C.±2° C. and about 35%±5% relative humidity, or after storage under any combination of such conditions, for a period of at least about 18 months, such as, e.g., about 18 months to about 24 months (aspect 127).

In aspects, the invention provides the composition of any one or more of aspect 1-aspect 127, wherein the composition comprises less than about 2.5% total impurities after storage at between about 15° C. and about 27° C. (e.g., between about 15° C. and about 27° C. and about 60% relative humidity), after storage at about 25° C.±2° C., e.g., after storage at about 25° C.±2° C. and about 40%±5% relative humidity, after storage at about 30° C.±2° C. and about 35%±5% relative humidity, or after storage under any combination of such conditions, for a period of at least about 24 months, such as, e.g., about 24 months to about 36 months (aspect 128).

In aspects, the invention provides the composition of any one or more of aspect 1-aspect 128, wherein the composition comprises less than about 2.5% total impurities after storage at between about 15° C. and about 27° C. (e.g., between about 15° C. and about 27° C. and about 60% relative humidity), after storage at about 25° C.±2° C., e.g., after storage at about 25° C.±2° C. and about 40%±5% relative humidity, after storage at about 30° C.±2° C. and about 35%±5% relative humidity, or after storage under any combination of such conditions, for a period of at least about 36 months (aspect 129).

In aspects, the invention provides a method of improving vision, the method comprising administering an effective amount of any one or more of the compositions provided in any one or more of aspect 1-aspect 129 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in vision (aspect 130).

In aspects, the invention provides a method of reducing visual impairment, the method comprising administering an effective amount of any one or more of the compositions provided in any one or more of aspect 1-aspect 129 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same reduction in visual impairment (aspect 131).

In aspects, the invention provides a method of treating an ophthalmic condition (e.g., an ocular condition or symptoms related thereto) selected from the group consisting of presbyopia, hyperopia, mydriasis, anisocoria, accommodative esotropia, myopia, and astigmatism, the method comprising administering an effective amount of any one or more of the compositions provided in any one or more of aspect 1-aspect 129 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement of the same ophthalmic condition (aspect 132).

In aspects, the invention provides a method of treating presbyopia (e.g., an presbyopia or symptoms related thereto), the method comprising administering an effective amount of any one or more of the compositions provided in any one or more of aspect 1-aspect 129 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in presbyopia (aspect 133).

In aspects, the invention provides a method of treating hyperopia (e.g., hyperopia or symptoms related thereto), the method comprising administering an effective amount of any one or more of the compositions provided in any one or more of aspect 1-aspect 129 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in hyperopia (aspect 134).

In aspects, the invention provides a method of treating mydriasis (e.g., mydriasis or symptoms related thereto), the method comprising administering an effective amount of any one or more of the compositions provided in any one or more of aspect 1-aspect 129 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in mydriasis (aspect 135).

In aspects, the invention provides a method of treating anisocoria (e.g., anisocoria or symptoms related thereto), the method comprising administering an effective amount of any one or more of the compositions provided in any one or more of aspect 1-aspect 129 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in anisocoria (aspect 136).

In aspects, the invention provides a method of treating accommodative esotropia (e.g., accommodative esotropia or symptoms related thereto), the method comprising administering an effective amount of any one or more of the compositions provided in any one or more of aspect 1-aspect 129 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in esotropia (aspect 137).

In aspects, the invention provides a method of treating myopia (e.g., myopia or symptoms related thereto), the method comprising administering an effective amount of any one or more of the compositions provided in any one or more of aspect 1-aspect 129 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in myopia (aspect 138).

In aspects, the invention provides a method of treating astigmatism (e.g., astigmatism or symptoms related thereto), the method comprising administering an effective amount of any one or more of the compositions provided in any one or more of aspect 1-aspect 129 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in astigmatism (aspect 139).

In aspects, the invention provides a method of improving, reducing, or treating any one or more of the ophthalmic conditions or symptoms related thereto provided in any one or more of aspect 130-aspect 139, wherein the method comprises the administration of 1 drop of composition to each affected eye, both eyes, or the dominant eye of the recipient once or twice daily over the course of an effective treatment period (aspect 140).

In aspects, the invention provides the method of aspect 140, wherein the method comprises the administration of 1 drop of the composition to each affected eye, both eyes, or the dominant eye of the recipient once daily over the course of an effective treatment period (aspect 141).

In aspects, the invention provides the method of any one or both of aspect 140 or aspect 141, wherein the effective treatment period is period of time lasting between 1 day and 5 years (aspect 142).

In aspects, the invention provides the method of aspect 142, wherein the effective treatment period is period of time lasting between 1 day and 3 years (aspect 143).

In aspects, the invention provides the method of aspect 143, wherein the effective treatment period is period of time lasting between 1 day and 1 years (aspect 144).

In aspects, the invention provides the method of aspect 144, wherein the effective treatment period is period of time lasting between 1 day and 6 months (aspect 145).

In aspects, the invention provides the method of aspect 145, wherein the effective treatment period is period of time lasting between 1 day and 3 months (aspect 146).

In aspects, the invention provides the method of aspect 146, wherein the effective treatment period is period of time lasting between 1 day and 1 months (aspect 147).

In aspects, the invention provides the method of aspect 147, wherein the effective treatment period is period of time lasting between 1 day and 1 weeks (aspect 148).

In aspects, the invention provides the method of aspect 148, wherein the effective treatment period is period of time lasting between 1 day and 1 week (aspect 149).

In aspects, the invention provides the method of aspect 140 or aspect 141, wherein the method comprises chronic treatment, wherein the effective treatment period is an indefinite period of time (aspect 150).

In aspects, the invention provides a method of improving vision by providing to a patient in need thereof an effective amount of a composition of any one or more of aspect 1-aspect 129, wherein the method is clinically demonstrated to be as effective or detectably or significantly more effective than treatment with the product approved under US Food and Drug Administration NDA Number 214028 (VUITY) for the same or similar indication (e.g., improving vision) and for at least substantially the same administration period (aspect 151).

In aspects, the invention provides a method of reducing visual impairment by providing to a patient in need thereof an effective amount of a composition of any one or more of aspect 1-aspect 129, wherein the method is clinically demonstrated to be as effective or detectably or significantly more effective than treatment with the product approved under US Food and Drug Administration NDA Number 214028 (VUITY) for the same or similar indication (e.g., reducing visual impairment) and for at least substantially the same administration period (aspect 152).

In aspects, the invention provides a method of treating presbyopia by providing to a patient in need thereof an effective amount of a composition of any one or more of aspect 1-aspect 129, wherein the method is clinically demonstrated to be as effective or detectably or significantly more effective than treatment with the product approved under US Food and Drug Administration NDA Number 214028 (VUITY) for the same or similar indication (e.g., presbyopia) and for at least substantially the same administration period (aspect 153).

In aspects, the invention provides a method of treating hyperopia by providing to a patient in need thereof an effective amount of a composition of any one or more of aspect 1-aspect 129, wherein the method is clinically demonstrated to be as effective or detectably or significantly more effective than treatment with the product approved under US Food and Drug Administration NDA Number 214028 (VUITY) for the same or similar indication (e.g., hyperopia) and for at least substantially the same administration period (aspect 154).

In aspects, the invention provides a method of treating mydriasis by providing to a patient in need thereof an effective amount of a composition of any one or more of aspect 1-aspect 129, wherein the method is clinically demonstrated to be as effective or detectably or significantly more effective than treatment with the product approved under US Food and Drug Administration NDA Number 214028 (VUITY) for the same or similar indication (e.g., mydriasis) and for at least substantially the same administration period (aspect 155).

In aspects, the invention provides a method of treating anisocoria by providing to a patient in need thereof an effective amount of a composition of any one or more of aspect 1-aspect 129, wherein the method is clinically demonstrated to be as effective or detectably or significantly more effective than treatment with the product approved under US Food and Drug Administration NDA Number 214028 (VUITY) for the same or similar indication (e.g., anisocoria) and for at least substantially the same administration period (aspect 156).

In aspects, the invention provides a method of treating accommodative esotropia by providing to a patient in need thereof an effective amount of a composition of any one or more of aspect 1-aspect 129, wherein the method is clinically demonstrated to be as effective or detectably or significantly more effective than treatment with the product approved under US Food and Drug Administration NDA Number 214028 (VUITY) for the same or similar indication (e.g., accommodative esotropia) and for at least substantially the same administration period (aspect 157).

In aspects, the invention provides a method of treating myopia by providing to a patient in need thereof an effective amount of a composition of any one or more of aspect 1-aspect 129, wherein the method is clinically demonstrated to be as effective or detectably or significantly more effective than treatment with the product approved under US Food and Drug Administration NDA Number 214028 (VUITY) for the same or similar indication (e.g., myopia) and for at least substantially the same administration period (aspect 158).

In aspects, the invention provides a method of treating astigmatism by providing to a patient in need thereof an effective amount of a composition of any one or more of aspect 1-aspect 129, wherein the method is clinically demonstrated to be as effective or detectably or significantly more effective than treatment with the product approved under US Food and Drug Administration NDA Number 214028 (VUITY) for the same or similar indication (e.g., astigmatism) and for at least substantially the same administration period (aspect 159).

In aspects, the invention provides a method of treating an ophthalmic condition (e.g., an ocular condition or symptoms related thereto) selected from the group consisting of presbyopia, hyperopia, mydriasis, anisocoria, accommodative esotropia, myopia, and astigmatism comprising administration of an effective amount of any one or more of the compositions described in any one or more of aspect 1-aspect 129, excluding aspects wherein compositions have a pH of greater than 5.5 (e.g., aspects 18-20), wherein the composition has a pH of between about 3.5 and 5.5 and wherein the method results in an detectably or significantly increased efficacy in treating the ophthalmic condition than the efficacy in treating the condition by administering at least substantially the same composition, comprising the same amount of pilocarpine compound and brimonidine compound, and having a pH of between about 5.6-about 8.5 (comparator composition) (aspect 160).

In aspects, the invention provides the method of aspect 160, wherein any difference between the composition used in the method and the comparator composition is related to the amount of one or more tonicity agents (aspect 161).

In aspects, the invention provides the method of aspect 161, wherein any difference between the composition used in the method and the comparator composition is related to the amount of sodium chloride (aspect 162).

In aspects, the invention provides a method of treating an ophthalmic condition (e.g., an ocular condition or symptoms related thereto) selected from the group consisting of presbyopia, hyperopia, mydriasis, anisocoria, accommodative esotropia, myopia, and astigmatism comprising administration of an effective amount of any one or more of the compositions described in any one or more of aspect 1-aspect 129, excluding aspects wherein compositions have a pH of greater than about 6.5 (e.g., aspects 15-17), wherein the composition has a pH of between about 6.5 and 8.5 and wherein the method results in an detectably or significantly increased efficacy in treating the ophthalmic condition than the efficacy in treating the condition by administering at least substantially the same composition, comprising the same amount of pilocarpine compound and brimonidine compound, and having a pH of between about 3.5-about 6.4 (comparator composition) (aspect 163).

In aspects, the invention provides the method of aspect 163, wherein any difference between the composition used in the method and the comparator composition is related to the amount of one or more tonicity agents (aspect 164).

In aspects, the invention provides the method of aspect 164, wherein any difference between the composition used in the method and the comparator composition is related to the amount of sodium chloride (aspect 165).

In aspects, the invention provides a method of treating an ophthalmic condition (e.g., an ocular condition or symptoms related thereto) selected from the group consisting of presbyopia, hyperopia, mydriasis, anisocoria, accommodative esotropia, myopia, and astigmatism comprising administration of an effective amount of any one or more of the compositions described in any one or more of aspect 1-aspect 129, wherein the method results in an detectably or significantly increased efficacy in treating the ophthalmic condition than the efficacy in treating the condition by administering at least substantially the same composition, comprising the same amount of pilocarpine compound and comprising no brimonidine (aspect 166).

In aspects, the invention provides a method of treating presbyopia or symptoms related thereto, the method comprising administration of an effective amount of a composition of any one or more of aspect 1-aspect 129, wherein the effective amount is 1-2 drops of the composition administered once or twice daily over an effective treatment period, wherein the method results in detectably or significantly reduced ocular blurring compared to treatment of presbyopia with the product approved under US Food and Drug Administration NDA Number 214028 (VUITY) for at least substantially the same administration period (aspect 167).

In aspects, the invention provides a method of treating presbyopia or symptoms related thereto, the method comprising administration of an effective amount of a composition of any one or more of aspect 1-aspect 129, wherein the effective amount is 1-2 drops of the composition administered once or twice daily over an effective treatment period, wherein the method results in detectably or significantly reduced ocular discomfort compared to treatment of presbyopia with the product approved under US Food and Drug Administration NDA Number 214028 (VUITY) for at least substantially the same administration period (aspect 168).

In aspects, the invention provides a method of treating presbyopia or symptoms related thereto, the method comprising administration of an effective amount of a composition of any one or more of aspect 1-aspect 129, wherein the effective amount is 1-2 drops of the composition administered once or twice daily over an effective treatment period, wherein the method results in detectably or significantly reduced eye pain compared to treatment of presbyopia with the product approved under US Food and Drug Administration NDA Number 214028 (VUITY) for at least substantially the same administration period (aspect 169).

In aspects, the invention provides a method of treating presbyopia or symptoms related thereto, the method comprising administration of an effective amount of a composition of any one or more of aspect 1-aspect 129, wherein the effective amount is 1-2 drops of the composition administered once or twice daily over an effective treatment period, wherein the method results in detectably or significantly reduced brow ache compared to treatment of presbyopia with the product approved under US Food and Drug Administration NDA Number 214028 (VUITY) for at least substantially the same administration period (aspect 170).

In aspects, the invention provides a method of treating presbyopia or symptoms related thereto, the method comprising administration of an effective amount of a composition of any one or more of aspect 1-aspect 129, wherein the effective amount is 1-2 drops of the composition administered once or twice daily over an effective treatment period, wherein the method results in detectably or significantly reduced blurry vision compared to treatment of presbyopia with the product approved under US Food and Drug Administration NDA Number 214028 (VUITY) for at least substantially the same administration period (aspect 171).

In aspects, the invention provides a method of treating presbyopia or symptoms related thereto, the method comprising administration of an effective amount of a composition of any one or more of aspect 1-aspect 129, wherein the effective amount is 1-2 drops of the composition administered once or twice daily over an effective treatment period, wherein the method results in detectably or significantly reduced light sensitivity compared to treatment of presbyopia with the product approved under US Food and Drug Administration NDA Number 214028 (VUITY) for at least substantially the same administration period (aspect 172).

In aspects, the invention provides a method of treating presbyopia or symptoms related thereto, the method comprising administration of an effective amount of a composition of any one or more of aspect 1-aspect 129, wherein the effective amount is 1-2 drops of the composition administered once or twice daily over an effective treatment period, wherein the method results in detectably or significantly reduced stinging compared to treatment of presbyopia with the product approved under US Food and Drug Administration NDA Number 214028 (VUITY) for at least substantially the same administration period (aspect 173).

In aspects, the invention provides a method of treating presbyopia or symptoms related thereto, the method comprising administration of an effective amount of a composition of any one or more of aspect 1-aspect 129, wherein the effective amount is 1-2 drops of the composition administered once or twice daily over an effective treatment period, wherein the method results in detectably or significantly reduced itching compared to treatment of presbyopia with the product approved under US Food and Drug Administration NDA Number 214028 (VUITY) for at least substantially the same administration period (aspect 174).

In aspects, the invention provides a method of manufacturing any one or more of the compositions of any one or more of aspect 1-aspect 129, wherein the method comprises (a) preparation of a polymer phase, (b) preparation of a drug phase, (c) filtration of the drug phase into the polymer phase, (d) filtering the composition resulting from (c), and (e) final packaging of the composition (aspect 175).

In aspects, the invention provides the method of manufacturing of aspect 175, wherein the composition(s) resulting from the method are used in any one or more of the methods of treatment in any one or more of aspects 130-174 (aspect 176).

In aspects, the invention provides a kit comprising a composition according to any one or more of aspect 1-aspect 129 and a device suitable for facilitating the delivery of the composition to a recipient eye (aspect 177).

In aspects, the invention provides the kit of aspect 177, wherein the device suitable for facilitating the delivery of the composition to a recipient eye is a container capable of delivering compositions held therein in a drop-by-drop manner (e.g., a dropper bottle) (aspect 178).

In aspects, the invention provides the kit of aspect 178, wherein the composition is provided within the delivery device/container (aspect 179).

In aspects, the invention provides the kit of any one or both of aspect 178 or aspect 179, wherein the kit comprises multiple doses of composition provided as a plurality of single dose containers, a single multi-dose container, or a plurality of multi-dose containers (aspect 180).

In aspects, the invention provides the kit of any one or more of aspect 177-aspect 180, wherein the composition is a composition manufactured according to any one or both of the methods of any one or both of aspect 175 or aspect 176 (aspect 181).

In aspects, the invention provides the kit of any one or more of aspect 177-aspect 181, wherein the kit is used in the method of treatment of any one or more of aspects 130-174 (aspect 182).

In aspects, the invention provides a composition comprising at least one pilocarpine compound and at least one brimonidine compound, wherein the composition has any one or more characteristics of aspect 1-aspect 129, wherein (a) the composition is utilized in any one or more of the methods of aspect 130-aspect 174, (b) the composition is manufactured according to a method described in any one or both of aspect 175-aspect 176, (c) the composition is present as a part of a kit according to any one or more of aspect 177-aspect 182, or (d) any combination of (a)-(c) (aspect 183).

In aspects, the invention provides a composition described in any one or more of the aspects in this Exemplary Aspects of the Invention section, wherein the composition demonstrates chemical stability, physical stability, or both chemical and physical stability, as measured by an indicator of stability described herein, when stored under United States Food and Drug Administration (U.S. FDA) accelerated stability test conditions for a period of at least about one month or under U.S. FDA long-term storage stability test conditions for a period of at least about one year (aspect 184).

In aspects, the invention provides a composition described in any one or more of the aspects in this Exemplary Aspects of the Invention section, wherein the composition demonstrates a rate of API uptake (absorption) by ophthalmic tissue, a total amount of API uptake (absorption) by ophthalmic tissue, a total concentration of API present in ophthalmic tissue measured at one or more points of time after administration, a retention of API in ophthalmic tissue, or any combination thereof, which is detectably or significantly better than/increased compared to a comparator or reference composition, wherein the comparator or reference composition comprises the same active pharmaceutical ingredients in the same amounts as in the composition upon initial storage, comprises at least most of the excipients as in the composition in approximately the same amounts excluding pH adjusting agents upon initial storage, or any or all thereof, but which has a pH which is at least about 25% greater than the pH of the composition (aspect 185).

In aspects, the invention provides a method of treating an ophthalmic condition or symptom related thereto in a mammalian eye, the method comprising administration of an effective amount of a composition described in any one or more of the aspects described in this Exemplary Aspects of the Invention section, wherein an effective amount of the composition is 1-2 drops of the composition to one or both eye(s) of the recipient once or twice daily, and wherein the method further optionally comprises repeating the administration of the composition for a number of times demonstrated to provide a significant clinical effect in visual improvement in a significant number of patients in a well-controlled and adequate study or that is shown to be bioequivalent to a product that has been demonstrated to achieve effectively the same improvement in vision (aspect 186).

In aspects, the invention provides the method of aspect 186, wherein the ophthalmic condition selected from the group consisting of presbyopia, hyperopia, mydriasis, anisocoria, accommodative esotropia, myopia, and astigmatism (aspect 187).

DETAILED DESCRIPTION OF THE INVENTION

For convenience, both combinations of elements/steps and individual elements/steps may be described in this section of this disclosure. Despite the inclusion of passages focused on specific elements/steps, any aspect, facet, embodiment, or other description of any particular step(s) or element(s) can be applied to any general description of the composition(s)/method(s) of the invention, or any other recited element(s)/step(s) thereof, which are provided in any part of this disclosure.

As used herein, uncontradicted, the word "exemplary" means "serving as an example, instance, or illustration." Uncontradicted, the content of the following detailed description is merely exemplary in nature and is not intended to limit application and uses. Any embodiment/aspect described herein as "exemplary" is not necessarily to be construed as preferred or advantageous over other embodiments.

COMPOSITIONS

In aspects, the invention provides pharmaceutically acceptable and ophthalmologically suitable composition(s) comprising a parasympathomimetic compound component, an alpha-2-adrenergic agonist component, and one or more excipients. In aspects, such composition(s) are suitable for ophthalmic administration, e.g., for the treatment of one or more conditions of the eye, such as impaired vision (improving vision or reducing impaired vision) or the treatment of a specific ophthalmic condition or symptoms related to the specific condition, such as, e.g., presbyopia. In aspects, the parasympathomimetic compound and alpha-2-adrenergic agonist components represent the only active pharmaceutical ingredients (APIs) in the composition.

In aspects, composition(s) provided by the invention comprise relative amount(s) of a limited buffer component (e.g., a buffer component comprising only select buffer constituent(s), a select number of select buffer constituent (s), or both, and active pharmaceutical ingredient(s), which is/are capable of being stably maintained (e.g., composition (s) maintaining an amount of API which is at least about 97% of an original amount, maintaining a level of impurity (ies) suitable for approval by a recognized regulatory body such as, e.g., the United States Food and Drug Administration), or both) for a commercially relevant period of time under typical storage conditions or conditions utilized for stability study(ies), including accelerated stability studies, known in the art. In aspects, storage conditions herein refer to conditions comprising a temperature of between about 15° C. and about 27° C. (e.g., between about 15° C. and about 27° C. and about 60% relative humidity); about 25° C.±2° C., e.g., about 25° C.±2° C. and about 40%±5% relative humidity (e.g., for long term storage); about 30° C.±2° C. and about 35%±5% relative humidity (e.g., for long term storage); about 30° C.±2° C. and about 65%±5% relative humidity; about 40° C.±2° C. and not more than ("NMT") about 25% relative humidity (e.g., for accelerated storage); or a combination of any or all such conditions. This is discussed further elsewhere herein. It can be understood that for long term storage, e.g., when stored at a point of use (after manufacturing), typically storage conditions are long term storage condition(s) (e.g., as opposed to accelerated storage conditions). Herein, a "commercially relevant period of time" is a period of time of at least about 1 month, e.g., ≥~6 weeks, ≥~2 months, ≥~10 weeks, ≥~3 months, ≥~6 months, ≥~9 months, ≥~12 months, ≥~18 months, ≥~24 months, ≥~28 months, ≥~32 months, or ≥~36 months.

In aspects, such composition(s) are suitable for ophthalmic administration for the treatment of one or more conditions of the eye, such as impaired vision (improving vision or reducing impaired vision) or a specific condition or symptoms related to the specific condition, such as, e.g., presbyopia.

Parasympathomimetic Compound Component (PCC)

In aspects, composition(s) provided by the invention comprise a parasympathomimetic compound component ("PCC") in addition to an alpha-2-adrenergic agonist component ("AAAC" or shortened in places herein to "AAC"). In aspects, the PCC comprises one or more parasympathomimetic agents (or parasympathomimetic drug). In aspects, the term "parasympathomimetic agent or drug" used herein refers to any cholinergic drug that enhances the effects mediated by acetylcholine in the central nervous system, the peripheral nervous system, or both. In aspects, a "parasympathomimetic agent or drug" is a muscarinic agonist. In aspects, a "parasympathomimetic agent or drug" is a muscarinic antagonist.

In aspects, the PCC can comprise any pharmaceutically acceptable and ophthalmologically suitable parasympathomimetic agent/drug. Examples of suitable cholinergic compounds are alpha androgenic agonists such as, e.g., acetylcholine, muscarine, pilocarpine, nicotine, suxamethonium, bethanechol, carbachol, methacholine, phenylpropanolamine, amphetamine, ephedrine, phentolamine, fenfluramine, etc. In certain aspects, suitable PCC constituents are muscarinic cholinergic agonists provided in ophthalmologically suitable form, such as, e.g., bethanechol compound(s), cevimeline compound(s), pilocarpine compound(s), methacholine compound(s), and xanomeline compound(s). In certain aspects, the PCC comprises one or more pilocarpine compounds. In certain aspects, the PCC comprises a single pilocarpine compound.

Pilocarpine Compounds

In aspects, the PCC of composition(s) provided by the invention comprises one or more pilocarpine compounds (compounds that comprise pilocarpine, including derivatives thereof, or that include another compound that is a pharmaceutically acceptable analog of pilocarpine that exhibits at least similar physiological/therapeutic effects as pilocarpine). Analogs of pilocarpine are known in the art (see, e.g., U.S. Pat. No. 5,025,027) and such analogs may be suitable in composition(s)/method(s) of the invention and other such analogs can be generated by application of routine method(s). However, in aspects, certain compounds or groups of compounds may offer one or more different properties, such that each such compound can be considered its own aspect or to define a category of aspects of the invention. In aspects, the PCC does not include analogs, only pilocarpine, pilocarpine derivatives (a molecule comprising a pilocarpine core and additional groups), or a related compound (e.g., a salt of either or both thereof). In aspects, a PCC only comprises pilocarpine or a related compound, such as a salt thereof.

Pilocarpine ($C_{11}H_{16}N_2O_2$) is a muscarinic cholinergic agonist having a molecular weight of about 208 Da having the structure provided below:

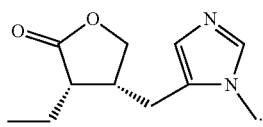

Pilocarpine

In aspects, the pilocarpine compound can be any pharmaceutically acceptable and ophthalmologically suitable pilocarpine compound, such as, e.g., any pharmaceutically acceptable and ophthalmologically suitable salt(s), solvate(s), hydrate(s), enantiomer(s), derivative(s), polymorph(s), and prodrug(s) thereof. In aspects, a pilocarpine compound is limited to one or some of these types of compound(s) but excludes other type(s) of any such compounds. E.g., in aspects, a pilocarpine compound does not include a polymorph, but does include two or more salts of pilocarpine.

Examples of pilocarpine salts include, e.g., the acetate, succinate, tartrate, bitartrate, dihydrochloride, salicylate, hemisuccinate, citrate, maleate, hydrochloride, carbamate, sulfate, nitrate, and benzoate salt forms of pilocarpine, and, e.g., quaternary pilocarpine salts (see, e.g., Wojciechowski thesis, University of Illinois, 1961; doi.org/10.1002/jps.2600501012), (1)-acyloxy-alkyl-pilocarpine salts described in U.S. Pat. No. 4,061,722A, and piloplex (see Ticho, et. Al. in "Piloplex, a new long-acting pilocarpine polymer salt. A long-term study," in British Journal of Ophthalmology, 1979, 63; 45-47), etc.

Pilocarpine enantiomers include, e.g., the (+)-1 and (−)-1 enantiomers of pilocarpine (see, e.g., Schmidt, Theresa et al. "Concise Synthesis of Both Enantiomers of Pilocarpine." Molecules (Basel, Switzerland) vol. 26, 12 3676. 16 Jun. 2021, doi:10.3390/molecules26123676).

Examples of pilocarpine derivatives include ophthalmologically suitable forms of quaternary pilocarpine derivatives described in, for example, Druzgala P, et. Al. in, "New water-soluble pilocarpine derivatives with enhanced and sustained muscarinic activity," Pharm Res. 1992 March; 9(3):372-7. Doi: 10.1023/a:1015847103862. PMID: 1614970; in, e.g., Ben-Bassat A A, et. Al., "Quaternary pilocarpine derivatives as potential acetylcholine antagonists. 2. Alterations in the lactone and imidazole moieties," J Med Chem. 1976 July; 19(7):928-33; and in, e.g., U.S. Pat. Nos. 5,530,136A, 4,835,174A, EP559700B1, etc. Pilocarpine derivatives also include, e.g., Pilo-OEG (Wang and Yang, described at innovationgateway.vcu.edu/technologies/biomedical/comeal-permeable-anti-glaucoma-drug) (Virginia Commonwealth University (VCU) tech number 19-080F).

Exemplary prodrugs of pilocarpine include, e.g., ophthalmologically suitable forms of various alkyl and aralkyl esters of pilocarpic acid described in, e.g., Bundgaard H, et. al. "Pilocarpine prodrugs I. Synthesis, physicochemical properties and kinetics of lactonization of pilocarpic acid esters," J Pharm Sci. 1986 January; 75(1):36-43. doi: 10.1002/jps.2600750109. PMID: 3958903; in, e.g., Bundgaard H, et. al. in "Pilocarpine prodrugs. II. Synthesis, stability, bioconversion, and physicochemical properties of sequentially labile pilocarpine acid diesters," J Pharm Sci. 1986 August; 75(8):775-83. doi: 10.1002/jps.2600750811. PMID: 3772750; in, e.g., Jarvinen, et. al. "Synthesis and identification of pilocarpic acid diesters, prodrugs of pilocarpine," 1991, Journal of Pharmaceutical and Biomedical Analysis, Vol. 9, Issue 6, pp. 457-464, DOI 10.1016/0731-7085(91)80247-7; in, e.g., EP0106541A2, etc.

Herein, uncontradicted, the term "pilocarpine" or "pilocarpine compound" refers to not only pilocarpine directly, but also its other pharmaceutically acceptable and ophthalmologically suitable salt(s), pharmaceutically acceptable and ophthalmologically suitable solvate(s), pharmaceutically acceptable and ophthalmologically suitable hydrate(s), pharmaceutically acceptable and ophthalmologically suitable enantiomer(s), pharmaceutically acceptable and ophthalmologically suitable derivative(s), pharmaceutically acceptable and ophthalmologically suitable polymorph(s), and pharmaceutically acceptable and ophthalmologically suitable prodrug(s) thereof, such as those exemplified above. However, as noted, any one of such types of pilocarpine compounds; or any combination(s) of two or more thereof, but, typically, less than all, of such compound types; each represent different aspect(s) of the invention, such that, uncontradicted, any description of aspect(s) relating to a pilocarpine compound can be interpreted as relating to any one, some, most, or all of such types of compounds being suitable or being actually present in the composition(s).

Pilocarpine Hydrochloride

In certain aspects, the composition(s) provided by the invention comprise a pilocarpine compound which is a pharmaceutically acceptable salt of pilocarpine. In aspects, the pharmaceutically acceptable salt of pilocarpine is pilocarpine hydrochloride. Pilocarpine hydrochloride ($C_{11}H_{17}ClN_2O_2$) is chemically (3S,4R)-3-ethyl-4-[(1-methyl-1H-imidazol-5-yl)methyl] oxolan-2-one hydrochloride, and has the following molecular structure:

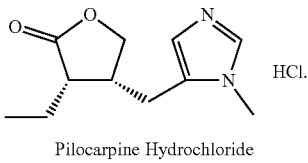

Pilocarpine Hydrochloride

In aspects, the PCC is present in composition(s) in a therapeutically effective amount (e.g., an effective amount). In aspects, the PCC is present in composition(s) provided by the invention in an amount representing between about 0.5% w/v to about 4% w/v, such as, for example, ~0.5% w/v-~3.8% w/v, ~0.5% w/v-~3.6% w/v, ~0.5% w/v-~3.4% w/v, ~0.5% w/v-~3.2% w/v, or ~0.5% w/v-~3% w/v, such as ~0.6% w/v-~4% w/v, ~0.7% w/v-~4% w/v, ~0.8% w/v-~4% w/v, ~0.9% w/v-~4% w/v, or ~1% w/v-~4% w/v, such as for example ~0.6% w/v-~3.8% w/v, ~0.7% w/v-~3.6% w/v, ~0.8% w/v-~3.4% w/v, ~0.9% w/v-~3.2% w/v, or, e.g., ~1% w/v-~3% w/v. In aspects, composition(s) comprise between about 1% w/v to about 2% w/v of a PCC, such as, e.g., about 1.25% w/v of a PCC or, e.g., ~1.5% w/v of a PCC.

In aspects, the PCC is present in composition(s) provided by the invention in an amount representing at least 1% w/v, such as, e.g., ≥~1.1% w/v, ≥~1.2% w/v, ≥~1.3% w/v, ≥~1.4% w/v, ≥~1.5% w/v, ≥~1.6% w/v, ≥~1.7% w/v, or ≥~1.8% w/v. In certain aspects, composition(s) comprise an amount of pilocarpine significantly greater than 1% w/v. such as e.g., an amount significantly greater than 1.1% w/v, 1.15% w/v, 1.2% w/v, 1.25% w/v, 1.3% w/v, 1.35% w/v, 1.4% w/v, or, e.g., significantly greater than 1.45% w/v, such as, e.g., at least about 1.5% w/v, ≥~1.55% w/v, ≥~1.6% w/v, ≥~1.65% w/v, ≥~1.7% w/v, ≥~1.75% w/v, ≥~1.8% w/v, ≥~1.85% w/v, ≥~1.9% w/v, 1.95% w/v, or ≥~2% w/v, ≥~2.1% w/v, ≥~2.2% w/v, ≥~2.3% w/v, ≥~2.4% w/v, or ≥~2.5% w/v, such as, e.g., between about 1.25% w/v and about 3% w/v or between about 1.25% w/v and about 2% w/v pilocarpine compound.

In aspects, the PCC is present in composition(s) provided by the invention in an amount of between about 1.1% w/v and about 1.7% w/v, such as, e.g., between about 1.2% w/v and about 1.6% w/v of a PCC, such as, e.g., about 1.5% w/v of a PCC or about 1.25% w/v of PCC. In aspects, the PCC is present in composition(s) provided by the invention in an amount no greater than 2.5% w/v, such as, e.g., being present in an amount which is ≤~2.4% w/v, ≤~2.3% w/v, ≤~2.2% w/v, ≤~2.1% w/v, ≤~2.0% w/v, ≤~1.9% w/v, ≤~1.8% w/v, ≤~1.7% w/v, or ≤~1.6% w/v, such as, e.g., ≤~1.55% w/v, ≤~1.5% w/v, ≤~1.45% w/v, ≤~1.4% w/v, ≤~1.35% w/v, or ≤~1.3% w/v. In aspects, composition(s) comprise no more than about 1.7% w/v of a pilocarpine compound and no less than about 1.1% w/v of a pilocarpine compound, in combination with an alpha-2-adrenergic agonist (AAA) component, described elsewhere herein.

In aspects, the PCC comprises two or more PCC constituents, wherein the total amount of such constituents is represented by the concentrations/amounts provided above. In aspects, composition(s) comprise a PCC comprising a single PCC constituent, wherein the total amount of such single constituent is represented by the concentrations/amounts provided above. In aspects, the PCC comprises a pharmaceutically acceptable and ophthalmologically suitable pilocarpine compound, such as a pharmaceutically acceptable and ophthalmologically suitable salt of pilocarpine, e.g., pilocarpine hydrochloride (pilocarpine HCL). In aspects, the PCC comprises a single constituent which is a pharmaceutically acceptable and ophthalmologically suitable pilocarpine compound, such as a pharmaceutically acceptable and ophthalmologically suitable salt of pilocarpine, e.g., pilocarpine HCl. In aspects, the single pilocarpine compound constituent, e.g., the pharmaceutically acceptable and ophthalmologically suitable salt of pilocarpine, e.g., pilocarpine HCl is present in composition(s) in the above-identified amounts. In aspects, composition(s) comprise pilocarpine hydrochloride (HCl) at a concentration of greater than 1% w/v, greater than 1.1% w/v, or, e.g., greater than about 1.15% w/v or, e.g., about 1.1% w/v to about 3.0% w/v, such as about 1% w/v-about 2% w/v, e.g., about 1% w/v-about 1.5% w/v, e.g., about 1.25% w/v, or about 1.5% w/v. In aspects, 1.25% w/v pilocarpine hydrochloride (or about 12.5 mg of pilocarpine hydrochloride) is equivalent to about 1.06% w/v pilocarpine free base (or about 10.6 mg pilocarpine free base). Such a conversion can be applied elsewhere as applicable herein, as is routinely understood in the art.

Alpha-2-Adrenerzic Agonist Component

In aspects, composition(s) provided by the invention comprise an alpha-2-adrenergic agonist compound ("AAA") component ("AAAC", or in places herein, shortened to "AAC") in addition to the PCC. In aspects, an AAA component comprises one or more compounds (compound(s)) characterizable as an alpha agonist. In aspects, composition(s) comprise an AAA component comprising one or more alpha-2-adrenergic agonist constituents (also referred to as alpha-2-agonists). In aspects, one or more alpha-2-adrenergic agonists/alpha-2-agonists can comprise any pharmaceutically acceptable and ophthalmologically suitable alpha-2-adrenergic agonists/alpha-2-agonists suitable for topical administration to a mammalian eye. In aspects, the one or more alpha-2-adrenergic agonist(s)/alpha-2-agonist constituents of an AAA component can comprise any pharmaceutically acceptable and ophthalmologically suitable alpha-2-adrenergic agonist/alpha-2-agonist suitable for topical administration which is capable of detectably or significantly reducing elevated IOP in a recipient eye, such as, e.g., the eye of a patient diagnosed with or suffering from open-angle glaucoma, ocular hypertension, or, e.g., an ocular condition such as presbyopia or related symptoms or other ophthalmic condition(s) described herein. In aspects, the alpha-2-adrenergic agonist/alpha-2-agonist is further characterizable as a 2-imidazoline derivative, a quinoxaline derivative, or both (e.g., a compound recognized as an alpha-2-adrenergic agonist/alpha-2-agonist and comprising such a chemical core structure as understood in the art).

In aspects, the AAA component of composition(s) provided by the invention comprise one or more alpha-2-adrenergic agonists/alpha-2-agonists selected from a group comprising amiloride, apraclonidine, brimonidine, clonidine (and its derivatives such as p-chloro and amino derivatives), detomidine, dexmedetomidine, dipivalylepi-nephrine, epinephrine, fadolmidine, guanabenz, guanfacine, isoproterenol, medetomidine, metaproterenol, mephentermine, methoxamine, methyldopa, naphazoline, norepinephrine, phenylephrine, rilmenidine, salbutamol, terbutaline, tetrahydrozoline, and xylazine and their pharmaceutically acceptable salts and prodrugs. In specific aspects, the one or more alpha-2-adrenergic agonists/alpha-2-agonists is a brimonidine compound.

Brimonidine Compounds

According to aspects, composition(s) provided by the invention comprise an AAA component comprising one or more brimonidine compound constituent(s). Brimonidine is a relatively selective alpha-2-adrenergic agonist (as that term is understood in the art) that is presently contained in a pharmaceutical product sold as a topical ophthalmic formulation (see, e.g., Alphagan P; 0.1% and 0.15%) for lowering elevated IOP in patients with open angle-glaucoma or ocular hypertension (see, e.g., Allergan, Inc.). Brimonidine is chemically 5-bromo-6-(2-imidazolidinylideneamino) quinoxaline (often present in an L-tartrate form), understood typically as having the structural formula:

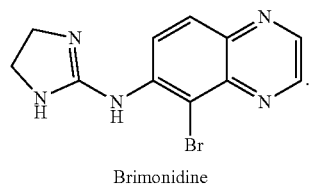 [SMILES: Brc1c(NC2=NCCN2)ccc2nccnc12]

Brimonidine

In aspects, composition(s) can comprise any pharmaceutically acceptable and ophthalmologically suitable brimonidine compound(s), including the base compound brimonidine, or a pharmaceutically acceptable enantiomer(s), pharmaceutically acceptable salt(s), pharmaceutically acceptable derivative(s), pharmaceutically acceptable polymorph(s), or pharmaceutically acceptable prodrug(s) thereof, or a combination of any or all thereof.

In aspects, the AAA component of composition(s) provided by the invention at least generally comprises, at least substantially comprises, or at least essentially comprises/consists of one or more salts of brimonidine, such as, e.g., brimonidine tartrate, or those disclosed in, e.g., U.S. Pat. No. 10,220,043 (KOWA).

In aspects, an AAA component of composition(s) comprises one or more derivatives of brimonidine, such as, e.g., one or more derivatives of brimonidine disclosed in U.S. Pat. No. 6,294,563.

In aspects, an AAA component of composition(s) comprises one or more prodrugs of brimonidine, such as, e.g., one or more sulfonyl prodrugs of brimonidine, such as those described in, e.g., Canadian Patent Document CA2603069.

In aspects, an AAA component of composition(s) at least generally comprises, at least substantially comprises, or at least essentially comprises, a salt of brimonidine. As used herein the term "brimonidine" or "brimonidine compound" should be interpreted to mean a brimonidine salt or any pharmaceutically acceptable and ophthalmologically suitable brimonidine compound disclosed in this section (or an equivalent thereof). In aspects, composition(s) at least generally comprise, at least substantially comprise, or at least essentially comprise (i.e., consist essentially of or consist of) brimonidine tartrate.

Herein, uncontradicted, the term "brimonidine" or "brimonidine compound" refers to not only brimonidine directly, but also its other pharmaceutically acceptable and ophthalmologically suitable enantiomer(s), pharmaceutically acceptable and ophthalmologically suitable salt(s), pharmaceutically acceptable and ophthalmologically suitable derivative(s), pharmaceutically acceptable and ophthalmologically suitable polymorph(s), or pharmaceutically acceptable prodrug(s) thereof such as those exemplified above. However, as noted, combinations of two or more thereof, but less than all, of such compound types; each individual compound type; and individual compound(s)/composition(s) described herein, each represent different aspect(s) of the invention and in cases exclude some or more of such other compounds.

Brimonidine Tartrate

According to aspects, an AAA component of composition(s) provided by the invention comprise brimonidine tartrate. Brimonidine tartrate is a relatively selective alpha-2-adrenergic agonist. Brimonidine tartrate is chemically known as 5-bromo-6-(2-imidazolidinylideneamino) quinoxaline L-tartrate. The empirical formula of brimonidine tartrate is $C_{11}H_{10}BrN_5$—$C_4H_6O_6$, and the compound has the following chemical structure:

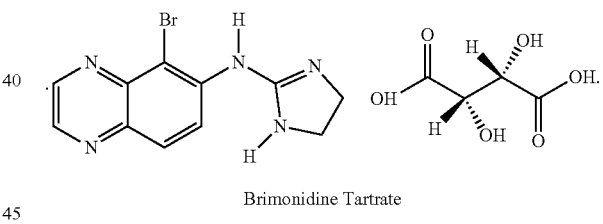

Brimonidine Tartrate

In aspects, composition(s) provided by the invention can comprise any pharmaceutically acceptable and ophthalmologically suitable amount of a brimonidine compound, e.g., a brimonidine salt, such as, e.g., brimonidine tartrate.

In aspects, composition(s) comprise at least (e.g., no less than or greater than) about 0.01% w/v of a brimonidine compound, e.g., a brimonidine salt, such as, e.g., brimonidine tartrate, such as, e.g., at least about 0.02% w/v, ≥~0.03% w/v, ≥~0.04% w/v, ≥~0.05% w/v, ≥~0.06% w/v, ≥~0.07% w/v, ≥~0.08% w/v, or, e.g., ≥~0.09% w/v, such as, e.g., ≥~0.095% w/v, or, e.g., ≥~0.1% w/v of a brimonidine compound, such as ≥~0.2% w/v, ≥~0.4% w/v, ≥~0.6% w/v, ≥~0.8% w/v, ≥~1% w/v, ≥~1.5% w/v, ≥~2% w/v, ≥~2.5% w/v, ≥~3% w/v, ≥~3.5% w/v, ≥~4% w/v, or ≥~4.5% w/v of a brimonidine compound.

In aspects, composition(s) comprise less than (e.g., no more/no greater than) 5% w/v of a brimonidine compound, e.g., a brimonidine salt, such as, e.g., brimonidine tartrate, such as, e.g., no more than about 4.5% w/v, ≤~4% w/v, ≤~3.5% w/v, ≤~3% w/v, ≤~2.5% w/v, ≤~2% w/v, ≤~1.5% w/v, ≤~1% w/v, ≤~0.8% w/v, ≤~0.6% w/v, ≤~0.4% w/v, ≤~0.35% w/v, ≤~0.3% w/v, ≤~0.25% w/v, ≤~0.2% w/v, ≤~0.18% w/v, ≤~0.15% w/v, or, e.g., ≤~0.1% w/v of a brimonidine compound, e.g., a brimonidine salt, such as, e.g., brimonidine tartrate.

In aspects, composition(s) can comprise between about 0.01% w/v to about 0.5% w/v of a brimonidine compound, such as, e.g., between about 0.01% w/v and about 0.45% w/v, ~0.01% w/v to (–) ~0.4% w/v, ~0.01% w/v–~0.35% w/v, ~0.01% w/v–~0.3% w/v, ~0.01% w/v–~0.25% w/v, ~0.01% w/v–~0.2% w/v, ~0.01% w/v–~0.15% w/v, or ~0.01% w/v–~0.1% w/v, such as between ~0.02% w/v–~0.5% w/v, ~0.04% w/v–~0.5% w/v, ~0.06% w/v–~0.5% w/v, ~0.08% w/v–~0.5% w/v, or ~0.1% w/v–~0.5% w/v, or, e.g., ~0.02% w/v–~0.5% w/v, e.g., ~0.03% w/v–~0.45% w/v, ~0.04% w/v–~0.4% w/v, ~0.05% w/v–~0.35% w/v, ~0.06% w/v–~0.3% w/v, ~0.07% w/v–~0.25% w/v, ~0.08% w/v–~0.2% w/v, or, e.g., ~0.1% w/v of a brimonidine compound, such as a brimonidine salt, e.g., brimonidine tartrate. In aspects, composition(s) provided by the invention comprise between about 0.05% w/v to about 0.15% w/v of a brimonidine compound, such as, e.g., a brimonidine salt, e.g., brimonidine tartrate, in combination with a PCC (described elsewhere herein). In aspects, a brimonidine compound is a salt of brimonidine, which, in aspects, is present in an amount that is approximately equivalent or equivalent to such an amount of free/free base brimonidine. For example, about 2 mg of brimonidine tartrate is equivalent to about 1.32 mg of free base brimonidine compound. Readers can readily similarly calculate other amounts of a brimonidine salt compound provided by such disclosure depending on the salt form used in the applicable composition.

Pilocarpine & Brimonidine Combinations

In aspects, composition(s) provided by the invention comprise a pharmaceutically acceptable and ophthalmologically suitable parasympathomimetic compound component (PCC) and a pharmaceutically acceptable and ophthalmologically suitable alpha-2-adrenergic agonist component (AAAC) in combination with one another (within a single composition). Such combination composition(s) can be referred to as "fixed dosage" combination products. Uncontradicted, the term "fixed dose" (AKA, "fixed-dose") is understood in the art as referring to a combination of two or more active ingredients (API(s)) within a single form of pharmaceutical administration, and does not necessarily impart any limitation on the relationship of dose(s) of such active ingredients, etc. See, e.g., Goodman et al. Expert Review of Pharmacoeconomics & Outcomes Research, 20:1, 1-26. Nonetheless, in aspects, fixed-dose combination(s) provided herein are characterized by specific amount(s) of APIs or relationship(s) (e.g., ratio(s)) of APIs.

In aspects, composition(s) provided by the invention comprise a pharmaceutically acceptable and ophthalmologically suitable fixed-dose combination of a PCC and an AAA component. In aspects, the PCC and the AAA component comprises, e.g., a pilocarpine compound and a brimonidine compound, respectively. In aspects, the PCC comprises a pilocarpine compound, e.g., pilocarpine hydrochloride. In aspects, the AAA component comprises a brimonidine compound, e.g., brimonidine tartrate. In aspects, composition(s) provided by the invention comprise, e.g., about 0.5% w/v to about 4% w/v of a PCC, such as, e.g., a pilocarpine compound, such as a pilocarpine salt, e.g., pilocarpine hydrochloride, such as, for example, an amount greater than about 1% w/v, such as, e.g., at least about 1.1% w/v. In aspects, composition(s) comprise between about 1% w/v to about 2% w/v of a PCC, such as, e.g., at least about 1.1% w/v and less than about 1.7% w/v of a PCC, such as, e.g., about 1.25% w/v of a PCC or about 1.5% w/v of a PCC, e.g., a pilocarpine compound, such as a pilocarpine salt, e.g., pilocarpine hydrochloride. In aspects, composition(s) provided by the invention further comprise, e.g., about 0.01% w/v to about 0.5% w/v of an AAA component, such as, e.g., ~0.02% w/v–~0.45% w/v, ~0.04% w/v–~0.4% w/v, ~0.06% w/v–~0.35% w/v, ~0.08% w/v–~0.3% w/v, ~0.09% w/v–~0.25% w/v, ~0.1% w/v–~0.2% w/v, or, e.g., ~0.1% w/v of an AAA component, such as, e.g., a brimonidine compound, such as a brimonidine salt, e.g., brimonidine tartrate.

Excipients

According to certain aspects, composition(s) provided by the invention comprise one or more excipients, which are a type of, or alternatively can be characterized as, a composition constituent/component or ingredient. In aspects, the one or more excipients can be any pharmaceutically acceptable and ophthalmologically acceptable excipient(s) provided that the excipient(s) does/do not detectably or significantly interfere with the activity or stability of the PCC or the AAA component or the activity or stability of any other excipient(s). Most, generally all, or all of the excipient(s) of composition(s) are typically characterized by one or more classes or components, which typically are defined by the function of such ingredient or component. Examples of the types of component(s)/ingredient(s) that can be present in composition(s) of the invention are described in turn in the following sections, but readers will understand that these disclosures can be combined in accordance with more general description(s) provided in the Summary, Exemplary Aspects, or other portions of this disclosure.

Penetration Enhancer Component (Penetration Enhancer(s))

In certain aspects, composition(s) provided by the invention comprise an effective amount of a penetration enhancer component (a part of a composition that comprises one or more penetration enhancer(s) in effective amounts for detectably or significantly enhancing penetration of other constituents, such as the PCC or compound(s) thereof; the AAA component or compound(s) thereof; or both the PCC and AAA component or compound(s) thereof). In aspects, a penetration enhancer component comprises any one or more pharmaceutically acceptable and ophthalmologically suitable penetration enhancer(s) (which can be referred to as penetration agents or penetration enhancing agents/constituents), which provide detectable or significant penetration enhancement effect of any one or more constituents of the PCC, one or more constituents of the AAA component, or one or more constituents of each of both the PCC and the AAA component. In aspects, the penetration enhancer component (e.g., constituents of the penetration enhancer component) is any pharmaceutically acceptable and ophthalmologically suitable compound capable of (when present in a suitable amount and under suitable conditions) (a) detectably or significantly increasing the amount of a PCC constituent, e.g., a pilocarpine compound, such as a salt of pilocarpine, e.g., pilocarpine HCl, which penetrates eye tissue in a given period of time (e.g., the period of time between doses, such as within a 24-hour period); (b) detectably or significantly increasing the amount of an AAA component constituent, e.g., a brimonidine compound, such as a salt of brimonidine, e.g., brimonidine tartrate, which penetrates eye tissue in a given period of time (e.g., the period of time between doses, such as within a 24-hour period); or (c) detectably or significantly increases the amount of a PCC constituent and an AAA component constituent which penetrates eye tissue in a given period of time (e.g., the period of time between doses, such as within a 24-hour period). In aspects, the penetration enhancer component or constituent(s) thereof is/are pharmaceutically acceptable and ophthalmologically suitable compound(s) which detectably or significantly increase the amount of a PCC constituent (e.g., pilocarpine HCl), AAA component constituent (e.g., brimonidine tartrate), or both, penetrating eye tissue within a 24-hour, 22-hour, 20-hour, 18-hour, 16-hour, 14-hour, 12-hour, 10-hour, 8-hour, 6-hour, 4-hour, 2-hour, or 1-hour period of time, such that a detectably or significantly greater amount of the PCC constituent(s) (e.g., pilocarpine HCl), AAA component constituent(s), (e.g., brimonidine tartrate), or both, is available within the eye tissue for treating the condition of the eye to which the treatment is directed. In aspects, the presence of a penetration enhancer component detectably or significantly increases the amount of a PCC constituent (e.g., pilocarpine HCl), an AAA component constituent (e.g., brimonidine tartrate), or both, which penetrates eye tissue over the amount of the same PCC constituent, AAA component constituent, or both, present in at least generally the same, at least substantially the same, at least essentially the same, or the same amount in a comparable composition lacking the penetration enhancer component or wherein such a penetration enhancer component is present in a detectably or significantly different amount.

In aspects, the penetration enhancer component or constituent(s) of the penetration enhancer component is or are any pharmaceutically acceptable and ophthalmologically suitable compound(s) capable of (a) detectably or significantly increasing the rate of penetration into an eye tissue of a PCC constituent, e.g., a pilocarpine compound, such as a salt of pilocarpine, e.g., pilocarpine HCl, (b) detectably or significantly increasing the rate of penetration into an eye tissue of an AAA component constituent, e.g., a brimonidine compound, such as a salt of brimonidine, e.g., brimonidine tartrate, or (c) detectably or significantly increasing the rate of penetration into an eye tissue of both a PCC constituent and an AAA component constituent. In aspects, a constituent of the penetration enhancer component detectably or significantly increases the amount of a PCC constituent, AAA component constituent, or both a PCC constituent and an AAA component constituent penetrating eye tissue per unit time compared to the amount per unit time of the same PCC constituent, AAA component constituent, or both the same PCC constituent and the same AAA component constituent present in at least generally the same, at least substantially the same, at least essentially the same, or the same amount in a comparable composition lacking the penetration component or comprising a penetration enhancement component in a detectably or significantly different amount.

In aspects, a penetration enhancer component constituent is a compound or composition capable of detectably or significantly enhancing penetration of an active pharmaceutical ingredient, e.g., a PCC constituent (e.g., a pilocarpine compound, e.g., a salt of pilocarpine, e.g., pilocarpine HCl), an AAA component constituent (e.g., a brimonidine compound, e.g., a salt of brimonidine, e.g., brimonidine tartrate) or both a PCC constituent and an AAA component constituent, in mammalian eye tissue (e.g., in human eye tissue, such as in the tissue of human patients). In some respects, a penetration enhancer component constituent can be any ophthalmologically suitable compound or mixture of compounds capable of exerting the effect of increasing the speed of penetration of an API present in the formulation (e.g., a pilocarpine compound, a brimonidine compound, or both) into ocular cells, e.g., corneal cells, or improving (e.g., increasing) the uptake or retention of an API present in the formulation (e.g., a pilocarpine compound, a brimonidine compound, or both) into ocular tissue or ocular cells. In aspects, a penetration enhancer detectably or significantly enhances penetration of an API, e.g., a pilocarpine compound, e.g., pilocarpine HCl, or, e.g., a brimonidine compound, e.g., brimonidine tartrate, or both a pilocarpine and a brimonidine compound, into ocular tissue by at least about 10%, ≥~20%, ≥~30%, ≥~40%, ≥~50%, ≥~60%, ≥~70%, ≥~80%, ≥~90%, or by ≥~100%, such as ≥~120%, ≥~140%, ≥~160%, ≥~180%, or at least approximately 200% or even more, over similar formulations lacking such a penetration enhancer (or, e.g., comprising a penetration enhancer component in a detectably or significantly different amount). In aspects, penetration can be measured or reflect the amount of API(s) in a tissue, such as ocular tissue; can reflect the penetration, dissemination, or, e.g., both penetration and dissemination of the API(s) throughout the tissue (e.g., the average amount throughout an entire tissue, the minimum amount throughout the tissue, or both, such as any of the amounts described herein or the presence of significant or detectable amount(s) of the API(s) as distributed through the tissue); or both.

In aspects, a penetration enhancer component of composition(s) can comprise any ophthalmologically suitable and pharmaceutically acceptable penetration enhancing agent which does not detectably or significantly interfere with the required functionality of any one or more other composition constituents, such as any one or more APIs or one or more excipients. In aspects, the penetration enhancer component can comprise, mostly comprise, generally consist of, substantially consist of, consist essentially of, or consist of a non-ionic penetration enhancer constituent (e.g., polysorbate 80.)

In aspects, exemplary constituent(s) of a penetration enhancer component comprise, e.g., one or more of pharmaceutically acceptable and ophthalmologically suitable polyoxyethylene sorbitan fatty acid esters, tocopheryl polyethylene glycol succinate (TPGS), poly-arginine, polyserine, tromethamine (tris), sesame seed oil or oils having similar compositions and functional characteristics suitable for ophthalmic use, etc. Exemplary polyoxyethylene sorbitan fatty acid esters include but not limited to polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65). In some aspects the polyoxyethylene sorbitan fatty acid ester can be a polyoxyethylene sorbitan oleate/polyoxyethylene sorbitan mono-oleate ester (e.g., polysorbate 80).

In aspects, additional compounds suitable for use in the present invention for increasing the penetration of an API of the composition within ocular tissue also can include quaternary ammonium compound(s), such as, e.g., ophthalmologically suitable quaternary ammonium salt(s). Quaternary ammonium compounds include ammonium salts in which organic radicals have been substituted for all four hydrogens of the original ammonium cation. Such compounds typically have a structure comprising a central nitrogen atom which is joined to four organic radicals and one acid radical. The organic radicals may be alkyl, aryl, or aralkyl, and the nitrogen can be part of a ring system. Examples of such compounds include benzalkonium chloride (e.g., CAS RN: 8001-54-5); benzethonium chloride CAS 121-54-0; cetalkonium chloride (e.g., CAS 122-18-9); cetrimide (e.g., CAS 8044-71-1); cetrimonium bromide (e.g., CAS 57-09-0); cetylpyridinium chloride (e.g., CAS 123-03-5); and stearalkonium chloride (e.g., CAS 122-19-0), provided that typically the quaternary ammonium compound included in any composition provided herein is of a nature and amount that is ophthalmologically safe.

In aspects, a penetration enhancer component can comprise benzalkonium chloride, benzethonium chloride, benzyltrimethylammonium chloride (also known as Triton B or trimethylbenzylammonium hydroxide), or lauryltrimethylammonium chloride (also known as dodecyltrimethylammonium chloride). In some embodiments, the ophthalmic formulations of the invention lack any quaternary ammonium salt.

In aspects, formulations described herein also or alternatively comprise polyoxyl n castor oils (n=35-40) or polyoxyl hydrogenated castor oils, such as for example polyethoxylated castor oils, e.g., polyoxyl 35 castor oil (e.g., Cremophor EL), polyoxyl 40 castor oil (e.g., Marlowet 40, Emulgin RO 40), a polyoxyethylene hydrogenated castor oil (such as, e.g., polyoxyethylene hydrogenated castor oil 10/polyoxyl 10 hydrogenated castor oil, polyoxyethylene hydrogenated castor oil 40/polyoxyl 40 hydrogenated castor oil (Cremophor RH 40), polyoxyethylene hydrogenated castor oil 50/polyoxyl 50 hydrogenated castor oil, and polyoxyethylene hydrogenated castor oil 60/polyoxyl 60 hydrogenated castor oil (Cremophor RH 60)). In aspects, one suitable polyoxyl castor oil is polyoxyl-35-castor oil. The term "cremophor" can be used in this disclosure as a convenient reference to mean any such type of castor oil-related compounds/compositions, groups of two or more (as a class), combinations thereof, and equivalents thereof.

In aspects, a penetration enhancer component can comprise, e.g., a polyoxyethylene polyoxypropylene glycol, e.g., a polyoxyethylene (160) polyoxypropylene (30) glycol (Pluronic F68), a polyoxyethylene (42) polyoxypropylene (67) glycol (Pluronic P123), a polyoxyethylene (54) polyoxypropylene (39) glycol (Pluronic P85); a polyoxyethylene (196) polyoxypropylene (67) glycol (Pluronic F127) and a polyoxyethylene (20) polyoxypropylene (20) glycol (Pluronic L-44); or a polyethyleneglycol fatty acid ester, such as mono-lauric acid polyethyleneglycol, monostearin acid ethylene glycol, monostearin acid polyethyleneglycol, the mono-oleic acid polyethyleneglycol, monostearin acid ethylene glycol, an ethylene glycol distearate, the distearic acid polyethyleneglycol, and diiso stearic-acid polyethyleneglycol. In aspects, a suitable compound is polyoxyl 40 stearate. In other aspects, a penetration enhancer component can comprise tyloxapol. In further aspects, poloxamers (block copolymers) of certain examples above, such as a polyoxyethylene-polyoxypropylene block copolymer (e.g., Pluronic F-68 from BASF) and polaxamines (copolymers of three long chains of ethylene oxide and a single chain of propylene oxide that are used as nonionic surfactants) are compounds suitable for penetration enhancer components of composition(s) herein. In certain aspects, composition(s) lack any constituent characterizable as a poloxamer, e.g., characterizable as a block copolymer (e.g., in certain aspects, composition(s) lack any poloxamer/block copolymer).

As noted above, any ingredient/constituent/excipient described herein typically is present in an effective amount (an amount that alone or in combination with other present agents provides a measurable or significant desired effect, such as penetration enhancement). Any ingredient/constituent described here with respect a component/composition comprising that ingredient/component, again, provides implicit support for corresponding aspects in which the described component mostly comprises, generally consists of, substantially consists of, consists essentially of, or consists only of the recited constituent, type of constituent, etc.

In aspects, composition(s) provided by the invention comprise a penetration enhancer component comprising one or more penetration enhancing agents, wherein the penetration enhancer component is present in the composition in a concentration representing between about 0.05% w/v to about 5% w/v of the composition, such as, e.g., ~0.1% w/v-~5% w/v, ~0.15% w/v-~5% w/v, ~0.2% w/v-~5% w/v, or ~0.25% w/v-~5% w/v, such as ~0.05% w/v-~5% w/v, ~0.05% w/v-~4.5% w/v, ~0.05% w/v-~4% w/v, ~0.05% w/v-~3.5% w/v, ~0.05% w/v-~3% w/v, ~0.05% w/v-~2.5% w/v, ~0.05% w/v-~2% w/v, ~0.05% w/v-~1.5% w/v, or ~0.05% w/v-~1% w/v, such as ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v of the composition or about 0.5% w/v of the composition.

In aspects, composition(s) provided by the invention comprise a penetration enhancer component comprising one or more penetration enhancing agents, wherein the penetration enhancer component is present in the composition in a concentration representing between about 0.005% w/v to about 0.01% w/v of the composition, such as, e.g., ~0.005% w/v-~0.009% w/v, or ~0.005% w/v-~0.008% w/v, such as, e.g., ~0.006% w/v-~0.01% w/v or ~0.007% w/v-~0.01% w/v, as in, e.g., between ~0.006% w/v-~0.009% w/v or ~0.007% w/v-~0.008% w/v of the composition, such as, e.g., ~0.007% w/v of the composition or ~0.0075% w/v of the composition.

In certain aspects, the penetration enhancer component comprises two or more constituents wherein the total concentration/amount of the two or more penetration enhancer component constituents is represented by the concentrations/amounts provided above. For example, In aspects, composition(s) comprise a penetration enhancer component comprising a first penetration enhancer constituent, e.g., polysorbate 80, present in an amount representing ~0.05% w/v-~5% w/v, ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v of the composition or about 0.5% w/v of the composition, and, optionally further, a second penetration enhancer constituent, e.g., benzalkonium chloride, present in an amount representing between about 0.005% w/v to about 0.01% w/v of the composition, such as, e.g., between ~0.006% w/v-~0.009% w/v or ~0.007% w/v-~0.008% w/v of the composition, such as ~0.007% w/v of the composition or ~0.0075% w/v of the composition. In aspects, composition(s) can comprise a penetration enhancer component comprising two or more constituents, such as, e.g., polysorbate 80 and benzalkonium chloride, wherein the penetration component comprises between about 0.05% w/v to about 1.1% w/v, such as between about 0.1% w/v-~0.6% w/v, such as, e.g., between about 0.2% w/v and about 0.6% w/v. This principle can be applied to combinations of any of the specific penetration enhancers described herein, any combination of classes of penetration enhancers, or any mixture thereof, and can include three or more of such compounds/classes of compounds. For example, composition(s) can comprise polysorbate 80, benzalkonium chloride, and, e.g., cremophor, wherein each provide, or the combination thereof provides, or both, detectable or significant penetration enhancement effect(s).

In aspects, the penetration enhancer component comprises/consists essentially of/consists of a single constituent wherein, in aspects, the single constituent is present in an amount represented by any of the recited concentration(s)/amount(s) provided above/herein.

In certain aspects, the penetration enhancer component comprises/consists essentially of (and, of course, by implication, alternatively consists of) two or more polyoxyethylene sorbitan fatty acid esters wherein the total amount of the two or more polyoxyethylene sorbitan fatty acid esters is represented by the concentrations/amounts above.

In aspects, the penetration enhancer component comprises/consists essentially of a single polyoxyethylene sorbitan fatty acid ester, wherein the total amount of the single polyoxyethylene sorbitan fatty acid ester is represented by the concentrations/amounts provided above. In certain aspects, the penetration enhancer component comprises a single constituent, the single constituent being a polyoxyethylene sorbitan fatty acid ester, such as, e.g., polysorbate 80, wherein the single polyoxyethylene sorbitan fatty acid ester, e.g., polysorbate 80, is, e.g., present in an amount representing ~0.05% w/v-~5% w/v, ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v or about 0.5% w/v of the composition.

In aspects, a single constituent of the penetration enhancer component is/consists essentially of polysorbate 80. In certain alternative aspects, the penetration enhancer component comprises a single constituent, wherein the single constituent is a quaternary ammonium compound, e.g., a quaternary ammonium salt, e.g., benzalkonium chloride, e.g., being present in an amount representing between about 0.005% w/v to about 0.01% w/v of the composition, such as, e.g., between ~0.006% w/v-~0.009% w/v or ~0.007% w/v-~0.008% w/v of the composition, such as, e.g., about 0.0075% w/v.

In aspects, one or more constituents of the penetration enhancer component can further provide one or more additional detectable or significant functionalities to a formulation/composition, such as, for example, a detectable or significant solubilization effect (such as is described elsewhere herein), detectable or significant demulcent effect, detectable or significant preservation effect, or any combination thereof. In aspects, one or more constituents of the penetration enhancer component can further provide a preservation/preservative effect. In one aspect, a penetration enhancing agent of the penetration enhancer component also provides a detectable or significant solubilization effect. In one aspect, a penetration enhancing agent of the penetration enhancer component also provides a detectable or significant demulcent effect. In one aspect, a penetration enhancing agent of the penetration enhancer component also provides both a detectable or significant solubilization enhancement effect and a detectable or significant demulcent effect. In one aspect, a penetration enhancing agent of the penetration enhancer component also provides a detectable or significant preservation effect and a detectable or significant solubilization effect. In certain aspects, a penetration enhancing agent of the penetration enhancer component does not provide a solubilization effect, does not provide a preservation effect, does not provide a demulcent effect, or does not provide any combination of such additional effects. That is, in aspects, a penetration enhancer and a solubilizing agent, or a penetration enhancer and a demulcent, or, e.g., a penetration agent and a preservation agent can be differing compounds.

In this and any other ingredient aspect of the invention, the invention also can be characterized as comprising a "means" for providing a recited function, here imparting/providing an effective, detectable, or significant penetration effect to one or more constituents of composition(s) of the invention. In such a respect, any known equivalents of such named agents can also be, e.g., are, incorporated into composition(s) or method(s) of the invention. As with other sections similarly described herein, any of the components of the invention can be, where suitable, described as means (e.g., the above-described penetration enhancement agents/compounds or components can be described as penetration enhancer means (or penetration means) or means for providing effective, detectable, or significant penetration activity/characteristics to one or more constituents of the composition).

Solubilization Component (Solubilizing Agent(s))

In aspects, composition(s) provided by the invention comprise an effective amount of a solubilization component. In aspects, the solubilization component comprises any one or more pharmaceutically acceptable and ophthalmologically suitable constituents (e.g., pharmaceutically acceptable and ophthalmologically suitable compounds) which detectably or significantly increase the solubilization of one or more other constituents of the composition, detectably or significantly increase the period of time that one or more other constituents of the composition remain solubilized, or both. In aspects, the solubilization component can comprise any one or more pharmaceutically acceptable or ophthalmologically suitable compounds capable of demonstrating such an effect. In aspects, a solubilizing agent of a solubilization component can be a surfactant, e.g., demonstrating detectable or significant surfactant properties/functions, e.g., in the context of the associated composition/formulation. In aspects, a solubilization component of a composition (e.g., a surfactant) can comprise any ophthalmologically suitable and pharmaceutically acceptable solubilizing agent (or, e.g., surfactant) which does not detectably or significantly interfere with the required functionality of any one or more other composition constituents.

In aspects, one or more constituents of the solubilization component can further provide one or more additional detectable or significant functionalities, such as, for example, detectable or significant penetration enhancement effect(s) (such as is described elsewhere herein), detectable or significant demulcent effect(s), or both. In one aspect, a solubilizing agent of the solubilizing component also provides detectable or significant penetration enhancement effect(s). In one aspect, a solubilizing agent of the solubilizing component also provides detectable or significant demulcent effect(s). In one aspect, a solubilizing agent of the solubilizing component also provides both detectable or significant penetration enhancement effect and detectable or significant demulcent effect. In certain aspects, a solubilizing agent of the solubilizing component does not provide either a penetration enhancement effect or a demulcent effect. In aspects, a penetration enhancer and a solubilizing agent, or a penetration enhancer and a demulcent, can be differing compounds.

In aspects, exemplary constituents of a solubilization component comprise, e.g., one or more of pharmaceutically acceptable and ophthalmologically suitable polyoxyethylene sorbitan fatty acid esters, tocopheryl polyethylene glycol succinate (TPGS), poly-arginine, polyserine, tromethamine (tris), sesame seed oil or oils having similar compositions and functional characteristics suitable for ophthalmic use, etc. Exemplary polyoxyethylene sorbitan fatty acid esters include but are not limited to polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65). In some aspects the polyoxyethylene sorbitan fatty acid ester can be a polyoxyethylene sorbitan oleate/polyoxyethylene sorbitan mono-oleate ester (e.g., polysorbate 80). In certain aspects, constituents of a solubilization component can comprise, e.g., one or more polyethoxylated castor oils, such as, e.g., polyethoxylated castor oils characterizable as cremophor(s).

In aspects, one or more compounds provided in the section entitled "Penetration Enhancer Component (Penetration Enhancer(s))" also have solubilization properties, and, thus, may be considered a constituent of a solubilization component.

In aspects, composition(s) provided by the invention comprise a solubilization component comprising one or more solubilizing agents, wherein the solubilization component is present in the composition in a concentration representing between about 0.05% w/v to about 5% w/v of the composition, such as, e.g., ~0.1% w/v–~5% w/v, ~0.15% w/v–~5% w/v, ~0.2% w/v–~5% w/v, or ~0.25% w/v–~5% w/v, such as ~0.05% w/v–~5% w/v, ~0.05% w/v–~4.5% w/v, ~0.05% w/v–~4% w/v, ~0.05% w/v–~3.5% w/v, ~0.05% w/v–~3% w/v, ~0.05% w/v–~2.5% w/v, ~0.05% w/v–~2% w/v, ~0.05% w/v–~1.5% w/v, or ~0.05% w/v–~1% w/v, such as ~0.1% w/v–~4% w/v, ~0.15% w/v–~3% w/v, ~0.2% w/v–~2% w/v, ~0.2% w/v–~1% w/v, or ~0.2% w/v–~0.5% w/v, such as for example about 0.1% w/v, about 0.15% w/v, about 0.2% w/v, about 0.25% w/v, about 0.3% w/v, about 0.35% w/v, about 0.4% w/v, about 0.45% w/v, or, e.g., about 0.5% w/v of the composition.

In certain aspects, the solubilization component comprises two or more constituents wherein the total concentration/amount of the two or more solubilization component constituents is represented by the concentrations/amounts provided above. For example, In aspects, composition(s) can comprise a solubilization component comprising a constituent characterizable as a polyethoxylated castor oil and tromethamine. In aspects, composition(s) can comprise, e.g., a polyethoxylated castor oil, e.g., cremophor, in an amount representing between about 0.1% w/v to about 0.5% w/v, such as, e.g., ~0.1% w/v–~0.4% w/v, or ~0.1% w/v–~0.3% w/v, such as, e.g., about 0.25% w/v of the composition. In aspects, composition(s) can comprise, e.g., tromethamine, in an amount representing between about 0.1% w/v to about 0.5% w/v, such as, e.g., ~0.1% w/v–~0.4% w/v, ~0.1% w/v–~0.3% w/v, or ~0.1% w/v–~0.2% w/v, such as, e.g., about 0.185% w/v of the composition. In aspects, composition(s) can comprise a solubilization component comprising at least two solubilization constituents, wherein the total amount of the at least two solubilization constituents represents between about 0.2% w/v to about 0.6% w/v of the composition, such as, e.g., ~0.3% w/v–~0.5% w/v, e.g., ~0.4% w/v or, e.g., ~0.435% w/v of the composition.

In aspects, the solubilization component comprises a single constituent wherein the single constituent is present in an amount represented by concentration(s)/amount(s) provided above. In certain aspects, the solubilization component comprises two or more polyoxyethylene sorbitan fatty acid esters wherein the total amount of the two or more polyoxyethylene sorbitan fatty acid esters is represented by concentration(s)/amount(s) provided above (or alternatively each is present in amount(s) provided above). In aspects, the solubilization component comprises a single polyoxyethylene sorbitan fatty acid ester, in aspects, wherein the total amount of the single polyoxyethylene sorbitan fatty acid ester is represented by concentration(s)/amount(s) provided above. In certain aspects, the solubilization component comprises a single constituent, the single constituent being a polyoxyethylene sorbitan fatty acid ester, such as, e.g., polysorbate 80, wherein, in aspects, the single polyoxyethylene sorbitan fatty acid ester, e.g., polysorbate 80, is present in an amount representing ~0.05% w/v–~5% w/v, ~0.1% w/v–~4% w/v, ~0.15% w/v–~3% w/v, ~0.2% w/v–~2% w/v, ~0.2% w/v–~1% w/v, or ~0.2% w/v–~0.5% w/v, such as for example about 0.25% w/v or about 0.5% w/v of the composition. In aspects, the single constituent of the solubilization component is polysorbate 80.

In this and any other ingredient aspect of the invention, the invention also can be characterized as comprising a "means" for providing a recited function, here imparting/providing an effective, detectable, or significant solubilization effect (e.g., increased solubilization) to one or more constituents of composition(s) of the invention. In such a respect, any known equivalents of such named agents can also be, e.g., are, incorporated into composition(s) or method(s) of the invention. As with other sections similarly described herein, any of the components of the invention can be, where suitable, described as means (e.g., the above-described solubilization agents/compounds or components can be described as solubilization means or means for providing effective, detectable, or significant solubilization activity/characteristics to one or more constituents of the composition.)

Combination Solubilization/Penetration Enhancer Component (Solubilizing Agent(s)/Penetration Enhancer(s))

In certain aspects, a single ingredient of composition(s) provided by the invention can be a constituent of both a penetration enhancer component and a solubilization component. E.g., in aspects, a single ingredient of composition (s) provided by the invention can be characterized as capable of providing both detectable and significant solubilization effect and detectable and significant penetration enhancement effect, such affects being described above in each of the solubilization component and penetration enhancer component sections, respectively. Therefore, in aspects, one or more compounds provided in the section entitled "Penetration Enhancer Component (Penetration Enhancer(s))," having penetration enhancing effect(s), can, in aspects be interpreted as being repeated in the section entitled "Solubilization Component (Solubilizing Agent(s))," having solubilization effect(s). Further, in aspects, one or more compounds provided in the section entitled "Solubilization Component (Solubilizing Agent(s))," having solubilization effect(s), can, in aspects, be interpreted as being repeated in the section entitled "Penetration Enhancer Component (Penetration Enhancer(s))," having penetration enhancing effect(s).

In aspects, one or more ingredients/constituents of composition(s) which provide both a detectable or significant penetration enhancing effect and a detectable or significant solubilization effect can further provide detectable or significant demulcent effect. In certain aspects, an ingredient providing both a detectable or significant penetration enhancing effect and a detectable or significant solubilization effect does not provide detectable or significant demulcent effect. That is, in aspects, a single ingredient providing both penetration enhancer functionality and solubilizing functionality, and a demulcent, can be different/differing compounds.

Exemplary combination solubilizer and the penetration enhancer compound(s) include, e.g., one or more of pharmaceutically acceptable and ophthalmologically suitable polyoxyethylene sorbitan fatty acid esters, tocopheryl polyethylene glycol succinate (TPGS), poly-arginine, polyserine, tromethamine (tris), sesame seed oil or oils having similar compositions and functional characteristics suitable for ophthalmic use, etc. Exemplary polyoxyethylene sorbitan fatty acid esters include but are not limited to polyoxyethylene sorbitan laurate (polysorbate 20), polyoxyethylene sorbitan palmitate (polysorbate 40), a polyoxyethylene sorbitan stearate (polysorbate 60), or a polyoxyethylene sorbitan tri stearate (polysorbate 65). In some aspects the polyoxyethylene sorbitan fatty acid ester can be a polyoxyethylene sorbitan oleate/polyoxyethylene sorbitan mono-oleate ester (e.g., polysorbate 80).

In aspects, composition(s) provided by the invention comprise a single ingredient providing both penetration enhancement and solubilization functionality, wherein the single ingredient is present in the composition in a concentration representing between about 0.05% w/v to about 5% w/v of the composition, such as, e.g., ~0.1% w/v-~5% w/v, ~0.15% w/v-~5% w/v, ~0.2% w/v-~5% w/v, or ~0.25% w/v-~5% w/v, such as ~0.05% w/v-~5% w/v, ~0.05% w/v-~4.5% w/v, ~0.05% w/v-~4% w/v, ~0.05% w/v-~3.5% w/v, ~0.05% w/v-~3% w/v, ~0.05% w/v-~2.5% w/v, ~0.05% w/v-~2% w/v, ~0.05% w/v-~1.5% w/v, or ~0.05% w/v-~1% w/v, such as ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v or about 0.5% w/v of the composition. In certain aspects, the single ingredient is a polyoxyethylene sorbitan fatty acid ester, such as, e.g., polysorbate 80, wherein the single polyoxyethylene sorbitan fatty acid ester, e.g., polysorbate 80, is present in an amount representing ~0.05% w/v-~5% w/v, ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v or about 0.5% w/v of the composition. In aspects, the single constituent of the solubilization component is polysorbate 80. In aspects, the single ingredient, e.g., the single polyoxyethylene sorbitan fatty acid ester, e.g., polysorbate 80, further provides detectable or significant demulcent effect.

In aspects, composition(s) can comprise, e.g., a polyethoxylated castor oil, e.g., a cremophor, in an amount representing between about 0.1% w/v to about 0.5% w/v, such as, e.g., ~0.1% w/v-~0.4% w/v, or ~0.1% w/v-~0.3% w/v, such as, e.g., about 0.25% w/v of the composition, wherein the cremophor provides both detectable or significant solubilization and penetration enhancement activity. In aspects, composition(s) can comprise both a polyethoxylated castor oil, e.g., a cremophor, and a polyoxyethylene sorbitan fatty acid ester, e.g., polysorbate 80, wherein a combination solubilization/penetration enhancer component comprises the two compounds in an amount representing about 0.1% w/v to about 1.8% w/v of the composition, such as, e.g., about 0.1% w/v to about 1% w/v, e.g., about 0.2% w/v to about 0.8% w/v, or, in aspects, e.g., 0.5% w/v to about 1% w/v, about 0.25% w/v, about 0.5% w/v, or, e.g., 0.75% w/v of the composition. In aspects, such a composition can further comprise one or more constituents which provide detectable or significant penetration enhancement activity (e.g., a penetration enhancing agent) or detectable or significant solubilization activity (e.g., a solubilization agent).

Demulcent Component (Demulcent(s))

In aspects, composition(s) provided by the invention comprise an effective amount of a demulcent component. In aspects, the demulcent component comprises any one or more pharmaceutically acceptable and ophthalmologically suitable constituents (e.g., pharmaceutically acceptable and ophthalmologically suitable compounds) which detectably or significantly increase the soothing effect of the composition; detectably or significantly reduce the degree of, or prevent, irritation caused by the composition or caused by one or more other constituents of the composition; detectably or significantly reduce the degree of, or prevent, inflammation caused by the composition or caused by one or more other constituents of the composition; or a combination thereof. In aspects, the demulcent component can comprise any one or more pharmaceutically acceptable or ophthalmologically suitable compounds capable of demonstrating such an effect.

In aspects, one or more constituents of the demulcent component can further provide one or more additional detectable or significant functionalities, such as, for example, detectable or significant penetration enhancement effect (such as is described elsewhere herein), detectable or significant solubilization effect, detectable or significant viscosity enhancing effect/thickening effect, or a combination thereof. That is, in one aspect, a demulcent constituent of the demulcent component also provides detectable or significant penetration enhancement effect. In one aspect, a demulcent constituent of the demulcent component also provides detectable or significant solubilization effect. In one aspect, a demulcent constituent of the demulcent component also provides detectable or significant viscosity enhancing/thickening effect. In one aspect, a demulcent constituent of the demulcent component also provides both detectable or significant penetration enhancement effect and detectable or significant solubilization effect. In one aspect, a demulcent constituent of the demulcent component also provides detectable or significant viscosity enhancing/thickening effect. In certain aspects, a demulcent constituent of the demulcent component does not provide a penetration enhancement effect, a solubilization effect, or a viscosity enhancing/thickening effect. That is, in aspects, a penetration enhancer and a demulcent, a solubilizer and a demulcent, or, e.g., a demulcent and a thickening agent can be differing compounds.

In aspects, a demulcent component of composition(s) can comprise any ophthalmologically suitable and pharmaceutically acceptable demulcent which does not detectably or significantly interfere with the required functionality of any one or more other composition constituents In aspects, exemplary constituents of a demulcent component comprise, e.g., a constituent which also provides detectable or significant penetration enhancement activity, solubilization activity, or both penetration enhancement activity and solubilization activity, such as, e.g., polysorbate 80. In some respects the polyoxyethylene sorbitan fatty acid ester can be a polyoxyethylene sorbitan oleate/polyoxyethylene sorbitan mono-oleate ester (e.g., polysorbate 80). In aspects, exemplary constituents of a demulcent component comprise, e.g., one or more polyols (sugar-like hydrogenated carbohydrates; sometimes referred to as polyhydric alcohols), e.g., polyols in liquid form, such as for example glycerin, polyethylene glycol 300, polyethylene glycol 400, polysorbate 80 as described previously, propylene glycol, etc.

In aspects, exemplary constituents of a demulcent component comprise, e.g., one or more of pharmaceutically acceptable and ophthalmologically suitable cellulose derivatives, such as, e.g., carboxymethylcellulose sodium, hydroxyethyl cellulose, hypromellose, methylcellulose, etc.

In alternative aspects, an exemplary constituent of a demulcent component is, e.g., a high-molecular-weight polysaccharide, e.g., dextran 70. In still further aspects, an exemplary constituent of a demulcent component is, e.g., gelatin. In yet further aspects, an exemplary constituent of a demulcent component is, e.g., polyvinyl alcohol (PVA). In aspects, an exemplary constituent of a demulcent component is, e.g., povidone.

In aspects, composition(s) provided by the invention comprise a demulcent component comprising one or more demulcent constituents, wherein the demulcent component is present in the composition in a concentration representing between about 0.01% w/v to about 5% or about 0.05% w/v to about 5% w/v of the composition, such as, e.g., ~0.1% w/v-~5% w/v, ~0.15% w/v-~5% w/v, ~0.2% w/v-~5% w/v, or ~0.25% w/v-~5% w/v, such as ~0.05% w/v-~5% w/v, ~0.05% w/v-~4.5% w/v, ~0.05% w/v-~4% w/v, ~0.05% w/v-~3.5% w/v, ~0.05% w/v-~3% w/v, ~0.05% w/v-~2.5% w/v, ~0.05% w/v-~2% w/v, ~0.05% w/v-~1.5% w/v, or ~0.05% w/v-~1% w/v, such as ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v of the composition.

In certain aspects, the demulcent component comprises two or more constituents wherein the total concentration/amount of the two or more demulcent component constituents is represented by the concentrations/amounts provided above. In aspects, the demulcent component comprises a single constituent wherein the single constituent is present in an amount represented by the concentrations/amounts provided above. In certain aspects, the demulcent component comprises two or more of polyoxyethylene sorbitan fatty acid esters wherein the total amount of the two or more polyoxyethylene sorbitan fatty acid esters is represented by the concentrations/amounts provided above. In aspects, the demulcent component comprises a single polyoxyethylene sorbitan fatty acid ester, wherein the total amount of the single polyoxyethylene sorbitan fatty acid ester is represented by the concentrations/amounts provided above. In certain aspects, the demulcent component comprises a single constituent, the single constituent being a polyoxyethylene sorbitan fatty acid ester, such as, e.g., polysorbate 80, wherein the single polyoxyethylene sorbitan fatty acid ester, e.g., polysorbate 80, is present in an amount representing ~0.05% w/v-~5% w/v, ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v, about 0.5% w/v, or, e.g., about 0.75% w/v of the composition. In aspects, the single constituent of the solubilization component is polysorbate 80.

In certain alternative aspects, composition(s) comprise a demulcent component wherein the demulcent component comprises a cellulose derivative in an amount of between about 0.2% w/v-about 2.5% w/v of a composition, typically in an amount of less than or equal to about 1% w/v. In aspects, composition(s) comprise a demulcent component wherein the demulcent component comprises dextran 70 in an amount of about 0.1% w/v of a composition. In aspects, a demulcent component comprising dextran 70 further comprises one or more additional demulcent constituents. In aspects, composition(s) comprise a demulcent component wherein the demulcent component comprises gelatin in an amount of about 0.01% w/v of a composition. In aspects, composition(s) comprise a demulcent component wherein the demulcent component comprises polyvinyl alcohol (PVA) in an amount of about 0.1% w/v-about 4% w/v of a composition. In aspects, composition(s) comprise a demulcent component wherein the demulcent component comprises povidone in an amount of about 0.1% w/v-about 2% w/v of a composition.

In this and any other ingredient aspect of the invention, the invention also can be characterized as comprising a "means" for providing a recited function, here imparting/providing an effective, detectable, or significant demulcent effect (e.g., soothing, or reduced irritation effect) to one or more constituents of composition(s) of the invention. In such a respect, any known equivalents of such named agents can also be, e.g., are, incorporated into composition(s) or method(s) of the invention. As with other sections similarly described herein, any of the components of the invention can be, where suitable, described as means (e.g., the above-described demulcent agents/compounds or components can be described as demulcent means or means for providing effective, detectable, or significant demulcent activity/characteristics to one or more constituents of the composition.)

In aspects, treatment of an ophthalmic condition/ocular condition with composition(s) provided by the invention comprising a demulcent component, e.g., comprising polysorbate-80 or one or more other demulcents of a demulcent component, detectably or significantly reduce or prevent inflammation, irritation, or both, over (as compared to) similar compositions (compositions comprising about the same or the same amount of most, generally all, substantially all, or all of the otherwise same ingredients), not comprising a demulcent.

Buffer Component (Buffer(s))

In aspects, composition(s) provided by the invention comprise an effective amount of a buffer component. In aspects, a buffer component can be referred to as a reduced buffer content component. In aspects, the presence of a buffer component, e.g., a reduced buffer component, yields a reduced buffer content composition. Herein, reference to a buffer component should be interpreted as, in aspects, also incorporating reference to the buffer component as a reduced buffer content component. In aspects, the buffer component comprises any one or more pharmaceutically acceptable and ophthalmologically suitable buffer system(s)/constituent(s) (e.g., pharmaceutically acceptable and ophthalmologically suitable system(s)/compound(s)/constituent(s)) which provide detectable or significant pH buffering effect, such that, e.g., the composition(s) maintain a pH within the pH ranges described herein for extended periods of time (e.g., a pH of between about 3-about 8.5, e.g., ~3-~7.5, ~3-~7, ~3-~6.5, ~3-~6, ~3-~5.5, ~3-~5, ~3-~4.5, e.g., ~3.5-~8.5, ~4-~8.5, ~4.5-~8.5, ~5-~8.5, ~5.5-~8.5, ~6-~8.5, ~6.5-~8.5, ~7-~8.5, or, e.g., ~7.5-~8.5, when stored under conditions comprising a temperature of between about 15° C. and about 27° C. (e.g., between about 15° C. and about 27° C. and about 60% relative humidity); when stored at about 25° C.±2° C., e.g., 25° C.±2° C. and about 40%±5% relative humidity (e.g., for long term storage); when stored at about 30° C.±2° C. and about 35%±5% relative humidity (e.g., for long term storage); when stored at about 30° C.±2° C. and about 65%±5% relative humidity; about 40° C.±2° C. and not more than ("NMT") about 25% relative humidity (e.g., for accelerated storage); or when stored at a combination of any or all such conditions for a period of at least about 1 month, e.g., ≥~3, ≥~6, ≥~9, ≥~12, ≥~18, ≥~24, or, e.g., at least about 36 months. In certain aspects, composition(s) comprise a buffer component comprising a single buffer system (or, e.g., a single compound, providing detectable or significant buffering capacity to the composition(s)). In certain aspects, composition(s) lack a buffer component.

In aspects, composition(s) provided by the invention comprise a buffer component characterizable as a reduced buffer content component. In aspects, "reduced buffer content", in reference to a component or a composition, refers to the presence of an amount of a buffer component which is detectably or significantly different, more specifically, is detectably or significantly less than (in terms of concentration) that of comparable reference product(s). In aspects, a reference product is a product can be a composition comprising at least mostly the same, at least generally the same, at least essentially the same, essentially the same, at least substantially the same, or the same active pharmaceutical ingredient(s) delivered by topical application. In aspects, a reference product can be a composition comprising at least mostly the same, at least generally the same, at least essentially the same, essentially the same, at least substantially the same, or the same active pharmaceutical ingredient(s) delivered by topical application, present in at least essentially the same, essentially the same, at least substantially the same, or the same amount(s). In aspects, a reference product can be a composition sharing one or more excipient(s). In aspects, a reference product can be a composition sharing one or more excipient(s) in the same amount(s). In aspects, a reference product can be a composition comprising (a) at least mostly the same, at least generally the same, at least essentially the same, essentially the same, at least substantially the same, or the same active pharmaceutical ingredient(s), (b) at least mostly the same, at least generally the same, at least essentially the same, essentially the same, at least substantially the same, or the same active pharmaceutical ingredient(s) present in at least essentially the same, essentially the same, at least substantially the same, or the same amount(s); (c) one or more of the same excipient(s); (d) one or more of the same excipient(s) in at least mostly the same, at least generally the same, at least essentially the same, essentially the same, at least substantially the same, or the same amount(s); or (e) any combination thereof, administered by topical application. In aspects, a reference composition can be a composition having demonstrated bioequivalence to any such composition(s) described herein, wherein bioequivalence is demonstrated in an appropriately conducted study acceptable by a recognized regulatory authority, such as the United States Food and Drug Administration.

In aspects, a buffer component of a composition can comprise any ophthalmologically suitable and pharmaceutically acceptable buffer which does not detectably or significantly interfere with the required functionality of any one or more other composition constituents. In aspects, exemplary constituents of a buffer component comprise, e.g., one or more buffer systems, e.g., one or more of a phosphate buffer (e.g., sodium phosphate), citrate buffer (e.g., sodium citrate compound, e.g., sodium citrate dihydrate), tris buffer, carbonate buffer (e.g., ammonium carbonate, sodium carbonate or sodium bicarbonate), succinate buffer, maleate buffer, a borate buffer, combinations of sodium hydroxide, potassium hydroxide, hydrochloric acid, lactic acid, phosphoric acid, sulfuric acid, etc. or combinations thereof. In specific aspects, composition(s) provided by the invention do not comprise a borate buffer, e.g., composition(s) do not comprise boric acid or sodium borate. In other specific aspects, composition(s) provided by the invention do not comprise a citrate buffer, e.g., composition(s) do not comprise a sodium citrate compound, e.g., sodium citrate dihydrate. In yet other specific aspects, composition(s) provided by the invention do not comprise a citrate buffer or a borate buffer, e.g., composition(s) provided by the invention do not comprise boric acid or sodium borate or a sodium citrate compound, e.g., sodium citrate dihydrate. As noted above disclosures of aspects based on "not comprising" an element provide simultaneous support for having very low amounts of an element, lacking an effective amount of an element, or lacking any detectable amount of such an element, etc.

In aspects, composition(s) comprise two or more active pharmaceutical ingredients and an amount of buffer component which is detectably or significantly less than the amount of buffer component present in a reference product, such a reference product being a composition approved under the United States Food and Drug Administration (U.S. FDA) NDA number 21408 (VUITY); notably wherein a product approved under U.S. FDA NDA number 21408 comprises a single API. In aspects, composition(s) comprise a buffer component which represents an amount which is at least about 2%, ≥~5%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, or, e.g., even ≥~95% less than a reference product, such as, e.g., a composition approved under U.S. FDA number 21408. In aspects, composition(s) comprise a buffer component which represents an amount which is at least about 2%, ≥~5%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, or, e.g., even ≥~95% less than a reference product which is a product comprising at least two APIs but which is otherwise at least generally the same, at least substantially the same, at least essentially the same, or is the same as a composition approved under U.S. FDA number 21408 (in, e.g., its constituents, amounts of constituents, or both).

In aspects, composition(s) comprise a buffer component which provides detectably or significantly different buffering capacity than that of a reference product, such as, e.g., a composition approved under U.S. FDA number 21408 or a product which is at least generally the same, at least substantially the same, at least essentially the same, or is the same as a composition approved under U.S. FDA number 21408 in, e.g., its constituents, amounts of constituents, or both. In aspects, composition(s) comprise a buffer component which provides a buffering capacity which is no more than about 95% of that of a reference product, such as a buffering capacity which is less than or equal to about 90%, ≤~85%, ≤~80%, ≤~75%, ≤~70%, ≤~65%, ≤~60%, ≤~55%, ≤~50%, ≤~45%, ≤~40%, ≤~35%, ≤~30%, ≤~25%, ≤~20%, ≤~15%, ≤~10%, or no more than, e.g., less than about 5% of the buffering capacity of a reference product. In aspects, composition(s) comprise a buffer component which provides a detectably or significantly reduced buffering capacity compared to the buffering capacity of a reference product, such as, e.g., a composition approved under U.S. FDA number 21408 or a product which is at least generally the same, at least substantially the same, at least essentially the same, or is the same as a composition approved under U.S. FDA number 21408 in, e.g., its constituents, amounts of constituents, or both.

In aspects, composition(s) can comprise a buffer component having the characteristic(s) described in any of the preceding paragraphs wherein the characteristic(s) is/are formed by a range of any of the specific cited values (e.g., a buffering capacity that is between about 30% and about 80% of a reference product). In aspects, a buffer having a pKa in a certain range (e.g., any one or more buffers or any buffer element(s)/compounds having a pKa of ~3-5, ~3-~4, or about 3) is reduced in a composition of the invention as compared to a reference product, such as a reference product described in the preceding paragraphs, by at least about 33%, at least about 50%, at least about 65%, ≥~75%, ≥~85%, ≥~90%, ≥~95%, or ~100%.

According to certain aspects, the invention provides a reduced buffering capacity composition(s) which provide/provides statistically significantly similar stability as a reference product, such as, e.g., a marketed composition, such as, e.g., a composition approved under U.S. FDA number 21408 or a product at least generally the same, at least substantially the same, at least essentially the same, or the same as a composition approved under U.S. FDA number 21048 in terms of its constituents, amount of constituent(s), or both, while comprising at least two active pharmaceutical ingredients and further while concurrently providing statistically significantly similar stability to such a reference product comprising a single API.

In aspects, composition(s) comprise an effective amount of a buffer component characterizable as a "uniform" buffer component. In aspects, a uniform buffer component is a buffer component wherein at least about 99% of the buffer component, such as ≥~99.25%, ≥~99.5%, or ≥~99.75% (or about 100%) of the buffer component, is composed of a single type of buffer (e.g., a single compound/constituent/agent). In aspects, a buffer component comprises a single buffer compound (single buffer constituent or single buffer agent).

In certain aspects, composition(s) comprise a buffer component (also referred to herein as a buffering component) in an amount such that the concentration of an active pharmaceutical ingredient in the composition, such as, e.g., a pilocarpine compound, or, e.g., the concentration of the total amount of active pharmaceutical ingredient in the composition, e.g., the amount of a pilocarpine compound and a brimonidine compound together, is at least about 1.5, at least about 2, at least about 2.5, or, e.g., at least about 3 times as high as, such as is at least about 3.5 times or, e.g., is at least about 4 times, at least about 4.5, at least about 5, at least about 5.5, or, e.g., is at least about 6 time higher than the concentration of the buffer component present in the composition. In certain aspects, composition(s) comprise a buffer/buffering component in an amount such that the concentration of one (e.g., a single, as in, e.g., a pilocarpine compound) or all (e.g., in total, as in, e.g., both a pilocarpine compound and a brimonidine compound) active pharmaceutical ingredient(s) in the composition is at least about 3.5, at least about 4, at least about 4.5, or, e.g., is at least about 5 times as high as, e.g., is at least 5 times higher than, the concentration of the buffer component present in the composition. In certain aspects, composition(s) comprise a buffer/buffering component in an amount such that the concentration of active pharmaceutical ingredient(s) in the composition is at least about 6, ≥~7, ≥~8, ≥~9, ≥~10, ≥~11, ≥~12, ≥~13, ≥~14, ≥~15, ≥~16, ≥~17, ≥~18, ≥~19, ≥~20, ≥~21, ≥~22, ≥~23, ≥~24, ≥~25, times as high as, e.g., is at least about 25 times higher than, the concentration of the buffer component present in the composition.

In certain aspects, composition(s) comprise a buffer/buffering component in an amount such that the concentration of active pharmaceutical ingredient(s) (e.g., one or, e.g., all API(s)) in the composition is at least about 26, ≥~27, ≥~28, ≥~29, ≥~30, ≥~31, ≥~32, ≥~33, ≥~34, ≥~35, ≥~36, ≥~37, ≥~38, ≥~39, or ≥~40, time as high as, e.g., is at least about 40 times higher than, the concentration of the buffer component present in the composition.

In certain aspects, composition(s) comprise a buffer/buffering component in an amount such that the concentration of active pharmaceutical ingredient(s) (e.g., one or, e.g., all API(s)) in the composition is at least about 41, ≥~42, ≥~43, ≥~44, ≥~45, ≥~46, ≥~47, ≥~48, ≥~49, or ≥~50, as times high as, e.g., is at least about 50 times higher than, the concentration of the buffer component present in the composition.

In certain aspects, composition(s) comprise a buffer/buffering component in an amount such that the concentration of active pharmaceutical ingredient(s) (e.g., one or, e.g., all API(s)) in the composition is at least about 51, ≥~52, ≥~53, ≥~54, ≥~55, ≥~56, ≥~57, ≥~58, ≥~59, or ≥~60, time as high as, e.g., is at least about 60 times higher than, the concentration of the buffer component present in the composition.

In certain aspects, composition(s) comprise a buffer/buffering component in an amount such that the concentration of active pharmaceutical ingredient(s) (e.g., one or, e.g., all API(s)) in the composition is less than about 5 times more than, less than about 4 times more than, less than about 3 times more than, or, e.g., is less than about 2.5 times, less than about 2 times, less than about 1.8 times, less than about 1.7 times, or, e.g., less than about 1.6 times more than, the concentration of the buffer component present in the composition. In certain specific aspects, composition(s) can comprise an amount of pilocarpine which is at least about 1.5 times greater than, but no more than (e.g., less than), about 4, about 3, or about no more than about 2.5 times as high as, the amount of buffer/buffering component in the composition.

In aspects, as is stated elsewhere herein, a buffer component can be, in aspects, characterizable as a uniform buffer component. In aspects, as is stated elsewhere herein, a buffer component is characterizable as a reduced buffer content buffer component (e.g., rendering reduced buffer content composition(s)).

In aspects, a buffer component can be selected (or characterized by), at least in part, to aid in or adding in (detectably or significantly promoting) the establishment of a target tonicity. In aspects, a buffer component can be selected or characterized by, at least in part, based upon the presence of one or more other constituents of the composition and, e.g., their concentration(s). For example, in aspects, sodium borate may be selected as a buffer as opposed to boric acid for composition(s) where, e.g., the presence of sodium borate confers a tonicity to the composition which is detectably or significantly different than that of boric acid, and which aids in the establishment of a target tonicity for the composition (e.g., an osmolality of between about 200 mOsm/Kg and about 500 mOsm/Kg, or, e.g., between about 200 mOsm/Kg and about 400 mOsm/Kg, such as, e.g., ~250-~400 mOsm/Kg, ~260-~390 mOsm/Kg, ~270-~380 mOsm/Kg, or, e.g., ~280-~370 mOsm/Kg, for example ~210-~390 mOsm/Kg, ~220 ~380 mOsm/Kg, ~230-~370 mOsm/Kg, ~240-~360 mOsm/Kg, or, e.g., ~250-~350 mOsm/Kg, such as ~270 mOsm/Kg-~330 mOsm/Kg).

In aspects, one or more constituents of the buffer component can further provide one or more additional detectable or significant functionalities, such as, for example, detectable or significant pH adjusting effects.

In aspects, composition(s) comprise a buffer component present in an amount no greater than 1% w/v of a composition, such as, e.g., in an amount no greater than about 0.95% w/v, ≤~0.9% w/v, ≤~0.85% w/v, ≤~0.8% w/v, or, e.g., ≤~0.75% w/v of a composition.

In aspects, composition(s) comprise a buffer component present in an amount no greater than about 0.7% w/v of a composition, such as, e.g., in an amount no greater than about 0.65% w/v, ≤~0.5% w/v, ≤~0.55% w/v, ≤~0.5% w/v, ≤~0.45% w/v, ≤~0.4% w/v, ≤~0.35% w/v, ≤~0.3% w/v, ≤~0.25% w/v, ≤~0.2% w/v, ≤~0.15% w/v, or, e.g., ≤~0.1% w/v of a composition.

In aspects, composition(s) comprise a buffer component present in an amount no greater than about 0.095% w/v of a composition, such as, e.g., in an amount no greater than about 0.09% w/v. ≤~0.085% w/v, ≤~0.08% w/v, ≤~0.075% w/v, ≤~0.07% w/v, ≤~0.065% w/v, ≤~0.06% w/v, ≤~0.055% w/v, ≤~0.05% w/v, ≤~0.045% w/v, ≤~0.04% w/v, ≤~0.035% w/v, or ≤~0.03% w/v, such as ≤~0.025% w/v of a composition.

In aspects, composition(s) provided by the invention comprise a buffer component comprising one or more buffering agents, wherein the buffer component is present in the composition in a concentration representing between about 0.005% w/v to about 1.5% w/v of the composition, such as, e.g., ~0.01% w/v-~0.5% w/v, ~0.015% w/v-~0.5% w/v, or ~0.02% w/v-~0.5% w/v, e.g., ~0.01% w/v-~0.4% w/v, ~0.01% w/v-~0.3% w/v, ~0.01% w/v-~0.2% w/v, ~0.01% w/v-~0.1% w/v, or ~0.01% w/v-~0.05% w/v. In one exemplary aspect, composition(s) comprise sodium citrate dihydrate in an amount of between about ~0.005% w/v-~0.09%, e.g., between about 0.01% w/v to about 0.05% w/v, such as about 0.02% w/v to about 0.03% w/v, e.g., about 0.022% w/v of the composition. In another exemplary aspect, composition(s) comprise sodium citrate dihydrate in an amount of between about 0.005% w/v to about 0.4% w/v, such as, e.g., ~0.005% w/v-~0.35% w/v, ~0.005% w/v-~0.3% w/v, or ~0.005% w/v-~0.25% w/v, such as ~0.05% w/v-~0.4% w/v, ~0.1% w/v-~0.4% w/v, ~0.15% w/v-~0.4% w/v, or, e.g., ~0.2% w/v-~0.4% w/v, such as, e.g., about 0.2% w/v of the composition.

According to certain aspects, composition(s) provided by the invention comprise a buffer component present in the composition in an amount representing significantly greater than 0.015% w/v of the composition(s). In aspects, composition(s) comprise a buffer component present in a concentration representing at least about 0.016% w/v, such as, e.g., an amount between about 0.017% w/v, 0.018% w/v, 0.019% w/v, 0.02% w/v, 0.021% w/v, 0.022% w/v, 0.023% w/v, 0.024% w/v, or 0.025% w/v and about 0.09% w/v. In one specific example, composition(s) comprise an amount of sodium citrate dihydrate which is significantly greater than 0.015% w/v.

In aspects, composition(s) provided by the invention comprise a buffer component comprising one or more buffering agents, wherein the buffer component is present in the composition in a concentration representing between about 0.01% w/v to about 1.5% w/v of the composition, such as, e.g., ~0.5% w/v-~5% w/v, ~0.6% w/v-~5% w/v, ~0.7% w/v-~5% w/v, ~0.8% w/v-~5% w/v, ~0.9% w/v-~5% w/v, or ~1% w/v-~5% w/v, e.g., ~0.5% w/v-~4.5% w/v, ~0.5% w/v-~4% w/v, ~0.5% w/v-~3.5% w/v, ~0.5% w/v-~3% w/v, ~0.5% w/v-~2.5% w/v, ~0.5% w/v-~2% w/v, ~0.5% w/v-~1.5% w/v, or ~0.5% w/v-~1% w/v. In one exemplary aspect, composition(s) comprise boric acid or sodium borate in an amount of between about 0.5% w/v-about 1.5% w/v, such as between ~0.75% w/v-~1.25% w/v, e.g., about 1% w/v of the composition. In another exemplary aspect, composition(s) comprise sodium borate in an amount of between about 0.5% w/v-about 1.5% w/v, such as between ~0.75% w/v-~1.25% w/v, e.g., about 1% w/v of the composition. In aspects, a first composition comprising an amount of pilocarpine compound, an amount of brimonidine compound, an amount of a preservation agent, optionally an amount of a penetration enhancer (other than e.g., a preservation agent which may provide detectable or significant penetration enhancement activity/effect), and an amount of a tonicity agent and having a pH of less than 6 comprises a buffer component comprising boric acid, while a second composition comprising the same amount of each of the pilocarpine compound, brimonidine compound, preservation agent, optional penetration enhancer, and tonicity agent having a pH of greater than 6 comprises a buffer component comprising sodium borate. In aspects, the first and second exemplary composition(s) comprise at least generally the same, at least substantially the same, at least essentially the same, essentially the same, or the same osmolality.

In certain specific aspects, composition(s) comprise a buffer component comprising a single buffer system, e.g., a single buffer compound/constituent. In certain specific aspects, no more than a single buffer constituent is present in the composition(s). In aspects, composition(s) can comprise a buffer component wherein the buffer component is a uniform buffer component as described herein, and at the at least primary (e.g., representing at least about 99% of the buffer component) buffer compound present in the buffer component has a pKa of less than about 5, such as, less than, e.g., no greater than, about 4.9, ≤~4.8, ≤~4.7, ≤~4.6, ≤~4.5, ≤~4.4, ≤~4.3, ≤~4.2, or ≤~4.1. In other aspects, composition(s) can comprise a buffer component wherein the buffer component is a uniform buffer component, and the at least primary buffer compound present in the buffer component has a pKa of less than, e.g., no greater than, about 4, such as less than about 3.9, ≤~3.8, ≤~3.7, ≤~3.6, ≤~3.5, ≤~3.4, ≤~3.3, ≤~3.2, or, e.g., ≤~3.1. In still other aspects, composition(s) can comprise a buffer component wherein the buffer component is a uniform buffer component, and the at least primary buffer compound present in the buffer component has a pKa of at least about 7.5, such as at least about 7.6, ≥~7.7, ≥~7.8, ≥~7.9, or ≥~8, such as at least about 8.1, ≥~8.2, ≥~8.3, ≥~8.4, ≥~8.5, ≥~8.6, ≥~8.7, ≥~8.8, or, e.g., ≥~8.9. In still other aspects, composition(s) can comprise a buffer component wherein the buffer component is a uniform buffer component, and the at least primary buffer compound present in the buffer component has a pKa of at least about 9, such as at least about 9.1, ≥~9.2, ≥~9.3, ≥~9.4, or, e.g., ≥~9.5.

In certain aspects, composition(s) can comprise a buffer component wherein the buffer component is a uniform buffer component, and the at least primary buffer compound present in the buffer component is a compound having at least two different ionizable functional groups, such as, e.g., 2 or 3 or more ionizable functional groups. In aspects, composition(s) comprise a buffer component, e.g., a uniform buffer component, comprising a compound having three different ionizable functional groups. In aspects, a compound having multiple ionizable functional groups can comprise pKa values of between about zero and about 12.

In aspects, a buffer compound of a buffer component, or, e.g., a compound having multiple ionizable functional groups, can comprise at least one pKa value of less than zero; between about 1 and about 3; about 3 and about 5; about 3 and about 8; about 8 and about 13; about 14 or higher; or, e.g., combinations of any or all thereof.

In aspects, a buffer compound of a buffer component, or, e.g., a compound having multiple ionizable functional groups, can comprise at least one pKa value of less than zero.

In aspects, a buffer compound of a buffer component, or, e.g., a compound having multiple ionizable functional groups, can comprise at least one pKa value of ~0-~12, ~0-~11, ~0-~10, ~0-~9, ~0-~8, ~0-~7, ~0-~6, ~0-~5, ~0-~4, ~0-~3, ~0-~2, or, e.g., ~0-~1.

In aspects, a buffer compound of a buffer component, or, e.g., a compound having multiple ionizable functional groups, can comprise at least one pKa value of ~1-~12, ~1-~11, ~1-~10, ~1-~9, ~1-~8, ~1-~7, ~1-~6, ~1-~5, ~1-~4, ~1-~3, or, e.g., ~1-~2.

In aspects, a buffer compound of a buffer component, or, e.g., a compound having multiple ionizable functional groups, can comprise at least one pKa value of ~2-~12, ~2-~11, ~2-~10, ~2-~9, ~2-~8, ~2-~7, ~2-~6, ~2-~5, ~2-~4, or, e.g., ~2-~3.

In aspects, a buffer compound of a buffer component, or, e.g., a compound having multiple ionizable functional groups, can comprise at least one pKa value of ~3-~12, ~3-~11, ~3-~10, ~3-~9, ~3-~8, ~3-~7, ~3-~6, ~3-~5, or, e.g., ~3-~4.

In aspects, a buffer compound of a buffer component, or, e.g., a compound having multiple ionizable functional groups, can comprise at least one pKa value of ~4-~12, ~4-~11, ~4-~10, ~4-~9, ~4-~8, ~4-~7, ~4-~6, or, e.g., ~4-~5.

In aspects, a buffer compound of a buffer component, or, e.g., a compound having multiple ionizable functional groups, can comprise at least one pKa value of ~5-~12, ~5-~11, ~5-~10, ~5-~9, ~5-~8, ~5-~7, or, e.g., ~5-~6.

In aspects, a buffer compound of a buffer component, or, e.g., a compound having multiple ionizable functional groups, can comprise at least one pKa value of ~6-~12, ~6-~11, ~6-~10, ~6-~9, ~6-~8, or, e.g., ~6-~7.

In aspects, a buffer compound of a buffer component, or, e.g., a compound having multiple ionizable functional groups, can comprise at least one pKa value of ~7-~12, ~7-~11, ~7-~10, ~7-~9, or, e.g., ~7-~8.

In aspects, a buffer compound of a buffer component, or, e.g., a compound having multiple ionizable functional groups, can comprise at least one pKa value of ~8-~12, ~8-~11, ~8-~10, or, e.g., ~8-~9.

In aspects, a buffer compound of a buffer component, or, e.g., a compound having multiple ionizable functional groups, can comprise at least one pKa value of ~9-~12, ~9-~11, or, e.g., ~9-~10.

In aspects, a buffer compound of a buffer component, or, e.g., a compound having multiple ionizable functional groups, can comprise at least one pKa value of ~10-~12, or, e.g., ~10-~11.

In aspects, a buffer compound of a buffer component, or, e.g., a compound having multiple ionizable functional groups, can comprise at least one pKa value of ~11-~12.

In aspects, a buffer compound of a buffer component, or, e.g., a compound having multiple ionizable functional groups, can comprise at least one pKa value of greater than 12.

In aspects, composition(s) of the invention are characterized by having a single buffer compound/element/agent having a PKa as indicated in any of the preceding ~20 paragraphs relating to pKa characteristics. In aspects, composition(s) exclude (are free of) buffering compounds having different pKa characteristics from a single buffering agent in the composition (e.g., in aspects the composition(s) comprising only a buffering agent with a PKa of ~8-9 or ~3 or ~4.5).

In aspects, a single buffer constituent of a composition can be any single buffer constituent described herein, such as boric acid, sodium borate, sodium citrate dihydrate, or, e.g., acetate or phosphate. In aspects, such single buffer component constituents can be present in the amounts described herein. In aspects, composition(s) do not comprise a buffer component. In aspects, composition(s) provided by the invention do not comprise any constituent characterizable as a buffer.

In one aspect, composition(s) comprise a buffer component, wherein the buffer component does not comprise a borate buffer (e.g., does not comprise boric acid or sodium borate) and, further, does not comprise a citrate buffer (e.g., does not comprise sodium citrate, e.g., does not comprise sodium citrate dihydrate). In aspects, such a buffer component which does not comprise a borate or citrate buffer can comprise one or more other buffer component constituents, such as, for example, an acetate buffer, a phosphate buffer, or both, in an amount described in this section. In aspects, such a buffer component which does not comprise a borate or a citrate buffer can comprise a buffer component comprising a single buffer component constituent, such as an acetate buffer or a phosphate buffer. In aspects, composition(s) comprise a buffer component, wherein the buffer component comprises a single buffer component constituent, and further wherein the single buffer component constituent is not a borate buffer or a citrate buffer, and where, in aspects, the single buffer component/constituent is present in an amount described in this section. In aspects, the single buffer constituent is an acetate buffer. In aspects, the single buffer constituent is an acetate buffer in an amount described in this section. In aspects, the single buffer constituent is a phosphate buffer. In aspects, the single buffer constituent is a phosphate buffer in an amount described in this section.

In this and any other ingredient aspect of the invention, the invention also can be characterized as comprising a "means" for providing a recited function, here imparting/providing an effective, detectable, or significant pH buffering effect. In such a respect, any known equivalents of such named agents can also be, e.g., are, incorporated into composition(s) or method(s) of the invention. As with other sections similarly described herein, any of the components of the invention can be, where suitable, described as means (e.g., the above-described buffering agents/compounds or components can be described as buffering means/buffer means or means for providing effective, detectable, or significant pH buffering activity/characteristics to the composition.)

Tonicity Component (Tonicity Agent(s))

In aspects, composition(s) provided by the invention comprise an effective amount of a tonicity component. In aspects, the tonicity component comprises any one or more pharmaceutically acceptable and ophthalmologically suitable constituents (e.g., pharmaceutically acceptable and ophthalmologically suitable compounds) which detectably or significantly modify or aid in the establishment of the tonicity of the composition. In aspects, the tonicity component can comprise any one or more pharmaceutically acceptable or ophthalmologically suitable compounds capable of demonstrating such an effect. In aspects, the tonicity agents/constituents of the tonicity component are suitable for establishing composition(s) having a targeted isotonic range, e.g., an osmolality of about 171 mOsm/Kg-about 1711 mOsm/K, such as, e.g., about 200 mOsm/Kg-about 1000 mOsm/K, about 250 mOsm/Kg-about 500 mOsm/Kg, or, e.g., about 280 mOsm/Kg to about 370 mOsm/Kg.

In aspects, a tonicity component of a composition can comprise any ophthalmologically suitable and pharmaceutically acceptable tonicity agent which does not detectably or significantly interfere with the required functionality of any one or more other composition constituents. In aspects, exemplary constituents of a tonicity component comprise, e.g., any one or more pharmaceutically acceptable and ophthalmologically suitable tonicity agents including, e.g., sodium chloride, potassium chloride, dextrose, glucose, glycerol, mannitol, other electrolytes, etc. In certain aspects, composition(s) comprise a tonicity component wherein the tonicity component does not comprise any constituent which may detectably or significantly promote microbial growth. In aspects, a tonicity component does not comprise a free monosaccharide. In aspects, a tonicity component does not comprise a free monosaccharide not characterizable as a sugar alcohol. In aspects, a tonicity component does not comprise any constituent characterizable as a glucose compound, e.g., glucose or D-glucose (dextrose).

In aspects, composition(s) provided by the invention comprise a tonicity component comprising one or more tonicity agents, wherein the tonicity component is present in the composition in a concentration representing between about 0.005% w/v to about 1% w/v of the composition, such as, e.g., ~0.005% w/v-~0.95% w/v, ~0.005% w/v-~0.9% w/v, ~0.005% w/v-~0.85% w/v, or ~0.005% w/v-~0.8% w/v, such as, e.g., ~0.05% w/v-~1% w/v, ~0.1% w/v-~1% w/v, ~0.2% w/v-~1% w/v, ~0.3% w/v-~1% w/v, ~0.4% w/v-~1% w/v, ~0.5% w/v-~1% w/v, ~0.6% w/v-~1% w/v, ~0.7% w/v-~1% w/v, or ~0.8% w/v-~1% w/v. In aspects, the tonicity component is present in composition(s) provided by the invention in an amount of between about 0.5% w/v and about 1% w/v of the composition.

In certain aspects, composition(s) provided by the invention comprise a tonicity component comprising one or more tonicity agents, wherein the tonicity component is present in the composition in a concentration representing between about 0.005% w/v to about 0.1% w/v of the composition, such as, e.g., ~0.005% w/v-~0.095% w/v, ~0.005% w/v-~0.09% w/v, ~0.005% w/v-~0.085% w/v, or ~0.005% w/v-~0.08% w/v, e.g., ~0.01% w/v-~0.1% w/v, ~0.02% w/v-~0.1% w/v, ~0.03% w/v-~0.1% w/v, ~0.04% w/v-~0.1% w/v, ~0.05% w/v-~0.1% w/v, ~0.06% w/v-~0.1% w/v, ~0.07% w/v-~0.1% w/v, or ~0.08% w/v-~0.1% w/v of the composition, such as, e.g., about 0.01% w/v or about 0.08% w/v of the composition.

In certain aspects, composition(s) provided by the invention comprise a tonicity component comprising one or more tonicity agents, wherein the tonicity component is present in the composition in a concentration representing between about 2% w/v to about 6% w/v of the composition, such as, e.g., ~2.5% w/v-~6% w/v, ~3% w/v-~6% w/v, ~3.5% w/v-~6% w/v, ~4% w/v-~6% w/v, or ~4.5% w/v-~6% w/v, e.g., ~2% w/v-~5.5% w/v, or ~2% w/v-~4.5% w/v, such as, e.g., ~2.5% w/v-~5.5% w/v, ~3% w/v-~5% w/v, ~3.5% w/v-~5% w/v, or ~4% w/v-~5% w/v, such as, e.g., ~4.5% w/v.

In certain aspects, composition(s) described herein comprise a tonicity component comprising on e or more tonicity agent(s), e.g., sodium chloride, in an amount representing less than about 0.5% w/v of the composition, such as, e.g., ≤~0.48% w/v, ≤~0.46% w/v, ≤~0.44% w/v, ≤~0.42% w/v, ≤~0.4% w/v, ≤~0.38% w/v, ≤~0.36% w/v, ≤~0.34% w/v, ≤~0.32% w/v, or, e.g., ≤~0.3% w/v of the composition. In certain aspects, composition(s) provided by the invention comprise a tonicity component comprising one or more tonicity agents, wherein the tonicity component, agent(s), or both, e.g., sodium chloride, is present in an amount of between about 0.005% w/v and about 0.36% w/v, such as, e.g., ~0.005% w/v-~0.35% w/v, ~0.005% w/v-~0.3% w/v, ~0.005% w/v-~0.25% w/v, ~0.005% w/v-~0.2% w/v, ~0.005% w/v-~0.15% w/v, ~0.005% w/v-~0.1% w/v, or, e.g., ~0.005% w/v-~0.05% w/v, such as, e.g., ~0.01% w/v-~0.36% w/v, ~0.02% w/v-~0.36% w/v, ~0.03% w/v-~0.36% w/v, ~0.04% w/v-~0.36% w/v, ~0.05% w/v-~0.36% w/v, ~0.06% w/v-~0.36% w/v, ~0.07% w/v-~0.36% w/v, or, e.g., ~0.08% w/v-~0.36% w/v, as in, e.g., ~0.01% w/v-~0.3% w/v, ~0.01% w/v-~0.2% w/v, or, e.g., ~0.01% w/v-~0.1% w/v.

In certain aspects, the tonicity component comprises two or more constituents wherein the total concentration/amount of the two or more tonicity component constituents is represented by the concentration(s)/amount(s) provided above. In aspects, the tonicity component comprises a single tonicity constituent wherein the single constituent is present in an amount represented by the concentrations/amounts provided above. In certain aspects, the tonicity component comprises a single constituent, the single constituent being sodium chloride.

Any aspect described herein as comprising a single element of a composition are to be understood as implicitly simultaneously disclosing composition(s) that consist essentially of such an element, at least in respect of any applicable component/function. Thus, for example, the preceding paragraph implicitly discloses a composition that comprising a tonicity constituent that consists essentially of sodium chloride (and, thus, can include other elements that do not materially modify, e.g., detract from or impair, the novel characteristics of the element, here sodium chloride, in the provided context).

In aspects, composition(s) provided by the invention comprise no more than about 0.1% w/v of a tonicity agent. In aspects, composition(s) provided by the invention comprise no more than about 0.1% w/v of sodium chloride. In aspects, sodium chloride is present in an amount representing between about 0.005% w/v to about 0.1% w/v of the composition, such as, e.g., ~0.005% w/v-~0.095% w/v, ~0.005% w/v-~0.09% w/v, ~0.005% w/v-~0.085% w/v, or ~0.005% w/v-~0.08% w/v, such as, e.g., ~0.01% w/v-about 0.1% w/v, ~0.02% w/v-~0.1% w/v, ~0.03% w/v-~0.1% w/v, ~0.04% w/v-~0.1% w/v, ~0.05% w/v-~0.1% w/v, ~0.06% w/v-~0.1% w/v, ~0.07% w/v-~0.1% w/v, or for example ~0.08% w/v-~0.1% w/v, such as, e.g., ~0.05% w/v-~0.1% w/v, ~0.07% w/v-~0.09% w/v, or, e.g., ~0.01% w/v or ~0.08% w/v of the composition. In certain aspects, the tonicity component comprises a single constituent, the single constituent being mannitol, wherein the mannitol is present in an amount representing between about 2% w/v to about 6% w/v, e.g., ~2.5% w/v-~5.5% w/v, ~3% w/v-~5% w/v, or ~3.5% w/v-~5% w/v, e.g., ~4% w/v-~5% w/v such as about 4.5% w/v.

Preservative Component (Preservation Agent(s))

In aspects, composition(s) provided by the invention comprise an effective amount of a preservative component. In aspects, the preservative component comprises any one or more pharmaceutically acceptable and ophthalmologically suitable constituents (e.g., pharmaceutically acceptable and ophthalmologically suitable compounds) which detectably or significantly increase the stability of the composition, detectably or significantly decrease the degradation of one or more other constituents of the composition (over a period of time/under storage conditions such as conditions comprising a temperature of between about 15° C. and about 27° C. (e.g., between about 15° C. and about 27° C. and about 60% relative humidity); about 25° C.±2° C., e.g., 25° C.±2° C. and about 40%±5% relative humidity (e.g., for long term storage); about 30° C.±2° C. and about 35%±5% relative humidity (e.g., for long term storage); about 30° C.±2° C. and about 65%±5% relative humidity; about 40° C.±2° C. and not more than ("NMT") about 25% relative humidity (e.g., for accelerated storage); or a combination of any or all such conditions or other condition(s) exemplified elsewhere herein or as is known in the art, detectably or significantly increase the period of time that the composition is considered safe and efficacious for use, detectably or significantly increases or extends shelf life by maintaining an amount of active pharmaceutical ingredient above a threshold, e.g., a PCC, e.g., pilocarpine HCl, or an AAA component, e.g., brimonidine tartrate, within desirable or acceptable limits, maintaining the level of any one or more impurities below an acceptable/suitable level, detectably or significantly impeding/inhibiting or preventing/restricting growth of bacteria or other microorganisms in the composition, or any such similar measures of composition stability/preservation, or any combination of some or all thereof. For example, in aspects, a preservative component comprises one or more pharmaceutically acceptable and ophthalmologically suitable constituents (e.g., pharmaceutically acceptable and ophthalmologically suitable compounds) which aid in maintaining, e.g., via reducing or preventing microbial contamination, at least about 95%, 95%, 97%, 98% or more of the API(s) of the composition, such as, e.g., a pilocarpine compound, a brimonidine compound, or both a pilocarpine compound and a brimonidine compound, when stored under conditions comprising a temperature of between about 15° C. and about 27° C. (e.g., between about 15° C. and about 27° C. and about 60% relative humidity); about 25° C.±2° C., e.g., 25° C.±2° C. and about 40%±5% relative humidity (e.g., for long term storage); about 30° C.±2° C. and about 35%±5% relative humidity (e.g., for long term storage); about 30° C.±2° C. and about 65%±5% relative humidity; about 40° C.±2° C. and not more than ("NMT") about 25% relative humidity (e.g., for accelerated storage); or a combination of any or all such conditions, for a period of at least about 1, 3, 6, 9, 12, 18, 24, or, e.g., at least about 36 months. As another example, in aspects, a preservative component comprises one or more pharmaceutically acceptable and ophthalmologically suitable constituents (e.g., pharmaceutically acceptable and ophthalmologically suitable compounds) which aid, e.g., via reducing or preventing microbial contamination, the composition in maintaining a level of total impurities which is less than about 2.5% after storage under conditions comprising a temperature of between about 15° C. and about 27° C. (e.g., between about 15° C. and about 27° C. and about 60% relative humidity); about 25° C.±2° C., e.g., 25° C.±2° C. and about 40%±5% relative humidity (e.g., for long term storage); about 30° C.±2° C. and about 35%±5% relative humidity (e.g., for long term storage); about 30° C.±2° C. and about 65%±5% relative humidity; about 40° C.±2° C. and not more than ("NMT") about 25% relative humidity (e.g., for accelerated storage); or a combination of any or all such conditions, for a period of at least about 1, 3, 6, 9, 12, 18, 24, or, e.g., at least about 36 months.

In aspects, the preservation component can comprise any one or more pharmaceutically acceptable/ophthalmologically suitable compounds capable of demonstrating any one or more of the above-described effects (e.g., to a detectable or significant level).

In aspects, one or more preservative agents of a preservation component provide one or more other detectably or significant functional activities, such as for example, providing detectable or significant penetration enhancement activity, such as, e.g., detectably or significantly enhancing the penetration of one or more PCC constituents, e.g., a pilocarpine compound, e.g., pilocarpine hydrochloride, detectably or significantly enhancing the penetration of one or more AAA component constituents, e.g., a brimonidine compound, e.g., brimonidine tartrate, or both a pilocarpine compound and a brimonidine compound into an ocular tissue. In aspects, one or more preservative agents of a preservation component provide detectable or significant solubilization activity, such as, e.g., detectably or significantly enhancing the solubilization of, or detectably or significantly maintaining the solubilization of, one or more composition constituents, e.g., one or more PCC constituents, e.g., a pilocarpine compound, e.g., pilocarpine hydrochloride, one or more AAA component constituents, e.g., a brimonidine compound, e.g., brimonidine tartrate, or, e.g., detectably or significantly maintaining the solubilization of both one or more PCC constituents and one or more AAA component constituents.

In aspects, the pharmaceutically acceptable and ophthalmologically suitable composition(s) provided by the invention comprise a preservative component comprising one or more preservation agents present in anti-microbially effective amounts, e.g., an amount capable of detectably or significantly inhibiting microbial growth. In aspects, a preservation component of a composition can comprise any ophthalmologically suitable and pharmaceutically acceptable preservative which does not detectably or significantly interfere with the required functionality of any one or more other composition constituents. In aspects, exemplary constituents of a preservative component comprise, e.g., hydrogen peroxide; sorbic acid; biquanides; quaternary ammonium salts such as benzalkonium chloride(s) (abbreviated herein as BKC, though in other literature other abbreviations such as BAC, BAK, or BZK may be used) and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; thiomersal, etc. In aspects, a preservative component can comprise benzalkonium chloride(s) (BKC), wherein the BKC provides detectable or significant penetration enhancement activity, detectable or significant preservation activity, detectable or significant solubilization effect(s), or any combination thereof. Benzalkonium chlorides, a class of quaternary ammonium compounds suitable for use in composition(s) herein, include, e.g., known as alkyl dimethyl benzyl ammonium chlorides (or ADBAC), alkyl dimethyl (phenylmethyl) chlorides, and ammonium alkyl dimethyl benzyl chlorides.

In aspects, composition(s) provided by the invention comprise a preservation component comprising one or more preservation agents, wherein the preservation component is present in the composition in a concentration representing between about 0.0001% w/v to about 0.02% w/v, such as, e.g., ~0.001% w/v–~0.015% w/v, ~0.001% w/v–~0.01% w/v, or ~0.001% w/v–~0.008% w/v, ~0.002% w/v–~0.02% w/v, ~0.004% w/v–~0.02% w/v, or ~0.006% w/v–~0.02% w/v, e.g., ~0.0005% w/v–~0.015% w/v, ~0.001% w/v–~0.01% w/v, ~0.002% w/v-~0.009% w/v, ~0.004% w/v-~0.008% w/v, or ~0.006% w/v-~0.008% w/v, such as, e.g., about 0.007% w/v or about 0.0075% w/v of the composition.

In aspects, a preservation component can comprise a quaternary ammonium salt, e.g., benzalkonium chloride, present in the formulation in a concentration of between about 0.0001% w/v to 0.02% w/v, such as between about 0.003% w/v to about 0.02% w/v, such as between about 0.005% w/v to about 0.02% w/v, or for example about 0.007% w/v or about 0.0075% w/v, or, e.g., about 0.01% w/v, or about 0.02% w/v. In aspects, composition(s) provided by the invention comprise benzalkonium chloride in an amount of less than about 0.01% w/v.

In aspects, antimicrobial effective amounts of a preservative may be determined by performing preservative efficacy tests or antimicrobial effectiveness tests. These tests are inter alia described in Chapter 51 of the United States Pharmacopeia 29-National Formulary 24 (USP 29-NF 24). In aspects, preservative agents of a preservation component are used in an amount within the concentration ranges described in standard reference books like Remington's Pharmaceutical Sciences and Handbook of Pharmaceutical Excipients (e.g., the $23^{rd}$ Edition thereof—Published in 2020).

In certain aspects, the preservation component comprises two or more constituents wherein the total concentration/amount of the two or more preservation component constituents is represented by the concentrations/amounts provided above. In aspects, the preservation component comprises a single constituent wherein the single constituent is present in an amount represented by the concentrations/amounts provided above, such as, e.g., benzalkonium chloride in amounts provided above.

In this and any other ingredient aspect of the invention, the invention also can be characterized as comprising a "means" for providing a recited function, here imparting/providing an effective, detectable, or significant preservation effect (e.g., increased stability of one or more constituents of the composition, maintenance of an acceptable level of impurities during composition storage, increased composition shelf life, etc.) of composition(s). In such a respect, any known equivalents of such named agents can also be, e.g., are, incorporated into composition(s) or method(s) of the invention. As with other sections similarly described herein, any of the components of the invention can be, where suitable, described as means (e.g., the above-described preservation agents/compounds or components can be described as preservation means or means for providing effective, detectable, or significant preservation activity/characteristics to the composition or one or more constituents of the composition).

Viscosity Enhancer Component (Viscosity Enhancing Agent(s), Thickening Agent(s), Gelling Agent(s))

In aspects, composition(s) provided by the invention comprise an effective amount of a viscosity enhancer component (also referred to as a thickening component or gelling/gel component). In aspects, certain constituent(s) of such a component may provide viscosity enhancement without forming a gel. In aspects, as is described herein, a viscosity enhancer component comprises a constituent which only detectably or significantly increases the viscosity of the composition after administration, e.g., after exposure to an environment associated with administration to a mammalian eye. Herein, in aspects, constituents of the composition which impart a viscosity enhancing effect, e.g., a detectably or significantly increased viscosity compared to the same composition without the constituent, or, e.g., a detectable or significant increase in viscosity after administration to a mammalian eye compared to the composition prior to administration to the mammalian eye, can be a component of the viscosity enhancer component. In aspects, the viscosity enhancer component comprises any one or more pharmaceutically acceptable and ophthalmologically suitable constituents (e.g., pharmaceutically acceptable and ophthalmologically suitable compounds) which detectably or significantly increase the viscosity, thickness, or gelling characteristics of the composition or of one or more other constituents of the composition. In certain aspects, one or more constituents of a viscosity enhancing component change form under certain conditions to modify the viscosity of the composition (such as, e.g., a gel forming agent of a composition.) In a specific example, one or more constituents of a viscosity enhancing component gels when ionic content increases, such that, e.g., the composition comprising the constituent is liquid when packaged, prior to administration (e.g., when in its final packaging), however when administered to/delivered to a mammalian eye, the composition thickens, e.g., gels/forms a gel. In certain aspects, the invention provides composition(s) specifically characterizable as a gel. In aspects, composition(s) comprising a thickening component are gel composition(s).

In aspects, one or more constituents of a thickening component can modify the viscosity of the composition after administration, such as, e.g., it/they do not detectably or significantly increase the viscosity of the composition prior to administration compared to an at least substantially similar composition lacking such constituent(s), but upon administration to a mammalian eye cause the detectable or significant increase in viscosity of the composition. In aspects, events upon administration which can cause a thickening agent constituent to increase the viscosity of the composition can be or include, e.g., (a) exposure to the environment of a mammalian eye to which the composition may be administered (or an environment, such as a test solution/media, that is substantially similar or the same in some, most, generally all, or all material respects), (b) exposure to an environment of at least about 28 degrees Celsius (° C.), such as the temperature of a mammalian eye to which it is administered, such as ≥~29° C. or ≥~30° C., e.g., 31° C., 32° C., 33° C., 34° C., or ≥~35° C., (c) exposure to an environment having an ionic strength that is detectably or significantly greater than that of one or more gelling agents present in the composition (e.g., gellan gum, or, e.g., guar gum); (d) exposure to an environment having a pH of greater than, about 4.5, e.g., ≥~4.6, ≥~4.7, ≥~4.8, ≥~4.9, ≥~5, ≥~5.1, ≥~5.2, ≥~5.3, ≥~5.4, or, e.g., ≥~5.5, or, e.g., combinations of any of (a)-(d). In aspects, upon exposure to such exemplified environments, a constituent can aid in or cause the formation of a viscoelastic gel. In aspects, the formation of such a gel in-situ (a) detectably or significantly increases the residence time of the APIs of the composition, (b) detectably or significantly enhances the bioavailability of the APIs of the composition, (c) detectably or significantly reduces the frequency of required dosing to achieve an at least generally equivalent, substantially equivalent, effectively equivalent, or equivalent efficacy in treatment of the target condition, (d) improves patient compliance with administration regimen(s), or (e) any combination thereof, compared to an at least generally equivalent, at least substantially equivalent, at least effectively equivalent, or equivalent composition lacking such a gelation in-situ.

According to certain aspects, the invention provides composition(s) comprising a viscosity enhancer component, wherein at least one constituent of the viscosity enhancer component is a gelling agent, wherein the gelling agent detectably or significantly increases the viscosity of the composition upon administration to the mammalian eye over the viscosity of the composition immediately prior to the administration of the composition to the mammalian eye within no more than about 20 seconds of making contact with the mammalian eye, such as, e.g., within ≤~18 seconds, ≤~16 seconds, ≤~14 seconds, ≤~12 seconds, ≤~10 seconds, ≤~8 seconds, ≤~6 seconds, ≤~4 seconds, or, ≤~2 seconds, such as within ≤~1 second of making contact with the mammalian eye.

In aspects, constituent(s) of a viscosity enhancer component detectably or significantly improve the form of the formulation for convenient administration (e.g., make the composition easier for a user to apply). In aspects, constituent(s) of a viscosity enhancer component detectably or significantly improve, e.g., increase, contact of the composition with eye tissue, or e.g., detectably or significantly increase the length of time the composition maintains contact with eye tissue following administration. In aspects, constituent(s) of a viscosity enhancer component detectably or significantly improves (e.g., detectably or significantly increases) bioavailability of active pharmaceutical ingredient(s) of the composition, such as, e.g., constituents of the PCC, such as a pilocarpine compound, e.g., a salt of pilocarpine, e.g., pilocarpine hydrochloride, constituents of the AAA component, such as a brimonidine compound, e.g., a salt of brimonidine, e.g., brimonidine tartrate, or, e.g., constituents of both the PCC and AAA component. In aspects, one or more constituents of the viscosity enhancer component can further provide one or more additional detectable or significant functionalities, such as, e.g., a detectable or significant demulcent effect.

In aspects, the viscosity enhancer component can comprise any one or more pharmaceutically acceptable or ophthalmologically suitable compounds capable of demonstrating such effect(s). In aspects, a viscosity enhancer component of a composition can comprise any ophthalmologically suitable and pharmaceutically acceptable viscosity enhancing agent which does not detectably or significantly interfere with the required functionality of any one or more other composition constituents.

In aspects, exemplary constituents of a viscosity enhancer component comprise, e.g., polymers containing, mostly composed, generally consisting of, or consisting of, hydrophilic groups such as monosaccharides and polysaccharides, ethylene oxide groups, hydroxyl groups, carboxylic acids, or other charged functional groups.

In aspects, exemplary polymer constituents of a viscosity enhancer component are high molecular weight polymers, e.g., polymers having a molecular weight of at least about 15,000 Daltons, such as, e.g., ≥~20,000 Daltons, ≥~30,000 Daltons, ≥~40,000 Daltons, or, e.g., ≥~50,000 Daltons, e.g., about 15,000 Daltons to about 50,000 Daltons.

In aspects, exemplary polymer constituents of a viscosity enhancer component have a molecular weight of at least about 50,000 Daltons, such as, e.g., ≥~60,000 Daltons, ≥~70,000 Daltons, ≥~80,000 Daltons, ≥~90,000 Daltons, or, e.g., ≥~100,000 Daltons, such as, e.g., ~50,000 Daltons to ~100,000 Daltons.

In aspects, exemplary polymer constituents of a viscosity enhancer component have a molecular weight of at least about 100,000 Daltons, such as, e.g., ≥~110,000 Daltons, ≥~120,000 Daltons, ≥~130,000 Daltons, ≥~140,000 Daltons, ≥~150,000 Daltons, ≥~160,000 Daltons, ≥~170,000 Daltons, ≥~180,000 Daltons, ≥~190,000 Daltons or, e.g., ≥~200,000 Daltons, such as, e.g., ~100,000 Daltons to ~200,000 Daltons.

In aspects, exemplary polymer constituents of a viscosity enhancer component have a molecular weight of at least about 200,000 Daltons, such as, e.g., ≥~210,000 Daltons, ≥~220,000 Daltons, ≥~230,000 Daltons, ≥~240,000 Daltons, ≥~250,000 Daltons, ≥~260,000 Daltons, ≥~270,000 Daltons, ≥~280,000 Daltons, ≥~290,000 Daltons, or ≥~300,000 Daltons, such as, e.g., ~200,000 Daltons-~300,000 Daltons.

In aspects, exemplary polymer constituents of a viscosity enhancer component have a molecular weight of at least about 300,000 Daltons, such as, e.g., ≥~310,000 Daltons, ≥~320,000 Daltons, ≥~330,000 Daltons, ≥~340,000 Daltons, ≥~350,000 Daltons, ≥~360,000 Daltons, ≥~370,000 Daltons, ≥~380,000 Daltons, ≥~390,000 Daltons, or, e.g., ≥~400,000 Daltons, such as, e.g., ~300,000 Daltons-~400,000 Daltons.

In aspects, exemplary polymer constituents of a viscosity enhancer component have a molecular weight of at least about 400,000 Daltons, such as, e.g., ≥~410,000 Daltons, ≥~420,000 Daltons, ≥~430,000 Daltons, ≥~440,000 Daltons, ≥~450,000 Daltons, ≥~460,000 Daltons, ≥~470,000 Daltons, ≥~480,000 Daltons, ≥~490,000 Daltons, or ≥~500,000 Daltons, such as, e.g., ~410,000 Daltons-~500,000 Daltons.

In certain aspects, exemplary polymer constituents of a viscosity enhancer component have a molecular weight of at least about 500,000 Daltons, such as ~500,000 Daltons-~1,500,000 Daltons, e.g., 500,000 Daltons-~1,250,000 Daltons, 500,000 Daltons-~1,000,000 Daltons, or 500,000 Daltons-~750,000 Daltons, e.g., 750,000 Daltons-~1,500,000 Daltons, 1,000,000 Daltons-~1,500,000 Daltons, or 1,250,000 Daltons-~1,500,000 Daltons. In certain aspects, exemplary polymer constituents of a viscosity enhancer component have a molecular weight of greater than 1,500,000 Daltons.

In certain aspects, exemplary polymer constituents of a viscosity enhancer component provide a detectable or significant increase in viscosity compared to the composition without the constituent(s), such as, e.g., an increase in viscosity over the composition without the constituent(s) either (a), while packaged, prior to use, (b) after administration to a mammalian eye (e.g., upon being placed under detectably or significantly different tonicity conditions), or (c) both (a) and (b), of at least about 0.5%, ≥~1%, ≥~3%, ≥~5%, ≥~10%, ≥~15%, ≥~20%, ≥~25%, ≥~30%, ≥~35%, ≥~40%, ≥~45%, or, e.g., ≥~50%.

In aspects, examples of suitable viscosity-enhancing agents include, e.g., sodium carboxymethylcellulose, hydroxypropylmethylcellulose, povidone, polyvinyl alcohol, polyethylene glycol, and gellan gum. In certain aspects, examples of suitable viscosity-enhancing agents include, e.g., agents capable of forming a gel in-situ, such as, e.g., a polymer such as a triblock copolymer poly (ethylene oxide)-b-poly (propylene oxide)-b-poly (ethylene oxide) (PEO-PPO-PEO) (e.g., pluronics or poloxamers), such as, e.g., the poloxamers 188 (F-68), 237 (F-87), 338 (F-108) and 407 (F-127), Pluronic F-127 (F-127) or Poloxamer 407 (P407) (copolymer PEO106-PPO70-PEO106); gellan gum, guar gum, xanthan gum, chitosan, xyloglucan (often referred to as tamarind seed polysaccharide (TSP), polyacrylic acid polymers (e.g., Carbopol), alginate (alginic acid), e.g., calcium alginate, sodium alginate, etc., pectin, carrageenan, cellulose derivatives such as, e.g., methyl cellulose, hydroxyethyl cellulose, hydroxypropyl methylcellulose (HPMC), sodium carboxymethyl cellulose (NaCMC), etc. In aspects, combinations of such agents can provide gelation activity, such as, e.g., a Carbopol and HPMC, or a Carbopol and chitosan, or, e.g., calcium alginate and HPMC, gellan gum with xanthan gum, HPMC, or Carbopol, gellan gum and carrageenan, etc. In aspects, a single agent can be present, such as, e.g., guar gum or, e.g., gellan gum. In certain aspects, formulations described herein lack any viscosity enhancer component, e.g., lack any thickening (e.g., viscosity-enhancing) compounds or agents/constituents.

In aspects, composition(s) provided by the invention comprise a viscosity enhancer component comprising one or more viscosity enhancing agents, wherein the viscosity enhancer component is present in the composition in a concentration representing between about 0.1% w/v to about 1% w/v of the composition, such as, e.g., ~0.1% w/v-~0.9% w/v, ~0.1% w/v-~0.8% w/v, ~0.1% w/v-~0.7% w/v, or ~0.1% w/v-~0.6% w/v, e.g., ~0.2% w/v-~1% w/v, ~0.3% w/v-~1% w/v, ~0.4% w/v-~1% w/v, ~0.5% w/v-~1% w/v, or ~0.6% w/v-~1% w/v, such as, e.g., ~0.2% w/v-~9% w/v, ~0.3% w/v-~0.8% w/v, ~0.4% w/v-~0.7% w/v, ~0.5% w/v-~0.7% w/v, or, e.g., about 0.6% w/v of the composition.

In certain aspects, the thickening component comprises two or more constituents wherein the total concentration/amount of the two or more thickening component constituents is represented by the concentrations/amounts provided above. In aspects, the solubilization component comprises a single constituent wherein the single constituent is present in an amount represented by the concentrations/amounts provided above. In certain aspects, the solubilization component comprises a single constituent, the single constituent being gellan gum, wherein the gellan gum, is present in an amount representing ~0.2% w/v-~9% w/v, ~0.3% w/v-~0.8% w/v, ~0.4% w/v-~0.7% w/v, ~0.5% w/v-~0.7% w/v, or, e.g., about 0.6% w/v of the composition.

In this and any other ingredient aspect of the invention, the invention also can be characterized as comprising a "means" for providing a recited function, here imparting/providing an effective, detectable, or significant viscosity enhancing, thickening, or gelling effect to composition(s) of the invention. In such a respect, any known equivalents of such named agents can also be, e.g., are, incorporated into composition(s) or method(s) of the invention. As with other sections similarly described herein, any of the components of the invention can be, where suitable, described as means (e.g., the above-described viscosity enhancing agents/compounds or components can be described as viscosity enhancing, thickening, or gelling means or means for providing effective, detectable, or significant viscosity enhancing, thickening, or gelling activity/characteristics to the composition.)

Chelation Component (Chelating Agent(s))

In aspects, composition(s) provided by the invention comprise a chelation component. In aspects, the chelation component comprises any one or more pharmaceutically acceptable and ophthalmologically suitable constituents (e.g., pharmaceutically acceptable and ophthalmologically suitable compounds) which detectably or significantly increase chelation within the composition, detectably or significantly supplement or enhance preservative efficacy, or a combination thereof, by forming stable water-soluble complexes (chelates) with alkaline earth and heavy metal ions. In aspects, the chelation component can comprise any one or more pharmaceutically acceptable or ophthalmologically suitable compounds capable of demonstrating such an effect. In aspects, a chelation component of a composition can comprise any ophthalmologically suitable and pharmaceutically acceptable chelating agent which does not detectably or significantly interfere with the required functionality of any one or more other composition constituents.

In aspects, exemplary constituents of a chelation component comprise, e.g., one or more of cromolyn, monomeric polyacids such as EDTA, cyclohexanediamine tetraacetic acid (CDTA), hydroxyethylethylenediamine triacetic acid (HEDTA), diethylenetriamine pentaacetic acid (DTPA), dimercaptopropane sulfonic acid (DMPS), dimercaptosuccmic acid (DMSA), aminotrimethylene phosphonic acid (ATPA), citric acid, any ophthalmologically acceptable salts thereof, and/or combinations of any two or more such compounds. In other aspects, a chelating agent can be a phosphate, such as, e.g., pyrophosphates, tripolyphosphates, and, hexametaphosphates; a chelating antibiotic such as chloroquine and tetracycline; a nitrogen-containing chelating agent containing two or more chelating nitrogen atoms within an imino group or in an aromatic ring (e.g., diimines, 2,2'-bipyridines, etc.); or for example a polyamine such as cyclam (1,4,7,11-tetraazacyclotetradecane), N—($C_1$-$C_{30}$ alkyl)-substituted cyclams (e.g., hexadecyclam, tetramethylhexadecylcyclam), diethylenetriamine (DETA), spermine, diethylnorspermine (DENSPM), diethylhomospermine (DEHOP), and deferoxamine (N'-[5-[[4-[[5-(acetylhydroxyamino) pentyl]amino]-1,4-dioxobutyl]hydroxyamino]pentyl]-N'-(5-aminopentyl)-N-hydroxybutanediamide; also known as desferrioxamine B and DFO).

In certain aspects, a chelation component of composition(s) provided by the invention comprise EDTA or an ophthalmologically suitable EDTA salt such as, e.g., diammonium EDTA, disodium EDTA, dipotassium EDTA, triammonium EDTA, trisodium EDTA, tripotassium EDTA, or calcium disodium EDTA. In certain aspects, composition(s) lack any one or more of EDTA or an EDTA salt.

In aspects, composition(s) provided by the invention comprise a chelation component comprising one or more chelating agents, wherein the chelation component is present in the composition in a concentration representing about 0.01% w/v to about 0.5% w/v, such as for example ~0.05% w/v-~0.5% w/v, ~0.1% w/v-~0.5% w/v, or ~0.2% w/v-~0.5% w/v, e.g., ~0.01% w/v-~0.45% w/v, ~0.01% w/v-~0.4% w/v, or ~0.01% w/v-~0.3% w/v, such as, e.g., about 0.1% w/v-about 0.4% w/v of the composition.

In certain aspects, the chelation component comprises two or more constituents wherein the total concentration/amount of the two or more chelation component constituents is represented by, e.g., concentration(s)/amount(s) provided above. In aspects, the chelation component comprises a single constituent wherein the single constituent is present in an amount represented by the concentrations/amounts provided above, such as, e.g., edetate disodium in amounts provided above.

In this and any other ingredient aspect of the invention, the invention also can be characterized as comprising a "means" for providing a recited function, here imparting/providing an effective, detectable, or significant chelating effect (e.g., forming stable water-soluble complexes (chelates) with alkaline earth and heavy metal ions) of composition(s). In such a respect, any known equivalents of such named agents can also be, e.g., are, incorporated into composition(s) or method(s) of the invention. As with other sections similarly described herein, any of the components of the invention can be, where suitable, described as means (e.g., the above-described chelating agents/compounds or components can be described as chelation means or means for providing effective, detectable, or significant chelation activity/characteristics to the composition or one or more constituents of the composition.)

pH Adjusting Component (pH Adjusting Agent(s))

In aspects, composition(s) provided by the invention comprise a pH adjusting component. In aspects, the pH adjusting component comprises any one or more pharmaceutically acceptable and ophthalmologically suitable constituents (e.g., pharmaceutically acceptable and ophthalmologically suitable compounds) which detectably or significantly alter or aid in the establishment of a target pH of the composition, such as a pH of between about 3 to about 6. In aspects, the pH adjusting component can comprise any one or more pharmaceutically acceptable or ophthalmologically suitable compounds capable of demonstrating such an effect. In aspects, a pH adjusting component of a composition can comprise any ophthalmologically suitable and pharmaceutically acceptable pH adjusting agent which does not detectably or significantly interfere with the required functionality of any one or more other composition constituents.

In aspects, one or more constituents of the pH adjusting component can further provide one or more additional detectable or significant functionalities, such as, for example, detectable or significant buffering effects. In aspects, a pH adjusting agent can be a compound different from a buffer/buffering agent.

In aspects, exemplary constituents of a buffer component comprise, e.g., one or more of sodium hydroxide, sodium carbonate, sodium bicarbonate, potassium hydroxide, ammonium carbonate, hydrochloric acid, lactic acid, phosphoric acid, sodium phosphate, sulfuric acid, etc. In aspects, such agents can be used to adjust the pH to a desirable/target range, such as, e.g., to between about 3 to about 6, such as ~3-~5, ~3.5-~5.5, ~4-~5.5, or ~4.5-~5.5, or, e.g., to between about 5 to about 8.5, such as ~5.5-~8.5, ~6.5-~8.5, or ~7-~8.5, such as ~7-~7.5. In aspects, the pH of the composition(s), e.g., composition(s) comprising a pilocarpine compound, e.g., pilocarpine HCl and a brimonidine compound, e.g., brimonidine tartrate, can be adjusted in any suitable manner by means of the addition of pH adjusting agents in an amount sufficient to establish and maintain a composition pH of, e.g., from about 3-about 8.5, such as, e.g., about 3-about 5.5, or, e.g., about 5-about 8.5, for example by addition of aqueous hydrochloric acid solutions or aqueous sodium hydroxide solutions. Such pH adjusting solutions can be diluted or concentrated in any suitable manner to achieve a desired effect/state. E.g., in aspects, suitable pH adjusting agents include 0.01 molar (M) hydrochloric acid, 0.1M hydrochloric acid, 1M hydrochloric acid, 2M hydrochloric acid, 3M hydrochloric acid, 4M hydrochloric acid, 5M hydrochloric acid, 6M hydrochloric acid (e.g., a 0.01-6 M, such as 0.1-5 M, e.g., 0.25-5 M, or 0.2-4 M hydrochloric acid), 0.01M sodium hydroxide, 0.1M sodium hydroxide, 1M sodium hydroxide, 2M sodium hydroxide, 3M sodium hydroxide, 4M sodium hydroxide, 5M sodium hydroxide (e.g., 0.01 M-55M sodium hydroxide, such as 0.2-5 M, 0.25-4 M, or 0.3-6M or 0.3-3M sodium hydrochloride), and 6M sodium hydroxide. In one aspect, suitable pH adjusting agents include either one of or a combination of hydrochloric acid or sodium hydroxide, e.g., 1M hydrochloric acid or 1M sodium hydroxide, which, in aspects, alternatively can be added to a composition to achieve a desired pH range.

In aspects, composition(s) provided by the invention can comprise a pH adjusting component comprising one or more pH adjusting agent(s), wherein the pH adjusting component is present in the composition(s) provided by the invention in an amount effective in providing the target pH. In aspects, such an amount can be considered a "trace amount," e.g., less than ~0.005% w/v, <0.004% w/v, <~0.003% w/v, <0.002% w/v, e.g., <~0.001% w/v. In aspects, such an amount can be an amount representing between about 0-about 0.01% w/v. In aspects, one or more pH adjusting agent(s) can be present in the composition(s) provided by the invention in an amount effective in providing the target pH, such amounts representing between about 0% w/v-about 0.1% w/v, such as, e.g., about 0.01% w/v, ~0.02% w/v, ~0.03% w/v, ~0.04% w/v, ~0.05% w/v, ~0.06% w/v, ~0.07% w/v, ~0.08% w/v, or, e.g., ~0.09% w/v.

In certain aspects, the pH adjusting component comprises two or more constituents wherein the total concentration/amount of the two or more pH adjusting component constituents within one or more ranges provided above. In aspects, the pH adjusting component comprises a single constituent wherein the single constituent is present in an amount within one or more ranges provided above. In aspects, composition(s) comprise sodium hydroxide, hydrochloric acid, or both sodium hydroxide and hydrochloric acid only in sufficient amounts to adjust pH during the manufacturing process (e.g., in an amount of less than 0.1% w/v, or, e.g., less than ~0.005% w/v.)

In this and any other ingredient aspect of the invention, the invention also can be characterized as comprising a "means" for providing a recited function, here imparting/providing an effective, detectable, or significant pH adjustment effect (e.g., pH establishment) to/of composition(s) of the invention. In such a respect, any known equivalents of such named agents can also be, e.g., are, incorporated into composition(s) or method(s) of the invention. As with other sections similarly described herein, any of the components of the invention can be, where suitable, described as means (e.g., the above-described pH adjusting agents/compounds or components can be described as pH adjusting means or means for providing effective, detectable, or significant pH adjustment activity/characteristics to the composition). In such aspects, it is understood that known equivalents to the recited elements provided herein also can be utilized/present in the place of such specifically named elements.

Antioxidant Component (Antioxidant(s))

In aspects, composition(s) comprise antioxidant(s) in effective amount(s). An "antioxidant" is typically understood as referring to a substance that preferentially reacts with oxygen, thereby detectably or significantly protecting other components of a composition to which it is added from premature degradation due to oxidation (e.g., protecting APIs that is known to be detectably/significantly susceptible to oxidation).

According to aspects, one or more antioxidant compounds can be present in composition(s) of the invention as an antioxidant component, which detectably or significantly improve API stability or reduce the amount of impurities, such as, e.g., providing for a composition which is stable under room temperature storage conditions, e.g., retains at least about 97% of the one or more PCC constituents, e.g., pilocarpine compound(s), retains at least about 97% of the one or more AAA component constituents, e.g., brimonidine compound(s), or retains at least about 97% of one or more PCC constituents and one or more AAA component constituents when stored at between about 15° C. and about 27° C. (e.g., between about 15° C. and about 27° C. and about 60% relative humidity); when stored at about 25° C.±2° C., e.g., 25° C.±2° C. and about 40%±5% relative humidity (e.g., for long term storage); about 30° C.±2° C. and about 35%±5% relative humidity (e.g., for long term storage); about 30° C.±2° C. and about 65%±5% relative humidity; about 40° C.±2° C. and not more than ("NMT") about 25% relative humidity (e.g., for accelerated storage); or a combination of any or all such conditions for at least about one month such as ≥~2 months or such as ≥~3 months, ≥~6 months, ≥~12 months, or, e.g., ≥~18 months, ≥~24 months, or ≥~36 months.

For example, composition(s) provided by the invention can comprise an antioxidant component comprising one or more antioxidant agents which detectably improve the stability of the one or more pilocarpine compound(s), one or more brimonidine compound(s), or both one or more pilocarpine compound(s) and one or more brimonidine compound(s), reduces the amount of composition impurities, enhances preservative effectiveness, or any or all thereof, at a period of at least 2 weeks post manufacturing, such as at a period ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or for even longer periods (e.g., ~3-~24, ~3-~18, ~3-18 12, ~3-~36, ~4-~12, ~4-18 24, ~4-~36, ~6-~12, ~6-~18, ~6-~24, or ~6-~36 months).

In aspects, the invention provides composition(s) comprising one or more pharmaceutically acceptable and ophthalmologically suitable antioxidant agents as constituents of an antioxidant component effective at pH range of between, e.g., ~3-~6, or, e.g., between ~5-~8.5, or effective within both ranges, e.g., effective at a pH range of between ~3-~8.5. In aspects, antioxidant compound(s) of the composition(s) herein do not detectably or significantly negatively impact any other component of the formulation, such as, e.g., they do not detectably or significantly reduce the efficacy of any one or more API(s), e.g., pilocarpine compound(s), brimonidine compound(s), or both.

In aspects any ophthalmologically suitable and pharmaceutically acceptable antioxidant can be used in methods of the invention/incorporated in composition(s) of the invention, in any suitably effective amount(s). In aspects, exemplary antioxidant(s) in a composition described herein can comprise, e.g., ascorbate compound(s) (e.g., sodium ascorbate, ascorbic acid, etc.), thiamine, pyridoxine, histidine, cysteine, glutathione, sodium bisulphite, sodium sulphite, sodium metabisulphite, sodium thiosulphite, sodium formaldehyde sulphoxylate, acetylcysteine, cysteine, thioglycerol, thioglycollic acid, thiolactic acid, thieurea, dihithreitol, propyl gallate, butylated hydroxyanisole, butylated hydroxytoluene, tertiary butyl hydroquinone, ascorbyl palmitate, nordihydroguaiaretic acid and alpha-tocopherol, any ophthalmologically acceptable salts thereof, or combinations of any two or more such compounds. In aspects, one or more antioxidant compound(s)/agent(s) can be present in the composition(s) provided by the invention in an amount representing between about 0.001 w/v. %-about 2 w/v. % of the composition, such as, e.g., ~0.001 w/v. %-~1.8 w/v. %, ~0.001 w/v. %-~1.6 w/v. %, ~0.001 w/v. %-~1.4 w/v. %, ~0.001 w/v. %-~1.2 w/v. %, ~0.08 w/v. %-~1 w/v. %, or. e.g., ~0.05-~1 w/v. % of the composition.

In this and any other ingredient aspect of the invention, the invention also can be characterized as comprising a "means" for providing a recited function, here imparting/providing an effective, detectable, or significant antioxidant effect to/of composition(s) of the invention. In such a respect, any known equivalents of such named agents can also be, e.g., are, incorporated into composition(s) or method(s) of the invention. As with other sections similarly described herein, any of the components of the invention can be, where suitable, described as means (e.g., the above-described antioxidant agents/compounds or components can be described as antioxidant means or means for providing effective, detectable, or significant antioxidant activity/characteristics to the composition.)

Carrier Component (Carrier Agent(s))

In aspects, composition(s) provided by the invention comprise a carrier component. In aspects, this component may be referenced as vehicle component. In aspects, the carrier component comprises any one or more pharmaceutically acceptable and ophthalmologically suitable constituents (e.g., pharmaceutically acceptable and ophthalmologically suitable carriers) which detectably or significantly maintain all constituents of the composition in deliverable form, such as in the form of a liquid, e.g., a solution, a suspension, or, e.g., a gel. In aspects, the carrier component can comprise any one or more pharmaceutically acceptable or ophthalmologically suitable carriers capable of performing such a function. In aspects, a carrier component of a composition can comprise any ophthalmologically suitable and pharmaceutically acceptable carrier which does not detectably or significantly interfere with the required functionality of any one or more other composition constituents.

In aspects, exemplary constituents of a carrier component comprise, e.g., one or more of a pharmaceutically acceptable and ophthalmologically suitable lipid (e.g., establishing a lipid vehicle), a gel (e.g., establishing a gel vehicle), an oil-based carrier (establishing an oil-based vehicle), a carrier in the form of an emulsion (establishing an emulsion vehicle), an emulsifier-containing carrier that forms an emulsion when mixed with other components, or, a carrier forming a solution vehicle, e.g., an aqueous carrier (water) to form an aqueous solution vehicle. In aspects, the carrier is an aqueous carrier. In aspects, the carrier is mostly, generally only, essentially only, substantially only, or only composed of water, e.g., water for injection (WFI) (a sterile, solute-free preparation of distilled water). In alternative aspects, other ophthalmologically suitable aqueous carriers which do not adversely affect the stability of the composition(s) may be used, such as, e.g., deionized water.

In certain aspects, the carrier is deuterated water, comprising an amount of deuteration which is detectably or significantly greater than that which is naturally occurring (e.g., that which is typically found in nature). In aspects, composition(s) do not comprise a deuterated carrier, such as, e.g., deuterated water. In certain common aspects, the carrier is water comprising no additional deuterium beyond that which is typically found in nature. In aspects, composition(s) comprise non-deuterated water, wherein "non-deuterated" describes water comprising no amount of deuteration beyond that which is typically naturally occurring. Uncontradicted, reference to "water" should be interpreted to mean non-deuterated water.

In aspects, composition(s) provided by the invention comprise a carrier component comprising one or more carriers, wherein the carrier component is present in a concentration representing at least about 60% w/v of the composition, such as, e.g., ≥~65% w/v, ≥~70% w/v, ≥~75% w/v, ≥~80% w/v, ≥~85% w/v, ≥~90% w/v, ≥~95% w/v of the composition.

In certain aspects, the carrier component comprises two or more constituents wherein the total concentration/amount of the two or more carrier component constituents is represented by the concentrations/amounts provided above. In aspects, the carrier component comprises a single constituent wherein the single constituent is present in an amount represented by the concentrations/amounts provided above. In certain aspects, the carrier component comprises a single constituent, the single constituent being water, or, e.g., water for injection (WFI), wherein the water is present in an amount representing ≥~70% w/v, ≥~75% w/v, ≥~80% w/v, ≥~85% w/v, ≥~90% w/v, or ≥~95% w/v of the composition. In aspects, the pharmaceutically acceptable and ophthalmologically suitable composition(s) are aqueous composition(s). In aspects, composition(s) provided by the invention typically comprise at least about 70% w/v water, and even more typically at least about 85% w/v-about 95% w/v water.

In this and any other ingredient aspect of the invention, the invention also can be characterized as comprising a "means" for providing a recited function, here imparting/providing an effective, detectable, or significant carrier function (e.g., vehicle) to/of composition(s) of the invention. In such a respect, any known equivalents of such named agents can also be, e.g., are, incorporated into composition(s) or method(s) of the invention. As with other sections similarly described herein, any of the components of the invention can be, where suitable, described as means (e.g., the above-described carriers or components can be described as carrier means or means for providing effective, detectable, or significant carrier or vehicle activity/characteristics to the composition.)

Composition(s) do not Include/are not Provided as

In certain aspects, composition(s) provided by the invention are characterizable by one or more ingredients/agents/constituents which are not present in the composition(s). For example, in one aspect, composition(s) are characterized by lacking any specific formulation elements, or elements and amounts, included in any of the cited patents described in the Background of this disclosure.

According to certain aspects of the invention, composition(s) provided by the invention do not comprise a chelating agent. In aspects, composition(s) provided by the invention do not comprise any compound which detectably or significantly increase chelation within the composition(s). In aspects, composition(s) do not comprise edetate disodium. In aspects, if composition(s) comprise edetate disodium, it is present in an amount which is significantly less than 0.5% w/v, e.g., <0.4% w/v, <0.3% w/v, <0.2% w/v, <0.1% w/v, <0.05% w/v, or, e.g., <0.01% w/v.

In certain embodiments, composition(s) provided by the invention do not comprise a polymer, such that composition(s) are characterizable as polymer-free. In certain embodiments, composition(s) provided as a solution do not comprise a polymer, such that composition(s) provided as a solution are characterizable as polymer-free.

In some specific embodiments, composition(s) are not provided in any form other than a solution. In certain alternative specific embodiments, composition(s) are not provided in any form other than a gel.

In aspects, composition(s) provided by the invention comprise less than about 0.001% w/v of a free monosaccharide, such as, e.g., less than about 0.0005% w/v, or, e.g., less than about 0.0001% w/v of a free monosaccharide. In some embodiments, composition(s) are characterizable as not comprising any free monosaccharide which is not characterizable as a sugar alcohol. In certain embodiments, composition(s) are characterizable as lacking any disaccharide. In aspects, composition(s) are characterizable as not comprising any oligosaccharide. In aspects, composition(s) do not comprise any free monosaccharide not characterizable as a sugar alcohol, do not comprise a disaccharide, and do not comprise an oligosaccharide. In aspects, composition(s) do not comprise any free monosaccharide, disaccharide, or oligosaccharide. In aspects, composition(s) do not comprise D-glucose. According to certain aspects, composition(s) provided by the invention comprise less than about 0.001% w/v, such as, e.g., ≤~0.0001% w/v, or, e.g., no detectable or significant amount of a free monosaccharide (e.g., glucose, fructose, etc.), disaccharide (e.g., maltose), oligosaccharide (e.g., an oligosaccharide higher than maltotriose), or, e.g., no detectable or significant amount of a combination of any or all thereof. In aspects, composition(s) provided herein comprise no amount of free monosaccharide, disaccharide, oligosaccharide, or, e.g., combination of any or all thereof, which detectably or significantly contribute(s) to therapeutic effect(s) of composition(s) herein.

In aspects, composition(s) do not comprise any agent which detectably or significantly promotes detectable or significant microbial growth, e.g., a glucose compound such as glucose or D-glucose (dextrose).

In aspects, composition(s) provided by the invention comprise only two pharmaceutically active ingredients, such as, e.g., a single constituent of a PCC, such as, e.g., a single pilocarpine compound, e.g., a salt of pilocarpine, e.g., pilocarpine HCl, and, e.g., a single constituent of an AAA component, such as, e.g., a single brimonidine compound, e.g., a salt of brimonidine compound, and brimonidine tartrate.

In aspects, composition(s) do not comprise an anti-inflammatory agent characterizable as a steroid. In aspects, composition(s) do not comprise an anti-inflammatory characterizable as a non-steroid anti-inflammatory drug (NSAID), such as, e.g., diclofenac or ketorolac. In specific examples, composition(s) do not comprise aceclidine.

In certain aspects, the PCC does not comprise, e.g., carbachol, bethanechol, methacholine, or muscarine compound(s) or combination(s) thereof. In certain aspects, the PCC does not comprise, e.g., pirenzepine, telenzepine, trihexyphenidyl, (+)(11-({2-[diethylaminomethyl]-1-piperdidinyl}acetyl)-5,11-di-hydro-6H-pyrido(2,3-b)(1,4) benzodiazepine-6-one, (+)5,11 dihydro-11-{[2-[(dipropylamino)methyl]-1piperdinyl)amino]carbonyl}-6H-pyrido(2,3-b)(1,4)benzodiazepine-6-one, himbacine, triptiramine, diphenylacetoxy-N-methylpiperidine ethiodide, (+)p-fluoro-hexahydro-sila-difenidol hydrochloride, or combination(s) of any or all thereof.

In aspects, composition(s) provided by the invention do not comprise more than a single buffer agent. In aspects, composition(s) provided by the invention lack any buffer component. In aspects, composition(s) provided by the invention comprise a buffer component which does not comprise a citrate buffer. In aspects, composition(s) provided by the invention comprise a buffer component which does not comprise a borate buffer. In aspects, composition(s) provided by the invention lack any buffer component comprising boric acid, sodium borate, or sodium citrate dihydrate. In aspects, composition(s) do not comprise a buffer agent having a pKa of less than about 8. In aspects, composition(s) do not comprise a buffer agent having a pKa of greater than about 5. In aspects, composition(s) do not comprise a buffer agent having a pKa of greater than about 4. In aspects, composition(s) only comprise a buffer agent having at least two pKa values, e.g., a buffer agent comprising two or more ionizable groups.

According to certain aspects, composition(s) are not provided as a solution. In certain aspects, composition(s) are not provided as a suspension. In aspects, composition(s) are provided as a gel (as opposed to, e.g., a suspension or a solution). In aspects, composition(s) are provided as solutions (as opposed to, e.g., a suspension or a gel). In aspects, composition(s) are only provided as suspensions (as opposed to, e.g., a solution or a gel).

In aspects, composition(s) do not comprise sodium hyaluronate, hydroxypropyl methylcellulose, or both sodium hyaluronate and hydroxypropyl methylcellulose, such as, e.g., may be provided for lubrication or other purposes. In aspects, composition(s) provided by the invention do not comprise detectable or significant amount(s) of one or more of hyaluronic acid or a pharmaceutically acceptable salt thereof, cellulose or a cellulose derivative, carboxymethyl cellulose sodium, hydroxyethyl cellulose, methylcellulose, dextran, gelatin, a polyol, glycerin, polyethylene glycol 300, polyethylene glycol 400, propylene glycol, polyvinyl alcohol, povidone, or, e.g., combinations of two or more thereof.

In aspects, composition(s) provided by the invention do not comprise a cholinesterase inhibitor. In aspects, composition(s) do not comprise, e.g., an organophosphate such as a metrifonate. In aspects, composition(s) do not comprise a carbamate such as phytostigmine (eserine), neostigmine (prostigmine), pyridostigmine, ambenonium, demarcarium, or rivastigmine. In aspects, composition(s) do not comprise a phenanthrene derivative such as galantamine. In aspects, composition(s) do not comprise a piperidine compound such as donepezil, tacrine (tetrahydroaminoacridine), edrophonium, huperzine A, or ladostigil. In aspects, composition(s) do not comprise a cholinesterase inhibitor such phospholine iodide (echothiophate), or diisopropylfluorophosphate. In aspects, composition(s) lack any derivative of such compounds.

In aspects, composition(s) do not comprise an alpha agonist other than brimonidine. In aspects, composition(s) do not comprise amiloride, apraclonidine, clonidine or clonidine derivatives such as p-chloro and amino derivatives, detomidine, dexmeetomidine, dipivalylepinephrine, epinephrine, guanabenz, guanfacine, isoproterenol, medetomide, metaproterenol, mephentermine, methoxamine, methyldopa, naphazoline, norepinephrine, phentolamine, phenylephrine, rilmenidine, salbutamol, terbutaline, tetrahydrozoline, and xylazine. In aspects, composition(s) lack any derivative of such compounds.

In aspects, composition(s) do not comprise a parasympathomimetic drug other than pilocarpine. In aspects, composition(s) do not comprise acetylcholine, muscarine, nicotine, suxmethonium, bethanechol, methacholine, phenylpropanolamine, amphetamine, ephedrine, phentolamine, or fenfluramine. In aspects, composition(s) do not comprise carbachol. In aspects, composition(s) do not comprise any derivative of such compounds.

In certain aspects, composition(s) do not comprise a carrier other than water, e.g., does not comprise one or more of vegetable oil(s), polyalkylene glycol(s), petroleum-based jelly, ethyl cellulose, ethyl oleate, carboxymethyl-cellulose, polyvinylpyrrolidone, isopropyl myristate, or other ophthalmologically suitable carriers known in the art other than water. In aspects, composition(s) do not comprise a deuterated carrier. In aspects, composition(s) do not comprise deuterated water, e.g., water comprising an amount of deuterium significantly greater than that which is found in nature.

In aspects, composition(s) do not comprise ophthalmic mucous penetrating particles, e.g., nanoparticles coated with a mucous penetrating agent.

In certain aspects, composition(s) do not comprise an emulsifier, e.g., an agent promoting the formation or maintenance of an emulsion. In aspects, composition(s) do not comprise, e.g., one or more of gelatin, egg yolk, casein, wool fat, cholesterol, acacia, tragacanth, chondrus, pectin, methyl cellulose, carboxymethylcellulose, bentonite, magnesium hydroxide, aluminum hydroxide, magnesium trisilicate, sodium lauryl sulfate, polyethylene glycol 400 monostearate, or combinations thereof. In certain aspects, composition(s) may comprise one or more such constituents.

In certain aspects, composition(s) do not comprise one or more hydrophilic monomers including monomeric acids such as acrylic, methacrylic, itaconic, crotonic, vinyl sulfonic, maleic, angelic, oleic, or alpha-chloro-acrylic acid, sulfoethyl-methacrylate, or vinyl pyrrolidone. In certain aspects, composition(s) do not comprise one or more hydrophobic monomers including alkyl acrylates, alkyl methacrylates, vinyl ethers, acrylonitrile, hydroxymethacrylate, styrene, and vinyl acetate.

In aspects, composition(s) do not comprise a component, compound, agent, constituent, etc. which significantly modifies the buffering capacity of a composition other than a buffering component or agent as described herein. In aspects, the only component or agent(s) which detectably or significantly modulate the buffering capacity of composition(s) herein is/are a buffer component/buffering agent(s) recognized in the art as buffer(s), such as those typically found in pharmaceutical formulations or, e.g., more specifically, ophthalmological composition(s).

In aspects, composition(s) lack any one or combination of any of the types of agents or specific compounds described herein as being included in composition(s) of the invention.

Ratios

According to aspects, any component(s) or compound(s)/agent(s) described herein can be present in composition(s) in therapeutically effective amount(s), compositionally compatible amount(s), or both. In aspects, any single component or compound/agent provided herein can be present in a relationship with, such as, e.g., in a ratio with, any one or more other single component or compound/agent. In aspects, any combination of component(s) or compound(s)/agent(s) provided herein can be present in a ratio with any other combination of component(s) or compound(s)/agent(s). In aspects, ratio(s) between such component(s) or compound(s)/agent(s) or combinations thereof can be established using any provided amount(s) for each disclosed herein, including, e.g., values within ranges of such amounts disclosed herein. To exemplify this disclosure, the following tables are provided. Table 1 below, e.g., illustrating a ratio array, demonstrates the types of ratios between components which the reader should understand to be encompassed by the disclosure herein. Table 2 below, also illustrating a ratio array, demonstrates types of ratios between agent(s)/constituent(s) which the reader should understand to be encompassed by the disclosure herein.

The reader should understand that the ratio arrays illustrated in Tables 1 and 2 are exemplary and do not necessarily disclose all possible ratios encompassed by this disclosure. For example, groups of such provided components can be, e.g., present in relationship to, e.g., as a ratio with, other one or more, e.g., groups, of provided components. For example, all excipients could be grouped and provided as a ratio to component(s), constituent(s), or groups of either or both component(s) and constituent(s), such as API(s). The parasympathomimetic compound component may be combined with the alpha-2-adrenergic agonist component to form an API component; and further the API component can be present in composition(s) in relationship to, e.g., in a ratio with, one or more other composition component(s), individual constituent(s), or both/combinations thereof. The arrays presented here, and, further, other such array(s) which could be generated by the disclosure herein (such as, e.g., between groups of component(s)/constituent(s)), should be interpreted as disclosing and encompassing any/all ratios which can be generated by the ranges for any such component(s)/constituent(s) provided here and elsewhere herein or which can be established using such disclosure (such as, e.g. when creating groups of components/constituents). Herein where any specific exemplary ratio is provided, composition(s) can also be described by the inverse of any such ratio or similar ratio provided to characterize formulations of certain aspects in this disclosure.

TABLE 1

Exemplary component ratios.

|  | PCC | AAC | PEC | SLC | SPC | DMC | BFC | TNC | PVC | VTC | CLC | PAC | AXC | CRC |
|---|---|---|---|---|---|---|---|---|---|---|---|---|---|---|
| PCC | — | AAC:PCC | PEC:PCC | SLC:PCC | SPC:PCC | DMC:PCC | BFC:PCC | TNC:PCC | PVC:PCC | VTC:PCC | CLC:PCC | PAC:PCC | AXC:PCC | CRC:PCC |
| AAC | PCC:AAC | — | PEC:AAC | SLC:AAC | SPC:AAC | DMC:AAC | BFC:AAC | TNC:AAC | PVC:AAC | VTC:AAC | CLC:AAC | PAC:AAC | AXC:AAC | CRC:AAC |
| PEC | PCC:PEC | AAC:PEC | — | SLC:PEC | SPC:PEC | DMC:PEC | BFC:PEC | TNC:PEC | PVC:PEC | VTC:PEC | CLC:PEC | PAC:PEC | AXC:PEC | CRC:PEC |
| SLC | PCC:SLC | AAC:SLC | PEC:SLC | — | SPC:SLC | DMC:SLC | BFC:SLC | TNC:SLC | PVC:SLC | VTC:SLC | CLC:SLC | PAC:SLC | AXC:SLC | CRC:SLC |
| SPC | PCC:SPC | AAC:SPC | PEC:SPC | SLC:SPC | — | DMC:SPC | BFC:SPC | TNC:SPC | PVC:SPC | VTC:SPC | CLC:SPC | PAC:SPC | AXC:SPC | CRC:SPC |
| DMC | PCC:DMC | AAC:DMC | PEC:DMC | SLC:DMC | SPC:DMC | — | BFC:DMC | TNC:DMC | PVC:DMC | VTC:DMC | CLC:DMC | PAC:DMC | AXC:DMC | CRC:DMC |
| BFC | PCC:BFC | AAC:BFC | PEC:BFC | SLC:BFC | SPC:BFC | DMC:BFC | — | TNC:BFC | PVC:BFC | VTC:BFC | CLC:BFC | PAC:BFC | AXC:BFC | CRC:BFC |
| TNC | PCC:TNC | AAC:TNC | PEC:TNC | SLC:TNC | SPC:TNC | DMC:TNC | BFC:TNC | — | PVC:TNC | VTC:TNC | CLC:TNC | PAC:TNC | AXC:TNC | CRC:TNC |
| PVC | PCC:PVC | AAC:PVC | PEC:PVC | SLC:PVC | SPC:PVC | DMC:PVC | BFC:PVC | TNC:PVC | — | VTC:PVC | CLC:PVC | PAC:PVC | AXC:PVC | CRC:PVC |
| VTC | PCC:VTC | AAC:VTC | PEC:VTC | SLC:VTC | SPC:VTC | DMC:VTC | BFC:VTC | TNC:VTC | PVC:VTC | — | CLC:VTC | PAC:VTC | AXC:VTC | CRC:VTC |
| CLC | PCC:CLC | AAC:CLC | PEC:CLC | SLC:CLC | SPC:CLC | DMC:CLC | BFC:CLC | TNC:CLC | PVC:CLC | VTC:CLC | — | PAC:CLC | AXC:CLC | CRC:CLC |
| PAC | PCC:PAC | AAC:PAC | PEC:PAC | SLC:PAC | SPC:PAC | DMC:PAC | BFC:PAC | TNC:PAC | PVC:PAC | VTC:PAC | CLC:PAC | — | AXC:PAC | CRC:PAC |
| AXC | PCC:AXC | AAC:AXC | PEC:AXC | SLC:AXC | SPC:AXC | DMC:AXC | BFC:AXC | TNC:AXC | PVC:AXC | VTC:AXC | CLC:AXC | PAC:AXC | — | CRC:AXC |
| CRC | PCC:CRC | AAC:CRC | PEC:CRC | SLC:CRC | SPC:CRC | DMC:CRC | BFC:CRC | TNC:CRC | PVC:CRC | VTC:CRC | CLC:CRC | PAC:CRC | AXC:CRC | — |

Abbreviations:
PCC (parasympathomimetic compound component);
AAC (alpha-2-adrenergic agonist component);
PEC (penetration enhancer component);
SLC (solubilization component);
SPC (combination solubilization/penetration enhancer component);
DMC (demulcent component);
BFC (buffer component);
TNC (tonicity component);
PVC (preservative component);
VTC (viscosity/thickening enhancement component);
CLC (chelation component);
PAC (pH adjusting component);
AXC (antioxidant component);
CRC (carrier component).

TABLE 2

Exemplary constituent ratios.

|  | PIL | BRM | BKC | PS80 | CRM | TMT | MAN | GEL | BOR | CIT | ACE | PHS | NCL | CAR |
|---|---|---|---|---|---|---|---|---|---|---|---|---|---|---|
| PIL | — | BRM:PIL | BKC:PIL | PS80:PIL | CRM:PIL | TMT:PIL | MAN:PIL | GEL:PIL | BOR:PIL | CIT:PIL | ACE:PIL | PHS:PIL | NCL:PIL | CAR:PIL |
| BRM | PIL:BRM | — | BKC:BRM | PS80:BRM | CRM:BRM | TMT:BRM | MAN:BRM | GEL:BRM | BOR:BRM | CIT:BRM | ACE:BRM | PHS:BRM | NCL:BRM | CAR:BRM |
| BKC | PIL:BKC | BRM:BKC | — | PS80:BKC | CRM:BKC | TMT:BKC | MAN:BKC | GEL:BKC | BOR:BKC | CIT:BKC | ACE:BKC | PHS:BKC | NCL:BKC | CAR:BKC |
| PS80 | PIL:PS80 | BRM:PS80 | BKC:PS80 | — | CRM:PS80 | TMT:PS80 | MAN:PS80 | GEL:PS80 | BOR:PS80 | CIT:PS80 | ACE:PS80 | PHS:PS80 | NCL:PS80 | CAR:PS80 |

TABLE 2-continued

Exemplary constituent ratios.

|     | PIL | BRM | BKC | PS80 | CRM | TMT | MAN | GEL | BOR | CIT | ACE | PHS | NCL | CAR |
|---|---|---|---|---|---|---|---|---|---|---|---|---|---|---|
| CRM | PIL: CRM | BRM: CRM | BKC: CRM | PS80: CRM | — | TMT: CRM | MAN: CRM | GEL: CRM | BOR: CRM | CIT: CRM | ACE: CRM | PHS: CRM | NCL: CRM | CAR: CRM |
| TMT | PIL: TMT | BRM: TMT | BKC: TMT | PS80: TMT | CRM: TMT | — | MAN: TMT | GEL: TMT | BOR: TMT | CIT: TMT | ACE: TMT | PHS: TMT | NCL: TMT | CAR: TMT |
| MAN | PIL: MAN | BRM: MAN | BKC: MAN | PS80: MAN | CRM: MAN | TMT: MAN | — | GEL: MAN | BOR: MAN | CIT: MAN | ACE: MAN | PHS: MAN | NCL: MAN | CAR: MAN |
| GEL | PIL: GEL | BRM; GEL | BKC: GEL | PS80: GEL | CRM: GEL | TMT: GEL | MAN: GEL | — | BOR: GEL | CIT: GEL | ACE: GEL | PHS: GEL | NCL: GEL | CAR: GEL |
| BOR | PIL: BOR | BRM: BOR | BKC: BOR | PS80: BOR | CRM: BOR | TMT: BOR | MAN: BOR | GEL: BOR | — | CIT: BOR | ACE: BOR | PHS: BOR | NCL: BOR | CAR: BOR |
| CIT | PIL: CIT | BRM: CIT | BKC: CIT | PS80: CIT | CRM: CIT | TMT: CIT | MAN: CIT | GEL: CIT | BOR: CIT | — | ACE: CIT | PHS: CIT | NCL: CIT | CAR: CIT |
| ACE | PIL: ACE | BRM: ACE | BKC: ACE | PS80: ACE | CRM: ACE | TMT: ACE | MAN: ACE | GEL: ACE | BOR: ACE | CIT: ACE | — | PHS: ACE | NCL: ACE | CAR: ACE |
| PHS | PIL: PHS | BRM: PHS | BKC: PHS | PS80: PHS | CRM: PHS | TMT: PHS | MAN: PHS | GEL: PHS | BOR: PHS | CIT: PHS | ACE: PHS | — | NCL: PHS | CAR: PHS |
| NCL | PIL: NCL | BRM: NCL | BKC: NCL | PS80: NCL | CRM: NCL | TMT: NCL | MAN: NCL | GEL: NCL | BOR: NCL | CIT: NCL | ACE: NCL | PHS: NCL | — | CAR: NCL |
| CAR | PIL: CAR | BRM; CAR | BKC: CAR | PS80: CAR | CRM: CAR | TMT: CAR | MAN: CAR | GEL: CAR | BOR: CAR | CIT: CAR | ACE: CAR | PHS: CAR | NCL: CAR | — |

Abbreviations:
PIL (pilocarpine compound(s));
BRM (brimonidine compound(s));
BKC (benzalkonium chloride);
PS80 (polysorbate 80);
CRM (cremophor compound(s));
TMT (tromethamine);
MAN (mannitol);
GEL (gellan gum);
BOR (borate buffer compound(s));
CIT (citrate buffer compound(s));
ACE (acetate buffer compound(s));
PHS (phosphate buffer compound(s));
NCL (sodium chloride (NaCl));
CAR (carrier).

Provided in Table 3 are exemplary amounts of exemplary component(s)/ingredient(s), which in aspects, can be/are present in composition(s) provided by the invention in a ratio with any one or more other component(s)/compound(s) disclosed, wherein such ratios can, in aspects, be a ratio formed by such disclosed amounts.

TABLE 3

Exemplary Ingredients and Exemplary Amounts from Which Ratio(s) Can be Derived

| Component/Compound Description | Exemplary Compound(s) (if component provided) | Exemplary Amount(s) (% w/v) |
|---|---|---|
| Parasympathomimetic compound component | Pilocarpine compound | 0.5-4 |
| Alpha-2-adrenergic agonist component | Brimonidine compound | 0.01-0.5 |
| Penetration enhancer component | Polysorbate 80, Benzalkonium chloride, Polyoxyl hydrogenated castor oil compound(s) | 0.003-5 |
| Solubilization Component | Polysorbate 80, Polyoxyl hydrogenated castor oil compound(s) | 0.05-5 |
| Combination solubilization/penetration enhancer component | Polysorbate 80 | 0.05-5 |
| Demulcent component | Polysorbate 80 | 0.01-5 |
| Buffer component | Acetate compound(s), Phosphate compound(s), citrate compound(s), borate compound(s) | 0.005-1.5 |
| Tonicity component | Sodium chloride, mannitol | 0.005-6 |
| Preservative component | Benzalkonium chloride | 0.0001-0.02 |
| Viscosity/thickening enhancement component | Gellan gum | 0.1-1 |
| Chelation component | EDTA compound(s) | 0.01-0.5 |
| pH adjusting component | Hydrochloric acid (HCl), Sodium hydroxide | Less than 0.1 |
| Antioxidant component | Ascorbate compound(s) | 0.001-2 |
| Carrier Component | Water | At least 60 |
| Pilocarpine compound(s) | Pilocarpine hydrochloride | 0.5-4 |
| Benzalkonium chloride | — | 0.0001-0.02 |
| Polysorbate 80 | — | 0.01-5 |
| Polyoxyl hydrogenated castor oil compound(s) | — | 0.05-0.8 |
| Tromethamine | — | 0.05-0.5 |
| Mannitol | — | 3-6 |
| Gellan gum | — | 0.1-1 |
| Borate buffer compound(s) | Boric acid, sodium borate | 0.5-1.5 |
| Citrate buffer compound(s) | Sodium citrate dihydrate | 0.005-0.4 |
| Acetate buffer compound(s) | Sodium acetate | 0.2-1.5 |
| Phosphate buffer compound(s) | Phosphoric acid | 0.005-1.5 |

TABLE 3-continued

Exemplary Ingredients and Exemplary Amounts
from Which Ratio(s) Can be Derived

| Component/Compound Description | Exemplary Compound(s) (if component provided) | Exemplary Amount(s) (% w/v) |
|---|---|---|
| Sodium Chloride | — | 0.01-0.1 |
| Carrier | Water | At least 60 |

Note:
In aspects, values in Table 3 represent the amounts of each respective component/ingredient's representative percentage by weight/volume (% w/v) of the composition(s). In other aspects, values in Table 3 represent the amounts of each respective component/ingredient's representative percentage by weight/weight (wt. %) of the composition(s).

In aspects, composition(s) herein comprise a ratio of PCC, such as, e.g., a pilocarpine compound, to an AAA component (AAC), such as, e.g., a brimonidine compound, of between about 1:0.01 and about 1:0.2, such as, e.g., ~1:0.01-~1:0.18, ~1:0.01-~1:0.16, ~1:0.01-~1:0.14, ~1:0.01-~1:0.12, ~1:0.01-~1:0.1, ~1:0.08-~1:0.06, ~1:0.01-~1:0.04, or, e.g., ~1:0.01-~1:0.02, such as for example ~1:0.02-~1:0.2, ~1:0.04-~1:0.2, ~1:0.06-~1:0.2, ~1:0.08-~1:0.2, ~1:0.1-~1:0.2, ~1:0.12-~1:0.2, ~1:0.14-~1:0.2, ~1:0.16-~1:0.2, or, e.g., ~1:0.18-~1:0.2, as in, for example, ~1:0.03-~1:0.18, ~1:0.04-~1:0.16, ~1:0.05-~1:0.14, ~1:0.05-~1:0.12, ~1:0.05-~1:0.1, or ~1:0.05-~1:0.08, such as ~1:0.06 or ~1:0.07. In aspects, such composition(s) are provided in the form of a solution.

In aspects, composition(s) herein composition(s) herein comprise a ratio of PCC, such as, e.g., a pilocarpine compound, to an AAA component (AAC), such as, e.g., a brimonidine compound, of between about 1:0.02 and about 1:0.4, such as, e.g., ~1:0.04-~1:0.4, ~1:0.06-~1:0.4, ~1:0.08-~1:0.4, ~1:0.1-~1:0.4, ~1:0.2-~1:0.4, or ~1:0.3-~1:0.4, such as, e.g., ~1:0.04-~1:0.3, ~1:0.04-~1:0.2, ~1:0.04-~1:0.1, ~1:0.04-~1:0.08, or ~1:0.04-~1:0.06, as in, e.g., ~1:0.03-~1:0.3, ~1:0.04-~1:0.2, ~1:0.05-~1:0.1, ~1:0.06-~1:0.9, or, e.g., ~1:0.07-~1:0.09, such as ~1:0.08. In aspects, such composition(s) are provided in the form of a gel.

In aspects, composition(s) herein comprise a ratio of PCC, such as, e.g., a pilocarpine compound, to an AAA component (AAC), such as, e.g., a brimonidine compound, of less than about 1:0.4, such as, e.g., ≤~1:0.3, ≤~1:0.2, ≤~1:0.1, ≤~1:0.09, ≤~1:0.08, or ≤~1:0.07. In aspects, composition(s) herein comprise a ratio of PCC, such as, e.g., a pilocarpine compound, to an AAA component (AAC), such as, e.g., a brimonidine compound, of greater than about 1:0.01, such as, e.g., ≥~1:1.02, ≥~1:1.03, ≥~1:1.04, ≥~1:1.05, ≥~1:1.06, or ≥~1:1.07. In certain aspects, such a composition is provided as a solution. In certain other aspects, such a composition is provided as a gel.

In aspects, composition(s) provided by the invention comprise a ratio of the total amount of API in the composition, consisting of a pilocarpine compound and a brimonidine compound, to the buffer component of about 6.4:about 1 to about 1:about 1.5; such as, e.g., about 3.8:1 to about 1:1.4; e.g., about 1:1, such as ~1.1:1, ~1.2:1, ~1.3:1, ~1.4:1, ~1.5:1, ~1.6:1, ~1.7:1, ~1.8:1, ~1.9:1, or, e.g., about 2:1. In aspects, compositions provided by the invention comprise a ratio of total amount of API in the composition, consisting of a pilocarpine compound and a brimonidine compound, to the buffer component is about 16:about 1-about 1:about 1.5, such as, e.g., about 9.5:1-about 1:1.4, or, e.g., about 5:1, ~4:1, ~3:1, ~2:1, ~1:1, or ~1:1.5, e.g., about 2:1 or about 2.1:1 or about 2.2:1. In aspects, the compositions provided by the invention comprise a ratio of the total amount of API in the composition, consisting of a pilocarpine compound and a brimonidine compound, to the buffer component, of between about 640:about 1 to about 2:about 1, such as, e.g., about 200:1-about 2:1, about 100:1-about 2:1, about 50:1-about 2:1 or, e.g., about 38:about 1-about 5.75:about 1, such as, e.g., ~20:1-~5.75:1, e.g., ~8:1. In aspects, such composition(s) are provided as a solution. In aspects, such composition(s) are provided as a gel.

In aspects, composition(s) provided by the invention comprise a ratio of the total amount of API in the composition, consisting of, e.g., a PCC and an AAA component, e.g., a pilocarpine compound and a brimonidine compound, to a buffer component, of between about 1:0.06-about 1:1.5, such as, e.g., ~1:0.06-~1:1.4, ~1:0.06-~1:1.3, ~1:0.06-~1:1.2, ~1:0.06-~1:1.1, ~1:0.06-~1:1, ~1:0.06-~1:0.09, ~1:0.06-~1:0.08, ~1:0.06-~1:0.07, or, e.g., ~1:0.06-~1:0.06, such as, e.g., ~1:0.07-~1:1.5, ~1:0.08-~1:1.5, ~1:0.09-~1:1.5, ~1:0.1-~1:1.5, ~1:0.2-~1:1.5, ~1:0.3-~1:1.5, ~1:0.4-~1:1.5, ~1:0.5-~1:1.5, or ~1:0.6-~1:1.5, as in, for example, ~1:0.07-~1:1.4, ~1:0.08-~1:1.3, ~1:0.09-~1:1.2, ~1:0.1-~1:1.1, ~1:0.1-~1:1, ~1:0.1-~1:0.9, ~1:0.1-~1:0.8, ~1:0.1-~1:0.7, or ~1:0.1-~1:0.6, such as for example ~1:0.6, ~1:0.5, ~1:0.4, or, ~1:0.1. In aspects, such composition(s) are provided in the form of a solution. In aspects, such composition(s) are provided as a gel.

In aspects, composition(s) provided by the invention comprise a ratio of the total amount of API in the composition, consisting of, e.g., a PCC and an AAA component, e.g., a pilocarpine compound and a brimonidine compound, to a buffer component, of less than about 1:1.5, such as, e.g., ≤~1:1.4, ≤~1:1.3, ≤~1:1.2, ≤~1:1.1, ≤~1:1, ≤~1:0.9, ≤~1:0.8, ≤~1:0.7, or, e.g., ≤~1:0.6. In aspects, composition(s) herein comprise a ratio of the total amount of API in the composition, consisting of, e.g., a PCC and an AAA component, e.g., a pilocarpine compound and a brimonidine compound, to a buffer component, of at least about 1:0.06, such as, e.g., ≥~1:0.08, ≥~1:0.1, ≥~1:0.2, ≥~1:0.3, ≥~1:0.4, ≥~1:0.5, or, e.g., ≥~1:0.6. In certain aspects, such composition(s) are provided in the form of a solution. In aspects, such composition(s) are provided as a gel.

In aspects, composition(s) provided by the invention comprise a ratio of PCC, such as, e.g., a pilocarpine compound, to buffer component, of between about 1:0.001 and about 1:3, such as, e.g., about 1:0.6. In aspects, compositions provided by the invention comprise a ratio of pilocarpine compound to the buffer component of about 6:about 1-about 1:about 2, such as, e.g., about 2:1 or about 1:1, e.g., about 1.1:1, about 1.2:1, about 1.3:1, about 1.4:1, about 1.5:1, about 1.6:1, about 1.7:1, about 1.8:1, or about 1.9:1, e.g., about 1:1.9, about 1:1.8, about 1:1.7, about 1:1.6, about 1:1.5, about 1:1.4, about 1:1.3, about 1:1.2, or, e.g., ~1:1.1, such as, e.g., about 1.25:about 1. In aspects, the ratio of the pilocarpine compound to the buffer component is between about, e.g., about 6:1-about 1:1.5, or, e.g., about 3.4:1-about 1:1.4, such as, e.g., about 1.5:1. In aspects, compositions having such ratios comprise a single buffer component constituent. In aspects, the single buffer constituent is boric acid or sodium borate. In aspects, such composition(s) are provided in the form of a solution. In aspects, such composition(s) are provided as a gel.

In aspects, compositions provided by the invention comprise a ratio of pilocarpine compound to the buffer component of about 600:about 1-about 12:about 1, such as, e.g., about 200:1 or about 50:1, e.g., about 50:1 to about 60:1, e.g., about 51:1, about 52:1, about 53:1, about 54:1, about 55:1, about 56:1, about 57:1, about 58:1, or about 59:1. In aspects, compositions comprise a ratio of pilocarpine compound to the buffer component of about 234:1-about 2.7:1, such as, e.g., about 10:1-about 2.5:1, about 7.5:1. In aspects, compositions having such ratios comprise a single buffer component constituent. In aspects, the single buffer constituent is sodium citrate dihydrate. In aspects, such composition(s) are provided as a solution. In aspects, such composition(s) are provided as a gel.

In aspects, compositions provided by the invention comprise a ratio of pilocarpine compound to the buffer component of about 1:about 1.5 to about 15:about 1, such as, e.g., about 1:1, about 2:1, about 3:1, about 7:1, about 10:1, or about 12:1, or, e.g., about 1.2:1, about 1.3:1, about 1.4:1, about 1.5:1, about 1.6:1, about 1.7:1, about 1.8:1, or about 1.9:1, such as between about 1.6:1 and about 1.7:1. In aspects, compositions provided by the invention comprise a ratio of pilocarpine compound to the buffer component of about 8.5:about 1 to about 1:about 1.4, such as, e.g., about 1:1, about 2:1, or, e.g., about 3:1, such as, e.g., about 2:1. In aspects, compositions having such ratios comprise a single buffer component constituent. In aspects, the single buffer constituent is an acetate buffer. In aspects, the single buffer component is a phosphate buffer. In aspects, such composition(s) are provided as a solution. In aspects, such composition(s) are provided as a gel.

In aspects, composition(s) provided by the invention comprise a ratio of PCC, such as, e.g., a pilocarpine compound, to buffer component, of between about 1:0.06 and about 1:1.5, such as, e.g., ~1:0.06-~1:1.4, ~1:0.06-~1:1.3, ~1:0.06-~1:1.2, ~1:0.06-~1:1.1, ~1:0.06-~1:1, ~1:0.06-~1:0.9, ~1:0.06-~1:0.8, ~1:0.06-~1:0.7, or ~1:0.06-~1:0.6, such as, for example, ~1:0.08-~1:1.5, ~1:0.09-~1:1.5, ~1:0.1-~1:1.5, ~1:0.2-~1:1.5, ~1:0.3-~1:1.5, ~1:0.4-~1:1.5, ~1:0.5-~1:1.5, ~1:0.6-~1:1.5, ~1:0.7-~1:1.5, or ~1:0.8-~1:1.5, as in, for example, ~1:0.08-~1:1.4, ~1:0.09-~1:1.2, ~1:0.1-~1:1, ~1:0.1-~1:0.9, or ~1:0.1-~1:1.8, such as, e.g., ~1:0.1, ~1:0.5, ~1:0.6, or ~1:0.7. In certain aspects, such composition(s) are provided in the form of a solution. In certain aspects, such composition(s) are provided in the form of a gel. In aspects, such ratio(s) can represent a ratio of PCC, e.g., pilocarpine compound, to borate. In aspects, such ratio(s) can represent a ratio of PCC, e.g., pilocarpine compound, to boric acid. In aspects, such ratio(s) can represent a ratio of PCC, e.g., pilocarpine compound, to a citrate buffer/citrate compound. In aspects, such ratio(s) can represent a ratio of PCC, e.g., pilocarpine compound, to an acetate buffer/acetate compound. In aspects, such ratio(s) can represent a ratio of PCC, e.g., pilocarpine compound, to a phosphate buffer/phosphate compound. In aspects, such composition(s) are provided as a solution. In aspects, such composition(s) are provided as a gel.

In aspects, composition(s) provided by the invention comprise a ratio of PCC, such as, e.g., a pilocarpine compound, to buffer component, of at least about 1:0.06, such as, e.g., ≥~1:0.08, ≥~1:0.1, ≥~1:0.2, ≥~1:0.3, ≥~1:0.4, ≥~1:0.5, or ≥~1:0.6. In aspects, composition(s) provided by the invention comprise a ratio of PCC, such as, e.g., a pilocarpine compound, to a buffer component, of less than about 1:1.5, such as, e.g., ≤~1.4, ≤~1.3, ≤~1.2, ≤~1.1, ≤~1, ≤~0.8, ≤~0.6, ≤~0.5, ≤~0.4, or, e.g., ≤~0.2. In certain aspects, such composition(s) are provided in the form of a solution. In certain aspects, such composition(s) are provided in the form of a gel. In aspects, such ratio(s) can represent a ratio of PCC, e.g., pilocarpine compound, to borate. In aspects, such ratio(s) can represent a ratio of PCC, e.g., pilocarpine compound, to boric acid. In aspects, such ratio(s) can represent a ratio of PCC, e.g., pilocarpine compound, to a citrate buffer/citrate compound. In aspects, such ratio(s) can represent a ratio of PCC, e.g., pilocarpine compound, to an acetate buffer/acetate compound. In aspects, such ratio(s) can represent a ratio of PCC, e.g., pilocarpine compound, to a phosphate buffer/phosphate compound. In aspects, such composition(s) are provided as a solution. In aspects, such composition(s) are provided as a gel.

In aspects, composition(s) provided by the invention comprise a ratio of brimonidine compound to the buffer component of about 1:about 2.5-about 1:about 30, such as, e.g., about 1:5, about 1:6, about 1:7, about 1:8, about 1:9, about 1:10, about 1:11, about 1:12, about 1:13, about 1:14, or, e.g., about 1:15, such as, e.g., about 1:10. In aspects, composition(s) provided by the invention comprise a ratio of AAA component, e.g., brimonidine compound, to a buffer component of about 40:about 1 to about 1:about 8, such as, e.g., about 10:1 to about 1:5, such as, e.g., about −4:1, ~3:1, ~2:1, ~1:1, ~1:2, ~1:3, or ~1:4, such as, e.g., about 1:2. In aspects, composition(s) provided by the invention comprise a ratio brimonidine compound to the buffer component of between about 1 to about 1-about 1:about 30, such as, e.g., about 1:1, about 1:2, about 1:3, about 1:4, about 1:5, about 1:6, about 1:7, about 1:8, about 1:9, about 1:10, about 1:11, or, e.g., about 1:12, such as between about 1:5-about 1:10, or, e.g., about 1:7.5. In certain aspects, such composition(s) are provided in the form of a solution. In aspects, such composition(s) are provided as a gel. In aspects, such ratio(s) can represent a ratio of AAC, e.g., brimonidine compound, to borate. In aspects, such ratio(s) can represent a ratio of AAC, e.g., brimonidine compound, to boric acid. In aspects, such ratio(s) can represent a ratio of AAC, e.g., brimonidine compound, to a citrate buffer/citrate compound. In aspects, such ratio(s) can represent a ratio of AAC, e.g., brimonidine compound, to an acetate buffer/acetate compound. In aspects, such ratio(s) can represent a ratio of AAC, e.g., brimonidine compound, to a phosphate buffer/phosphate compound. In aspects, such composition(s) are provided as a solution. In aspects, such composition(s) are provided as a gel.

In aspects, composition(s) provided by the invention comprise a ratio of AAA component (AAC) to buffer component of between about 1:0.01 and about 1:30, such as, e.g., ~1:0.01-~1:25, ~1:0.01-~1:20, ~1:0.01-~1:15, ~1:0.01-~1:12, ~1:0.01-~1:10, ~1:0.01-~1:8, ~1:0.01-~1:6, ~1:0.01-~1:4, or ~1:0.01-~1:2, such as, e.g., ~1:0.015-~1:28, ~1:0.02-~1:28, ~1:0.03-~1:28, ~1:0.04-~1:28, ~1:0.05-~1:28, ~1:0.1-~1:28, ~1:0.5-~1:28, ~1:1-~1:28, ~1:2-~1:28, ~1:5-~1:28, ~1:7.5-~1:28, or, e.g., ~1:10-~1:28, such as, e.g., ~1:0.01-~1:10, ~1:0.015-~1:9, ~1:0.02-~1:8, ~1:0.1-~1:6, ~1:0.5-~1:5, ~1:1-~1:4, ~1:1-~1:3, or, e.g., ~1:2. In aspects, composition(s) provided by the invention comprise a ratio of AAA component (AAC) to buffer component of between about 1:1 and about 1:30, such as, e.g., ~1:1-1:25, ~1:1-1:20, ~1:1-1:15, ~1:1-1:10, ~1:1-1:7.5, ~1:1-~1:5, ~1:1-1:2.5, such as, e.g., ~1:2-~1:30, ~1:3-~1:30, ~1:4-~1:30, ~1:5-~1:30, ~1:6-~1:30, ~1:7-~1:30, ~1:8-~1:30, ~1:9-~1:30, or ~1:10-~1:30, such as, e.g., ~1:2-~1:25, ~1:3-~1:20, ~1:4-~1:15, or ~1:5-~1:10, such as, e.g., ~1:2, ~1:7.5, or, e.g., ~1:10. In certain aspects, such composition(s) are provided in the form of a solution. In aspects, such composition(s) are provided as a gel. In aspects, such ratio(s) can represent a ratio of AAC, e.g., brimonidine compound, to borate. In aspects, such ratio(s) can represent a ratio of AAC, e.g., brimonidine compound, to boric acid. In aspects, such ratio(s) can represent a ratio of AAC, e.g., brimonidine compound, to a citrate buffer/citrate compound. In aspects, such ratio(s) can represent a ratio of AAC, e.g., brimonidine compound, to an acetate buffer/acetate compound. In aspects, such ratio(s) can represent a ratio of AAC, e.g., brimonidine compound, to a phosphate buffer/phosphate compound. In aspects, such composition(s) are provided as a solution. In aspects, such composition(s) are provided as a gel.

In aspects, composition(s) herein comprise a ratio of AAA component (AAC) to buffer component of at least about 0.01, ≥~0.02, ≥~0.05, ≥~0.1, ≥~0.5, ≥~1, ≥~2.5, ≥~5, ≥~7.5, ≥~10, ≥~12.5, ≥~15, ≥~17.5, ≥~20, or ≥~22.5. In aspects, composition(s) herein comprise a ratio of AAA component (AAC) to buffer component of less than about 1:30, such as, e.g., ≤~1:25, ≤~1:20, ≤~1:17.5, ≤~1:15, ≤~1:12.5, ≤~1:10, ≤~1:7.5, ≤~1:5, ≤~1:2.5, ≤~1:1, ≤~1:0.5, ≤~1:0.1, or ≤~1:0.05. In certain aspects, such composition(s) are provided in the form of a solution. In aspects, such composition(s) are provided as a gel. In aspects, such ratio(s) can represent a ratio of AAC, e.g., brimonidine compound, to borate. In aspects, such ratio(s) can represent a ratio of AAC, e.g., brimonidine compound, to boric acid. In aspects, such ratio(s) can represent a ratio of AAC, e.g., brimonidine compound, to a citrate buffer/citrate compound. In aspects, such ratio(s) can represent a ratio of AAC, e.g., brimonidine compound, to an acetate buffer/acetate compound. In aspects, such ratio(s) can represent a ratio of AAC, e.g., brimonidine compound, to a phosphate buffer/phosphate compound. In aspects, such composition(s) are provided as a solution. In aspects, such composition(s) are provided as a gel.

In aspects, composition(s) provided by the invention comprise a ratio of total amount of API of the composition, consisting of a pilocarpine compound and a brimonidine compound, to benzalkonium chloride of about 50 to about 1-about 650:about 1, such as, e.g., about 57:1, about 95:1, about 384:1, or, e.g., about 634:1, such as, e.g., between about 175:1-about 230:1, e.g., about 229:1, about 214:1, about 193:1, about 180:1. In aspects, composition(s) provided by the invention comprise a total amount of API, such as, e.g., an API component comprising a PCC and an AAA component (AAC), such a total amount of API in aspects comprising a pilocarpine compound and a brimonidine compound, wherein the ratio of the total API to preservative component, penetration enhancer component, or both, such as, e.g., a ratio of the total API to a quaternary ammonium salt compound providing one or more such activity(ies), e.g., benzalkonium chloride (e.g., in aspects a total API to benzalkonium chloride ratio), of between about 1:0.0009 and about 1:05, such as, e.g., ~1:0.0009-~1:0.045, ~1:0.0009-~1:0.04, ~1:0.0009-~1:0.03, ~1:0.0009-~1:0.02, ~1:0.0009-~1:0.01, or, e.g., ~1:0.0009-~1:0.005, such as, e.g., ~1:0.001-~1:0.05, ~1:0.002-~1:0.05, ~1:0.003-~1:0.05, ~1:0.004-~1:0.05, or ~1:0.005-~1:0.05, as in, e.g., ~1:0.001-~1:0.01, ~1:0.002-~1:0.009, ~1:0.003-~1:0.008, such as 1:0.004-1:0.007, for example about 1:0.004, 1:0.005, or about 1:0.006. In aspects, such composition(s) are provided as a solution. In aspects, such composition(s) are provided as a gel.

In aspects, composition(s) comprise a ratio of total amount of API to quaternary ammonium salt compound, e.g., benzalkonium chloride, which is at least about 1:0.0009, e.g., ≥~1:0.001, ≥~1:0.0015, ≥~1:0.002, ≥~1:0.0025, ≥~1:0.003, ≥~1:0.0035, ≥~1:0.004, ≥~1:0.0045, ≥~1:0.005, ≥~1:0.0055, or ≥~1:0.006. In aspects, composition(s) comprise a ratio of total amount of API to quaternary ammonium salt compound, e.g., benzalkonium chloride, which is less than about 1:0.05, such as, e.g., ≤~0.04, ≤~0.03, ≤~0.02, ≤~0.01, ≤~0.009, ≤~0.008, ≤~0.007, ≤~0.006, or, e.g., ≤~0.005. In aspects, such composition(s) are provided as a solution. In aspects, such composition(s) are provided as a gel.

In aspects, composition(s) provided by the invention comprise a ratio of pilocarpine compound to benzalkonium chloride of about 1000:about 1-about 50:about 1, such as, e.g., about 567:1, about 367:1, about 85:1, about 55:1, about 50:1, about 150:1, about 330:1, about 400:1, or, e.g., about 215:1-about 167:1, such as, e.g., about 214:1, about 200:1, about 178:1, or about 167:1. In aspects, composition(s) provided by the invention comprise a ratio of PCC, e.g., a pilocarpine compound, to preservative component, penetration enhancer component, or both, such as, e.g., a ratio of the PCC to a quaternary ammonium salt compound providing one or both such activity(ies), e.g., benzalkonium chloride (BKC) (e.g., in aspects, a total pilocarpine compound to BKC ratio), of between about 1:0.001 and about 1:0.04, such as, e.g., ~1:0.001-~1:0.03, ~1:0.001-~1:0.02, ~1:0.001-~1:0.01, ~1:0.001-~1:0.009, ~1:0.001-~1:0.008, ~1:0.001-~1:0.007, or ~1:0.001-~1:0.006, such as, e.g., ~1:0.002-~1:0.04, ~1:0.003-~1:0.04, ~1:0.004-~1:0.04, ~1:0.005-~1:0.04, or ~1:0.006-~1:0.04, as in, e.g., ~1:0.0015-~1:0.02, ~1:0.002-~1:0.01, ~1:0.0025-~1:0.01, ~1:0.003-~1:0.009, or ~1:0.004-~1:0.008, as in, e.g., ~1:0.004, ~1:0.005, or, e.g., ~1:0.006. In aspects, such composition(s) are provided as a solution. In aspects, such composition(s) are provided as a gel.

In aspects, composition(s) provided by the invention comprise a ratio of PCC, e.g., a pilocarpine compound, to quaternary ammonium salt compound, e.g., benzalkonium chloride, which is less than about 1:0.04, such as, e.g., ≤~0.03, ≤~0.02, ≤~0.01, ≤~0.009, ≤~0.008, ≤~0.007, ≤~0.006, or ≤~0.005. In aspects, composition(s) provided by the invention comprise a ratio of PCC, e.g., a pilocarpine compound, to quaternary ammonium salt compound, e.g., benzalkonium chloride, which is greater than about 1:0.001, such as, e.g., ≥~0.0015, ≥~0.002, ≥~0.0025, ≥~0.003, ≥~0.0035, ≥~0.004, ≥~0.0045, such as ≥~0.005. In aspects, such composition(s) are provided as a solution. In aspects, such composition(s) are provided as a gel.

In aspects, composition(s) provided by the invention comprise a ratio of brimonidine compound to benzalkonium chloride of about 2 to about 1-about 70:about 1, such as, e.g., about 2.5:1, about 10:1, about 17:1, or about 67:1, such as, e.g., about 11:1, about 12:1, about 13:1, about 14:1, about 15:1, about 16:1, or, e.g., about 17:1, such as about 13.3:1, or about 14.3:1. In aspects, composition(s) provided by the invention comprise a ratio of AAA component (AAC), e.g., brimonidine compound, to preservative component, penetration enhancer component, or both, such as, e.g., a ratio of the AAC to a quaternary ammonium salt compound providing one or both such activity(ies), e.g. benzalkonium chloride (e.g., in aspects, a total brimonidine compound to benzalkonium chloride ratio), of between about 1:0.015 and about 1:0.4, such as, e.g., ~1:0.015-~1:0.3, ~1:0.015-~1:0.2, ~1:0.015-~1:0.1, ~1:0.015-~1:0.09, ~1:0.015-~1:0.08, or, e.g., ~1:0.015-~1:0.07, such as, e.g., ~1:0.02-~1:0.4, ~1:0.03-~1:0.4, ~1:0.04-~1:0.4, ~1:0.05-~1:0.4, ~1:0.06-~1:0.4, or ~1:0.07-~1:0.4, as in, for example, ~1:0.02-~1:0.3, ~1:0.03-~1:0.2, ~1:0.04-~1:0.1, ~1:0.05-~1:0.09, or ~1:0.06-~1:0.08, such as, e.g., ~1:0.07 or about 1:0.075. In aspects, such composition(s) are provided as a solution. In aspects, such composition(s) are provided as a gel.

In aspects, composition(s) provided by the invention comprise a ratio of AAA component (AAC), e.g., brimonidine compound, to quaternary ammonium salt compound, e.g., benzalkonium chloride, which is at least about 1:0.015, such as, e.g., ≥~1:0.02, ≥~1:0.03, ≥~1:0.04, ≥~1:0.05, ≥~1:0.06, or ≥~1:0.07. In aspects, composition(s) provided by the invention comprise a ratio of quaternary ammonium salt. e.g., benzalkonium chloride, to brimonidine compound, of at least about 1:3, such as, e.g., ≥~1:3.5, ≥~1:4, ≥~1:4.5, ≥~1:5, ≥~1:5.5, ≥~1:6, ≥~1:6.5, ≥~1:7, ≥~1:7.5, or, e.g., ≥~1:8.

In aspects, composition(s) provided by the invention comprise a ratio of AAA component (AAC), e.g., brimonidine compound, to quaternary ammonium salt compound, e.g., benzalkonium chloride, which is less than about 1:0.4, such as, e.g., ≤~1:0.3, ≤~1:0.2, ≤~1:0.1, ≤~1:0.09, ≤~1:0.085, or ≤~1:0.08. In aspects, such composition(s) are provided as a solution. In aspects, such composition(s) are provided as a gel.

According to aspects, composition(s) provided by the invention comprise a ratio of total API (e.g., total API comprising a PCC (e.g., a pilocarpine compound) and an AAA component (AAC) (e.g., a brimonidine compound)) to tonicity component, e.g., sodium chloride, of between about 1:0.001 and about 1:0.1, such as, e.g., ~1:0.001-~1:0.095, ~1:0.001-~1:0.09, ~1:0.001-~1:0.08, ~1:0.001-~1:0.07, ~1:0.001-~1:0.06, or ~1:0.001-~1:0.05, such as, e.g., ~1:0.002-~1:0.1, ~1:0.004-~1:0.1, ~1:0.006-~1:0.1, ~1:0.008-~1:0.1, ~1:0.01-~1:0.1, ~1:0.02-~1:0.1, ~1:0.03-~1:0.1, ~1:0.04-~1:0.1, ~1:0.05-~1:0.1, or ~1:0.06-~1:0.1, such as, e.g., ~1:0.002-~1:0.09, ~1:0.004-~1:0.08, ~1:0.005-~1:0.05, or ~1:0.01-~1:0.04, as in, e.g., ~1:0.006, ~1:0.007, ~1:0.04, or ~1:0.05. In aspects, such composition(s) are provided as a solution. In aspects, such composition(s) are provided as a gel.

In aspects, composition(s) provided herein comprise a ratio of total API to tonicity component, e.g., sodium chloride, which is at least about ≥~1:0.001, such as, e.g., ≥~1:0.002, ≥~1:0.004, ≥~1:0.006, ≥~1:0.008, ≥~1:0.01, ≥~1:0.02, ≥~1:0.03, or ≥~1:0.04. In aspects, composition(s) provided herein comprise a ratio of total API to tonicity component, e.g., sodium chloride, which is less than about 1:0.1, such as, e.g., ≤~1:0.08, ≤~1:0.07, ≤~1:0.06, ≤~1:0.05, ≤~1:0.04, ≤~1:0.03, ≤~1:0.02, ≤~1:0.01, ≤~1:0.008, ≤~1:0.007, or, e.g., ≤~1:0.006. In aspects, such compositions are provided as a solution. In aspects, such composition(s) are provided as a gel.

In aspects, composition(s) provided by the invention comprise a ratio of PCC, e.g. pilocarpine compound, to tonicity component, e.g., sodium chloride, of between about 1:0.001 and about 1:0.1, such as, e.g., ~1:0.001-~1:0.095, ~1:0.001-~1:0.09, ~1:0.001-~1:0.08, ~1:0.001-~1:0.07, ~1:0.001-~1:0.06, or ~1:0.001-~1:0.05, such as, e.g., ~1:0.002-~1:0.1, ~1:0.004-~1:0.1, ~1:0.006-~1:0.1, ~1:0.008-~1:0.1, ~1:0.01-~1:0.1, ~1:0.02-~1:0.1, ~1:0.03-~1:0.1, ~1:0.04-~1:0.1, ~1:0.05-~1:0.1, or ~1:0.06-~1:0.1, such as, e.g., ~1:0.002-~1:0.09, ~1:0.004-~1:0.08, ~1:0.005-~1:0.05, or ~1:0.01-~1:0.04, as in, e.g., ~1:0.006, ~1:0.007, ~1:0.04, or ~1:0.05. In aspects, such composition(s) are provided as a solution. In aspects, such composition(s) are provided as a gel.

In aspects, composition(s) provided by the invention comprise a ratio of PCC, e.g., pilocarpine compound, to tonicity component, e.g., sodium chloride, which is at least about 1:0.001, such as, e.g., ≥~1:0.003, ≥~1:0.005, ≥~1:0.007, ≥~1:0.01, ≥~1:0.02, ≥~1:0.03, ≥~1:0.04, or ≥~1:0.05. In aspects, composition(s) provided by the invention comprise a ratio of PCC, e.g., pilocarpine compound, to tonicity component, e.g., sodium chloride, which less than about 1:0.1, such as, e.g., ≤1:0.09, ≤1:0.08, ≤1:0.07, ≤1:0.06, ≤1:0.05, ≤1:0.04, ≤1:0.03, ≤1:0.02, ≤1:0.01, or, e.g., ≤1:0.007, ≤1:0.006, or ≤1:0.005. In aspects, such composition(s) are provided as a solution. In aspects, such composition(s) are provided as a gel.

In aspects, composition(s) provided by the invention comprise a ratio of AAA component (AAC), e.g., a brimonidine compound, to tonicity component, e.g., sodium chloride, which between about 1:0.02 and about 1:2, such as, e.g., ~1:0.02-~1:2, ~1:0.04-~1:2, ~1:0.06-~1:2, ~1:0.08-~1:2, ~1:0.1-~1:2, ~1:0.2-~1:2, ~1:0.4-~1:2, ~1:0.6-~1:2, ~1:0.8-~1:2, or ~1:1-~1:2, such as, e.g., ~1:0.02-~1:1.5, ~1:0.02-~1:1.4, ~1:0.02-~1:1.2, ~1:0.02-~1:1, ~1:0.02-~1:0.8, ~1:0.02-~1:0.6, ~1:0.02-~1:0.4, ~1:0.02-~1:0.2, or ~1:0.02-~1:0.1, as in, e.g., ~1:0.04-~1:1.5, ~1:0.06-~1:1, ~1:0.08-~1:0.8, or ~1:0.1-~1:0.7, such as, for example, about 1:0.1, about 1:0.8, or, e.g., about 1:0.7. In aspects, such composition(s) are provided as a solution. In aspects, such composition(s) are provided as a gel.

In aspects, composition(s) provided by the invention comprise a ratio of AAA component (AAC), e.g., a brimonidine compound, to tonicity component, e.g., sodium chloride, which is at least about 1:0.02, such as, e.g., ≥~1:0.04, ≥~1:0.06, ≥~1:0.08, ≥~1:0.1, ≥~1:0.2, ≥~1:0.3, ≥~1:0.4, ≥~1:0.5, ≥~1:0.6, ≥~1:0.7, or, e.g., ≥~1:0.8. In aspects, composition(s) provided by the invention comprise a ratio of AAA component (AAC), e.g., brimonidine compound, to tonicity component, e.g., sodium chloride, which is at least about 1:1, such as, e.g., at least about 1:1.05, ≥~1:1.1, ≥~1:1.15, ≥~1:1.2, ≥~1:1.25, ≥~1:1.3, ≥~1:1.35, ≥~1:1.4, ≥~1:1.45, or, e.g., ≥1:1.5. 1: In aspects, composition(s) provided by the invention comprise a ratio of AAA component (AAC), e.g., brimonidine compound, to tonicity component, e.g., sodium chloride, which less than about 1:2, such as, e.g., ≤~1:1.5, ≤~1:1.3, ≤~1:1.1, ≤~1:1, ≤~1:0.8, ≤~1:0.7, ≤~1:0.6, ≤~1:0.5, ≤~1:0.4, ≤~1:0.3, ≤~1:0.2, or, e.g., ≤~1:0.1. In aspects, such composition(s) are provided as a solution. In aspects, such composition(s) are provided as a gel.

In aspects, composition(s) provided by the invention comprise a ratio of tonicity component, e.g., sodium chloride, to a preservative component, penetration enhancer component, or both, such as, e.g., a ratio of the tonicity component to a quaternary ammonium salt compound providing one or both such activity(ies), e.g., benzalkonium chloride (e.g., in aspects, a ratio of sodium chloride to benzalkonium chloride) of between about 1:0.03 and about 1:4, such as, e.g., ~1:0.03-~1:3, ~1:0.03-~1:2, ~1:0.03-~1:1, ~1:0.03-~1:0.8, ~1:0.03-~1:0.6, ~1:0.03-~1:0.4, ~1:0.03-~1:0.2, ~1:0.03-~1:0.1, or ~1:0.03-~1:0.09, such as, e.g., ~1:0.04-~1:4, ~1:0.06-~1:4, ~1:0.08-~1:4, ~1:0.1-~1:4, ~1:0.2-~1:4, ~1:0.6-~1:4, ~1:0.8-~1:4, ~1:1-~1:4, as in, for example, ~1:0.04-~1:3, ~1:0.06-~1:2, ~1:0.07-~1:1, ~1:0.08-~1:0.9, or ~1:0.1-~1:0.8, e.g., ~1:0.1, ~1:0.7, or, e.g., ~1:0.8. In aspects, such composition(s) are provided as a solution. In aspects, such composition(s) are provided as a gel.

In aspects, composition(s) provided by the invention comprise a ratio of tonicity component, e.g., sodium chloride, to quaternary ammonium salt compound, e.g., benzalkonium chloride, which is at least about 1:0.03, such as, e.g., ≥~0.04, ≥~0.06, ≥~0.08, ≥~0.1, ≥~0.2, ≥~0.6, ≥~0.7, or, e.g., ≥~0.8. In aspects, composition(s) provided by the invention comprise a ratio of tonicity component, e.g., sodium chloride, to quaternary ammonium salt, e.g., benzalkonium chloride, which is less than about 1:4, such as, e.g., ≤~1:3, ≤~1:2, ≤~1:1, ≤~1:0.8, ≤~1:0.7, ≤~1:0.6, ≤~1:0.5, ≤~1:0.4, ≤~1:0.3, ≤~1:0.2, or, e.g., ≤~1:0.1. In aspects, such composition(s) are provided as a solution. In aspects, such composition(s) are provided as a gel.

In aspects, composition(s) provided by the invention comprise a ratio of pilocarpine compound to penetration enhancer component of about 430:about 1-about 4:about 1, such as, e.g., about 400:1, about 300:1, about 200:1, about 243:1, about 227:1, about 150:1, 145:1, about 133:1, or, e.g., about 20:1, about 16:1, about 12:1, or less than about 10:1, such as, e.g., about 9:1, ~8:1, ~7:1, ~6:1, ~5:1, or, e.g., ~4:1. In aspects, composition(s) can comprise, for example, any one or more of polysorbate 80, benzalkonium chloride, cremophor, or, e.g., tromethamine. In aspects, one or more of polysorbate 80, benzalkonium chloride, cremophor, or, e.g., tromethamine provide detectable or significant penetration enhancement activity.

In aspects, composition(s) provided by the invention comprise a ratio of brimonidine compound to penetration enhancer component of about 30:about 1 to about 1:about 15, such as, e.g., about 29:1, about 27:1, about 7:1, or, e.g., about 1:10, about 1:5, about 1:3, or, e.g., about 1:1. In aspects, compositions can comprise, for example, any one or more of polysorbate 80, benzalkonium chloride, cremophor, or, e.g., tromethamine. In aspects, one or more of polysorbate 80, benzalkonium chloride, cremophor, or, e.g., tromethamine provide detectable or significant penetration enhancement activity.

In aspects, composition(s) provided by the invention comprise a ratio of total amount of API in the composition, consisting of a pilocarpine compound and a brimonidine compound, to penetration enhancer component of about 460:1 to about 1:1, such as, e.g., about 430:1, about 350:1, about 300:1, about 275:1, about 250:1, about 200:1, about 175:1, about 160:1, about 150:1, about 140:1, or, about 120:1, about 100:1, about 75:1, about 50:1, or, e.g., less than about 20:1, e.g., ~18:1, ~16:1, ~14:1, ~12:1, ~10:1, ~8:1, ~6:1, ~4:1, ~2:1, or, e.g., about 1:1. In aspects, composition (s) can comprise, for example, any one or more of polysorbate 80, benzalkonium chloride, cremophor, or, e.g., tromethamine. In aspects, one or more of polysorbate 80, benzalkonium chloride, cremophor, or, e.g., tromethamine provide detectable or significant penetration enhancement activity.

In certain specific aspects, composition(s) comprise one or more polyethoxylated castor oil(s), e.g., cremophor. In aspects, composition(s) comprise a ratio of polyethoxylated castor oil(s) to brimonidine of, e.g., between about 1:0.06 and about 1:4, such as, e.g., ~1:0.06-~1:3, ~1:0.06-~1:2, or, e.g., ~1:0.06-~1:1, as in, e.g., ~1:0.08-~1:4, ~1:1-~1:4, ~1.5-~1:4, ~1:2-~1:4, ~1:2.5-~1:4, or, e.g., ~1:3-~1:4, such as, e.g., ~1:0.08-~1:3.5, ~1:0.09-~1:3, ~1:0.1-~1:2.5, ~1:0.2-~1:2, or, e.g., ~1:0.2-~1:1, ~1:0.2-~1:0.5, such as, e.g., ~1:0.4. In aspects, such composition(s) are provided as a gel.

Additional Means/Steps for Performing Functions

In aspects, composition(s) provided by the invention comprise one or more means for performing one or more specific functions and methods of the invention include steps for performing functions. In general, any element described herein as a "means" for performing a function can also, wherever suitable, serve as a "step for" performing a function in the context of methods of the invention, and vice versa. E.g., a component described herein as a means for preserving a composition also simultaneously and implicitly supports a method of making such a composition comprising a step of preserving a composition and a kit comprising a means for delivering a composition implicitly and simultaneously provides a step for delivering the composition comprising the use of such delivery means.

In one aspect, composition(s) provided by the invention comprise means for enhancing penetration of one or more composition constituents, in aspects such means for penetration enhancement detectably or significantly improving the penetration into an eye tissue of one or more active pharmaceutical ingredients, e.g., PCC constituent, AAA component constituent, or both, e.g., pilocarpine compound, e.g., salt of pilocarpine, e.g., pilocarpine hydrochloride, brimonidine compound, e.g., salt of brimonidine, e.g., brimonidine tartrate, or both ("penetration enhancement means"). Support for penetration enhancement means can be found in, e.g., the section entitled "Penetration Enhancer Component (Penetration Enhancer(s))."

In one aspect, composition(s) provided by the invention comprise means for solubilization of one or more composition constituents, in aspects such means for solubilization detectably or significantly improving the solubilization of one or more composition constituents, e.g., one or more active pharmaceutical ingredients, e.g., PCC constituent, AAA component constituent, or both, e.g., pilocarpine compound, e.g., salt of pilocarpine, e.g., pilocarpine hydrochloride, brimonidine compound, e.g., salt of brimonidine, e.g., brimonidine tartrate, or both, detectably or significantly maintaining the solubilization of one or more composition constituents for a detectably or significantly longer period of time, or both ("solubilization means"). Support for solubilization means can be found in, e.g., the section entitled "Solubilization Component (Solubilizing Agent(s))."

In one aspect, composition(s) provided by the invention comprise means for solubilization of one or more composition constituents, in aspects such means for solubilization detectably or significantly improving the solubilization of one or more composition constituents, e.g., one or more active pharmaceutical ingredients, e.g., PCC constituent, AAA component constituent, or both, e.g., pilocarpine compound, e.g., salt of pilocarpine, e.g., pilocarpine hydrochloride, brimonidine compound, e.g., salt of brimonidine, e.g., brimonidine tartrate, or both, in aspects such means detectably or significantly maintaining the solubilization of one or more composition constituents for a detectably or significantly longer period of time (than substantially similar or identical compositions lacking such means—substantially similar in this respect and in some aspects typically meaning either about the same amount, same amount, or significantly similar amount of most, generally all, essentially all or all relevant ingredients), or both, and, further or alternatively, in aspects, detectably or significantly improving the penetration into an eye tissue of one or more active pharmaceutical ingredients, e.g., PCC constituent, AAA component constituent, or both, e.g., pilocarpine compound, e.g., salt of pilocarpine, e.g., pilocarpine hydrochloride, brimonidine compound, e.g., salt of brimonidine, e.g., brimonidine tartrate, or both ("penetration enhancement and solubilization means"). Support for penetration enhancement and solubilization means can be found in, e.g., the section entitled "Combination Solubilization/Penetration Enhancer Component (Solubilizing Agent(s)/Penetration Enhancer(s))."

In one aspect, composition(s) provided by the invention comprise means for soothing irritation caused by one or more composition constituents, such means for soothing detectably or significantly reducing or preventing irritation or inflammation caused by one or more composition constituents ("demulcent means"). Support for demulcent means can be found in, e.g., the section entitled "Demulcent Component (Demulcent(s))."

In aspects, composition(s) provided by the invention comprise a means of buffering a composition, in aspects such a means capable of maintaining the pH of compositions between about 3 to about 6 for an extended period of time, e.g., at least about 1 month, ~3 months, ~6 months, ~12 months, ~18 months, ~24 months, or, e.g., at least about 36 months when stored at room temperature. In certain aspects, compositions provided by the invention lack such a means of buffering pH ("buffering means"). In aspects, such buffering means are described in, e.g., the section entitled "Buffer Component (Buffer(s))."

In one aspect, composition(s) provided by the invention comprise means for providing a suitable tonicity of the composition(s), providing a suitable osmolality of the composition(s), e.g., means for providing composition(s) which, in aspects, do not cause detectable or significant ocular irritation due to tonicity when provided according to instructions ("tonicity means"). Support for tonicity means can be found in, e.g., the section entitled "Tonicity Component (Tonicity Agent(s))."

In one aspect, composition(s) provided by the invention comprise means for preserving the composition(s), e.g., detectably or significantly inhibiting microbial growth, in aspects detectably or significantly reducing the number of impurities or detectably or significantly improving the stability of the compositions such that compositions remain safe and suitable for administration after storage of at least about 1 month, e.g., ~2 months, or e.g., ~3 months or more after manufacturing at room temperature (25° C. and about 60% relative humidity) ("preservation means"). Support for preservation means can be found in, e.g., the section entitled "Preservative Component (Preservation Agent(s))."

In one aspect, composition(s) provided by the invention comprise means for increasing viscosity, such means for viscosity enhancement in aspects detectably or significantly increasing the thickness or viscosity of a composition, or, e.g., detectably or significantly modifying the nature of the composition such as, e.g., providing the composition as a gel ("viscosity enhancer means" or "thickening means"). Support for viscosity enhancer/thickening means can be found in, e.g., the section entitled "Viscosity Enhancer/Thickening Component (Viscosity Enhancing Agent(s)/Thickening Agent(s))."

In one aspect, composition(s) provided by the invention comprise means for chelation, in aspects such means for chelation detectably or significantly improving the stability of one or more active pharmaceutical ingredients, e.g., one or more PCC constituents, AAA constituent, or both, e.g., pilocarpine compound, e.g., salt of pilocarpine, e.g., pilocarpine hydrochloride, brimonidine compound, e.g., salt of brimonidine, e.g., brimonidine tartrate, or both, detectably enhancing the effectiveness of one or more preservatives, or any combination thereof ("chelation means"). Support for chelation means can be found in, e.g., the section entitled "Chelation Component (Chelating Agent(s))."

In one aspect, composition(s) provided by the invention comprise means for adjusting the pH of the composition(s), in aspects providing a suitable or target pH of the composition(s) of between about, e.g., 3-about 8.5, e.g., between about 3-about 5.5, or, e.g., between about 5-about 8.5 ("pH adjusting means"). Support for pH adjusting means can be found in, e.g., the section entitled "pH Adjusting Component (pH Adjusting Agent(s)).

In one aspect, composition(s) provided by the invention comprise means for protecting API(s) from oxidation, e.g., means for providing antioxidant protection of API(s), such means for antioxidant protection of API(s) which in aspects detectably or significantly improving the stability of the one or more pilocarpine compound(s), brimonidine compound(s), or both, detectably or significantly reducing impurities detected at time points 2 weeks, 1 months, 2 months, or 3 months or more (e.g., 6, 12, 18, 24, or 36 months) after manufacturing, or any combination thereof ("antioxidant means"). Support for antioxidant means can be found in, e.g., the section entitled "Antioxidant Component (Antioxidant(s))."

In one aspect, composition(s) provided by the invention comprise means for providing compositions of the invention as liquid compositions (e.g., solutions, gels, etc.), e.g., providing a carrier for the API(s) and any one or more other excipients of the composition(s) ("carrier means"). Support for carrier means can be found in, e.g., the section entitled "Carrier Component (Carrier Agent(s))."

COMPOSITION CHARACTERISTICS

Lacking Borate Buffer, Citrate Buffer, or Both Buffer(s)

In certain specific aspects, composition(s) provided by the invention are characterizable as being free of boric acid, free of sodium borate, free of sodium citrate (e.g., sodium citrate dihydrate), or free of any borate buffer, citrate buffer, or any or all thereof. In particular, in aspects, the invention provides pharmaceutically acceptable and ophthalmologically suitable composition(s) comprising pilocarpine compound(s), e.g., pilocarpine HCl, and brimonidine compound(s), e.g., brimonidine tartrate, wherein the composition is free of borate (boric acid or sodium borate) buffer(s). In other particular aspects, the invention provides pharmaceutically acceptable and ophthalmologically suitable composition(s) comprising pilocarpine compound(s), e.g., pilocarpine HCl, and brimonidine compound(s), e.g., brimonidine tartrate, wherein the composition is free of citrate buffer(s). In still further particular aspects, the invention provides pharmaceutically acceptable and ophthalmologically suitable composition(s) comprising pilocarpine compound(s), e.g., pilocarpine HCl, and brimonidine compound(s), e.g., brimonidine tartrate, wherein the composition is free of both boric acid or sodium borate buffer(s) and citrate buffer(s).

In one general aspect, the invention provides pharmaceutically acceptable and ophthalmologically suitable composition(s) comprising a pilocarpine compound, a brimonidine compound, and one or more pharmaceutically acceptable excipients, such as, e.g., one or more of a penetration-enhancer, preservative, chelating agent, tonicity agents, buffers or pH-adjusting agent, preservatives, and water, or some, most, substantially all, or all thereof, wherein the composition(s) is/are free of boric acid or sodium borate or citrate buffers. In one aspect, the invention provides pharmaceutically acceptable and ophthalmologically suitable ophthalmic composition(s) comprising a pilocarpine compound and a brimonidine compound and one or more pharmaceutically acceptable excipients, wherein the composition(s) is/are free of boric acid or sodium borate or citrate buffers and maintains a pH of about 3 to about 8.5, such as, e.g., specifically a targeted pH range of about 3 to about 5.5, or, alternatively, a targeted pH range of about 5 to about 8.5, for a period of at least about 1 month.

In a further specific aspect, the invention provides pharmaceutically acceptable and ophthalmologically suitable ophthalmic composition(s) comprising a pilocarpine compound, e.g., pilocarpine HCl, in a concentration of about 1% w/v to about 3% w/v, a brimonidine compound, e.g., brimonidine tartrate, in a concentration of about 0.05% w/v to about 0.2% w/v, boric acid in a concentration of about 0.5% w/v to about 1.5% w/v, one or more tonicity agent(s) in a concentration of about 0.01% w/v to about 0.1% w/v, benzalkonium chloride in an amount of about 0.003% to about 0.02% w/v, water, and one or more buffers or pH-adjusting agents, wherein the composition(s) is/are free of citrate buffer, e.g., free of sodium citrate. In another specific aspect, the invention provides pharmaceutically acceptable and ophthalmologically suitable ophthalmic composition(s) comprising a pilocarpine compound, e.g., a salt of pilocarpine, e.g., pilocarpine hydrochloride, in a concentration from about 1.0% w/v to 3.0% w/v, a brimonidine compound, e.g., brimonidine tartrate, in a concentration of about 0.05% w/v to about 0.2% w/v, sodium citrate in a concentration from about 0.005% w/v to about 0.4% w/v, one or more tonicity agent(s) in a concentration from about 0.01% w/v to about 0.1% w/v, benzalkonium chloride in an amount from about 0.003% to about 0.02% w/v, water, and one or more buffers or pH-adjusting agents, wherein the composition(s) is/are free of boric acid. In certain aspects, such composition(s) can comprise sodium citrate dihydrate in an amount of about 0.005% w/v to about 0.4% w/v. In another specific aspect, the invention provides pharmaceutically acceptable and ophthalmologically suitable ophthalmic composition(s) comprising a pilocarpine compound, e.g., pilocarpine HCl, in a concentration of about 1.0% w/v to 3.0% w/v, a brimonidine compound, e.g., brimonidine tartrate, in a concentration of about 0.05% w/v to about 0.2% w/v, optionally a penetration enhancer in a concentration from about 0.1% w/v to about 3.0% w/v, one or more tonicity agent(s) in a concentration of about 0.01% w/v to about 0.1% w/v, benzalkonium chloride in an amount from about 0.003% to about 0.02% w/v, water, and one or more buffers or pH-adjusting agents, wherein the composition(s) is/are free of boric acid, sodium borate, or citrate buffers. In aspects, composition(s) free of both a boric acid or sodium borate buffer and a citrate buffer comprise(s) a buffer component comprising a single buffer constituent, such as, e.g., an acetate buffer or a phosphate buffer.

In aspects, the invention provides pharmaceutically acceptable and ophthalmologically suitable composition(s) for treating one or more ocular condition(s) comprising a pilocarpine compound, e.g., a salt of pilocarpine, e.g., pilocarpine hydrochloride, in an amount of about 1% w/v-about 3% w/v; a brimonidine compound, e.g., a salt of brimonidine, e.g., brimonidine tartrate; a solubilization component in an amount of between about 0.1% w/v-about 0.7% w/v; a preservation component in an amount of about 0.003% w/v-about 0.02% w/v; a tonicity component in an amount of between about 3.5% w/v-about 5.5% w/v; and a viscosity enhancement component (thickening component) in an amount of about 0.1% w/v-about 1% w/v, wherein the composition(s) is/are free of boric acid, sodium borate, or citrate buffers. In aspects, the composition(s) further comprise(s) a buffer component, wherein the buffer component is free of boric acid, sodium borate, or citrate buffers, however, comprises a single alternative buffer constituent, such as, e.g., an acetate buffer or a phosphate buffer.

Ready-to Use (RTU)

In aspects, composition(s) provided by the invention are provided in ready-to-use (RTU) form, and do not require dilution or further modification prior to administration. In aspects, composition(s) is/are stored in a healthcare setting and is/are ready for immediate administration to a subject, such as a human patient. In aspects, the composition(s), is/are stored in a home setting, and is/are ready for immediate administration to a subject.

In aspects, composition(s) provided by the invention are fixed-dose composition(s), such fixed-dose composition(s) comprising a PCC and an AAA component, such as, e.g., comprising a pilocarpine compound and a brimonidine compound.

pH

Uncontradicted, as used herein, the term "pH" is the conventional measurement unit of hydrogen ion activity in a solution at room temperature (about 25° C.).

In aspects, composition(s) provided by the invention have a pH of between about 3 and about 8.5, such as, e.g., ~3-~8, ~3-~7.5, ~3-~7, ~3-~6.5, ~3-~6, ~3-~5.5, or ~3-~5, such as, e.g., ~3.5-~8.5, ~4-~8.5, ~4.5-~8.5, ~5-~8.5, ~5.5-~8.5, or ~6-~8.5.

In aspects, composition(s) provided by the invention have a pH of about 3 to about 6, such as, e.g., ~3.5-~6, ~4-~6, ~4.5-~6, or ~5-~6, e.g., ~3-~5.5, ~3-~5, ~3-~4.5, or ~3-~4, such as, e.g., ~3.5-~5.5, ~4-~5, or, e.g., about 4 to ~4.5, or, e.g., ~4-~6, ~4.5-~6, ~5-~6, or, e.g., ~5-~5.5, such as about 5.

In aspects, composition(s) provided by the invention have a pH of about 5 to about 8.5, such as, e.g., ~5.5-~8.5, ~6-~8.5, ~6.5-~8.5, ~7-~8.5, ~7.5-~8.5, or, e.g., ~8-~8.5, such as, for example, ~5-~8, ~5-~7.5, ~5-~7, ~5-~6.5, ~5-~6, or, e.g., ~5-~5.5.

In aspects, composition(s) comprise a pH of, e.g., ~4-~7, ~5-~6, ~5.2-~5.7, ~7-~8, or, e.g., ~7.2-~7.6.

In aspects, the pH of the composition(s) provided by the invention, such as, e.g., pilocarpine and brimonidine compound composition(s), will be affected by the concentration of each of the ingredients during manufacturing. Hence, in aspects, the pH of the composition(s) can be adjusted during manufacturing to attain the target pH ranges described above, such as, e.g., ~3-~8.5, such as ~3-~6, or alternatively ~5-~8.5. In aspects, the pH of composition(s) provided by the invention is maintained from the time of establishment during manufacturing (e.g., the final pH adjustment during manufacturing or, e.g., the pH at the time of packaging) to the time of administration to the recipient mammalian eye when stored at controlled room temperature, e.g., at a temperature of about 15° C. to 25° C.+/−2° C., for a period of at least about 1 month, such as, e.g., for a period of about 1-about 36 months or more.

In aspects, one or more characteristics of the composition(s) described in this disclosure, such as, e.g., viscosity, efficacy, etc. is detectably or significantly different, such as, e.g., statistically significantly different, at the composition's pH as compared to an at least generally equivalent, at least substantially equivalent, at least essentially equivalent, or equivalent (in terms of API(s) present, excipient(s) present, amounts of API(s) present, amount(s) of excipient(s) present, or a combination thereof) second composition provided at a second pH (a reference composition having a pH that is different by +about 0.7 pH units, +about 1 pH units, +~1.2 pH units, +~1.5 pH units, +~1.7 pH units, +~2 pH units, or +~2.5 pH units as compared to the composition of the invention). For example, in an aspect, a composition of the invention has a relatively low pH of about 3-5, 3.5-5, 3.8-5, 4-5, 4.2-5, or about 4.5-5, such as about 3-4.5, 3-4.2, 3-4, or 3-4.8 or ~4-4.8, ~4-4.5, ~3.5-4.5, or ~3.2-4.2 or ~3.2-~4.6 (e.g., a pH of about 4.5 or about 5) and exhibits one or more statistically significant functional or physiologically different characteristics (e.g., retention of one or more API(s) in tissue(s)), as compared to a substantially identical/equivalent composition having a pH that is at least 1, at least 1.5, at least 2, at least 2.2, at least 2.4, or at least 2.7 pH units higher than the inventive composition (e.g., a pH of greater than 6.5, greater than 6.7, or about 7 or higher). In aspects, composition(s) comprise one or more characteristic(s) such as, e.g., viscosity, efficacy, etc. which is detectably or significantly different from other composition(s) wherein the only difference between such first and second compositions is in the pH of the composition(s); the amount of pH adjusting agent(s) present in each composition; the amount of tonicity agent(s) present in each composition; the tonicity agent(s) itself/themselves present in each composition; or, e.g., a combination thereof. Improved properties of such composition, as also further exemplified described herein, reflect one of the unexpected/surprising aspects of certain compositions of the invention.

In aspects, a first composition and a second composition can have pH levels which differ by least about, e.g., ≥~10%, ≥~15%, ≥~15%, ≥~20%, ≥~25%, ≥~30%, ≥~35%, ≥~40%, ≥~45%, ≥~50%, ≥~55%, or, e.g., ≥~60%, such as ≥~65%, ≥~70%, ≥~75%, ≥~80%, ≥~85%, ≥~90%, ≥~95%, or, e.g., ≥~100% higher, such as, e.g., ≥~110%, ≥~120%, ≥~130%, ≥~140%, ≥~150%, ≥~160%, ≥~170%, or, e.g., ≥~180%, as compared to one or more reference compositions (e.g., compositions disclosed in any of the patent references cited and incorporated herein), such as a second/reference composition having a pH which is higher or lower than another composition by such an amount. In aspects, a first composition and a second composition can have pH levels which differ from one another by, e.g., between about 10% and about 180%, such as, e.g., ~10%-~160%, ~10%-~140%, ~10%-~120%, ~10%-~100%, ~10%-~80%, or ~10%-~60%. In aspects, such a difference in pH can be a difference of, e.g., ~15%-~180%, ~20%-~180%, ~25%-~180%, 30%-~180%, ~35%-~180%, ~40%-~180%, ~45%-~180%, ~50%-~180%, or, e.g., by ~55%-~80%.

In aspects, one or more characteristic(s), e.g., performance characteristics (functional/therapeutic or physiochemical), of two (or more) composition(s) differing in their pH levels from one another by such amounts described in the preceding paragraph is/are statistically or significantly, e.g., statistically significantly, different from one another. In aspects, such two (or more) compositions can otherwise be at least generally the same, at least substantially the same, at least essentially the same, or, e.g., the same as one another in at least most other respects, such as, e.g., in the API(s) present in each, the amount(s) of API(s) present in each, the excipient(s) present in each, the amount(s) of API(s) present in each, or any combination of any or all thereof.

In aspects, composition(s) herein are characterizable as having a characteristic, e.g., a performance characteristic, which is detectably or significantly, e.g., statistically significantly, different from that of a comparator composition, wherein the comparator composition has a detectably or significantly different pH, such as, e.g., a pH which is at least about, e.g., 10%, ≥~15%, ≥~15%, ≥~20%, ≥~25%, ≥~30%, ≥~35%, ≥~40%, ≥~45%, ≥~50%, ≥~55%, or, e.g., ≥~60%, such as ≥~65%, ≥~70%, ≥~75%, ≥~80%, ≥~85%, ≥~90%, ≥~95%, or, e.g., ≥~100% higher, such as, e.g., ≥~110%, ≥~120%, ≥~130%, ≥~140%, ≥~150%, ≥~160%, ≥~170%, or, e.g., ≥~180% different (e.g., higher or lower).

Further, in aspects herein, one or more characteristic(s) of composition(s) provided by the invention is being formulated, stored, or administered at/comprising relatively "lower" pH are compared to second/reference composition(s) at or comprising, e.g., a "higher" pH, or vice versa. In aspects, such a difference in pH should be interpreted as such pH levels differing from one another by amounts (percentages) provided in this section.

In aspects, differences in, physiochemical characteristics of compositions of the invention as compared to such second/reference compositions, e.g., in terms of viscosity, efficacy, etc. as cited herein, can be determined by e.g., any suitable measure or method of the same known in the art, e.g., via method(s), procedure(s), using equipment, applying protocol(s), or performing test(s) routinely utilized or performed by those in the art to measure such characteristic(s). For example, in aspects, efficacy of a treatment using composition(s) herein can determined be any suitable measure of efficacy known in the art, such as any one or more tests of vision (visual impairment, visual acuity, visual capability, etc.) cited herein or recognized as appropriate by those knowledgeable in the field of ophthalmology.

According to certain aspects, composition(s) herein demonstrate a rate of API uptake (absorption) by ophthalmic tissue, a total amount of API uptake (absorption) by ophthalmic tissue, a total concentration of API present in ophthalmic tissue measured at one or more points of time after administration, a retention of API in ophthalmic tissue, or any combination thereof, which is detectably or significantly better than/increased compared to a comparator or reference composition, wherein the comparator or reference composition comprises the same active pharmaceutical ingredients in the same amounts as in the composition upon initial storage, comprises at least most of the excipients as in the composition in approximately the same amounts excluding pH adjusting agents upon initial storage, or any or all thereof, but which has a pH which is at least about 25% greater than the pH of the composition, such as, e.g., ≥~27%, ≥~28%, ≥~29%, ≥~30%, ≥~35%, ≥~40%, ≥~45%, ≥~50%, ≥~75%, ≥~100%, ≥~125%, ≥~150%, ≥~175%, or, e.g., ≥~200% greater than the pH of the composition(s). In aspects, comparator/reference composition(s) have excipients which are the same, essentially the same, substantially the same, generally the same, and mostly the same as composition(s) described herein, such as, e.g., in terms of the number(s) of excipients, type(s) or class(es) of excipients, amount(s) of each excipient(s), or combinations of any or all thereof. In aspects, comparator/reference composition(s) share the same API(s), share the same API(s) in the same amount(s), or both.

In aspects, composition(s) of the invention comprising brimonidine compound(s) and pilocarpine compound(s), when provided at a pH of between about 3 and about 6, such as, e.g., ~3.5-~5.5 has/have a detectably or significantly, e.g., statistically significantly, different efficacy in treating a targeted condition compared to that of an at least generally equivalent, at least substantially equivalent, at least essentially equivalent, or equivalent (in terms of API(s) present, excipient(s) present, amount(s) of API(s) present, amount(s) of excipient(s) present, or a combination thereof) second composition provided at a pH of between about 7 and about 8.5 (e.g., a pH of 6.6-9, 6.8-8.8, 7-9, or 7-8). In aspects, composition(s) of the invention comprising brimonidine compound(s) and pilocarpine compound(s), when provided at a pH of between about 7 and about 8.5, has/have a detectably or significantly, e.g., statistically significantly, different efficacy in treating a targeted condition compared to that of an at least generally equivalent, at least substantially equivalent, at least essentially equivalent, or equivalent (in terms of API(s) present, excipient(s) present, amount(s) of API(s) present, amount(s) of excipient(s) present, or a combination thereof) second composition provided at a pH of between about 3 and about 6, such as, e.g., ~3.5-~5.5. Aspects of the invention include compositions that are maintained at such pH levels during the product's shelf life (e.g., 2 years, 1.5 years, 1 year, 6 months, etc.) or are stored for a relevant period of time at such pH prior to administration (e.g., at least 3, at least 6, at least 9, at least 12, at least 15, at least 18, at least 24, at least 30, or at least 36 months).

In aspects, composition(s) comprising brimonidine compound(s) and pilocarpine compound(s) provided by the invention, when provided at a pH of between about 7 and about 8.5, provide an absorption efficacy of the brimonidine compound(s) which is detectably or significantly greater, e.g., statistically significantly greater, than that of the pilocarpine compound(s). Readers will understand that any description of a composition using the phrase "when provided" means that such a composition is an aspect of the invention (i.e., a composition maintained at such a pH, such as for any of the periods described in the preceding paragraph).

In aspects, administration of composition(s) comprising brimonidine compound(s) and pilocarpine compound(s) provided by the invention to mammalian eye(s), when compositions comprise (e.g., are provided at) a pH of between about 7 and about 8.5, results in a detectably or significantly, e.g., statistically significantly, higher concentration of brimonidine compound(s) present in ophthalmic tissue of the mammalian eye(s) when measured at a given period of time after administration (e.g., a period of time of about 1 minute, ~2 minutes, ~5 minutes, ~15 minutes, ~30 minutes, ~45 minutes, ~1 hours, ~1.5 hours, ~2 hours, ~3 hours, ~4 hours, ~5 hours, ~6 hours, ~7 hours, ~8 hours, ~9 hours, ~10 hours, ~11 hours, ~12 hours, ~14 hours, ~16 hours, ~18 hours, ~20 hours, ~22 hours, or, e.g., ~24 hours, or, e.g., another suitable identifiable period of time after a first administration of composition(s) and prior to a second administration of composition(s)) compared to the concentration of pilocarpine compound(s) in the ophthalmic tissue of the mammalian eye present after the same period of time. Readers will understand that suitability in this context will vary with the effect that is the subject of the analysis/difference in the compositions.

In aspects, administration of composition(s) provided by the invention having a pH of between about 7 and about 8.5 and comprising brimonidine compound(s) and pilocarpine compound(s) to a mammalian eye results in a detectably or significantly, e.g., a statistically significantly, higher relative amount of brimonidine absorbed by ocular tissue (e.g., corneal tissue) at a given period of time after administration (e.g., a time of administration such as that described above) compared to the relative amount of pilocarpine absorbed by ocular tissue within the same time period that occurs with the administration of a second/reference composition at a markedly/substantially different pH (e.g., a pH differing by 0.5, 1, 1.5, 1.7, 2, or 2.5 units). In this paragraph, "relative amount" refers to the percent of the total amount of each respective API administered which is absorbed and present in ocular tissue at the time of measure.

In aspects, composition(s) provided by the invention having a pH of between about 7 and about 8.5 and comprise effective amounts of brimonidine compound(s) and pilocarpine compound(s) wherein the pH of the composition provides for a detectably or significantly, e.g., statistically significantly, higher (e.g., faster) rate of absorption, e.g., uptake) of the brimonidine compound(s) of the compositions into or by the ocular tissue of a recipient mammalian eye (e.g., in a cornea) than that of the pilocarpine compound(s).

In aspects, the amount of brimonidine compound(s) retained in ophthalmic tissue is detectably or significantly greater than, e.g., is statistically significantly greater than, the amount of pilocarpine compound(s) retained in the ophthalmic tissue of mammalian eye(s) when the compound(s) are administered to the mammalian eye(s) as component(s)/constituent(s) of composition(s) provided by the invention having a pH of between about 7 and about 8.5. In aspects, the amount of brimonidine compound(s) retained in ophthalmic tissue when administered as a component of composition(s) provided by the invention having a pH of between about 7 and about 8.5 is detectably or significantly greater than, e.g., statistically significantly greater than, the amount of brimonidine compound(s) retained in ophthalmic tissue when administered as a component of composition(s) provided by the invention having a pH of between about 3 and about 6.

According to certain aspects, the concentration in ocular tissue, amount in ocular tissue, rate of absorption by ocular tissue, retention within ocular tissue, or combination of any or all thereof, of brimonidine compound(s) when administered to mammalian eye(s) as component(s)/constituent(s) of composition(s) provided by the invention herein having a pH of between about 7 and about 8.5 is detectably or significantly higher than or increased compared to (e.g., statistically significantly higher than or increased compared to) an at least generally the same, at least substantially the same, at least essentially the same, or the same (in terms of API(s) present, amount(s) of API(s) present, excipient(s) present, amount(s) of API(s) present, or any combination of any or all thereof) composition having a pH of between about 3 and about 6, such as a pH of between about 5 and about 6, e.g., a pH of about 5.

In aspects, composition(s) comprising brimonidine compound(s) and pilocarpine compound(s) provided by the invention, when provided at a pH of between about 3.5 and about 6, such as, e.g., between about 4 and about 6, e.g., at a pH of about 5, provide an absorption efficacy of the pilocarpine compound(s) which is detectably or significantly greater, e.g., statistically significantly greater, than that of the brimonidine compound(s).

In aspects, administration of composition(s) comprising brimonidine compound(s) and pilocarpine compound(s) provided by the invention to mammalian eye(s), when compositions comprise (e.g., are provided at) a pH of between about 3 and about 6, such as, e.g., a pH of about 5, results in a detectably or significantly, e.g., statistically significantly, higher concentration of pilocarpine compound(s) present in the ophthalmic tissue of the mammalian eye(s) when measured at a given period of time after administration (e.g., a period of time of about 1 minute, ~2 minutes, ~5 minutes, ~15 minutes, ~30 minutes, ~45 minutes, ~1 hours, ~1.5 hours, ~2 hours, ~3 hours, ~4 hours, ~5 hours, ~6 hours, ~7 hours, ~8 hours, ~9 hours, ~10 hours, ~11 hours, ~12 hours, ~14 hours, ~16 hours, ~18 hours, ~20 hours, ~22 hours, or, e.g., ~24 hours, or, e.g., another identifiable period of time after a first administration of composition(s) and prior to a second administration of composition(s)) compared to the concentration of brimonidine compound(s) in the ophthalmic tissue of the mammalian eye present after the same period of time.

In aspects, administration of composition(s) provided by the invention having a pH of between about 3 and about 6, such as, e.g., about 5, and comprising brimonidine compound(s) and pilocarpine compound(s) to a mammalian eye results in a detectably or significantly, e.g., statistically significantly, higher relative amount of pilocarpine absorbed by ocular tissue at a given period of time after administration (e.g., a time of administration such as that described elsewhere herein) compared to the relative amount of brimonidine absorbed by (typically the same) ocular tissue within the same time period (e.g., in the cornea). In this paragraph, "relative amount" refers to the percent of the total amount of each respective API administered which is absorbed and present in ocular tissue at the time of measure.

In aspects, composition(s) provided by the invention having a pH of between about 3 and about 6, such as, e.g., about 5, and comprising effective/suitable amounts of brimonidine compound(s) and pilocarpine compound(s), provide for a detectably or significantly, e.g., statistically significantly, higher (e.g., faster) rate of absorption, e.g., uptake) of the pilocarpine compound(s) into or by the ocular tissue of a recipient mammalian eye than that of the brimonidine compound(s) in the composition.

In aspects, the amount of pilocarpine compound(s) retained in ophthalmic tissue is detectably or significantly greater than, e.g., is statistically significantly greater than, the amount of brimonidine compound(s) retained in the ophthalmic tissue of mammalian eye(s) when the compound(s) are administered to the mammalian eye(s) as component(s)/constituent(s) of composition(s) provided by the invention having a pH of between about 3 and about 6, such as, e.g., a pH of about 5. In aspects, the amount of pilocarpine compound(s) retained in ophthalmic tissue when administered as a component of composition(s) provided by the invention having a pH of between about 3 and about 6, such as, e.g., a pH of about 5, is detectably or significantly greater than, e.g., statistically significantly greater than, the amount of pilocarpine compound(s) retained in ophthalmic tissue when administered as a component of composition(s) provided by the invention having a pH of between about 7 and about 8.5.

According to certain aspects, the concentration in ocular tissue, amount in ocular tissue, rate of absorption by ocular tissue, retention within ocular tissue, or combination of any or all thereof, of pilocarpine compound(s) when administered to mammalian eye(s) as component(s)/constituent(s) of composition(s) provided by the invention herein having a pH of between about 3 and about 6, such as, e.g., a pH of about 5, is detectably or significantly higher than or increased compared to (e.g., statistically significantly higher than or increased compared to) an at least generally the same, at least substantially the same, at least essentially the same, or the same (in terms of API(s) present, amount(s) of API(s) present, excipient(s) present, amount(s) of API(s) present, or any combination of any or all thereof) composition having a pH of between about 3 and about 6, such as a pH of about 5.

In aspects, the composition(s) provided within the lower pH range(s) recited here, e.g., less than a pH of 6, such as, e.g., between about 3 and about 6, is/are detectably or significantly (such as, e.g., statistically significantly) more efficacious in treating one or more target conditions than an at least generally equivalent, at least substantially equivalent, at least essentially equivalent, or equivalent (in terms of API(s) present, excipient(s) present, amounts of API(s) present, amount(s) of excipient(s) present, or a combination thereof) second composition(s) provided within the higher pH range(s) recited here, such as e.g., a pH of greater than 6, such as, e.g., between about 6 and about 8.5.

In certain particular exemplary aspects, composition(s) provided by the invention comprise brimonidine compound(s) and pilocarpine compound(s) (as typical, implicitly such statements mean that these APIs are administered in effective and suitable amounts), wherein the concentration in ocular tissue, amount in ocular tissue, rate of absorption by ocular tissue, retention within ocular tissue, or combination of any or all thereof, of pilocarpine compound(s) in the composition, when the composition is administered to mammalian eye(s), is detectably or significantly higher than or increased compared to (e.g., statistically significantly higher than or increased compared to) an at least generally the same, at least substantially the same, at least essentially the same, or the same (in terms of API(s) present, amount(s) of API(s) present, excipient(s) present, amount(s) of API(s) present, or any combination of any or all thereof) comparator composition, but wherein the comparator composition has a pH which is at least about 10% higher, such as, e.g., ≥~15%, ≥~15%, ≥~20%, ≥~25%, ≥~30%, ≥~35%, ≥~40%, ≥~45%, ≥~50%, ≥~55%, or, e.g., ≥~60%, such as ≥~65%, ≥~70%, ≥~75%, ≥~80%, ≥~85%, ≥~90%, ≥~95%, or, e.g., ≥~100% higher, such as, e.g., ≥~110%, ≥~120%, ≥~130%, ≥~140%, ≥~150%, ≥~160%, ≥~170%, or, e.g., ≥~180% higher, as in a comparator composition having a pH which is between about 10% and about 180% higher, ~10%-~160%, ~10%-~140%, ~10%-~120%, ~10%-~100%, ~10%-~80%, or ~10%-~60% higher, e.g., ~15%-~180%, ~20%-~180%, ~25%-~180%, 30%-~180%, ~35%-~180%, ~40%-~180%, ~45%-~180%, ~50%-~180%, or, e.g., by ~55%-~80% higher.

In one exemplary aspect, composition(s) provided by the invention comprise brimonidine compound(s) and pilocarpine compound(s), wherein the concentration in ocular tissue, amount in ocular tissue, rate of absorption by ocular tissue, retention within ocular tissue, or combination of any or all thereof, of pilocarpine compound(s), when the composition is administered to mammalian eye(s), is detectably or significantly higher than or increased compared to (e.g., statistically significantly higher than or increased compared to) an at least generally the same, at least substantially the same, at least essentially the same, or the same (in terms of API(s) present, amount(s) of API(s) present, excipient(s) present, amount(s) of API(s) present, or any combination of any or all thereof) composition having a pH of between about 7 and about 8.5.

In aspects, composition(s) provided within the higher pH range(s) recited here, e.g., greater than a pH of 6, such as, e.g., between about 6 and about 8.5, is/are detectably or significantly (such as, e.g., statistically significantly) more efficacious in treating one or more target conditions than an at least generally equivalent, at least substantially equivalent, at least essentially equivalent, or equivalent (in terms of API(s) present, excipient(s) present, amount(s) of API(s) present, amount(s) of excipient(s) present, or a combination thereof) to second composition(s) provided within the lower pH range(s) recited here, such as, e.g., a pH of less than about 6, such as, e.g., between about 3 and about 6, e.g., a pH of between about 5 and 6, such as a pH of about 5. In aspects, composition(s) provided within the lower pH range(s) recited herein, e.g., less than a pH of 6, such as, e.g., between about 3 and about 6, such as between about 5 and about 6, e.g., about 5, is/are detectably or significantly (such as, e.g., statistically significantly) more efficacious in treating one or more target conditions than an at least generally equivalent, at least substantially equivalent, at least essentially equivalent, or equivalent (in terms of API(s) present, excipient(s) present, amount(s) of API(s) present, amount(s) of excipient(s) present, or a combination thereof) to second composition(s) provided with the higher pH range(s) recited here, such as, e.g., a pH of higher than 6, such as between about 6 and about 8.5, such as a pH of between about 7 and about 7.5.

Osmolality

In aspects, composition(s) provided by the invention are characterizable as isotonic. In aspects, composition(s) provided by the invention have an osmolality of between about 171 milliosmoles per kilogram (mOsm/Kg) and about 1171 mOsm/Kg, such as, e.g., ~171 mOsm/Kg-~1100 mOsm/Kg, ~171 mOsm/Kg-~1000 mOsm/Kg, ~171 mOsm/Kg-~900 mOsm/Kg, ~171 mOsm/Kg-~800 mOsm/Kg, ~171 mOsm/Kg-~700 mOsm/Kg, ~171 mOsm/Kg-~600 mOsm/Kg, ~171 mOsm/Kg-~500 mOsm/Kg, or ~171 mOsm/Kg-~400 mOsm/Kg.

In aspects, composition(s) provided by the invention have an osmolality of between about 180 mOsm/Kg-about 1171 mOsm/Kg, such as, e.g., ~200 mOsm/Kg-~1171 mOsm/Kg, ~220 mOsm/Kg-~1171 mOsm/Kg, ~240 mOsm/Kg-~1171 mOsm/Kg, ~260 mOsm/Kg-~1171 mOsm/Kg, ~280 mOsm/Kg-~1171 mOsm/Kg, ~300 mOsm/Kg-~1171 mOsm/Kg, ~320 mOsm/Kg-~1171 mOsm/Kg, ~340 mOsm/Kg-~1171 mOsm/Kg, ~360 mOsm/Kg-~1171 mOsm/Kg, ~380 mOsm/Kg-~1171 mOsm/Kg, or, e.g., ~400 mOsm/Kg-~1171 mOsm/Kg, e.g., ~200 mOsm/Kg-~1000 mOsm/Kg.

In aspects, composition(s) provided by the invention have an osmolality of between about 200 mOsm/Kg and about 500 mOsm/Kg, or, e.g., between about 200 mOsm/Kg and about 400 mOsm/Kg, such as, e.g., ~250-~400 mOsm/Kg, ~260-~390 mOsm/Kg, ~270-~380 mOsm/Kg, or, e.g., ~280-~370 mOsm/Kg, for example ~210-~390 mOsm/Kg, ~220 ~380 mOsm/Kg, ~230-~370 mOsm/Kg, ~240-~360 mOsm/Kg, or, e.g., ~250-~350 mOsm/Kg. In aspects, the invention provides composition(s) comprising a tonicity agent component such that the composition comprises an isotonic range (e.g., an osmolality) within a range provided here.

Viscosity

In aspects, composition(s) provided by the invention, after manufacture and while in storage at between about 15° C.-about 27° C., have a viscosity of less than about 75 cps, e.g., in aspects, a viscosity of less than about 70 cps, less than about 65 cps, less than about 60 cps or less than about 50 cps. In aspects, composition(s) provided by the invention in the form of composition(s) capable of forming gel(s) comprise a viscosity after manufacture and while in storage of between about 15° C.-about 27° C. which is detectably or significantly less than the viscosity of the composition(s) after administration to a mammalian eye. That is, in aspects, composition(s) provided by the invention, when provided in the form of composition(s) capable for forming gel(s), form(s) gel(s) having a higher viscosity after administration to a mammalian eye which is detectably or significantly greater than the viscosity of the composition(s) after manufacture and while in storage of between about 15° C.-about 27° C., prior to administration. In aspects, composition(s) after administration to a mammalian eye can comprise a viscosity of greater than about 15 cps, such as, e.g., greater than about 20 cps, about 30 cps, about 40 cps, about 50 cps, about 60 cps, about 70 cps, about 80 cps, about 90 cps, or, e.g., greater than about 100 cps. In aspects, composition(s) have at least generally, at least substantially, at least essentially, essentially, or the same viscosity after administration to a mammalian eye as prior to administration (e.g., after manufacture and during storage at about 15° C.-about 27° C.). In certain aspects, at any time during storage at about 15° C.-about 27° C. and after administration to mammalian eye, the composition(s) has/have a viscosity of between about 1 and about 150 cps, e.g., ~1 cps-~140 cps, ~1 cps-~130 cps, ~1 cps-~120 cps, ~1 cps-~110 cps, or, e.g., in aspects, ~1 cps-~100 cps.

Stability

Uncontradicted, the term "stable" or "stable composition" as used herein, refers to a pilocarpine compound composition provided by the invention having sufficient physical and chemical stability to allow storage at a convenient temperature, such as between about 0° C. and about 50° C., for a commercially reasonable period of time, such as a period of time of at least about 2 weeks, ~1 month, ~6 weeks, ~2 months, ~3 months, ~6 months, ~12 months, ~18 months, ~24 months, ~30 months, or, e.g., at least about 35 months.

In aspects, composition(s) of the invention are stable. In aspects, composition(s) of the invention exhibit physical stability, chemical stability, or both, over any of the periods of storage described herein. The term "physical stability" typically refers to maintenance of color, dissolved oxygen level, head space oxygen level, and particulate matter, and the term "chemical stability" typically relates to formation of drug-related impurities in terms of total impurity, single maximum individual impurity, and maximum individual unknown impurity. For the purpose of the present invention chemical stability also includes maintenance of pH of the finished formulation. In aspects, composition(s) provided by the invention demonstrate stability required for commercially relevant times after manufacturing, such as for at least about 1, 3, 6, 9, 12, 18, 24 or 36 months, during which composition(s) is/kept in its/their original packaging under specified storage condition. The term "shelf life" refers to the amount of time the ophthalmic composition(s) may be stored without detectable or significant loss of potency and/or dissolution profile. Preferably, the shelf life refers to the amount of time the ophthalmic composition(s) may be stored without a loss of more than 2%, 5%, 8% or 10% of the potency and/or dissolution. Composition(s) of the invention, in aspects, exhibit such shelf-life characteristic. Herein, uncontradicted, the term "room temperature" refers to controlled room temperature as between 15° C. to 25° C.+/−2° C.

Herein, storage conditions, stability test conditions, or both, are storage conditions that comply with/are established by the stability guidance provided by the United States Food and Drug Administration (US FDA) for ophthalmic products, such products often (e.g., typically) being stored in semipermeable container(s) (see, e.g., "Guidance for Industry—Q1A(R2) Stability Testing of New Drug Substances and Products", U.S. Department of Health and Human Services, Food and Drug Administration, Center for Drug Evaluation and Research (CDER), Center for Biologics Evaluation and Research (CBER); November 203; ICH; Revision 2.) or other well-known storage/stability evaluation condition guidance provided by other recognized regulatory authorities (including US FDA) which may vary from any of the various stability test/storage conditions recited specifically herein. Accordingly, in aspects, composition(s) provided in the invention demonstrate chemical stability, physical stability, or both (e.g., in terms of maintaining an amount of API(s), maintaining pH, maintaining an acceptable level of impurities, etc.) when stored under a storage condition defined as appropriate for ophthalmic products, e.g., ophthalmic products stored in a semipermeable container, by a recognized regulatory authority, e.g., the United States Food and Drug Administration. Uncontradicted, storage conditions specifically identified in this disclosure include, e.g., about 25° C.±2° C. and about 40%±5% relative humidity (e.g., for long term storage); about 30° C.±2° C. and about 35%±5% relative humidity (e.g., for long term storage); about 30° C.±2° C. and about 65%±5% relative humidity; about 40° C.±2° C. and not more than ("NMT") about 25% relative humidity (e.g., for accelerated storage), according to the U.S. FDA Guidance for Industry document cited above. In aspects, composition(s) provided by the invention demonstrate chemical and physical stability, such as, e.g., as determined by maintaining an amount of API(s) relative to the amount of API(s) present upon initial storage, as determined by maintaining the pH within an appropriate range relative to the pH of the composition(s) upon initial storage, as determined by maintaining a level of one, more than one, or total impurities below 2.5%, or, e.g., any combination of any or all thereof, when stored under United States Food and Drug Administration (U.S. FDA) accelerated stability test conditions for a period of at least about one month or under U.S. FDA long-term storage stability test conditions for a period of at least about one year.

In one aspect, the invention provides pharmaceutically acceptable and ophthalmologically suitable composition(s) comprising less than about 2.5% of total impurities, such as, e.g., ≤~2% total impurities, ≤~1.5%, ≤~1%, or ≤~0.5% total impurities. The term "impurity" refers to an undesired substance in a composition which may be present in an initial composition and/or may be formed after a certain period of shelf life of composition(s). These impurities may, e.g., be formed via degradation of one or more components of composition(s). Sources of degradation can include, but are not limited to, oxidation, light, ultraviolet light, moisture, heat, changes in pH, and composition component interactions.

In aspects, the invention provides composition(s) described herein, wherein the composition(s) comprise(s) less than about 2.5% total impurities, e.g., less than about 2%, less than about 1.5%, less than about 1%, or, e.g., less than about 0.5% total impurities after storage at between about 15° C. and about 27° C. (e.g., between about 15° C. and about 27° C. and about 60% relative humidity); when stored at between about 25° C.±2° C., e.g., about 25° C.±2° C. and about 40%±5% relative humidity (e.g., for long term storage); about 30° C.±2° C. and about 35%±5% relative humidity (e.g., for long term storage); about 30° C.±2° C. and about 65%±5% relative humidity; about 40° C.±2° C. and not more than ("NMT") about 25% relative humidity (e.g., for accelerated storage); or a combination of any or all such conditions, for a period of at least about 1 month, e.g., ≥~3 months, ≥~6 months, ≥~9 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

In one aspect, the invention provides pharmaceutically acceptable and ophthalmologically suitable composition(s) which remain stable and retain at least about 90%, such as, e.g., ≥~92%, ≥~94%, ≥~96%, ≥~98%, or even ≥~99% of the labelled concentration of pilocarpine compound, e.g., pilocarpine hydrochloride, the labelled concentration of brimonidine compound, e.g., brimonidine tartrate, or both the labelled concentration of pilocarpine and brimonidine compounds after storage under typical and/or accelerated conditions.

In aspects, the invention provides composition(s) as described herein, wherein the composition(s) maintain(s) at least about 98%, e.g., at least about 99%, of the pilocarpine compound, the brimonidine compound, or both when stored at between about 15° C. and about 27° C. (e.g., between about 15° C. and about 27° C. and about 60% relative humidity); when stored at about 25° C.±2° C., e.g., when stored at about 25° C.±2° C. and about 40%±5% relative humidity (e.g., for long term storage); about 30° C.±2° C. and about 35%±5% relative humidity (e.g., for long term storage); about 30° C.±2° C. and about 65%±5% relative humidity; about 40° C.±2° C. and not more than ("NMT") about 25% relative humidity (e.g., for accelerated storage); or a combination of any or all such conditions, for at least about one month, such as, e.g., ≥~3 months, ≥~6 months, ≥~9 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

In certain aspects, composition(s) having a first pH (e.g., one of the pH level characteristics described elsewhere herein) demonstrate chemical stability, physical stability, which is at least generally the same or equivalent to, is at least substantially the same or equivalent to, is at least essentially the same or equivalent to, is essentially the same or equivalent to, is the same or equivalent to, or is detectably or significantly better than (e.g., higher or improved compared to) composition(s) having a second pH which is at least about 10%, ≥~20%, ≥~30%, ≥~40%, ≥~50%, ≥~60%, ≥~70%, ≥~80%, ≥~90%, ≥~100%, ≥~110%, ≥~120%, ≥~130%, ≥~140%, ≥~150%, ≥~160%, ≥~170%, ≥~180%, ≥~190%, or ≥~200% greater than that of the first composition(s) (i.e., the composition of the invention at issue) (e.g., where the inventive composition has a pH that is less than 7, 6.5, or 6, and typically has a pH that is at least 0.5, 1, 1.2, 1.5, 1.7, 2, 2.2, or 2.5 pH units less than a comparator composition, such as a composition that is substantially similar but has a pH of greater than 6.5, 6.7, 6.8, or 7). In aspects, such enhanced/improved or other stability characteristic of the inventive composition is reflected in/characterized by, e.g., an ability to retain at least about 97% of API(s), an ability to maintain a level of impurity(ies) below 2.5%, an ability to maintain pH, ability to maintain form (e.g., as a solution, suspension, gel, etc.) or, e.g., combination(s) thereof when compositions are stored under long-term, short-term, or long-term and short-term storage condition(s), such as, e.g., about 25° C.±2° C. and about 40%±5% relative humidity (e.g., for long term storage); about 30° C.±2° C. and about 35%±5% relative humidity (e.g., for long term storage); about 30° C.±2° C. and about 65%±5% relative humidity (e.g., for intermediate storage, as appropriate/required by U.S. FDA standard(s)); about 40° C.±2° C. and not more than ("NMT") about 25% relative humidity (e.g., for accelerated storage); or a combination of any or all such conditions, for a period of at least about 1 month, such as, e.g., ≥~3 months, ≥~6 months, ≥~9 months, ≥~12 months, ≥~18 months, ≥~24 months, ≥~28 months, ≥~32 months, or, e.g., at least about 36 months.

In aspects, compositions of the invention are characterized as having a pH that provides for a significantly or detectable improvement in one or more characteristics as compared to a composition at a neutral pH, near neutral pH (a pH of 5.5-7, 6-7, or 6.5-7), or a basic pH (a pH of above 7), such as better retention in an ocular tissue (of one or more APIs), better stability, or other condition as described herein.

Dosage Forms & Administration Rates

In aspects, pharmaceutically acceptable and ophthalmologically suitable composition(s) provided by the invention can be provided as, e.g., formulated as, solutions, suspensions, ointments, creams, gels, sprays, and other dosage forms suitable for topical ophthalmic administration. In aspects, composition(s) provided by the invention are topically applied compositions. In aspects, composition(s) provided by the invention are injectable compositions or are formulated to be suitable for administration by injection. In aspects, composition(s) provided by the invention can be suitable for topical delivery as drops or implantation in or on a subject's eye or tissue surrounding the eye, e.g., suitable for implantation into a subconjunctival space, naso-lacrimal duct, or vitreous body of the subject.

In aspects, composition(s) provided by the invention are aqueous solutions. In aspects, composition(s) provided as aqueous solutions provide ease of use of such compositions including as a patient's ability to easily administer such compositions by means of instilling a suitable dose of the solutions to affected eye(s). In aspects, aqueous composition(s) provided by the invention are typically more than about 50% w/v, e.g., ≥~55% w/v, ≥~60% w/v, ≥~65% w/v, ≥~70% w/v, ≥~75% w/v, ≥~80% w/v, ≥~85% w/v, or ≥~90% w/v water, and at least generally all, substantially all, or all components of the formulation are fully dissolved such that a clear, aqueous solution is provided.

In aspects, pharmaceutically acceptable and ophthalmologically suitable composition(s) provided by the invention are provided as a liquid solution, wherein compositions are administered as drops to affected eye(s). In aspects, compositions are administered as about 1 to about 3 drops, such as, e.g., about 1 to about 2 drops, e.g., about 1, about 2, or about 3 drops of the composition to each affected eye per dose/administration. Typically, a single administration comprises no more than about 2 drops of composition, such as about 1 or about 2 drops of composition per administration. In aspects, exact amounts to be administered can be determined by an overseeing physician, e.g., optometrist. In aspects, a typical drop size is between about 5 µL and about 100 µL, such as, e.g., ~5 µL-~75 µL, or ~5 µL-about 50 µL, such as, e.g., ~10 µL-~100 µL or, e.g., ~25 µL-~100 µL, for example ~25 µL-~70 µL, or, e.g., ~20 µL-~60 µL.

In certain aspects, pharmaceutically acceptable and ophthalmologically suitable composition(s) provided by the invention are provided as a gel. In aspects, composition(s) provided as a gel increase the amount of time the composition(s) contact(s) eye tissue, leading to, in aspects, an increased bioavailability of active ingredient(s) contained therein (i.e., a detectable or significant improvement in bioavailability of the API(s)).

According to certain aspects, pharmaceutically acceptable and ophthalmologically suitable composition(s) provided by the invention are controlled release compositions, such as, e.g., characterizable as slow-release composition(s).

In aspects, composition(s) are administered as a single administration. In other aspects, composition(s) are administered as a plurality of administrations, such as, e.g., 5, 10, 20, 30, 40, or 50 or more administrations, such as, e.g., daily administration for a period of days, weeks, months, or years (e.g., 1, 2, 3, 4, or 5 years or longer). In aspects, multiple administrations are separated from one another by a period of at least about 1 minute, such as at least about 30 minutes or longer, such as, e.g., at least about 1 hour or longer, or such as 24 hours or longer.

In aspects, an effective treatment period is a period of about 1 day, about 1 day-about 1 week, about 1 week to about 1 month, about 1 week to about 3 months, about 1 week to about 6 months, about 1 week to about 9 months, about 1 month to about 1 year, about 1 year to about 5 years, or longer. In certain aspects, compositions provided by the invention are used as a chronic treatment, e.g., in treating a chronic condition, such that the effective treatment period is an indefinite period (e.g., treatment is ongoing with no defined end point.) In aspects, composition(s) provided by the invention are used in treatment of a chronic condition, wherein treatment is for a period of at least 5 years or longer, e.g., ~10, ~15, ~20, or ~25 years or more.

The ophthalmic composition(s) may be applied to each affected eye, both eyes, or the dominant eye of the recipient over the course of an effective treatment period. Exact application may vary depending on the target indication, the tolerance or goals of the recipient, the aim of the attending physician/treatment provider, or any combination thereof.

Methods of Use

Method of Improving Vision

In one aspect, the invention provides pharmaceutically acceptable and ophthalmologically suitable composition(s) described herein, e.g., composition(s) comprising a PCC, e.g., a pilocarpine compound, and an AAA component, e.g., brimonidine compound, and methods for their use in improving vision, reducing visual impairment, treating a vision-related ophthalmic condition, or combinations thereof. In aspects, composition(s) provided by the invention and methods of their use described herein can be provided to or for any patient in need thereof or suffering from a condition benefiting from the provision of compositions or methods described herein. In aspects, a suitable patient is a patient who wears corrective eyeglasses (spectacles) who cannot or will not use progressive lenses or bifocal lenses. In aspects, a suitable patient is a patient who has undergone cataract surgery. In aspects, a suitable patient is a patient who has developed presbyopia after a corneal procedure. In aspects, a suitable patient is a patient who has mono- or multi-focal intraocular lenses. In aspects, a suitable patient is a patient using contact lenses and does not tolerate mono vision contact lenses. In aspects, a suitable patient is a patient using contact lenses and does not tolerate multifocal contact lenses. In aspects, a suitable patient is a patient suffering from higher order aberration after corneal surgery. In aspects, a suitable patient is a patient suffering from hyperopia or tropias. In aspects, a suitable patient is a patient who does not tolerate a change in spectacle prescription or experiences rapid changes in spectacle prescription.

In one aspect, the invention provides pharmaceutically acceptable and ophthalmologically suitable composition(s) described herein, e.g., composition(s) comprising a PCC, e.g., a pilocarpine compound, and an AAA component, e.g., brimonidine compound, and methods for their use in treating an ophthalmic condition benefitting from the receipt of a suitable amount of such composition(s), wherein such condition(s) include one or more of, e.g., reduced vision, vision impairment, presbyopia, hyperopia, mydriasis, anisocoria, and accommodative esotropia, myopia, astigmatism (or symptoms related to, e.g., presbyopia, hyperopia, mydriasis, anisocoria, accommodative esotropia, myopia, or related to e.g., astigmatism), Adie's tonic pupil, or other causes of parasympathetic denervation, accommodative insufficiency, and complications arising after refractive surgery, such as decentered ablations following LASIK or PRK, conical scars, hazing, refractive errors, etc., and further wherein the method comprises administration of an effective amount of such composition(s). In aspects, composition(s) provided by the invention are suitable for administration to any subject benefiting from the administration thereof, e.g., any mammal with an ophthalmic condition benefitting from the receipt of an effective/suitable amount of such compositions. In aspects, a suitable recipient is an adult human. In aspects, a suitable recipient is an adult human suffering from or diagnosed with, e.g., reduced vision, vision impairment, presbyopia, hyperopia, mydriasis, anisocoria, and accommodative esotropia, myopia, astigmatism (or symptoms related to, e.g., presbyopia, hyperopia, mydriasis, anisocoria, accommodative esotropia, myopia, or related to e.g., astigmatism), Adie's tonic pupil, or other causes of parasympathetic denervation, accommodative insufficiency, and complications arising after refractive surgery, such as decentered ablations following LASIK or PRK, conical scars, hazing, refractive errors, etc. In aspects, composition(s) provided by the invention are suitable for administration to children (in this and similar other aspects, "suitability" or "suitable for" in regards to characteristics of a composition refers to, i.a., the characteristic of demonstrated suitability in terms of efficacy and safety, e.g., demonstrated through clinical trials to be sufficiently suitable (safe and effective) to treat the indicated condition, act in the indicated population/setting, or both, e.g., in a significant number of patients in such studies). In aspects, composition(s) provided by the invention are not suitable for administration to children. In aspects, composition(s) provided by the invention are suitable for administration to children for whom other interventions are unsuitable, undesirable, or insufficient. Determinations of suitable and efficacy in such aspects can be determined by, e.g., scientific evidence, such as, for example, determination of bioequivalence to a product having such effects, or determination of such effectives through one or more scientific studies, such as one or more adequate, well-controlled, studies, which would be suitable for submission to U.S. FDA in connection with approval of a pharmaceutical product, wherein a suitably significant effect is observed.

According to one specific aspect, the invention provides a method of treating an ophthalmic condition or symptom related thereto, the ophthalmic condition selected from the group consisting of presbyopia, hyperopia, mydriasis, anisocoria, accommodative esotropia, myopia, and astigmatism. In aspects, the invention provides such a method wherein the method comprises administration of a therapeutically effective amount of any composition described herein, wherein an effective amount of the composition is about 1 drop or about 2 drops, e.g., 1-2 drops, such as, in aspects, no more than about 2 drops, of the composition(s) to the mammalian eye. In aspects, such compositions(s) are administered once or twice daily, such as no more than about twice per day. In aspects, such method(s) further comprise optionally repeating administration of the composition(s) for a number of times demonstrated to provide a significant clinical effect in visual improvement, e.g., a significant clinical effect in vision, such as, e.g., a number of times demonstrated to provide a clinically relevant improvement in vision, in a significant number of patients in a well-controlled and adequate study or that is shown to be bioequivalent to a product that has been demonstrated to achieve effectively the same improvement in vision.

Method of Modulating Physiological Properties of the Eye

In one aspect, the invention provides pharmaceutically acceptable and ophthalmologically suitable composition(s) described herein, e.g., composition(s) comprising a PCC, e.g., a pilocarpine compound, and an AAA component, e.g., brimonidine compound, and methods for their use in detectably or significantly modulating one or more physiological properties of a mammalian eye, one or more physiological properties of a mammalian eye, or both, wherein the method comprises administration of an effective amount of composition(s) described herein. In one aspect, the invention provides a method of detectably or significantly modulating one or more physiological properties of a mammalian eye comprising administering to the patient an effective amount of a pharmaceutically acceptable and ophthalmologically suitable ophthalmic composition comprising a pilocarpine compound, e.g., a salt of pilocarpine, e.g., pilocarpine hydrochloride, in a concentration of about 1.0% w/v to about 3.0% w/v, a brimonidine compound, e.g., a salt of brimonidine, e.g., brimonidine tartrate, in a concentration of about 0.05% w/v to about 02% w/v, optionally a penetration enhancer in a concentration from about 0.1% w/v to about 3.0% w/v, one or more tonicity agents in a concentration from about 0.01% w/v to about 0.1% w/v, benzalkonium chloride in an amount from about 0.003% to about 0.02% w/v, water, and one or more buffers or pH-adjusting agents, wherein the composition is free of boric acid buffers e.g., free of boric acid or sodium borate, free of citrate buffers, e.g., free of sodium citrate dihydrate, or free of both borate and citrate buffers.

In aspects, the invention provides a method of detectably or significantly modulating one or more physiological conditions of a mammalian eye comprising administering to the patient an effective amount of a pharmaceutically acceptable and ophthalmologically suitable ophthalmic composition described herein. In aspects, the invention provides a method of detectably or significantly modulating one or more physiological conditions of a mammalian eye comprising administering to the patient an effective amount of a pharmaceutically acceptable and ophthalmologically suitable ophthalmic composition comprising a pilocarpine compound, e.g., a salt of pilocarpine, e.g., pilocarpine hydrochloride, which, in aspects, is in an amount of about 1% w/v-about 3% w/v and, in aspects, also or alternatively administering a brimonidine compound, e.g., a salt of brimonidine, e.g., brimonidine tartrate, a solubilization component in an amount of between about 0.1% w/v-about 0.7% w/v, wherein optionally such compounds are both administered in a fixed-dose dosage form (e.g., a gel or solution); and, wherein, in aspects, such a method includes administering such API(s) with an effective amount of a preservation component (e.g., in an amount of about 0.003% w/v-about 0.02% w/v); a tonicity component (e.g., in an amount of between about 3.5% w/v-about 5.5% w/v); and a viscosity enhancement component (thickening component) (e.g., in an amount of about 0.1% w/v-about 1% w/v), wherein, in aspects, the composition is free of borate buffers e.g., free of boric acid and free of sodium borate, free of citrate buffers, e.g., free of sodium citrate dihydrate, or free of both borate and citrate buffers.

In aspects, a physiological property of a mammalian eye that is treated/modified or modulated by methods of the invention can be any physiological property participating in, affecting, contributing to, affected by, impaired by, damaged by, or otherwise associated with an ophthalmic condition treatable with the compositions herein, e.g., ocular conditions such as, e.g., reduced vision, presbyopia, hyperopia, mydriasis, anisocoria, accommodative esotropia, myopia, and, e.g., astigmatism.

Method of Treating an Ocular Condition

In aspects, efficacy of treatment(s) (e.g., any efficacy of method(s) described herein) can be measured using any method known in the art. In aspects, method(s) described herein can comprise repeated administration of compositions) for a number of times demonstrated to provide a clinically relevant improvement in vision, such as in a significant number of recipients in a well-controlled and adequate study or, e.g., that is shown to be bioequivalent to a product that has been demonstrated to achieve effectively the same improvement in one or more measures of vision. In certain aspects, one or more measures of vision, e.g., the efficacy of treatment described herein, can be assessed using e.g., as applicable to the target indication being treated, measure(s)/method(s) such as: (a) subjects having uncorrected distance and near visual acuity taken using a standard eye chart (e.g., Snellen chart at distance and Jaeger charts at near), or early treatment diabetic retinopathy study (ETDRS) chart, wherein results can be converted to decimal notation using Halliday's conversion chart; (b) clinical evaluation of the depth of field obtained using standard wavefront aberrometry or other techniques in the art using modification/adjustment of spectacle prescription in refractor head/trial frame; (c) change in pupil size (as measured by infrared imaging system used for checking alignment during auto-refractometry); (d) pupil appearance (e.g., visual inspection for equality of size, shape, reactivity to light, direct and consensual accommodation); (e) non-invasive objective assessments of $3^{rd}$, $4^{th}$ and $5^{th}$ ocular higher order aberrations (e.g., coma, spherical aberration, and trefoil) conducted using standard wavefront aberrometry; or (f) other known methods as appropriate. In aspects, any improvement in, e.g., vision, can be, for example, determined by use of one or more such method(s) or other method(s) recognized as appropriate by those in the art. In aspects, composition(s) provided herein demonstrate a significant clinical effect in visual improvement, e.g., a significant clinical effect in vision, such as, e.g., a clinically relevant improvement in vision in a significant number of patients in a well-controlled and adequate study or that is shown to be bioequivalent to a product that has been demonstrated to achieve effectively the same improvement in vision. In aspects, such effect(s) are demonstrable by use of one or more measurement(s) described in this paragraph or elsewhere herein or otherwise recognized as appropriate by those in the art.

In one aspect, the invention provides a method of treating an ocular condition in a patient comprising administering to the patient an effective amount of a composition described herein, e.g., an ophthalmic composition comprising a pilocarpine compound, e.g., a salt of pilocarpine, e.g., pilocarpine hydrochloride, and a brimonidine compound, e.g., a salt of brimonidine, e.g., brimonidine tartrate. In aspects, the invention provides methods for treating a patient diagnosed with any one or more such conditions.

Uncontradicted, "Treating" or "treatment" as used herein (and as well-understood in the art) can include any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure, etc.), fully or partially remove the disease's underlying cause, shorten a disease's duration, or a combination of any or all thereof.

In one aspect, the invention provides a method of treating an ocular condition comprising administering to the patient an effective amount of a composition described herein, e.g., an effective amount of a pharmaceutically acceptable and ophthalmologically suitable ophthalmic composition comprising a pilocarpine compound, e.g., a salt of pilocarpine, e.g., pilocarpine hydrochloride, in a concentration of about 1.0% w/v to about 3.0% w/v, a brimonidine compound, e.g., a salt of brimonidine, e.g., brimonidine tartrate, in an amount of about 0.05% w/v to about 0.2% w/v, optionally a penetration enhancer in a concentration from about 0.1% w/v to about 3.0% w/v, one or more tonicity agents in a concentration from about 0.01% w/v to about 0.1% w/v, benzalkonium chloride in an amount from about 0.003% to about 0.02% w/v, water, and one or more buffers or pH-adjusting agents, wherein the composition is free of borate buffers e.g., free of boric acid or sodium borate, free of citrate buffers, e.g., free of sodium citrate dihydrate, or free of both borate and citrate buffers.

In aspects, the invention provides a method of treating an ocular condition comprising administering to the patient an effective amount of a composition described herein, e.g., an effective amount of a pharmaceutically acceptable and ophthalmologically suitable ophthalmic composition comprising a pilocarpine compound, e.g., a salt of pilocarpine, e.g., pilocarpine hydrochloride, in an amount of about 1% w/v-about 3% w/v; a brimonidine compound, e.g., a salt of brimonidine, e.g., brimonidine tartrate, in an amount of about 0.05% w/v-about 0.2% w/v; a solubilization component in an amount of between about 0.1% w/v-about 0.7% w/v; a preservation component in an amount of about 0.003% w/v-about 0.02% w/v; a tonicity component in an amount of between about 3.5% w/v-about 5.5% w/v; and a viscosity enhancement component (thickening component) in an amount of about 0.1% w/v-about 1% w/v, wherein the composition is free of borate buffers e.g., free of boric acid or sodium borate, free of citrate buffers, e.g., free of sodium citrate dihydrate, or free of both borate and citrate buffers.

The term "ocular condition" as used herein includes any condition, disease, or impairment which affects or involves the eye or one of the parts or regions of the eye, including optical conditions causing refractive errors in the eye. Uncontradicted, use of the term "ocular condition" includes one or more symptoms related to the composition, such as, e.g., symptom(s) related to presbyopia. Ocular conditions include, but are not limited to presbyopia, hyperopia, mydriasis, anisocoria, and accommodative esotropia, myopia, astigmatism, Adie's tonic pupil, or other causes of parasympathetic denervation, accommodative insufficiency, and complications arising after refractive surgery, such as decentered ablations following LASIK or PRK, corneal scars, hazing, refractive errors, etc. In aspects, compositions provided by the invention can be suitable for patients who have received cataract implants with intra-ocular implant lenses, laser eye surgery (laser-assisted in situ keratomileusis (LASIK), or implantation of a phakic intra-ocular implants. In aspects, compositions may be suitable in pediatric conditions, such as, e.g., squint in childhood, where eye surgery is not recommended.

In certain aspects, composition(s) provided by the invention may find use in the treatment of other conditions, such as, e.g., extreme skin conditions such as ichthyosis, multiple allergy syndrome, or one or more conditions related to diabetes.

Exemplary Target/Treatable Conditions

In aspects, the invention provides a method of treating presbyopia, including one or more symptom of presbyopia, the method comprising administering an effective amount of any one or more of the compositions described herein, for an effective treatment period, e.g., about 1 day to about 5 years or longer. In aspects, the degree or extent of presbyopia is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of presbyopia at the start of treatment (or, e.g., the degree of presbyopia present without treatment). In certain aspects, a single administration of a composition provided by the invention corrects presbyopia for a period of at least about 1 hours, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours. In aspects, such improvement is in a significant number of patients, as determined by one or more adequate and well-controlled clinical studies. This principle can be applied to any other clinical/therapeutic improvement/effect described in this disclosure.

In aspects, the invention provides a method of treating hyperopia, including one or more symptoms of hyperopia, the method comprising administering an effective amount of any one or more of the compositions described herein, for an effective treatment period, e.g., about 1 day to about 5 years or longer. In aspects, the degree or extent of hyperopia is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of hyperopia at the start of treatment (or, e.g., the degree of hyperopia present without treatment). In certain aspects, a single administration of a composition provided by the invention corrects hyperopia for a period of at least about 1 hours, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours.

In aspects, the invention provides a method of treating mydriasis, including one or more symptoms of mydriasis, the method comprising administering an effective amount of any one or more of the compositions described herein, for an effective treatment period, e.g., about 1 day to about 5 years or longer. In aspects, the degree or extent of mydriasis is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of mydriasis at the start of treatment (or, e.g., the degree of mydriasis present without treatment). In certain aspects, a single administration of a composition provided by the invention corrects mydriasis for a period of at least about 1 hours, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours.

In aspects, the invention provides a method of treating anisocoria, including one or more symptoms of anisocoria, the method comprising administering an effective amount of any one or more of the compositions described herein, for an effective treatment period, e.g., about 1 day to about 5 years or longer. In aspects, the degree or extent of anisocoria is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of anisocoria at the start of treatment (or, e.g., the degree of anisocoria present without treatment). In certain aspects, a single administration of a composition provided by the invention corrects anisocoria for a period of at least about 1 hours, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours.

In aspects, the invention provides a method of treating accommodative esotropia, including one more symptom(s) of accommodative esotropia, the method comprising administering an effective amount of any one or more of the compositions described herein, for an effective treatment period, e.g., about 1 day to about 5 years or longer. In aspects, the degree or extent of accommodative esotropia is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of accommodative esotropia at the start of treatment (or, e.g., the degree of accommodative esotropia present without treatment). In certain aspects, a single administration of a composition provided by the invention corrects accommodative esotropia for a period of at least about 1 hours, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours.

In aspects, the invention provides a method of treating myopia, including one or more symptoms of myopia, the method comprising administering an effective amount of any one or more of the compositions described herein, for an effective treatment period, e.g., about 1 day to about 5 years or longer. In aspects, the degree or extent of myopia is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of myopia at the start of treatment (or, e.g., the degree of myopia present without treatment). In certain aspects, a single administration of a composition provided by the invention corrects myopia for a period of at least about 1 hour, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours.

In aspects, the invention provides a method of treating astigmatism, including one or more symptoms of astigmatism, the method comprising administering an effective amount of any one or more of the compositions described herein, for an effective treatment period, e.g., about 1 day to about 5 years or longer. In aspects, the degree or extent of astigmatism is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of astigmatism at the start of treatment (or, e.g., the degree of astigmatism present without treatment). In certain aspects, a single administration of a composition provided by the invention corrects astigmatism for a period of at least about 1 hours, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours.

In one aspect, the invention provides a pharmaceutically acceptable and ophthalmologically suitable composition comprising a pilocarpine compound, e.g., a salt of pilocarpine, e.g., pilocarpine HCl, for use in the treatment of an ocular condition (including one or more symptoms related to the ocular condition) selected from the group consisting of presbyopia, hyperopia, mydriasis, anisocoria, accommodative esotropia, myopia, and astigmatism, wherein (a) the composition is stable for a period of at least about 1 month, at least about 3 months, or at least about six months, (b) the ocular condition is improved by one or more measures of improvement known and accepted by the art for the condition being treated by at least about 15%, such as, e.g., at least about 20%, or, e.g., at least about 25% throughout (e.g., after the first, second, third, fifth, or, e.g., tenth administration of the composition, or at the end of the treatment period, and (c) wherein the composition is free of boric acid or sodium borate buffer, citrate buffer, or both.

Comparable Or Improved Effects/Reduced Side Effects

In aspects, the invention provides pharmaceutically acceptable and ophthalmologically suitable composition(s) comprising a pilocarpine compound and a brimonidine compound and being free of borate buffer (boric acid or sodium borate), citrate buffer (e.g., sodium citrate), or both, wherein treatment with the pharmaceutically acceptable and ophthalmologically suitable composition(s) provides equivalent or detectably or significantly improved clinical outcomes in treating visual impairment (e.g., in improving vision) when compared to treatment with the product approved under US Food and Drug Administration NDA Number 214028 (VUITY) (or a substantially similar product or a bioequivalent product) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of reducing visual impairment (e.g., in improving vision) by providing to a patient in need thereof an effective amount of composition(s) described herein, wherein the method is clinically demonstrated to be as effective or detectably or significantly more effective than treatment with the product approved under US Food and Drug Administration NDA Number 214028 (VUITY) for the same or similar indication (e.g., reducing visual impairment) and for at least substantially the same administration period.

In aspects, the invention provides pharmaceutically acceptable and ophthalmologically suitable composition(s) comprising a pilocarpine compound and a brimonidine compound and being free of borate buffer (boric acid, sodium borate), citrate buffer (e.g., sodium citrate), or both, wherein treatment with the pharmaceutically acceptable and ophthalmologically suitable composition provides equivalent or detectably or significantly improved clinical outcomes in treating presbyopia or one or more symptoms thereof when compared to treatment with the product approved under US Food and Drug Administration NDA Number 214028 (VUITY) (and, as noted above, this and similar aspects also implicitly disclose also or alternative comparison against substantially similar products or other bioequivalent products) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating presbyopia or one or more symptoms thereof by providing to a patient in need thereof an effective amount of composition(s) described herein, wherein the method is clinically demonstrated to be as effective or detectably or significantly more effective than treatment with the product approved under US Food and Drug Administration NDA Number 214028 (VUITY) for the same or similar indication (e.g., presbyopia) and for at least substantially the same administration period.

In aspects, the invention provides pharmaceutically acceptable and ophthalmologically suitable composition(s) comprising a pilocarpine compound and a brimonidine compound and being free of borate buffer (boric acid, sodium borate), citrate buffer (e.g., sodium citrate), or both, wherein treatment with the pharmaceutically acceptable and ophthalmologically suitable composition(s) provide(s) equivalent or detectably or significantly improved clinical outcomes in treating hyperopia when compared to treatment with the product approved under US Food and Drug Administration NDA Number 214028 (VUITY) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating hyperopia by providing to a patient in need thereof an effective amount of composition(s) described herein, wherein the method is clinically demonstrated to be as effective or detectably or significantly more effective than treatment with the product approved under US Food and Drug Administration NDA Number 214028 (VUITY) for the same or similar indication (e.g., hyperopia) and for at least substantially the same administration period.

In aspects, the invention provides pharmaceutically acceptable and ophthalmologically suitable composition(s) comprising a pilocarpine compound and a brimonidine compound and being free of borate buffer (boric acid, sodium borate), citrate buffer (e.g., sodium citrate), or both, wherein treatment with the pharmaceutically acceptable and ophthalmologically suitable composition provides equivalent or detectably or significantly improved clinical outcomes in treating mydriasis when compared to treatment with the product approved under US Food and Drug Administration NDA Number 214028 (VUITY) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating mydriasis by providing to a patient in need thereof an effective amount of composition(s) described herein, wherein the method is clinically demonstrated to be as effective or detectably or significantly more effective than treatment with the product approved under US Food and Drug Administration NDA Number 214028 (VUITY) for the same or similar indication (e.g., mydriasis) and for at least substantially the same administration period.

In aspects, the invention provides pharmaceutically acceptable and ophthalmologically suitable composition(s) comprising a pilocarpine compound and a brimonidine compound and being free of borate buffer (boric acid, sodium borate), citrate buffer (e.g., sodium citrate), or both, wherein treatment with the pharmaceutically acceptable and ophthalmologically suitable composition provides equivalent or detectably or significantly improved clinical outcomes in treating anisocoria when compared to treatment with the product approved under US Food and Drug Administration NDA Number 214028 (VUITY) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating anisocoria by providing to a patient in need thereof an effective amount of a composition described herein, wherein the method is clinically demonstrated to be as effective or detectably or significantly more effective than treatment with the product approved under US Food and Drug Administration NDA Number 214028 (VUITY) for the same or similar indication (e.g., anisocoria) and for at least substantially the same administration period.

In aspects, the invention provides pharmaceutically acceptable and ophthalmologically suitable composition(s) comprising a pilocarpine compound and brimonidine compound and being free of borate buffer (boric acid, sodium borate), citrate buffer (e.g., sodium citrate), or both, wherein treatment with the pharmaceutically acceptable and ophthalmologically suitable composition provides equivalent or detectably or significantly improved clinical outcomes in treating accommodative esotropia when compared to treatment with the product approved under US Food and Drug Administration NDA Number 214028 (VUITY) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating accommodative esotropia by providing to a patient in need thereof an effective amount of a composition described herein, wherein the method is clinically demonstrated to be as effective or detectably or significantly more effective than treatment with the product approved under US Food and Drug Administration NDA Number 214028 (VUITY) for the same or similar indication (e.g., accommodative esotropia) and for at least substantially the same administration period.

In aspects, the invention provides pharmaceutically acceptable and ophthalmologically suitable composition(s) comprising a pilocarpine compound and brimonidine compound and being free of borate buffer (boric acid, sodium borate), citrate buffer (e.g., sodium citrate), or both, wherein treatment with the pharmaceutically acceptable and ophthalmologically suitable composition provides equivalent or detectably or significantly improved clinical outcomes in treating myopia when compared to treatment with the product approved under US Food and Drug Administration NDA Number 214028 (VUITY) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating myopia by providing to a patient in need thereof an effective amount of composition(s) described herein, wherein the method is clinically demonstrated to be as effective or detectably or significantly more effective than treatment with the product approved under US Food and Drug Administration NDA Number 214028 (VUITY) for the same or similar indication (e.g., myopia) and for at least substantially the same administration period.

In aspects, the invention provides pharmaceutically acceptable and ophthalmologically suitable composition(s) comprising a pilocarpine compound and brimonidine compound and being free of borate buffer (boric acid, sodium borate), citrate buffer (e.g., sodium citrate), or both, wherein treatment with the pharmaceutically acceptable and ophthalmologically suitable composition provides equivalent or detectably or significantly improved clinical outcomes in treating astigmatism when compared to treatment with the product approved under US Food and Drug Administration NDA Number 214028 (VUITY) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating astigmatism by providing to a patient in need thereof an effective amount of composition(s) described herein, wherein the method is clinically demonstrated to be as effective or detectably or significantly more effective than treatment with the product approved under US Food and Drug Administration NDA Number 214028 (VUITY) for the same or similar indication (e.g., astigmatism) and for at least substantially the same administration period.

In aspects, the invention provides a method of treating presbyopia including symptoms thereof, the method comprising administration of an effective amount of composition(s) described herein, wherein the method results in detectably or significantly reduced ocular blurring compared to treatment of presbyopia with the product approved under US Food and Drug Administration NDA Number 214028 (VUITY) for at least substantially the same administration period.

In aspects, the invention provides a method of treating presbyopia including symptoms thereof, the method comprising administration of an effective amount of a composition(s) described herein, wherein the method results in detectably or significantly reduced ocular discomfort compared to treatment of presbyopia with the product approved under US Food and Drug Administration NDA Number 214028 (VUITY) for at least substantially the same administration period.

In aspects, the invention provides a method of treating presbyopia including symptoms thereof, the method comprising administration of an effective amount of (s)composition(s) described herein, wherein the method results in detectably or significantly reduced eye pain compared to treatment of presbyopia with the product approved under US Food and Drug Administration NDA Number 214028 (VUITY) for at least substantially the same administration period.

In aspects, the invention provides a method of treating presbyopia including symptoms thereof, the method comprising administration of an effective amount of a composition(s) described herein, wherein the method results in detectably or significantly reduced brow ache compared to treatment of presbyopia with the product approved under US Food and Drug Administration NDA Number 214028 (VUITY) for at least substantially the same administration period.

In aspects, the invention provides a method of treating presbyopia including symptoms thereof, the method comprising administration of an effective amount of (s)composition(s) described herein, wherein the method results in detectably or significantly reduced blurry vision compared to treatment of presbyopia with the product approved under US Food and Drug Administration NDA Number 214028 (VUITY) for at least substantially the same administration period.

In aspects, the invention provides a method of treating presbyopia including symptoms thereof, the method comprising administration of an effective amount of composition(s) described herein, wherein the method results in detectably or significantly reduced light sensitivity compared to treatment of presbyopia with the product approved under US Food and Drug Administration NDA Number 214028 (VUITY) for at least substantially the same administration period.

In aspects, the invention provides a method of treating presbyopia including symptoms thereof, the method comprising administration of an effective amount of composition(s) described herein, wherein the method results in detectably or significantly reduced stinging compared to treatment of presbyopia with the product approved under US Food and Drug Administration NDA Number 214028 (VUITY) for at least substantially the same administration period.

In aspects, the invention provides a method of treating presbyopia including symptoms thereof, the method comprising administration of an effective amount of composition(s) described herein, wherein the method results in detectably or significantly reduced itching compared to treatment of presbyopia with the product approved under US Food and Drug Administration NDA Number 214028 (VUITY) for at least substantially the same administration period.

In aspects, the invention provides a composition described herein, e.g., pharmaceutically acceptable and ophthalmologically suitable ophthalmic composition(s) of a pilocarpine compound, e.g., a salt of pilocarpine, e.g., pilocarpine HCl, a brimonidine compound, e.g., a salt of brimonidine, e.g., brimonidine tartrate, the composition(s) being free of boric acid, sodium borate, sodium citrate, or any combination thereof, wherein treatment with the pharmaceutically acceptable and ophthalmologically suitable composition provides detectably or significantly reduced risk of poor illumination, retinal detachment, adhesions (synechiae) between the iris and the lens in patients who have iritis when using the composition, hypersensitivity, headache, conjunctival hyperemia, blurred vision, eye pain, visual impairment, eye irritation, lacrimation, or any combination thereof compared to treatment with the product approved under US Food and Drug Administration NDA Number 214028 (VUITY) for at least substantially the same administration period.

In aspects, the invention provides composition(s) described herein, e.g., a pharmaceutically acceptable and ophthalmologically suitable ophthalmic composition of a pilocarpine compound, e.g., a salt of pilocarpine, e.g., pilocarpine HCl, a brimonidine compound, e.g., a salt of brimonidine, e.g., brimonidine tartrate, the composition being free of boric acid, sodium borate, sodium citrate, or any combination thereof, wherein treatment with the pharmaceutically acceptable and ophthalmologically suitable composition results in no detectable or significant impact on night vision, no detectable or significant reduction in visual field, or both.

In aspects, the invention provides composition(s) which detectably or significantly outperform the product approved under US Food and Drug Administration NDA Number 214028 (VUITY) in one or more respects related to composition pharmacokinetics related to pilocarpine, total API, or both. In aspects, composition(s) provided by the invention demonstrate a mean $C_{max} \geq 1.95$ ng/mL at day 30 of use (e.g., significantly greater, or greater by about 10%, 15%, 20%, 25%, 33%, 50%, 100% or more). In aspects, composition(s) provided by the invention demonstrate a mean $AUC_{0-t,ss} \geq 4.14$ ng*hr/mL at day 30 of use (e.g., significantly greater, or greater by about 10%, 15%, 20%, 25%, 33%, 50%, 100% or more). In aspects, composition(s) provided by the invention demonstrate a median $T_{max} \leq 0.3$ hours post dose at day 30 of use (e.g., significantly lower/lesser, such as reduced by about 10%, 15%, 20%, 25%, 33%, or 50%). In further aspects, the invention provides composition(s) wherein the proportion of patients gaining 3-lines or more in mesopic DCNVA, without losing more than 1 line (5 letters) of CDVA at Day 30, hour 3, is $\geq 26\%$ (e.g., is significantly greater than such value).

In aspects, any composition described in this disclosure can be used in the methods described in this section. However, for purposes of exemplification, compositions according to Exemplary Formulation A, Exemplary Formulation B, Exemplary Formulation C, and Exemplary Formulation D of Examples 1 and 2 may be particularly suitable for use in such methods, such as, e.g., Compositions 1-8 of Examples 3 and 6.

Methods of Manufacturing

In one aspect, the invention provides a process for preparing pharmaceutically acceptable and ophthalmologically suitable composition(s) described herein, e.g., composition(s) comprising a pilocarpine compound, e.g., a salt of pilocarpine, e.g., pilocarpine hydrochloride, in a concentration of about 1.0% w/v to 3.0% w/v, a brimonidine compound, e.g., a salt of brimonidine, e.g., brimonidine tartrate, in a concentration of about 0.05% w/v-about 0.2% w/v, optionally a penetration enhancer in a concentration from about 0.1% w/v to about 3.0% w/v, one or more tonicity agents in a concentration from about 0.01% w/v to about 0.1% w/v, benzalkonium chloride in an amount from about 0.003% to about 0.02% w/v, water, and one or more buffers or pH-adjusting agents, wherein the composition(s) is/are free of boric acid, sodium borate, or citrate buffers (e.g., free of boric acid, free of sodium citrate, e.g., sodium citrate dihydrate, or free of boric acid, sodium borate, and sodium citrate, e.g., sodium citrate dihydrate). In aspects, such composition(s) is/are characterized by lacking one, two, or more of such recited elements or comprising such elements but in different effective amounts.

In aspects, the invention provides a process for preparing pharmaceutically acceptable and ophthalmologically suitable composition(s) described herein, e.g., composition(s) comprising a pilocarpine compound, e.g., a salt of pilocarpine, e.g., pilocarpine hydrochloride, in an amount of about 1% w/v-about 3% w/v; a brimonidine compound, e.g., a salt of brimonidine, e.g., brimonidine tartrate, a solubilization component in an amount of between about 0.1% w/v-about 0.7% w/v; a preservation component in an amount of about 0.003% w/v-about 0.02% w/v; a tonicity component in an amount of between about 3.5% w/v-about 5.5% w/v; and a viscosity enhancement component (thickening component) in an amount of about 0.1% w/v-about 1% w/v, water, and one or more buffers or pH-adjusting agents, wherein the composition is free of boric acid or citrate buffers (e.g., free of boric acid, free of sodium borate, free of sodium citrate, e.g., sodium citrate dihydrate, or free of boric acid, sodium borate, and sodium citrate, e.g., sodium citrate dihydrate.)

In aspects, composition(s) provided by the invention are prepared by using any suitable technique, many of which are known to those skilled in the art, the steps of which can be combined in any order. In describing methods of manufacturing provided by the invention, references to order of operations/steps may be present. It should be understood that steps of described manufacturing process(es) can be performed in any suitable order, provided that the end product is at least substantially, at least generally, or essentially the same.

According to certain aspects, the invention provides a method of manufacturing (e.g., a manufacturing process for) composition(s) described herein, wherein the process is a non-aseptic process, and wherein the method of manufacturing comprises a terminal sterilization step. In aspects, composition(s) are terminally sterilized using moist heat. Terminal sterilization can be used to destroy all viable microorganisms within the final, sealed container containing the pharmaceutical composition. In aspects, an autoclave is used to accomplish terminal heat-sterilization of compositions in their final packaging. Typical autoclave cycles in the pharmaceutical industry to achieve terminal sterilization of the final product are about 121° C. for at least about 10 minutes. In aspects, facilities, equipment, procedures, and personnel participating in the method of manufacturing, e.g., participating in the processing, meet GMP rules and guidelines for non-aseptic processes.

According to alternative aspects, the invention provides a method of manufacturing (e.g., a manufacturing process for) composition(s) described herein, wherein the process is an aseptic process. In aspects, sterility is maintained during the manufacturing process by use of sterile materials and a controlled working environment. In aspects, all containers and apparatus utilized in the process are sterilized, preferably by heat sterilization, prior to use, e.g., prior to filling. In aspects, a sterilized container is filled under aseptic conditions, such as by passing the composition through a filter. Therefore, in aspects, composition(s) can be sterile filled into a container to avoid the heat stress of terminal sterilization. In aspects, facilities, equipment, procedures, and personnel participating in the method of manufacturing, e.g., participating in the processing, meet GMP rules and guidelines for aseptic processing.

In aspects, the invention provides a method of manufacturing composition(s) described herein, wherein the method comprises (a) preparation of a bulk composition, (b) offline filtration of the bulk composition, (c) online filtration of the bulk composition, and (d) final packaging of the composition. In aspects, composition(s) resulting from the method can be used in any one or more of the methods of treatment described herein.

In aspects, the invention provides a method of manufacturing composition(s) described herein, wherein the method comprises (a) preparation of a polymer phase, (b) preparation of a drug phase, (c) filtration of the drug phase into the polymer phase, (d) filtering the composition resulting from (c), and (e) final packaging of the composition. In aspects, composition(s) resulting from the method can be used in any one or more of the methods of treatment described herein.

In aspects, the invention provides pharmaceutically acceptable and ophthalmologically suitable composition(s) comprising pilocarpine compound(s), e.g., a salt of pilocarpine, e.g., pilocarpine HCl, and brimonidine compound(s), e.g., a salt of brimonidine, e.g., brimonidine tartrate, and methods of their manufacture, wherein the composition resulting from the method of manufacturing is aseptically distributed into single dose or multidose containers. Further, in aspects, the invention provides packaging of such single or multidose containers into kits for distribution to an end user.

Specific examples of manufacturing process(es) suitable for manufacturing composition(s) provided by the invention are found in, e.g., Examples 4, 5, and 7 of this disclosure.

According to some aspects, the invention provides a first method of manufacturing composition(s) described herein comprising the following steps.

In aspects, the first step(s) in a manufacturing process comprises the preparation of a bulk solution.

In aspects, preparation of a bulk solution comprises, e.g., (a) collecting water, e.g., WFI, in a manufacturing vessel at a temperature of between about 65° C. to about 85° C., such as, e.g., about 70° C.-about 80° C., or, e.g., not less than about 70° C.; (b) cooling the water for injection to about 15° C. to about 30° C., such as about 20° C.-about 25° C.; and (c) bubbling 0.2 μm filtered nitrogen through the WFI and continuing to bubble 0.2 μm filtered nitrogen through the WFI until the dissolved oxygen content of the WFI is less than or equal to about 2 ppm, such as, e.g., ≤~1.5 ppm, ≤~1 ppm, or, e.g., ≤~0.5 ppm. In aspects, the manufacturing process comprises continuing to bubble 0.2 μm filtered nitrogen through the WFI during bulk solution manufacturing.

In aspects, preparation of the bulk solution is continued by transferring between about 50-about 70 Kg of WFI, e.g., about 60 Kg of WFI, into a separate holding vessel. In aspects, this reserved WFI can be used in other manufacturing steps, such as, e.g., the preparation of pH adjusting agents (such as, e.g., 0.1N hydrochloric acid, 0.1N sodium hydroxide, or both), and for, e.g., bringing the final composition up to a final target volume.

In aspects, bulk solution preparation can continue by mixing the WFI with a suitable mixing device/stirrer, set at a speed appropriate for attaining sufficient mixing. In aspects, mixing speed can be adjusted according to the vessel geometry and mixing/stirring dynamics exhibited by the solution/composition throughout manufacture.

In aspects, bulk solution preparation can continue by adding the required quantity of a preservation agent, e.g., benzalkonium chloride. In aspects, the container comprising the preservation agent, e.g., benzalkonium chloride to be added is rinsed one or more times, e.g., once, twice, three times, four times, or, e.g., five times, with a sufficient amount of WFI sufficient to rinse the container, e.g., an amount such as, e.g., about 30 mL to about 70 mL, or, e.g., about 50 mL each time. In aspects, mixing/stirring is continued during the addition of the rinse solution back into the vessel after each rinse.

In aspects, bulk solution preparation can continue by adding the required quantity of a penetration agent. In aspects, this step is omitted in the manufacturing process of a composition which does not comprise a penetration agent. In aspects, a penetration agent, such as, e.g., polysorbate 80, is added, and the container used to add the penetration agent, e.g., polysorbate 80, is rinsed one or more times, e.g., once, twice, three times, four times, or, e.g., five times, with an amount of WFI sufficient to rinse the container, e.g., an amount such as, e.g., about 30 mL to about 70 mL, or, e.g., about 50 mL each time. In aspects, mixing/stirring is continued during the addition of the rinse solution back into the vessel after each rinse.

In aspects, bulk solution preparation can continue by adding the required amount of buffer agent(s), such as, e.g., citrate buffer or borate buffer or, e.g., acetate buffer or a phosphate buffer. In aspects, mixing/stirring is continued during the addition of the components, and is continued for a sufficient period to ensure the buffer constituents are completely dissolved, such as, for example, a period of time of, e.g., about 5 minutes, about 10 minutes, about 15 minutes, about 20 minutes, about 25 minutes, about 30 minutes, etc.

In aspects, bulk solution preparation can continue by adding the required amount of tonicity agent(s), such as, e.g., sodium chloride. In aspects, mixing/stirring is continued during the addition of the components and is continued for a sufficient period of time to ensure the buffer constituents are completely dissolved, such as, for example, a period of time of, e.g., about 5 minutes, about 10 minutes, about 15 minutes, about 20 minutes, about 25 minutes, or at least about 30 minutes or more.

In aspects, bulk solution preparation can continue by adding the required amount of PCC, such as, e.g., pilocarpine compound(s), e.g., salt(s) of pilocarpine, e.g., pilocarpine HCl, and the container used to add the PCC (e.g., pilocarpine HCl) is rinsed one or more times, e.g., once, twice, or three times with an amount of WFI sufficient to rinse the container, e.g., an amount such as, e.g., about 10 mL to about 40 mL, e.g., about 15-about 35 mL, or, e.g., about 25 mL each time. In aspects, mixing/stirring is continued during the addition of the rinse solution back into the vessel after each rinse. In aspects, mixing is continued for a sufficient period of time to ensure complete dissolution of the PCC, e.g., pilocarpine HCl, such as, e.g., a period of at least about 10 minutes, about 15 minutes, about 20 minutes, about 25 minutes, about 30 minutes, at least about 35 minutes, or, e.g., at least about 40 minutes or more.

In aspects, bulk solution preparation can continue by adding the required amount of AAA component, such as, e.g., brimonidine compound(s), e.g., salt(s) of brimonidine, e.g., brimonidine tartrate, and the container used to add the AAA component (e.g., brimonidine tartrate) is rinsed one or more times, e.g., once, twice, or three times with an amount of WFI sufficient to rinse the container, e.g., an amount such as, e.g., about 10 mL to about 40 mL, e.g., about 15-about 35 mL, or, e.g., about 25 mL each time. In aspects, mixing/stirring is continued during the addition of the rinse solution back into the vessel after each rinse. In aspects, mixing is continued for a sufficient period of time to ensure complete dissolution of the AAA component, e.g., brimonidine tartrate, such as, e.g., a period of at least about 10 minutes, about 15 minutes, about 20 minutes, about 25 minutes, about 30 minutes, at least about 35 minutes, or, e.g., at least about 40 minutes or more.

In aspects, preparation of the bulk solution can continue by bringing the composition up to a target volume, e.g., a volume of about 85 L-95L, such as, e.g., about 90 L. In aspects, the volume is brought up using WFI set aside as described above. In aspects, the solution is mixed for a sufficient period of time to ensure composition uniformity, such as, e.g., for a period of at least about 20 minutes, at least about 25 minutes, at least about 30 minutes, or at least about 35 minutes, e.g., about 30-32 minutes.

In aspects, preparation of the bulk solution can continue by performing a visual check of the solution for clarity, to ensure, e.g., that there are no visible undissolved particles in the solution.

In aspects, preparation of the bulk solution is pH adjusted using one or more pH adjusting agents. In aspects, pH of the solution is adjusted by the addition or one or more pH adjusting agents, with the solution sufficiently mixed after each addition such that the composition has a uniform pH prior to (a) sampling for pH, and (b) applying further pH adjustment as needed. In aspects, pH is adjusted to a pH of between about 4.4 to about 4.6, such as, e.g., about 4.4, about 4.5, or about 4.6 using the pH adjusting agent(s). In aspects, the pH is adjusted to a pH of between about 7 to about 8.5, such as, e.g., about 7.1, about 7.2, about 7.3, about 7.4, about 7.5, about 7.6, about 7.7, about 7.8, about 7.9, or, e.g., about 8.

In aspects, preparation of the bulk solution is completed by bringing up the volume of the solution to a final volume of, e.g., about 100L, with WFI reserved as described above. In aspects, the resulting solution is mixed for a sufficient period of time to ensure composition uniformity, such as, e.g., a period of at least about 10 minutes, at least about 15 minutes, at least about 20 minutes, at least about 25, or at least about 30 minutes. In aspects, a final pH check is performed to ensure that the composition pH is between about 4.4-about 4.6, such as, e.g., about 4.5.

In aspects, once the bulk solution is complete, offline filtration is performed. In aspects, the filtration is performed under laminar air flow.

In aspects, the second step(s) in a manufacturing process comprises the preparation of a bulk solution.

In aspects, after completion of the preparation of the bulk solution, the filtration process is initiated under controlled conditions, such as, e.g., under laminar air flow (LAF). In aspects, prior to initiation of the filtration process, a cartridge filter, e.g., a 0.2 μm capsule or cartridge filter, is integrity tested using an industry standard integrity test, such as, e.g., a water bubble point test, against the filter manufacturer's specification. In one aspect, an exemplary acceptable result is a pressure of not less than about 46 psi under a filtration pressure limit of between about 0.8 kg/cm² to about 1.8 kg/cm².

In aspects, prior to the start of filtration activity, the filtration unit is flushed with a sufficient amount of bulk solution to flush the unit, such as, e.g., about 200-250 mL, e.g., about 180 mL, about 200 mL, about 210 mL, about 220 mL, or e.g., about 230 mL of the bulk solution. In aspects, the bulk solution can be held inside of the filtration unit for a period of time during the flush, such as about 1.5 minutes, about 2 minutes, about 2.5 minutes, or about 3 minutes during the flush. In aspects, the bulk solution used for the flush is discarded after the flush. In aspects, the flushing procedure is repeated a number of times, such as one more time, two more times, three more times, four more times, or five or more times. In aspects, flushing is conducted a total of about 3 times.

In aspects, upon completion of flushing, filtration of the bulk solution is initiated. In aspects, the bulk solution is filtered through the pre-sterilized, tested, and flushed 0.2 μm capsule or cartridge filter. In aspects, all filtrate is collected in a sterile receiving vessel.

In aspects, upon completion of filtration, the filtrate within the sterile receiving vessel is overlayed with nitrogen, such as, e.g., 0.2 μm-filtered nitrogen.

In aspects, the receiving vessel can be transferred to a storage area, e.g., a sterile storage area, and stored under controlled conditions, e.g., controlled temperature and air flow conditions (e.g., under laminar air flow) until initiation of the filling activity.

In aspects, a post-filtration integrity test of the filter can be performed. In aspects, the post-filtration integrity test of the filter can be a water bubble point test. In aspects, an acceptable result is a pressure of not less than 39.2 psi under a filtration pressure limit of between about 0.8 kg/cm² to about 1.8 kg/cm².

In certain aspects, upon completion of the first filtration process is followed by a second filtration, wherein, prior to the initiation of filling and capping activity, the bulk solution is filtered through another filter, e.g., another 0.2μ pre-sterilized capsule or cartridge filter.

In aspects, pre-integrity filter testing is performed using an industry-accepted standard integrity test, such as, e.g., a water bubble point test, against the filter manufacturer's specification. In aspects, an acceptable result is a pressure of not less than about 46 psi under a filtration pressure limit of between about 0.8 kg/cm² to about 1.8 kg/cm². Upon passing the integrity test, in aspects the filter is then connected to the filling line through a pre-sterilized vessel, e.g., buffer tank.

In aspects, prior to the initiation of filtration activity, the filter/filtration unit is flushed with a sufficient volume of water to flush the filter, such as, e.g., about 200-about 250 mL of bulk solution, such as, e.g., about 180 mL, about 190 mL, about 200 mL, about 210 mL, about 220 mL, or, e.g., about 230 mL of the bulk solution. In aspects, the bulk solution is held within the filtration unit for a period of time during flushing, such as about 1.5 minutes, about 2 minutes, about 2.5 minutes, or, e.g., about 3 minutes, during this flushing process. In aspects, the flush and is then discarded. In aspects, the flushing process is repeated a number of times, such as at least one more time, at least two more times, at least 3 more times, at least four more times, or, e.g., at least five more times. In aspects, the flushing process is performed at least two additional times for a total of at least about 3 flushes, with the bulk solution used for flushing discarded after each flush.

In aspects, after discarding the filter flush solution, the entire quantity of remaining bulk solution is filtered into the sterile vessel, e.g., the sterile buffer tank.

In aspects, upon completing the filtration, the filling activity is then initiated. In aspects, upon the completion of the filling activity, a post-filtration integrity test of the filter is performed using an industry standard integrity test, such as, e.g., a water bubble point test. In aspects, an acceptable result is a pressure of not less than about 39.2 psi under a filtration pressure limit of between about 0.8 kg/cm² to about 1.8 kg/cm².

In aspects, the final step of a method of manufacturing composition(s) described herein is the process of filling and capping the composition(s).

In aspects, suitable sterile containers, such as, e.g., sterile vials, bottles such as, e.g., dropper bottles, are each filled to a target fill volume, such as, e.g., a volume of between about 1 mL and about 10 mL, such as a volume of between about 1 mL and about 5 mL, or, e.g., a volume of between about 1 mL and about 3 mL, such as a volume of about 2 mL to about 3 mL, e.g., a target volume of about 2.6 mL to about 2.8 mL (about 2.62 g to about 2.82 g), such as about 2.7 mL (about 2.72 g).

In aspects, after filling, the head space of each container is flushed with nitrogen, e.g., filtered nitrogen. In aspects, a minimum nitrogen flow is established, such as, e.g., a minimum nitrogen flow of about 1.5 L/min, about 2 L/min, about 2.5 L/min, or, e.g., about 3 L/min. In aspects, this step comprises placing associated container (e.g., vial, bottle, etc.), such as the nozzle of the bottle, and capping the bottle.

According to some aspects, the invention provides a second method of manufacturing a composition described herein comprising the following steps.

In aspects, a first ("filter number 1") and a second ("filter number 2") filter, e.g., 0.2 μm capsule filter, are each integrity-tested using an industry standard filter integrity test, e.g., a water bubble point test, against the filter manufacturer's specification(s). In aspects, an acceptable result of each test is a pressure of not less than about 46.0 psi under a filtration pressure limit of between about 0.8 kg/cm² to about 1.8 kg/cm². In aspects, upon completion of integrity testing, filters are flushed with a sufficient amount of nitrogen to remove any residual water from the filter pores.

In aspects, upon passing the integrity test, the outlet of filter number 2 is connected to the inlet of filter number 1 using a suitable connection mechanism, such as tubing, e.g., Pharma 50 silicone tubing, of a suitable length. Such length can be any suitable length for the manufacturing configuration, such as, e.g., a length of about 40 cm, about 50 cm, about 60 cm, about 70 cm, or about 80 cm. In aspects, the outlet of filter number 1 is connected to a valve, e.g., a diaphragm valve. In aspects, the inlet of filter number 2 is connected to a suitable connection mechanism, such as, e.g., tubing, for example Pharma 50 silicone tubing, of suitable length for the manufacturing configuration, such as, for example, a length of about 1.5 meters, 2 meters, 2.5 meters, 3 meters, or, e.g., about 3.5 meters, e.g., in aspects, about 2.30 meters. In aspects, the entire assembly is sterilized using a suitable sterilization method, e.g., autoclaving. During sterilization, e.g., while autoclaving, in aspects, the diaphragm valve is maintained in an open position. In aspects, upon completion of sterilization, e.g., after autoclaving, the diaphragm valve is closed under aseptic conditions. In aspects, the entire assembly is then connected to an empty manufacturing vessel (e.g., a "reactor vessel").

In aspects, the manufacturing vessel/reactor vessel is sterilized with a sufficient amount of water, e.g., water for injection (WFI), such as, e.g., about 100 Kg, about 110 Kg, about 120 Kg, about 130 Kg, about 140 Kg, or, e.g., about 150 Kg of WFI. In aspects, this establishes a sterilized "reactor vessel".

In aspects, a sufficient amount of WFI, e.g., about 120 Kg of WFI, at a temperature of not less than about 70° C., e.g., a temperature of between about 70° C.-about 80° C., is collected in a manufacturing vessel, such as, e.g., a stainless-steel (SS) manufacturing vessel.

In aspects, the WFI is cooled, for example to a temperature of about 20° C.-about 25° C., such as, e.g., by circulating the water through a water jacket. In aspect, while cooling, e.g., simultaneously with cooling, nitrogen, e.g., 0.2μ-filtered nitrogen, is passed (e.g., bubbled) through the WFI, with all WFI collected in the manufacturing vessel.

In aspects, the dissolved oxygen content of the WFI is tested one or more times, e.g., the WFI is routinely tested, to ensure that the WFI reaches a dissolved oxygen content of no more than about 2 ppm, e.g., no more than about 1.5 ppm, no more than about 1 ppm, or, e.g., no more than about 0.5 ppm.

In aspects, nitrogen bubbling is continued throughout the manufacturing process of one or more solutions of the method.

After completion of empty reactor sterilization, about 50 Kg, e.g., between about 50 Kg to about 70 Kg, of the about 120 Kg of WFI is transferred to a second manufacturing vessel, e.g., a stainless-steel manufacturing vessel. In aspects, this reserved WFI is used for one or more steps of the method, such as, e.g., used in the preparation of a drug phase, bringing composition(s) up to volume, or both, as is described further below.

In aspects, the establishment of a polymer phase is a first step(s) of the method of manufacturing.

In aspects, while maintaining the temperature of the remaining about 70 Kg (e.g., between about 50 to about 70 Kg) of WFI in the reactor vessel at about 70° C. to about 80° C., such as about 73° C. to about 78° C., a suitable stirrer (mixer) is established in the reactor vessel. In aspects, the suitable stirrer can be any stirrer suitable for the manufacturing configuration. In aspects, the stirrer/mixer is set to a stirrer speed of about 50 rpm to about 200 rpm, such as, e.g., about 75 rpm to about 175 rpm. In aspects, the mixing speed can be adjusted as necessary based on/according to the equipment being used in the manufacturing process, the batch volume, etc., e.g., according to the vessel geometry and the stirring dynamics during manufacture of the batch.

In aspects, the required quantity of a viscosity enhancer component, e.g., a gelling agent, e.g., gellan gum NF (national formulary), is added to the reactor vessel. In aspects, stirring is maintained at a sufficient speed, e.g., about 125 rpm±about 50 rpm, for a sufficient time, e.g., for at least about 30 minutes, such as about 60 mins, or for a sufficient time to ensure complete dissolution of the gellan gum. In aspects, the solution is maintained at a temperature of between about 70° C. and about 80° C., such as, e.g., 73° C. and about 78° C., during continuous stirring.

In aspects, after complete dissolution of the viscosity enhancer component, e.g., gellan gum, the solution is cooled to a temperature of between about 20° C. and about 25° C. In aspects, cooling is conducted under constant stirring. In aspects, this establishes the "polymer phase." In aspects, the polymer phase is sterilized at a set temperature, such as, e.g., a temperature of about 122.0° C., or a period, e.g., for at least about 20 minutes. In aspects, constant stirring continues during this period, e.g., at a suitable speed, such as a speed of about 125 rpm±about 50 rpm.

In aspects, upon completion of sterilization, the polymer phase is cooled, such as, e.g., to a temperature of about 20° C. to about 30° C., e.g., 25° C. In aspects, while cooling, when the temperature of the polymer phase reaches a set temperature, such as, e.g., a temperature of between about 50° C. to about 70° C., such as, e.g., about 60° C., the stirring speed is increased to a suitable increased mixing speed, e.g., a stirring speed of about 250 rpm±50 rpm. In aspects, the method of manufacturing continues with a second step(s) of preparing a drug phase solution.

In aspects, an amount of reserved WFI, e.g., about 50 kg of the reserved, cooled WFI, is collected in a suitable manufacturing vessel. In aspects, a suitable stirrer/mixer is established in the manufacturing vessel. In aspects, the mixer is set to a suitable stirring speed for the manufacturing configuration being used, e.g., a stirring speed of, e.g., about 200 rpm to about 400 rpm, such as, e.g., about 250 rpm to about 350 rpm. In aspects, the mixing speed can be adjusted as necessary based on/according to the equipment being used in the manufacturing process, the batch size being manufactured, or both, e.g., according to the vessel geometry and the stirring dynamics during the manufacture of the batch.

In aspects, the total required quantity of PCC, e.g., pilocarpine compound(s), e.g., salt(s) of pilocarpine, e.g., pilocarpine HCl, is added to the manufacturing vessel. In aspects, the total required quantity of AAA component, e.g., brimonidine compound(s), e.g., salt(s) of brimonidine, e.g., brimonidine tartrate, is added to the manufacturing vessel. In aspects, the addition of the APIs is followed by the addition of the total required quantity of a preservative component, e.g., benzalkonium chloride. In aspects, the resulting composition is mixed for a sufficient period of time to ensure that the two components are completely dissolved.

In aspects, a penetration enhancer component constituent, if present in the composition, such as, e.g., polysorbate 80, is added to the manufacturing vessel. In aspects, the resulting composition is mixed for a sufficient period of time to ensure that the entire penetration enhancer component, e.g., polysorbate 80, is completely dissolved.

In aspects, upon the complete dissolution of the PCC (e.g., pilocarpine HCl), the AAA component (e.g., brimonidine tartrate), preservative component (e.g., benzalkonium chloride), and penetration enhancer component (e.g., polysorbate 80) (if present in the composition), a solubilization component constituent (such as, e.g., surfactant), e.g., cremophor, is added to the solution. In aspects, the resulting composition is mixed for a suitable period of time to allow the cremophor to completely dissolve.

In aspects, upon the complete dissolution of the solubilization constituent, e.g., cremophor, the total required quantity of a tonicity component, e.g., mannitol, is added to the solution. In aspects, the resulting composition is mixed for a suitable period of time to allow the tonicity component, e.g., mannitol, to completely dissolve.

Upon the complete dissolution of the mannitol, the total required quantity of a second solubilizer, e.g., a solubilizer which in aspects may also be characterizable as a penetration enhancer, e.g., tromethamine, is added to the solution. In aspects, the resulting composition is mixed for a sufficient period of time to ensure complete dissolution of the component, e.g., tromethamine. In aspects, such a period of time can be, e.g., at least about 5 minutes, at least about 10 minutes, at least about 15 minutes, or, e.g., at least about 20 min.

In aspects, the composition is then checked for clarity. In aspects, clarity is evaluated using visual inspection. In aspects, stirring/mixing is continued until visual clarity of the solution is achieved.

In aspects, the volume of the composition is then brought to between about 50 L and about 60 L, e.g., to about 55 L (if, e.g., an exemplary batch size of about 100 L is being manufactured; it should be understood that this and other steps of the methods of manufacturing described here can be adjusted as needed for the batch size being manufactured) using, e.g., previously reserved WFI. In aspects, the composition is then stirred for a sufficient period of time to ensure composition uniformity, such as for at least about 5 minutes, at least about 10 minutes, at least about 15 minutes, at least about 20 minutes, at least about 25 minutes, or, e.g., at least about 30 minutes. In aspects, this establishes the "drug phase".

In aspects, an industry standard sampling protocol is used to sample and test the drug phase to ensure that the phase meets pre-established specification(s). Upon acceptance, in aspects, the drug phase is transferred to the sterilized polymer phase via aseptic filtration (see below).

In aspects, the method of manufacturing next comprises a step of aseptic filtration. As has been previously stated, references to order of operation, e.g., "next" as used here, should not be interpreted as limiting. In aspects, manufacturing steps/processes described can be performed in any suitable order provided the resulting composition comprises the characteristic(s) described herein.

In aspects, aseptic filtration of the drug phase into the sterile polymer phase is performed at a filtration pressure of between about, e.g., 0.8 Kg/cm$^2$-about 1.8 Kg/cm$^2$.

In aspects, prior to beginning the aseptic filtration, the weight of the drug phase is noted. In aspects, an amount of drug phase, e.g., about 50 Kg to ~60 Kg, e.g., about 55 Kg of the drug phase (which can be referred to as the "concentrated drug phase"), is filtered into the reactor vessel containing the polymer phase through 2 sterilized 0.2 µm filters connected in series.

In aspects, WFI is passed through the filters a number of times, such as about two times or about three times with, e.g., between about 2 L and about 3 L of WFI used each time, such as, e.g., about 2.5 L of WFI each time. In aspects, the filtrate added to the reactor vessel each time to ensure all required drug phase is added into the reactor vessel. In aspects, the resulting composition is then stirred for a sufficient period of time (and at a suitable speed) to ensure composition uniformity. In aspects for example, the composition is mixed for at least about 45 minutes, at least about 50 minutes, at least about 55 minutes, at least about 60 minutes, at least about 65 minutes, at least about 75 minutes, at least about 80 minutes, or, e.g., at least about 85 minutes, such as, e.g., about 1 hour, at a suitable speed, such as, e.g., a speed of about 150 rpm-about 350 rpm, or, e.g., a speed of about 200 rpm to about 300 rpm, to ensure composition uniformity.

In aspects, a post-filtration integrity test of the filter is performed using an industry standard filter integrity test, e.g., a water bubble point test. In aspects, an acceptable result is a pressure of not less than about 34.8 psi under a filtration pressure limit of between about 0.8 kg/cm$^2$ to about 1.8 kg/cm$^2$.

In aspects, the composition is pH adjusted using one or more pH adjusting agents. In aspects, pH of the solution is adjusted by the addition or one or more pH adjusting agents, with the solution sufficiently mixed after each addition such that the composition has a uniform pH prior to (a) sampling for pH, and (b) applying further pH adjustment as needed. In aspects, pH is adjusted to a pH of between about 4.4 to about 4.6, such as, e.g., about 4.4, about 4.5, or about 4.6 using the pH adjusting agent(s).

In aspects, the method of manufacturing further comprises a final combined composition (bulk solution) filtration step.

In aspects, filtration of the final combined composition (bulk solution) is then performed using a suitable filter, e.g., such as an 8 µm filter, such as, e.g., an 8 µm PP2 MidiCap® filter (Sartorius).

In aspects, prior to initiating filtration activity, a sterilized filter, e.g., a sterilized 8.0 µm filter, e.g. a sterilized 8 µm polypropylene filter, is flushed with a sufficient amount of bulk solution, such as, e.g., about 80 mL to about 140 mL of bulk solution, e.g., about 100 mL to about 120 mL of bulk solution, a number of times such as about 2 times, about 3 times, about 4 times, or, e.g., about 5 times. In aspects, during each flush, the composition is held in the filtration unit for an extended period of time, such as about 1 minute, about 2 minutes, about 3 minutes, about 4 minutes, or, e.g., about 5 minutes, prior to discarding each flush. In aspects, upon completion of the flushing process, filtration of the bulk solution is performed. In aspects, the filtrate collected in a sterile receiving vessel.

In aspects, a final step of the method is filling and capping step(s).

In aspects, suitable sterile containers, such as sterile vials or, e.g., sterile bottles, such as, e.g., dropper bottles, are each filled to a suitable volume, such as, e.g., a volume of between about 1 mL and about 10 mL, such as, e.g., a volume of between about 1 mL and about 5 mL, e.g. about 1 mL to about 3 mL, or, e.g., a volume of about 2 mL to about 3 mL, such as, e.g., to a volume of between about 2.6 mL and about 2.8 mL (about 2.62 g to about 2.82 g), such as about 2.7 mL (about 2.72 g).

In aspects, after filling, the head space of each container, e.g., vial or bottle, is flushed with nitrogen, e.g., filtered nitrogen. In aspects, a minimum nitrogen flow is utilized for flushing, such as, e.g., a minimum nitrogen flow of about 1 L/min, about 1.5 L/min, about 2 L/min, about 2.5 L/min, or, e.g., about 3 L/min. In aspects, this step comprises placing all container components, e.g., a bottle nozzle, and capping the bottle.

Product-by-Process Aspects

In aspects, the invention provides composition(s) described herein, e.g., composition(s) comprising about 1% w/v-about 3% w/v of a pilocarpine compound, e.g., a salt of pilocarpine, e.g., pilocarpine HCl, about 0.05% w/v-about 0.2% of a brimonidine compound, e.g., a salt of brimonidine, e.g., brimonidine tartrate, about 0.003% w/v-about 0.02% w/v benzalkonium chloride, about 0.5% w/v-about 1.5% w/v boric acid or sodium citrate or, alternatively, about 0.005% w/v-about 0.4% w/v sodium citrate dihydrate, or, as yet a third alternative, not comprising boric acid, sodium citrate, or sodium citrate dihydrate, about 0.01% w/v-about 0.1% w/v sodium chloride, optionally about 0.05% w/v-about 0.5% w/v of a penetration enhancer such as, e.g., polysorbate 80, a sufficient amount of pH adjusting agent(s) to establish the pH of the composition at between about 3.5-about 5.5, or, alternatively, to about 7-about 7.5, and water, the composition made by a process comprising (a) preparing a bulk composition, (b) offline filtering the bulk composition, (c) online filtering the bulk composition, and (d) packaging of the final composition, wherein the process is either an aseptic process or a non-aseptic process.

In aspects, the invention provides composition(s) described herein, e.g., composition(s) comprising between about 0.5% w/v-about 2.5% w/v of a pilocarpine compound, e.g., a salt of pilocarpine, e.g., pilocarpine HCl, about 0.05% w/v-about 0.25 w/v of a brimonidine compound, e.g., a salt of brimonidine, e.g., brimonidine tartrate, about 0.05% w/v-about 0.8 w/v of a polyethoxylated castor oil (e.g., cremophor), about 0.003% w/v-about 0.02% w/v of benzalkonium chloride, about 0.05% w/v-about 0.5% w/v tromethamine, about 3% w/v-about 6% w/v mannitol, about 0.1% w/v-about 1% w/v gellan gum, a sufficient amount of pH adjusting agent(s) to establish the pH of the composition at between about 3.5-about 5.5, or, alternatively, to about 7-about 7.5, and water, the composition made by a process comprising (a) preparing a polymer phase, (b) preparing a drug phase, (c) filtering the drug phase into the polymer phase, (d) filtering the composition resulting from (c), and (e) packaging the final composition, wherein the process is either an aseptic process or a non-aseptic process. In aspects, the process is an aseptic process.

In aspects, the invention provides composition(s) described herein, e.g., composition(s) comprising about 1% w/v-about 3% w/v of a PCC, e.g., a pilocarpine compound, e.g., a salt of pilocarpine, e.g., pilocarpine HCl, about 0.05% w/v-about 0.2% w/v of an AAA component, e.g., a brimonidine compound, e.g., a salt of brimonidine, e.g., brimonidine tartrate, about 0.003% w/v-about 0.02% w/v of a preservation agent, about 0.5% w/v-about 1.5% w/v borate buffer or, alternatively, about 0.005% w/v-about 0.09% w/v citrate buffer, or, as yet a third alternative, not comprising either borate buffer (e.g., not comprising boric acid or sodium borate) or citrate buffer (e.g., not comprising sodium citrate dihydrate), about 0.01% w/v-about 0.1% w/v tonicity component, optionally about 0.05% w/v-about 0.5% w/v of a penetration enhancer such as, e.g., polysorbate 80, a sufficient amount of pH adjusting agent(s) to establish the pH of the composition at between about 3.5-about 5.5 or, alternatively to establish the pH of the composition at between about 7-about 7.5, and a carrier, e.g., an aqueous carrier such as WFI, the composition made by a process comprising (a) preparing a bulk composition, (b) offline filtering the bulk composition, (c) online filtering the bulk composition, and (d) packaging of the final composition, wherein the process is either an aseptic process or a non-aseptic process, and, further, wherein the composition (a) maintains its established pH within acceptable limits (e.g., between 4-5 or between 7-7.5, according to its established pH during its manufacture), (b) retains at least about 95%, such as, e.g., at least about 97%, about 98%, or, e.g., at least about 99% of the original PCC, AAA component, or both when stored at between about 15° C. and about 27° C. (e.g., between about 15° C. and about 27° C. and about 60% relative humidity); when stored at about 25° C.±2° C., e.g., when stored at about 25° C.±2° C. and about 40%±5% relative humidity (e.g., for long term storage); when stored at about 30° C.±2° C. and about 35%±5% relative humidity (e.g., for long term storage); about 30° C.±2° C. and about 65%±5% relative humidity; when stored at about 40° C.±2° C. and not more than ("NMT") about 25% relative humidity (e.g., for accelerated storage); or when stored at a combination of any or all such conditions, (c) comprises less than about 2.5% total impurities, e.g., less than about 2%, less than about 1.5%, less than about 1%, or, e.g., less than about 0.5% total impurities after storage at between about 15° C. and about 27° C. (e.g., between about 15° C. and about 27° C. and about 60% relative humidity); after storage at about 25° C.±2° C., e.g., after storage at about 25° C.±2° C. and about 40%±5% relative humidity (e.g., for long term storage); after storage at about 30° C.±2° C. and about 35%±5% relative humidity (e.g., for long term storage); after storage at about 30° C.±2° C. and about 65%±5% relative humidity; after storage at about 40° C.±2° C. and not more than ("NMT") about 25% relative humidity (e.g., for accelerated storage); or after storage at a combination of any or all such conditions, or (d) any combination of or all of (a), (b), and (c) for a period of at least about 1 month, such as, e.g., ≥~3 months, ≥~6 months, ≥~9 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

In aspects, the invention provides composition(s) comprising between about 0.5% w/v-about 2.5% w/v of a PCC, e.g., a pilocarpine compound, e.g., a salt of pilocarpine, e.g., pilocarpine HCl, about 0.05% w/v-about 0.2% w/v of an AAA component, e.g., a brimonidine compound, e.g., a salt of brimonidine, e.g., brimonidine tartrate, about 0.05% w/v-about 0.8 w/v of a first solubilizer, e.g., a surfactant solubilizer (e.g., cremophor), about 0.003% w/v-about 0.02% w/v of a preservation component, about 0.05% w/v-about 0.5% w/v a second solubilizer, e.g., a solubilizer further characterizable as a penetration enhancer, about 3% w/v-about 6% w/v tonicity component, about 0.1% w/v-about 1% w/v thickening component, a sufficient amount of pH adjusting agent(s) to establish the pH of the composition at between about 3.5-about 5.5 or, alternatively to establish the pH of the composition at between about 7-about 7.5 and water, the composition(s) made by a process comprising (1) preparing a polymer phase, (2) preparing a drug phase, (3) filtering the drug phase into the polymer phase, (4) filtering the composition resulting from (3), and (5) packaging the final composition, wherein the process is either an aseptic process or a non-aseptic process, e.g., an aseptic process, and, further, wherein the composition (a) its established pH within acceptable limits (e.g., between 4-5 or between 7-7.5, according to its established pH during its manufacture), (b) retains at least about 95%, such as, e.g., at least about 97%, about 98%, or, e.g., at least about 99% of the original PCC, AAA component, or both when stored at between about 15° C. and about 27° C. (e.g., between about 15° C. and about 27° C. and about 60% relative humidity); when stored at about 25° C.±2° C., e.g., when stored at about 25° C.±2° C. and about 40%±5% relative humidity (e.g., for long term storage); when stored at about 30° C.±2° C. and about 35%±5% relative humidity (e.g., for long term storage); when stored at about 30° C.±2° C. and about 65%±5% relative humidity; when stored at about 40° C.±2° C. and not more than ("NMT") about 25% relative humidity (e.g., for accelerated storage); or when stored at a combination of any or all such conditions, (c) comprises less than about 2.5% total impurities, e.g., less than about 2%, less than about 1.5%, less than about 1%, or, e.g., less than about 0.5% total impurities after storage at between about 15° C. and about 27° C. (e.g., between about 15° C. and about 27° C. and about 60% relative humidity); after storage at about 25° C.±2° C., e.g., after storage at about 25° C.±2° C. and about 40%±5% relative humidity (e.g., for long term storage); after storage at about 30° C.±2° C. and about 35%±5% relative humidity (e.g., for long term storage); after storage at about 30° C.±2° C. and about 65%±5% relative humidity; after storage at about 40° C.±2° C. and not more than ("NMT") about 25% relative humidity (e.g., for accelerated storage); or (d) any combination of or all of (a), (b), and (c), for a period of at least about 1 month, such as, e.g., ≥~3 months, ≥~6 months, ≥~9 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

Packaging/Delivered Form and Kits

In aspects, composition(s) provided by the invention can be provided with, e.g., contained within, a delivery device suitable for administering the composition. In aspects, such a delivery device can be any suitable delivery device capable of maintaining the composition(s) therein in sterile form prior to administration and, further, capable of preventing detectable or significant degradation of the compositions during shipping or storage. In aspects, composition(s) can be provided with, e.g., contained within, dropper bottle(s), squeeze bottle(s), vials, and the like which are commonly known in the art.

According to certain embodiments, pharmaceutically acceptable and ophthalmologically suitable composition(s) provided by the invention can be packaged in any suitable packaging, such suitability being at least in part defined by protecting the compositions held therein from degradation, contamination, or both. In certain aspects, suitable packaging materials are materials which exhibit less than about 20%, such as <~18%, <~16%, <~14%, <~12%, <~10%, <~8%, <~6%, <~4%, <~2% or even less sorption of a PCC constituent, such as, e.g., a pilocarpine compound, or more specifically pilocarpine HCl, an AAA component, such as, e.g., a brimonidine compound, or more specifically brimonidine tartrate, or both. In some respects, suitable materials include but may not be limited to packaging material made of select polyolefins, such as, e.g., DuPont® 20 LDPE, Chevron 5502 HDPE, Atofina 3020 PP, polypropylene homopolymers, low ethylene content (<8%) polypropylenes, and polymers (HDPE, PP) with low content of additives (<5%) and with low flexural modulus (<200 kpsi). In some respects, a suitable material is an EP-quality LDPE which, in further aspects, may contain no additives. In aspects, suitable packaging can comprise a polypropylene container provided that that polypropylene container is not packaged in a bag/container containing an iron oxide oxygen scavenger.

In certain aspects, the packaging can comprise or can be mostly comprised of (e.g., comprise in an amount ≥~10%, ≥~20%, ≥~30%, ≥~40%, or ≥~50%, such as, e.g., comprise in an amount ≥~60%, ≥~70%, ≥~80%, ≥~90% or more) an ultraviolet-light blocking agent or material. In aspects, such a material can be capable of blocking ≥~1%, ≥~5%, ≥~10%, ≥~20%, ≥~30%, ≥~40%, or ≥~50%, such as, e.g., ≥~60%, ≥~70%, ≥~80%, ≥~90% or more of the ultraviolet light in the environment from entering the container. In aspects, composition(s) described herein can be packaged in, stored, in, or both packaged and stored in a container wherein the container significantly reduces exposure of the composition to UV B radiation, such as by at least about 50%, at least about 65%, at least about 75%, at least about 90%, at least about 95%, or at least 99%. In aspects, the packaging material of composition(s) described herein is semi- or completely opaque, while in alternative aspects, the packaging is semi- or completely clear. In aspects, packaging can comprise different parts wherein one component of the packaging comprises a first material and one or more components of the packaging contain a second (or more) material(s).

In certain aspects, packaging can be selected based on the method of delivery of the compositions herein (e.g., composition(s) provided as a gel can be provided in suitable packaging for gels wherein compositions provided as a liquid can be provided in suitable packaging for liquids, e.g., in a user-friendly dropper bottle; in aspects, a composition in gel form can also or alternatively be provided in a dropper bottle for drop-by-drop administration.) In aspects, the composition(s) provided by the invention are stored in vials capable of being penetrated by a needle such that compositions can be extracted from such vials and administered by injection. In aspects, composition(s) are provided in pre-filled injection devices, such as, e.g., pre-filled syringes. In aspects, the compositions of the invention are stored in a packaging that facilitates the delivery of the composition as eye drops.

In one aspect, ophthalmic composition(s) provided by the invention comprise a pilocarpine compound, e.g., pilocarpine hydrochloride, a brimonidine compound, e.g., brimonidine tartrate, and one or more pharmaceutically acceptable excipient(s), and are provided in single-dose bottles. In an alternative aspect, such composition(s) are provided in multi-dose bottles, such as multi-dose eye dropper bottles. In aspects, such multi-dose bottles allow for the composition, e.g., provided as a solution to be dropped into the recipient's eye(s), to be applied as liquid drops over a course of treatment, such as, e.g., over the course of many days, several weeks, months, or longer.

In aspects, the average force required to release one or more drops of the compositions described herein from a dropper bottle (a standard bottle common in the art for dispensing liquid in droplet form), by compressing the middle section of the storage body of such a dropper bottle, ranges between about 1.7-2.8 Kg for release of the first drop, e.g., between about 1.7-2.6, ~1.7-2.4, ~1.7-2.2, or between about ~1.7-2.0 Kg. In aspects, successive drops can require more tension, such as can require an additional ~20-30% of force for release of the second drop, and, e.g., an additional force of ~24-50% for release of the third drop.

In aspects, composition(s) provided by the invention are administered by injection. In aspects, composition(s) are provided in packaging which is accessible via a needle such that composition(s) can be withdrawn by a needle in preparation for injection. In aspects, composition(s) are provided in pre-filled injection devices, such as pre-filled syringes. In aspects, one or more pre-filled syringes are provided in a kit as is described further elsewhere herein. In aspects, injection devices can comprise between about 0.25 mL-about 5 mL of composition, though typically up to about 1 mL, such as, e.g., between ~0.5-~5 mL, ~0.75-~5 mL, ~1-~5 mL, ~1.25-~5 mL, ~1.5-~5 mL, ~1.75-~5 mL, ~2-~5 mL, ~2.25-~5 mL, ~2.5-~5 mL, ~2.75-~5 mL, ~3-~5 mL, ~3.25-~5 mL, ~3.5-~5 mL, ~3.75-~5 mL, ~4-~5 mL, ~4.25- ~5 mL, ~4.5-~5 mL, or, e.g., ~4.75-~5 mL, such as for example ~0.25-~4.5 mL, ~0.25-~4 mL, ~0.25-~3.5, ~0.25-~3.5 mL, ~0.25-~3 mL, ~0.25-~2.5 mL, ~0.25-~2 mL, ~0.25-~1.5 mL, or, e.g., ~0.25-~1 mL of composition, as in, e.g., ~0.1 mL, ~0.15 mL, ~0.2 mL, ~0.25 mL, ~0.3 mL, ~0.35 mL, ~0.4 mL, ~0.45 mL, ~0.5 mL, ~0.55 mL, ~0.6 mL, ~0.7 mL, ~0.75 mL, ~0.8 mL, ~0.85 mL, ~0.9 mL, or, e.g., ~1 mL of composition.

In aspects, composition(s) are provided in single dose or multi-dose packaging.

In aspects, a single dose package comprises a single dose of composition within a single dose administration container. In aspects, a multi-dose package comprises a plurality of single dose administration containers. In aspects, a multidose package comprises a plurality of doses within a single administration container. For example, a multi-dose package can be, e.g., a single dropper bottle comprising sufficient volume of composition to administer the composition multiple times over the course of an administration period, such as (but certainly not limited to) administration of about 1-3×/day over a period of about 1-7 days, ~1 week-~1 month, ~1 month-~3 months, ~3 months-~6 months, or, e.g., ~6 months-~1 year.

In aspects, packaging of composition(s) is any suitable packaging which effectively provides compositions with a shelf life of at least about 1 month, such as, e.g., ≥~3 weeks, ≥~4 weeks (1 month), ≥~5 weeks, ≥~6 weeks, ≥~7 weeks, ≥~8 weeks (2 months), ≥~9 weeks, ≥~10 weeks, ≥~11 weeks, ≥~12 weeks (3 months), ≥~13 weeks, ≥~14 weeks, ≥~15 weeks, ≥~16 weeks (4 months), or more, such as ≥~5 months, ≥~6 months, ≥~7 months, ≥~8 months, ≥~9 months, ≥~10 months, ≥~11 months, or ≥~12 months (1 year), or even longer, such as, ≥~18 months, ≥~24 months (2 years), ≥~30 months, or, e.g., ≥~36 months (3 years) or longer.

The term "shelf life" has been described elsewhere herein. In aspects, shelf life refers to a period of time wherein any API of the composition loses more than about 10%, such as, e.g., ≤~9%, ≤~8%, ≤~7%, ≤~6%, ≤~5%, ≤~4%, ≤~3%, ≤~2%, or, e.g., ≤~1%, of the potency while in storage after manufacturing and prior to use.

Kits (Collections of Compositions and Administration Devices)

In aspects, the invention provides kits comprising one or more pilocarpine and brimonidine compound composition(s) described herein and one or more delivery devices for such compounds. In aspects, a kit provided by the invention can comprise a single delivery device comprising a single composition, the composition present in an amount representative of a single dose. In aspects, a kit provided by the invention can comprise a single delivery device comprising a single composition, the composition present in an amount representative of multiple doses, e.g., 2 or more, 3 or more, 5 or more, 10 or more 20 or more, 30 or more, or, e.g., 50 or more doses. In aspects, a kit provided by the invention can comprise a plurality of delivery devices comprising a single composition, the composition present in an amount representative of a single dose. In aspects, a kit provided by the invention can comprise a plurality of delivery devices comprising a single composition, the composition present in an amount representative of a multiple doses, e.g., 2 or more, 3 or more, 5 or more, 10 or more 20 or more, 30 or more, or, e.g., 50 or more doses. In aspects, a kit provided by the invention can comprise multiple compositions in multiple delivery devices, wherein at least one ingredient of at least one composition varies from that of at least one other composition in either presence or amount. In aspects, a kit provided by the invention can comprise multiple compositions in multiple delivery devices, wherein the amount of at least one composition in one delivery device varies from the amount of at least one other composition in at least one other delivery device. In aspects, a dose can be a single drop. In aspects, a dose can be 2 drops. In aspects, a dose can be 3 drops. Typically, a dose is one or two drops, e.g., a single drop.

In aspects, the invention provides a kit wherein composition(s) are pre-filled in a delivery device, and a kit comprises one or more pre-filled delivery devices and one or more additional components to facilitate administration of the composition(s). For example, in aspects, the invention provides a kit wherein composition(s) are provided in one or more pre-filled containers which facilitate administration of the composition(s) by drops, such as, e.g., one or more pre-filled dropper bottles as described herein. In alternative aspects, the invention provides a kit wherein composition(s) are pre-filled in a syringe and the kit comprises one or more needles to facilitate delivery of the compositions by injection, such as, e.g., for administration by intracameral injection. In aspects, the invention provides a composition which is formulated for injection and contained in an injection delivery device, a device adapted for injection delivery, or is packaged with an injection delivery device.

In aspects, the invention provides for a kit as described in this section, wherein the kit has a shelf life when stored at controlled room temperature of between about 15° C. to 27° C., e.g., about 25° C.+/−2° C., for at least about 1 month, e.g., ~2, ~3, ~4, ~5, or at least ~6 months (e.g., 6-36 months.)

Stored at Room Temperature

In aspects, composition(s) provided by the invention, e.g., composition(s) in final packaged form, such as, e.g., composition(s) provided as a component of a kit, are stable when stored at standard room temperature, that is, controlled room temperature of between about 15° C. to 27° C., e.g., about 25° C.+/−2° C., for a period of at least about 1 month, e.g., ≥~3, ≥~6, ≥~9, ≥~12, ≥~18, ≥~24, ≥~28, ≥~33, or, e.g., ≥~36 months.

REPRESENTATIVE EXPERIMENTS/EMBODIMENTS ("EXAMPLES")

The following detailed exemplary expository descriptions or experiments involving embodiments, applications, or related principles, of or otherwise related to the invention ("Examples") are provided to assist readers in further understanding aspects of the invention or principles related to the invention or practice of aspects of the invention.

Any particular materials, methods, steps, and conditions employed/described in the following Examples, and any results thereof, are merely intended to further illustrate aspects of the invention. These Examples reflect exemplary embodiments of the invention, and the specific methods, findings, principles of such Examples, and the general implications thereof, can be combined with any other part of this disclosure. However, readers should understand that the invention is not limited by these Examples or any part thereof.

Example 1

Tables 4, 5, and 6, below, provide exemplary Formulation A, exemplary Formulation B, and exemplary Formulation C, respectively, each providing a list of ingredients suitable for compositions of the present invention provided in the form of a solution(s).

TABLE 4

Exemplary Formulation A. Pilocarpine and Brimonidine Solution + Boric Acid (without Citrate).

| No. | Ingredient | Percentage (w/v) in Composition |
|---|---|---|
| 1 | Pilocarpine Compound | 1-3 |
| 2 | Brimonidine Tartrate | 0.05-0.2 |
| 3 | Benzalkonium Chloride (BKC) | 0.003-0.02 |

TABLE 4-continued

Exemplary Formulation A. Pilocarpine and Brimonidine Solution + Boric Acid (without Citrate).

| No. | Ingredient | Percentage (w/v) in Composition |
|---|---|---|
| 4 | Boric Acid or Sodium Borate (pH dependent) | 0.5-1.5 |
| 5 | Sodium Chloride | 0.005-0.1 |
| 6 | OPTIONAL: Penetration Enhancer | 0.05-0.5 |
| 7 | pH Adjusting Agent(s) (e.g., Sodium Hydroxide, Hydrochloric Acid) | QS to Adjust pH to 5.5-7.5 |
| 8 | Water for Injection | QS to 100% Volume |

TABLE 5

Exemplary Formulation B. Pilocarpine and Brimonidine Solution + Sodium Citrate Dihydrate (without Boric Acid).

| No. | Ingredient | Percentage (w/v) in Composition |
|---|---|---|
| 1 | Pilocarpine Compound | 1-3 |
| 2 | Brimonidine Tartrate | 0.05-0.2 |
| 3 | Benzalkonium Chloride (BKC) | 0.003-0.02 |
| 4 | Sodium Citrate Dihydrate | 0.005-0.4 |
| 5 | Sodium Chloride | 0.005-0.1 |
| 6 | OPTIONAL: Penetration Enhancer | 0.05-0.5 |
| 7 | pH Adjusting Agent(s) (e.g., Sodium Hydroxide, Hydrochloric Acid) | QS to Adjust pH to 5.5-7.5 |
| 7 | Water for Injection | QS to 100% Volume |

TABLE 6

Exemplary Formulation C. Pilocarpine and Brimonidine Solution without Boric Acid or Sodium Citrate Dihydrate.

| No. | Ingredient | Percentage (w/v) in Composition |
|---|---|---|
| 1 | Pilocarpine Compound | 1-3 |
| 2 | Brimonidine Tartrate | 0.05-0.2 |
| 3 | Benzalkonium Chloride (BKC) | 0.003-0.02 |
| 4 | Sodium Acetate or Sodium Phosphate (pH dependent) | 0.2-1.5 |
| 5 | Sodium Chloride | 0.005-0.1 |
| 6 | OPTIONAL: Penetration Enhancer | 0.05-0.5 |
| 7 | pH Adjusting Agent(s) (e.g., Sodium Hydroxide, Hydrochloric Acid) | QS to Adjust pH to 5.5-7.5 |
| 7 | Water for Injection | QS to 100% Volume |

Example 2

Table 7 below provide exemplary Formulation D provided as a gel, providing a list of ingredients suitable for a composition of the present invention provided in gel form.

TABLE 7

Exemplary Formulation D. Pilocarpine and Brimonidine Gel.

| No. | Ingredient | Percentage (w/v) in Composition |
|---|---|---|
| 1 | Pilocarpine Compound (Note: equivalent to 12.72 mg/mL of base when present at, e.g., 1.25% w/v) | 0.5-2.5 |
| 2 | Brimonidine Tartrate (Note: 2 mg of brimonidine tartrate is equivalent to about 1.32 mg of free base brimonidine compound) | 0.05-0.2 |
| 3 | Cremophor | 0.05-0.8 |
| 4 | Benzalkonium chloride (BKC) | 0.003-0.02 |
| 5 | Tromethamine | 0.05-0.5 |
| 6 | Mannitol | 3-6 |
| 7 | Gellan gum | 0.1-1 |
| 8 | OPTIONAL: Penetration Enhancer | 0.05-1 |
| 9 | pH Adjusting Agent(s) | Q.S. to Adjust pH to 3.5-8.5 |
| 10 | Water for Injection | QS to 100% Volume |

Example 3

Table 8 below provides specific examples of suitable compositions according to Formulations A, B, and C of Example 1, provided as solutions. Notably, each of the compositions below are exemplified as being suitable at two different pH levels: compositions having the provided ingredients and having a pH of about 5.5 and compositions having the provided ingredients and having a pH of about 7.4.

TABLE 8

Exemplary Compositions of the Invention Provided as Solutions.

| Ingredient | Comp. 1: PH* + BT** without Citrate | Comp. 2: PH + BT without Borate | Comp. 3: PH + BT without Borate or Citrate Buffers | Comp. 4: PH + BT + PE***, without Citrate | Comp. 5: PH + BT + PE, without Borate | Comp. 6: PH + BT + PE without Borate or Citrate Buffers |
|---|---|---|---|---|---|---|
| | Percentage (w/v) in Composition | | | | | |
| Pilocarpine HCl (PH) | 1.5 | 1.5 | 1.5 | 1.5 | 1.5 | 1.5 |
| Brimonidine Tartrate (BT) | 0.1 | 0.1 | 0.1 | 0.1 | 0.1 | 0.1 |
| Benzalkonium Chloride (BKC) | 0.007 | 0.007 | 0.007 | 0.007 | 0.007 | 0.007 |
| Boric Acid Sodium Borate | 1 (pH 5.5)† 1 (pH 7.4)† | — | — | 1 (pH 5.5)† 1 (pH 7.4)† | — | — |
| Sodium Citrate Dihydrate | — | 0.2 | — | — | 0.2 | — |

TABLE 8-continued

Exemplary Compositions of the Invention Provided as Solutions.

| Ingredient | Comp. 1: PH* + BT** without Citrate | Comp. 2: PH + BT without Borate | Comp. 3: PH + BT without Borate or Citrate Buffers | Comp. 4: PH + BT + PE***, without Citrate | Comp. 5: PH + BT + PE, without Borate | Comp. 6: PH + BT + PE without Borate or Citrate Buffers |
|---|---|---|---|---|---|---|
| | Percentage (w/v) in Composition | | | | | |
| Acetate Buffer (Sodium Acetate) (pH 5.5) or Phosphate Buffer (Sodium Phosphate) (pH 7.4)‡ | — | — | 0.75 | — | — | 0.75 |
| Penetration Enhancer (PE), e.g., Polysorbate 80 | — | — | — | 0.25 | 0.25 | 0.25 |
| Sodium Chloride | 0.01 | 0.08 (pH 5.5) †† 0.01 (pH 7.4) †† | 0.08 | 0.07 | 0.08 (pH 5.5) †† 0.01 (pH 7.4) †† | 0.08 |
| Sodium Hydroxide | Q.S. to Adjust pH to 5.5 or 7.4 per final pH target | Q.S. to Adjust pH to 5.5 or 7.4 per final pH target | Q.S. to Adjust pH to 5.5 or 7.4 per final pH target | Q.S. to Adjust pH to 5.5 or 7.4 per final pH target | Q.S. to Adjust pH to 5.5 or 7.4 per final pH target | Q.S. to Adjust pH to 5.5 or 7.4 per final pH target |
| Hydrochloric Acid | Q.S. to Adjust pH to 5.5 or 7.4 | Q.S. to Adjust pH to 5.5 or 7.4 | Q.S. to Adjust pH to 5.5 or 7.4 | Q.S. to Adjust pH to 5.5 or 7.4 | Q.S. to Adjust pH to 5.5 or 7.4 | Q.S. to Adjust pH to 5.5 or 7.4 |
| Water for Injection | QS to 100% volume per final pH target | QS to 100% volume per final pH target | QS to 100% volume per final pH target | QS to 100% volume per final pH target | QS to 100% volume per final pH target | QS to 100% volume per final pH target |

*"PH" = pilocarpine hydrochloride.
**"BT" = brimonidine tartrate.
***"PE" = penetration enhancer.
†Sodium borate is used in solutions having a pH of 7.4, while boric acid is used in solutions having a pH of 5.5. No solution is exemplified here as comprising both sodium borate and boric acid.
††The concentration of sodium chloride will vary depending on the compositions of solutions at the two pH levels and is present in amounts which achieve the same osmolality in each solution.
‡Sodium acetate buffer is an exemplified buffer in solutions having a pH target of 5.5. Sodium phosphate buffer is an exemplified buffer in solutions having a pH target of 7.4.

Example 4

The following manufacturing process can be used to manufacture Composition 1, Composition 2, or Composition 3 of Table 8, Example 3.

Part 1. Bulk Solution Manufacturing

The manufacturing vessel/reactor vessel is sterilized with about 120 kg of water for injection (WFI). This establishes a sterilized "reactor vessel".

About 120 kg of water for injection (WFI) at a temperature of not less than about 70° C., e.g., at a temperature of between 70° C.-80° C., is collected in a manufacturing vessel, such as, e.g., a stainless-steel (SS) manufacturing vessel.

The WFI is cooled to about 20° C.-about 25° C., such as by circulating the water through a water jacket. While cooling, e.g., simultaneously with cooling, 0.2μ-filtered nitrogen is bubbled through the WFI, with all WFI collected in the manufacturing vessel.

The dissolved oxygen content of the WFI is routinely tested to ensure that the WFI reaches a dissolved oxygen content of no more than 2 ppm.

Nitrogen bubbling is continued throughout the bulk solution manufacturing process.

About 50 kg of WFI is transferred into a separate holding vessel. This WFI is used for rinsing, preparation of 0.1N hydrochloric acid (for pH adjustment), and preparation of 0.1N sodium hydroxide solution (for pH adjustment), and for bringing the final composition up to a target final volume.

A suitable stirrer is set to a speed of about 400 rpm±about 100 rpm within the manufacturing vessel containing about 70 kg of WFI. The mixing speed is adjusted as necessary based on/according to the equipment and batch, e.g., vessel geometry and the stirring dynamics during the manufacture of the batch.

The total required quantity of benzalkonium chloride (BKC) solution is added to the manufacturing vessel. The container used to add the BKC is rinsed multiple times, e.g., about 5 times, with approximately 50 mL of WFI each time. The rinses are added to the manufacturing vessel. Stirring is continued for at least about 10 minutes, such as for about 15 to 17 minutes, or for a sufficient time to ensure complete dissolution and composition uniformity.

The total required quantity of buffer, such as either citrate buffer, borate buffer, or, e.g., acetate buffer or phosphate buffer (acetate and phosphate buffers being used for solutions having lower and higher pH range targets, respectively, as appropriate) are added to the manufacturing vessel. In compositions lacking a buffer, this step is omitted. Stirring is continued for at least about 10 minutes, such as for about 15 minutes, or for a sufficient time to ensure complete dissolution of any buffer component/ingredient and composition uniformity.

The total required quantity of sodium chloride is added to the manufacturing vessel and stirring is continued to ensure its complete dissolution.

The total required quantity of pilocarpine HCl is added to the manufacturing vessel. The container used to add the pilocarpine HCl is rinsed multiple times, e.g., about 3 times, with approximately 25 mL WFI each time. The rinses are added to the manufacturing vessel. Stirring is continued for at least about 15 minutes, such as for about 30 minutes, or for a sufficient time to ensure complete dissolution of the pilocarpine HCl and uniformity.

The total required quantity of brimonidine tartrate is added to the manufacturing vessel. The container used to add the brimonidine tartrate is rinsed multiple times, e.g., about 3 times, with approximately 25 mL of WFI each time. The rinses are added to the manufacturing vessel. Stirring is continued for at least about 15 minutes, such for about 30 minutes, or for a sufficient time to ensure complete dissolution of the brimonidine tartrate and uniformity.

The volume in the manufacturing vessel is brought up to a volume of about 90 L (e.g., about 90 Kg) using the reserved WFI. The resulting composition in the manufacturing vessel is stirred for at least about 15 minutes, such as for about 30 to about 32 minutes or for a sufficient amount of time to ensure composition uniformity.

The composition (e.g., the solution) is checked for visual clarity to ensure that there are no undissolved particles in the solution. Stirring is continued until visual clarity is achieved. The resulting solution is referred to as the bulk solution.

The pH of the bulk solution is checked. If required, the pH of the bulk solution is adjusted to about 5.5 or to a range limited to between about 5.1 to about 5.9, or, alternatively, to about 7.4 or to a range limited to between about 7.1 to about 7.9 (depending on the final pH target for the composition) using 0.1N sodium hydroxide solution or 0.1N hydrochloric acid solution. The bulk solution is mixed for about 5 minutes after every addition of sodium hydroxide or hydrochloric acid before measuring the pH during pH adjustment.

The final volume of the bulk solution in the manufacturing vessel is brought up to a final volume of about 100 L (e.g., about 100 Kg), using reserved WFI. The resulting bulk solution is stirred for at least about 10 minutes such as about 15 minutes, or for a sufficient time to ensure uniformity of the bulk solution. The final bulk solution is checked to confirm that the pH of the solution is about 5.5 or, alternatively, is about 7.4 (as described above). The pH of the solution is adjusted, if necessary, with stirring and final pH confirmation repeated, as necessary.

Part 2. Filtration
2.1 Offline Filtration

After completion of the preparation of the bulk solution, the filtration process is initiated under laminar air flow (LAF).

Prior to initiation of the filtration process, a 0.2 µm capsule or cartridge filter is integrity tested using a water bubble point test against the filter manufacturer's specification. The result should be a pressure of not less than 46 psi under a filtration pressure limit of between about 0.8 kg/cm$^2$ to about 1.8 kg/cm$^2$.

Prior to the start of filtration activity, the filtration unit is flushed with about 200 mL to about 220 mL of the bulk solution. The bulk solution is held inside of the filtration unit for about 2 minutes during the flush. The bulk solution used for the flush is then discarded. The flushing procedure is repeated two additional times for a total of 3 flushes.

After flushing, filtration of the bulk solution is initiated. The bulk solution is filtered through the pre-sterilized, tested, and flushed 0.2 µm capsule or cartridge filter. All filtrate is collected in a sterile receiving vessel.

Upon completion of filtration, the filtrate within the sterile receiving vessel is overlayed with 0.2 µm-filtered nitrogen.

The receiving vessel is transferred to a sterile storage area and stored under laminar air flow until initiation of the filling activity.

A post-filtration integrity test of the filter is performed using a water bubble point test. The result should be a pressure of not less than 39.2 psi under a filtration pressure limit of between about 0.8 kg/cm$^2$ to about 1.8 kg/cm$^2$.

2.1 Online Filtration

Prior to the initiation of filling and capping activity, the bulk solution is filtered through another 0.2µ pre-sterilized capsule or cartridge filter.

Pre-integrity filter testing is performed using a water bubble point test against the filter manufacturer's specification. The result should be a pressure of not less than 46 psi under a filtration pressure limit of between about 0.8 kg/cm$^2$ to about 1.8 kg/cm$^2$. The filter is then connected to the filling line through a pre-sterilized vessel, e.g., buffer tank.

Prior to the initiation of filtration activity, the filter/filtration unit is flushed with about 200 to about 220 mL of the bulk solution. The bulk solution is held within the filtration unit for about 2 minutes during this flushing process and is then discarded. The flushing process is repeated at least two additional times for a total of at least about 3 flushes, with the bulk solution used for flushing discarded after each flush.

After completely discarding the filter flush solution, the entire quantity of remaining bulk solution is filtered into the sterile vessel, e.g., the sterile buffer tank.

The filling activity is then initiated.

Upon the completion of the filling activity, a post-filtration integrity test of the filter is performed using a water bubble point test. The result should be a pressure of not less than 39.2 psi under a filtration pressure limit of between about 0.8 kg/cm$^2$ to about 1.8 kg/cm$^2$.

Part 3. Filling and Capping

Suitable sterile containers, such as sterile vials, are each filled to a volume of between about 2.6 mL to about 2.8 mL (about 2.62 g to about 2.82 g), such as about 2.7 mL (about 2.72 g).

After filling, the head space of each vial is flushed with filtered nitrogen, e.g., using a minimum nitrogen flow of about 2 L/min.

Example 5

The following manufacturing process can be used to manufacture Composition 4, Composition 5, or Composition 6 of Table 7, Example 3.

Part 1. Bulk Solution Manufacturing

The manufacturing vessel/reactor vessel is sterilized with about 120 kg of water for injection (WFI). This establishes a sterilized "reactor vessel".

About 120 kg of water for injection (WFI) at a temperature of not less than about 70° C. is collected in a manufacturing vessel, such as, e.g., a stainless-steel (SS) vessel.

The WFI is cooled to about 20° C.-about 25° C., such as by circulating the water through a water jacket. While cooling, e.g., simultaneously with cooling, 0.2µ-filtered nitrogen is bubbled through the WFI, with all WFI collected in the manufacturing vessel.

The dissolved oxygen content of the WFI is routinely tested to ensure that the WFI reaches a dissolved oxygen content of no more than 2 ppm.

Nitrogen bubbling is continued throughout bulk solution manufacturing.

About 50 kg of WFI is transferred into a separate holding vessel. This WFI is used for rinsing, preparation of 0.1N hydrochloric acid (for pH adjustment), and preparation of 0.1N sodium hydroxide solution (for pH adjustment), and for bringing the final composition up to a target final volume.

A suitable stirrer is set to a speed of about 400 rpm±about 100 rpm within the manufacturing vessel containing about 70 kg of WFI. The mixing speed is adjusted as necessary based on/according to the equipment and batch, e.g., vessel geometry and the stirring dynamics.

The total required quantity of benzalkonium chloride (BKC) solution is added to the manufacturing vessel. The container used to add the BKC is rinsed multiple times, e.g., about 5 times, with approximately 50 mL of WFI each time. The rinses are added to the manufacturing vessel. Stirring is continued for at least about 10 minutes, such as for about 15 to 17 minutes, or for a sufficient time to ensure complete dissolution and composition uniformity.

The total required quantity of polysorbate 80 is added to the manufacturing vessel. The container used to add the polysorbate 80 is rinsed multiple times, e.g., about 5 times, with approximately 50 mL of WFI each time. The rinses are added to the manufacturing vessel under stirring. Stirring is continuous from the beginning of the process to the end of the process, unless otherwise indicated.

The total required quantity of buffer, such as, e.g., either citrate buffer, borate buffer, or acetate buffer or phosphate buffer (acetate and phosphate buffers selected based upon the target pH range of the solution) are added to the manufacturing vessel. In compositions lacking a buffer, this step is omitted. Stirring is continued for at least about 10 minutes, such as for about 15 minutes, or for a sufficient time to ensure complete dissolution of any buffer component/ ingredient and composition uniformity.

The total required quantity of sodium chloride is added to the manufacturing vessel and stirring is continued to ensure its complete dissolution.

The total required quantity of pilocarpine HCl is added to the manufacturing vessel. The container used to add the pilocarpine HCl is rinsed multiple times, e.g., about 3 times, with approximately 25 mL WFI each time. The rinses are added to the manufacturing vessel. Stirring is continued for at least about 15 minutes, such as for about 30 minutes, or for a sufficient time to ensure complete dissolution of pilocarpine HCl and composition uniformity.

The total required quantity of brimonidine tartrate is added to the manufacturing vessel. The container used to add the brimonidine tartrate is rinsed multiple times, e.g., about 3 times, with approximately 25 mL WFI each time. The rinses are added to the manufacturing vessel. Stirring is continued for at least about 15 minutes, such as for about 30 minutes, or for a sufficient time to ensure complete dissolution of brimonidine tartrate and uniformity.

The volume in the manufacturing vessel is brought up to a volume of about 90 L (e.g., about 90 Kg) using the reserved WFI. The resulting composition in the manufacturing vessel is stirred for at least about 15 minutes, such as for about 30 to about 32 minutes or for a sufficient amount of time to ensure composition uniformity.

The composition (e.g., the solution) is checked for visual clarity to ensure that there are no undissolved particles in the solution. Stirring is continued until visual clarity is achieved. The resulting solution is referred to as the bulk solution.

The pH of the bulk solution is checked. If required, the pH of the bulk solution is adjusted to about 5.5 (e.g., to a pH within a range limited to about 5.1 to about 5.9) or, alternatively, to about 7.4 (e.g., to a pH within a range limited to about 7.1 to about 7.9) using 0.1N sodium hydroxide solution or 0.1N hydrochloric acid solution. The bulk solution is mixed for about 5 minutes after each addition of sodium hydroxide or hydrochloric acid before measuring the pH during pH adjustment.

The final volume of the bulk solution in the manufacturing vessel is brought up to a final volume of about 100 L (e.g., about 100 Kg), using reserved WFI. The resulting bulk solution is stirred for at least about 10 minutes such as about 15 minutes, or for a sufficient time to ensure uniformity of the bulk solution. The final bulk solution is checked to confirm that the pH of the solution is about 5.5, or alternatively, is about 7.4 (as described above). The pH of the solution is adjusted, if necessary, with stirring and final pH confirmation repeated, as necessary.

Part 2. Filtration 2.1 Offline Filtration

After completion of the preparation of the bulk solution, the filtration process is initiated under laminar air flow (LAF).

Prior to initiation of the filtration process, a 0.2 μm capsule or cartridge filter is integrity tested using a water bubble point test against the filter manufacturer's specification. The result should be a pressure of not less than 46 psi under a filtration pressure limit of between about 0.8 kg/cm$^2$ to about 1.8 kg/cm$^2$.

Prior to the start of filtration activity, the filtration unit is flushed with about 200 mL to about 220 mL of the bulk solution. The bulk solution is held inside of the filtration unit for about 2 minutes during the flush. The bulk solution used for the flush is then discarded. The flushing procedure is repeated two additional times for a total of 3 flushes.

After flushing, filtration of the bulk solution is initiated. The bulk solution is filtered through the pre-sterilized, tested, and flushed 0.2 μm capsule or cartridge filter. All filtrate is collected in a sterile receiving vessel.

Upon completion of filtration, the filtrate within the sterile receiving vessel is overlayed with 0.2 μm-filtered nitrogen.

The receiving vessel is transferred to a sterile storage area and stored under laminar air flow until initiation of the filling activity.

A post-filtration integrity test of the filter is performed using a water bubble point test. The result should be a pressure of not less than 39.2 psi under a filtration pressure limit of between about 0.8 kg/cm$^2$ to about 1.8 kg/cm$^2$.

2.2 Online Filtration

Prior to the initiation of filling and capping activity, the bulk solution is filtered through another 0.2μ pre-sterilized capsule or cartridge filter.

Pre-integrity filter testing is performed using a water bubble point test against the filter manufacturer's specification. The result should be a pressure of not less than 46 psi under a filtration pressure limit of between about 0.8 kg/cm$^2$ to about 1.8 kg/cm$^2$. The filter is then connected to the filling line through a pre-sterilized vessel, e.g., buffer tank.

Prior to the initiation of filtration activity, the filter/ filtration unit is flushed with about 200 to about 220 mL of the bulk solution. The bulk solution is held within the filtration unit for about 2 minutes during this flushing process and is then discarded. The flushing process is repeated at least two additional times for a total of at least about 3 flushes, with the bulk solution used for flushing discarded after each flush.

After completely discarding the filter flush solution, the entire quantity of remaining bulk solution is filtered into the sterile vessel, e.g., the sterile buffer tank.

The filling activity is then initiated.

Upon the completion of the filling activity, a post-filtration integrity test of the filter is performed using a water bubble point test. The result should be a pressure of not less than 39.2 psi under a filtration pressure limit of between about 0.8 kg/cm² to about 1.8 kg/cm².

Part 3. Filling and Capping

Suitable sterile containers, such as sterile vials, are each filled to a volume of about 2.6 mL to about 2.8 mL (~2.62 g-~2.82 g), such as about 2.7 mL (about 2.72 g).

After filling, the head space of each vial is flushed with filtered nitrogen, e.g., using a minimum nitrogen flow of about 2 L/min.

Example 6

Table 9 below provides specific examples of suitable compositions according to Formulation D of Example 2, provided as a gel.

TABLE 9

Exemplary Compositions of the Invention Provided as a Gel.

| Ingredient | Comp. 7: Pilocarpine + Brimonidine Gel | Comp. 8: Pilocarpine + Brimonidine Gel + PE* |
|---|---|---|
| | (Percentage (w/v) in Composition) | |
| Pilocarpine HCl | 1.25 | 1.25 |
| Brimonidine Tartrate | 0.1 | 0.1 |
| Cremophor | 0.25 | 0.25 |
| Benzalkonium Chloride (BKC) | 0.0075 | 0.0075 |
| Tromethamine | 0.185 | 0.185 |
| Mannitol | 4.5 | 4.5 |
| Gellan Gum | 0.6 | 0.6 |
| Polysorbate 80 | — | 0.5 |
| Sodium Hydroxide | Q.S. to Adjust pH to 4.5 | Q.S. to Adjust pH to 4.5 |
| Hydrochloric Acid | Q.S. to Adjust pH to 4.5 | Q.S. to Adjust pH to 4.5 |
| Water for Injection | QS to 100% Volume | QS to 100% Volume |

*"PE" = penetration enhancer.

Example 7

The following manufacturing process can be used to manufacture Composition 7 or Composition 8, of Table 9, Example 6.

Part 1. Bulk Solution Manufacturing
1.1 Preparation of Polymer Phase Solution

A first (filter no. 1) and a second (filter no. 2) 0.2 μm capsule filter are each integrity-tested using a water bubble point test against the filter manufacturer's specification(s). The result of each test should be a pressure of not less than 46.0 psi under a filtration pressure limit of between about 0.8 kg/cm² to about 1.8 kg/cm². Upon completion of integrity testing, filters are flushed with nitrogen to remove any residual water from the filter pores.

The outlet of filter no. 2 is connected to the inlet of filter No. 1 using a suitable connection mechanism, such as Pharma 50 silicone tubing of a suitable length, such as about 60 cm. The outlet of filter no. 1 is connected to a diaphragm valve. The inlet of filter no. 2 is connected to a suitable connection mechanism, such as Pharma 50 silicone tubing of suitable length, such as about 2.30 meters. The entire assembly is sterilized using a suitable sterilization method such as autoclaving. During sterilization, e.g., while autoclaving, the diaphragm valve is maintained in an open position. Upon completion of sterilization, e.g., after autoclaving, the diaphragm valve is closed under aseptic conditions. The entire assembly is then connected to an empty manufacturing vessel (e.g., a "reactor vessel").

The manufacturing vessel/reactor vessel is sterilized with about 120 kg of water for injection (WFI). This establishes a sterilized "reactor vessel" or "SIP vessel".

About 120 kg of water for injection (WFI) at a temperature of not less than about 70° C. is collected in a manufacturing vessel, such as, e.g., a stainless-steel (SS) vessel.

The WFI is cooled to about 20° C.-about 25° C., such as by circulating the water through a water jacket. While cooling, e.g., simultaneously with cooling, 0.2μ-filtered nitrogen is bubbled through the WFI, with all WFI collected in the manufacturing vessel.

The dissolved oxygen content of the WFI is routinely tested to ensure that the WFI reaches a dissolved oxygen content of no more than 2 ppm.

Nitrogen bubbling is continued throughout bulk solution manufacturing.

After completion of empty reactor sterilization, about 50 Kg of the 120 Kg of WFI is transferred to a second manufacturing vessel, e.g., a stainless-steel manufacturing vessel, to be used in the preparation of a drug phase and bringing composition(s) up to volume.

While maintaining the temperature of the remaining about 70 Kg WFI in the reactor vessel between about 73° C. and 78° C., a suitable stirrer in the reactor vessel is set to a stirrer speed of about 125 rpm±about 50 rpm. The mixing speed is adjusted as necessary based on/according to the equipment and batch, e.g., vessel geometry and the stirring dynamics during the manufacture of the batch.

The required quantity of gellan gum NF (national formulary) is added to the reactor vessel and stirring is maintained at about 125 rpm±about 50 rpm for at least about 30 minutes, such as about 60 mins, or for a sufficient time to ensure complete dissolution of the gellan gum. The solution is maintained at a temperature of between about 73° C. and about 78° C. during the continuous stirring.

After complete dissolution of gellan gum, the solution is cooled to between about 20° C. and about 25° C. under constant stirring. This establishes the "polymer phase".

The polymer phase is sterilized at a set temperature of about 122.0° C. for about 20 minutes while constantly stirring at speed of about 125 rpm±about 50 rpm.

Upon completion of sterilization, the polymer phase is cooled to about 25° C. While cooling, when the temperature of the polymer phase reaches about 60° C., the stirring speed is increased to a stirring speed of about 250 rpm±50 rpm.

1.2 Preparation of Drug Phase Solution

About 50 Kg of the reserved, cooled WFI is collected in a suitable manufacturing vessel. A suitable stirrer in the manufacturing vessel is set to a stirring speed of about 300 rpm±50 rpm. The mixing speed is adjusted as necessary based on/according to the equipment and batch, e.g., vessel geometry and the stirring dynamics during the manufacture of the batch.

The total required quantity of pilocarpine HCl is added to the manufacturing vessel, followed by the addition of the total required quantity brimonidine tartrate, which is then followed by the addition of the total required quantity of benzalkonium chloride to the manufacturing vessel. The resulting composition is mixed until the three components are completely dissolved. As indicated elsewhere herein, in some embodiments of this process, the order of the addition of components can be in an order other than what is specifically exemplified.

The total required quantity of polysorbate 80 is added to the manufacturing vessel. The resulting composition is mixed until the polysorbate 80 is completely dissolved. In compositions lacking polysorbate 80, this step is omitted.

Upon the complete dissolution of the pilocarpine HCl, brimonidine tartrate, benzalkonium chloride, and polysorbate 80 (if present), the total required quantity of cremophor is added to the solution. The resulting composition is mixed for a suitable period of time to allow complete dissolution of cremophor.

Upon the complete dissolution of the cremophor, the total required quantity of mannitol is added to the solution. The resulting composition is mixed for a suitable period of time to allow the mannitol to completely dissolve.

Upon the complete dissolution of the mannitol, the total required quantity of tromethamine is added to the solution. The resulting composition is mixed for a sufficient period of time, such as about 10 minutes, to ensure complete dissolution of the tromethamine.

The composition is checked for clarity. Stirring is continued until visual clarity is achieved.

The volume is then brought to about 55 L using previously reserved WFI. The composition is then stirred for about 15 minutes or for a sufficient period of time to ensure composition uniformity. This establishes the "drug phase".

An industry standard sampling protocol is used to sample and test the drug phase to ensure that the phase meets pre-established specification(s). Upon acceptance, the drug phase is transferred to the sterilized polymer phase via aseptic filtration (see below).

1.3 Aseptic Filtration of Drug Phase into Sterile Polymer Phase

Aseptic filtration of the drug phase into the sterile polymer phase is performed at a filtration pressure of between about 0.8 Kg/cm²-about 1.8 Kg/cm².

Prior to beginning the aseptic filtration, the weight of the drug phase is noted. About 55 Kg of the drug phase (which can be referred to as the "concentrated drug phase") is filtered into the reactor vessel containing the polymer phase through the two sterilized 0.2 μm filters connected in series.

WFI is then passed through the filters a number of times, such as about two times with about 2.5 L of WFI each time, and the filtrate added to the reactor vessel each time to ensure all required drug phase is added into the reactor vessel. The resulting composition is then stirred for about 1 hour at a speed of about 250 rpm±about 50 rpm, or for a sufficient period of time (and at a suitable speed) to ensure composition uniformity.

A post-filtration integrity test of the filter is performed using a water bubble point test. The result should be a pressure of not less than 34.8 psi under a filtration pressure limit of between about 0.8 kg/cm² to about 1.8 kg/cm².

The pH of the composition is adjusted using one or more pH adjusting agents. The pH of the solution is adjusted by the addition or one or more pH adjusting agents, with the solution sufficiently mixed after each addition such that the composition has a uniform pH prior to (a) sampling for pH, and (b) applying further pH adjustment as needed. Composition pH is adjusted to a pH of between about 4.4 to about 4.6, such as, e.g., about 4.4, about 4.5, or about 4.6 using the pH adjusting agent(s).

Part 2. Filtration

Filtration of the final combined composition (bulk solution) is then performed using a suitable filter such as an 8 μm PP2 MidiCap® filter (Sartorius).

Before initiating filtration activity, a sterilized 8.0 μm polypropylene filter is flushed with about 100 mL to about 120 mL of bulk solution a number of times such as about 3 times. During each flush, the composition is held in the filtration unit for an extended period of time, such as about 2 minutes, prior to discarding each flush. Upon completion of flushing, filtration of the bulk solution is performed with the filtrate collected in a sterile receiving vessel.

Part 3. Filling and Capping

Suitable sterile containers, such as sterile vials, are each filled to a volume of between about 2.6 mL to about 2.8 mL (about 2.62 g to about 2.82 g), such as about 2.7 mL (about 2.72 g).

After filling, the head space of each vial is flushed with filtered nitrogen, e.g., using a minimum nitrogen flow of about 2 L/min.

The invention claimed is:

1. A pharmaceutically acceptable and ophthalmologically suitable gel composition for treating an ocular condition via administration to a mammalian eye, the composition comprising (1) a pilocarpine compound in an amount greater than 1% w/v; (2) a brimonidine compound in an amount of between 0.05% w/v and 0.2% w/v, and (3) at least one polyethoxylated castor oil, wherein the w/v ratio of the at least one polyethoxylated castor oil to the brimonidine compound is between about 1:0.06 and about 1:4.

2. The composition of claim 1, wherein the pilocarpine compound is a salt of pilocarpine.

3. The composition of claim 2, wherein the pilocarpine compound is pilocarpine hydrochloride.

4. The composition of claim 1, wherein the composition comprises pilocarpine hydrochloride in an amount of between 1.15% w/v and 1.7% w/v.

5. The composition of claim 1, wherein the composition comprises pilocarpine hydrochloride in an amount representing 1.5% w/v of the composition.

6. The composition of claim 1, wherein the brimonidine compound is a salt of brimonidine.

7. The composition of claim 6, wherein the brimonidine compound is brimonidine tartrate.

8. The composition of claim 7, wherein the composition comprises brimonidine tartrate in an amount between 0.05% w/v and 0.15% w/v of the composition.

9. The composition of claim 8, wherein the composition comprises brimonidine tartrate in an amount representing about 0.1% w/v of the composition.

10. The composition of claim 1, wherein the w/v ratio of the at least one polyethoxylated castor oil to the brimonidine compound is between about 1:0.06 and about 1:1.

11. The composition of claim 10, wherein the w/v ratio of the at least one polyethoxylated castor oil to the brimonidine compound is between about 1:0.2 and about 1:0.5.

12. The composition of claim 1, wherein the pH of the composition is maintained between about 3.5 and about 8.5 when stored at between about 15° C. and about 25° C.+/−2° C. for a period of at least about 3 months.

13. The composition of claim 1, wherein the composition further comprises a tonicity component, and further wherein the tonicity component comprises a sugar alcohol.

14. The composition of claim 13, wherein the tonicity component comprises mannitol in an amount representing about 3% w/v to about 6% w/v of the composition.

15. The composition of claim 1, wherein the composition further comprises an effective amount of a preservation component.

16. The composition of claim 15, wherein the preservation component comprises an effective amount of one or more quaternary ammonium salts.

17. The composition of claim 16, wherein the one or more quaternary ammonium salts is benzalkonium chloride.

18. The composition of claim 17, wherein the composition comprises benzalkonium chloride in an amount of between about 0.003% w/v and about 0.02% w/v of the composition.

19. The composition of claim 18, wherein the composition comprises benzalkonium chloride in an amount of between about 0.007% w/v and about 0.008% w/v of the composition.

20. A method of treating an ophthalmic condition or symptom related thereto in a mammalian eye, the method comprising administration of an effective amount of the composition of claim 1.

21. The method of claim 20, wherein an effective amount of the composition is 1-2 drops of the composition to one or both eye(s) of the recipient once or twice daily.

22. The method of claim 20, wherein the ophthalmic condition is selected from the group consisting of presbyopia, hyperopia, mydriasis, anisocoria, accommodative esotropia, myopia, and astigmatism.

* * * * *